(12) United States Patent
Shelton, IV et al.

(10) Patent No.: US 12,232,726 B2
(45) Date of Patent: Feb. 25, 2025

(54) SURGICAL INSTRUMENT WITH MULTIPLE PROGRAM RESPONSES DURING A FIRING MOTION

(71) Applicant: Cilag GmbH International, Zug (CH)

(72) Inventors: Frederick E. Shelton, IV, Hillsboro, OH (US); Jason L. Harris, Lebanon, OH (US); Michael J. Vendely, Lebanon, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/587,265

(22) Filed: Feb. 26, 2024

(65) Prior Publication Data

US 2024/0252168 A1 Aug. 1, 2024

Related U.S. Application Data

(63) Continuation of application No. 17/592,197, filed on Feb. 3, 2022, now Pat. No. 11,931,028, which is a
(Continued)

(51) Int. Cl.
*A61B 17/072* (2006.01)
*A61B 17/068* (2006.01)
(Continued)

(52) U.S. Cl.
CPC .......... *A61B 17/072* (2013.01); *A61B 17/068* (2013.01); *A61B 17/07207* (2013.01); *A61B 17/32* (2013.01); *A61B 2017/00004* (2013.01); *A61B 2017/00017* (2013.01); *A61B 2017/00022* (2013.01); *A61B 2017/00137* (2013.01); *A61B 2017/00398* (2013.01); *A61B 2017/0046* (2013.01); *A61B 2017/00477* (2013.01); *A61B 2017/00734* (2013.01);
(Continued)

(58) Field of Classification Search
CPC . A61B 17/068; A61B 17/0686; A61B 17/072; A61B 17/07207; A61B 17/115; A61B 2017/00004; A61B 2017/00017; A61B 2017/00022; A61B 2017/00234; A61B 2017/00367; A61B 2017/00398; A61B 2017/07278; A61B 2017/07271; A61B 2017/07214; A61B 34/30; A61B 34/71; A61B 90/98
USPC .............. 227/19, 175.1, 175.2, 176.1, 180.1; 606/1, 139, 153, 213, 219
See application file for complete search history.

(56) References Cited

U.S. PATENT DOCUMENTS

| | | | |
|---|---|---|---|
| 5,395,033 A | 3/1995 | Byrne et al. | |
| 6,953,139 B2 * | 10/2005 | Milliman | A61B 17/07207 227/19 |

(Continued)

FOREIGN PATENT DOCUMENTS

EP 2364651 B1 11/2016

*Primary Examiner* — Scott A Smith

(57) ABSTRACT

A surgical instrument. The surgical instrument includes an elongated channel configured to support a staple cartridge, an anvil pivotably connected to the elongated channel, a knife mechanically coupled to the staple cartridge, an electric motor and a control circuit electrically connected to the electric motor. The control circuit is configured to change a firing motion of the surgical instrument based on a combination of events.

20 Claims, 95 Drawing Sheets

Related U.S. Application Data continuation of application No. 16/506,399, filed on Jul. 9, 2019, now Pat. No. 11,284,891, which is a continuation of application No. 15/130,571, filed on Apr. 15, 2016, now Pat. No. 10,357,247.

(51) Int. Cl.
  *A61B 17/32* (2006.01)
  *A61B 17/00* (2006.01)
  *A61B 90/00* (2016.01)

(52) U.S. Cl.
  CPC ............. *A61B 2017/07214* (2013.01); *A61B 2017/07257* (2013.01); *A61B 2017/07271* (2013.01); *A61B 2017/07278* (2013.01); *A61B 2090/065* (2016.02); *A61B 2090/0811* (2016.02)

(56) References Cited

U.S. PATENT DOCUMENTS

| | | |
|---|---|---|
| 7,845,537 B2 | 12/2010 | Shelton, IV et al. |
| 8,210,411 B2 | 7/2012 | Yates et al. |
| 8,505,799 B2 | 8/2013 | Viola et al. |
| 8,523,043 B2 | 9/2013 | Ullrich et al. |
| 8,608,044 B2 | 12/2013 | Hueil et al. |
| 8,608,045 B2 | 12/2013 | Smith et al. |
| 8,627,993 B2 | 1/2014 | Smith et al. |
| 8,657,174 B2 | 2/2014 | Yates et al. |
| 8,840,603 B2 | 9/2014 | Shelton, IV et al. |
| 8,851,354 B2 | 10/2014 | Swensgard et al. |
| 8,960,520 B2 | 2/2015 | McCuen |
| 9,044,227 B2 | 6/2015 | Shelton, IV et al. |
| 9,072,535 B2 | 7/2015 | Shelton, IV et al. |
| 9,113,880 B2 | 8/2015 | Zemlok et al. |
| 9,179,912 B2 | 11/2015 | Yates et al. |
| 9,345,481 B2 | 5/2016 | Hall et al. |
| 9,629,629 B2 | 4/2017 | Leimbach et al. |
| 9,737,301 B2 | 8/2017 | Baber et al. |
| 9,808,244 B2 | 11/2017 | Leimbach et al. |
| 9,987,095 B2 | 6/2018 | Chowaniec et al. |
| 10,335,145 B2 | 7/2019 | Harris et al. |
| 10,357,247 B2 | 7/2019 | Shelton, IV et al. |
| 10,405,859 B2 | 9/2019 | Harris et al. |
| 10,426,467 B2 | 10/2019 | Miller et al. |
| 10,456,137 B2 | 10/2019 | Vendely et al. |
| 10,492,783 B2 | 12/2019 | Shelton, IV et al. |
| 10,828,028 B2 | 11/2020 | Harris et al. |
| 11,045,199 B2 * | 6/2021 | Mozdzierz ..... A61B 17/320016 |
| 11,179,150 B2 | 11/2021 | Yates et al. |
| 11,284,891 B2 | 3/2022 | Shelton, IV et al. |
| 11,607,239 B2 | 3/2023 | Swensgard et al. |
| 11,931,028 B2 * | 3/2024 | Shelton, IV ........... A61B 17/32 |
| 2008/0296346 A1 | 12/2008 | Shelton, IV et al. |
| 2009/0090763 A1 | 4/2009 | Zemlok et al. |
| 2010/0069942 A1 | 3/2010 | Shelton, IV |
| 2011/0174861 A1 | 7/2011 | Shelton, IV et al. |
| 2011/0204119 A1 * | 8/2011 | McCuen ............. A61B 17/068 227/175.1 |
| 2014/0001231 A1 | 1/2014 | Shelton, IV et al. |
| 2014/0263541 A1 | 9/2014 | Leimbach et al. |
| 2014/0263552 A1 | 9/2014 | Hall et al. |
| 2015/0053737 A1 | 2/2015 | Leimbach et al. |

* cited by examiner

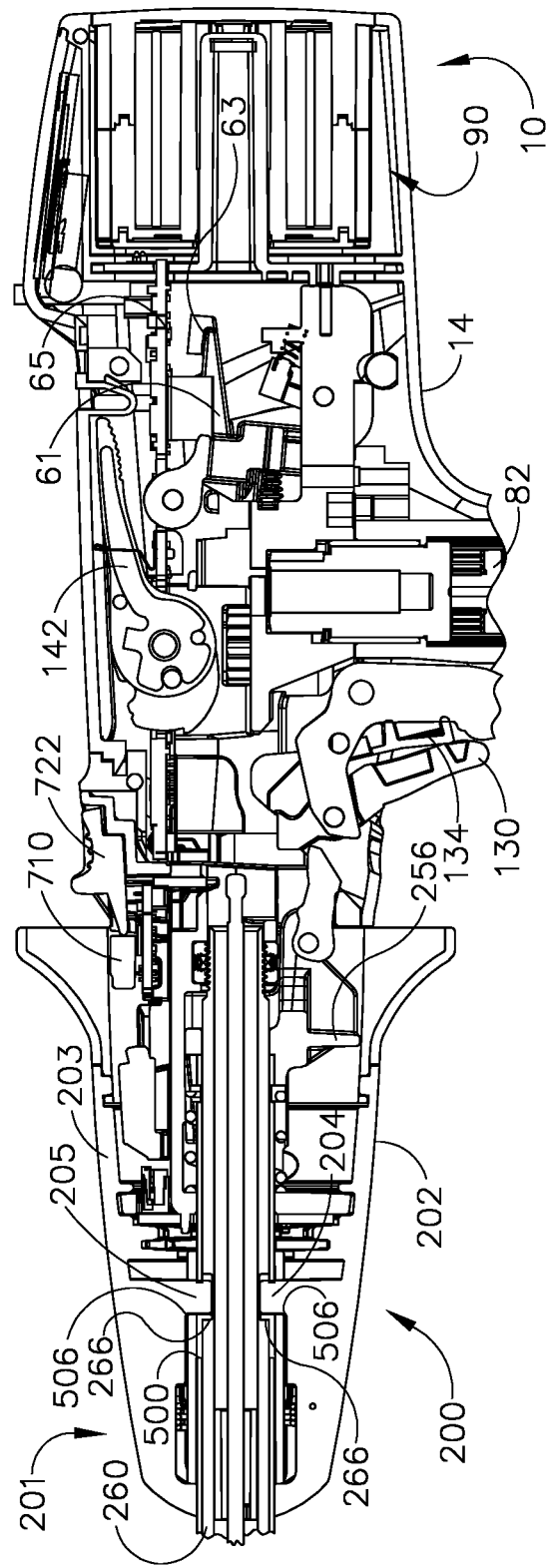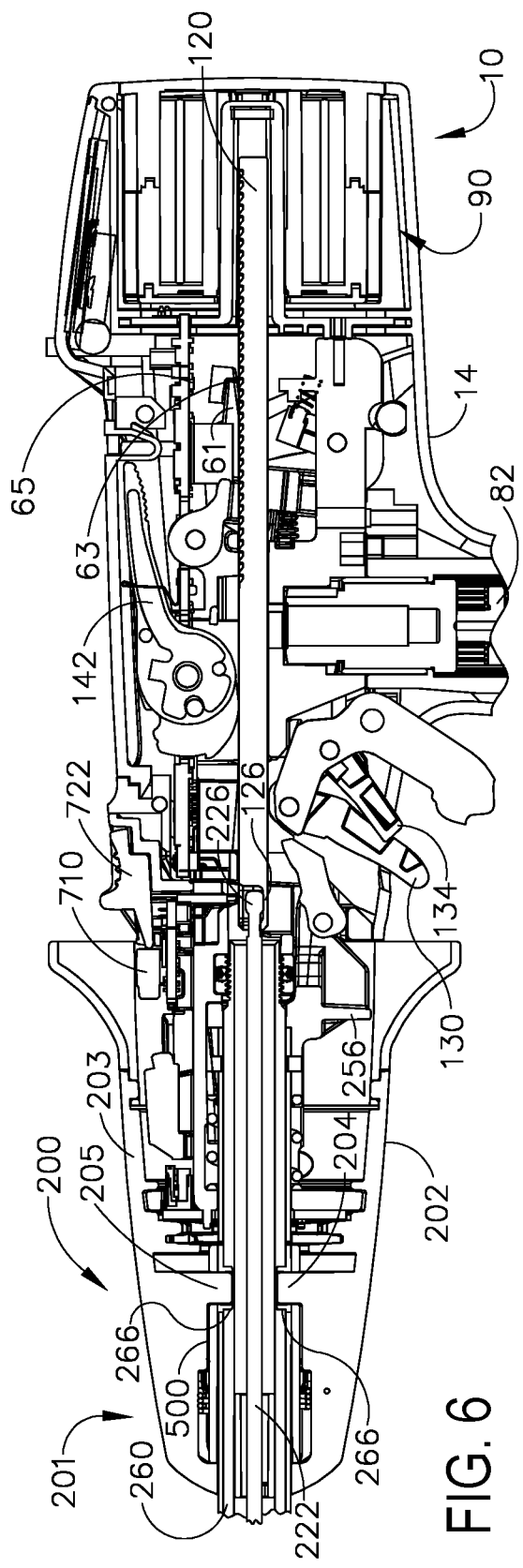

FIG. 13

FIRED
RIGHT SIDE

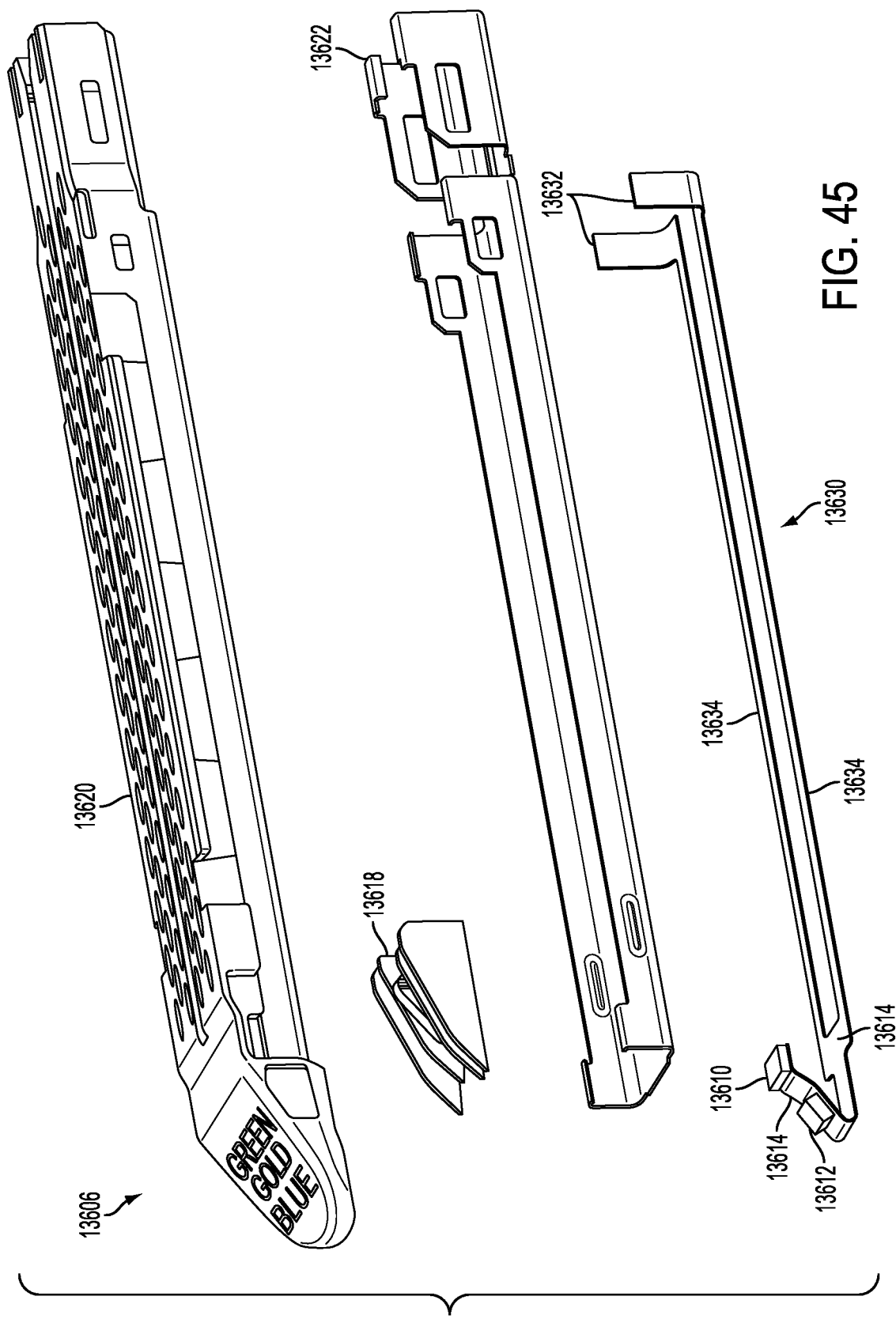

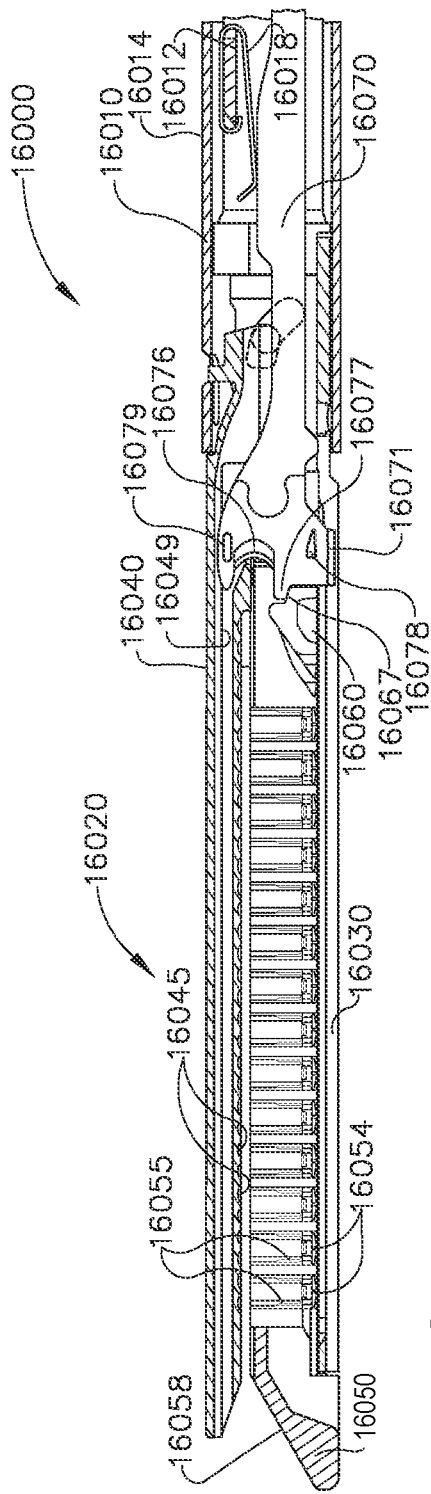
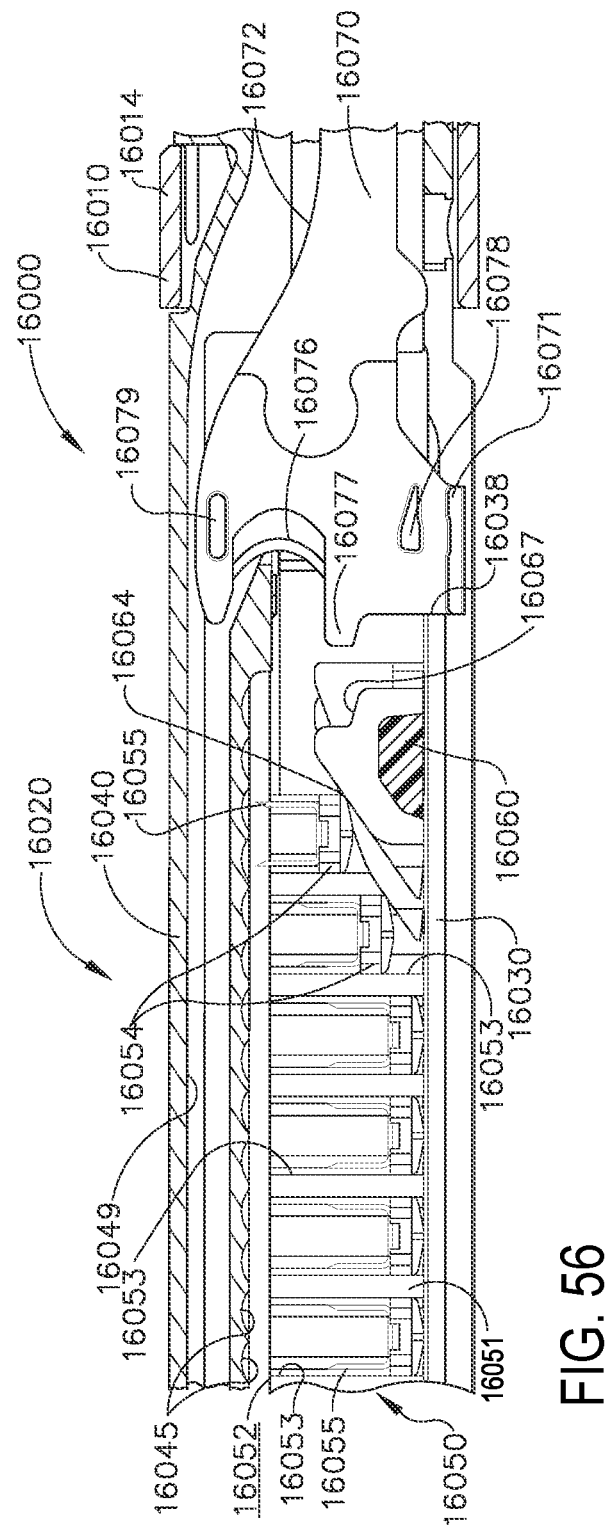
FIG. 55
FIG. 56

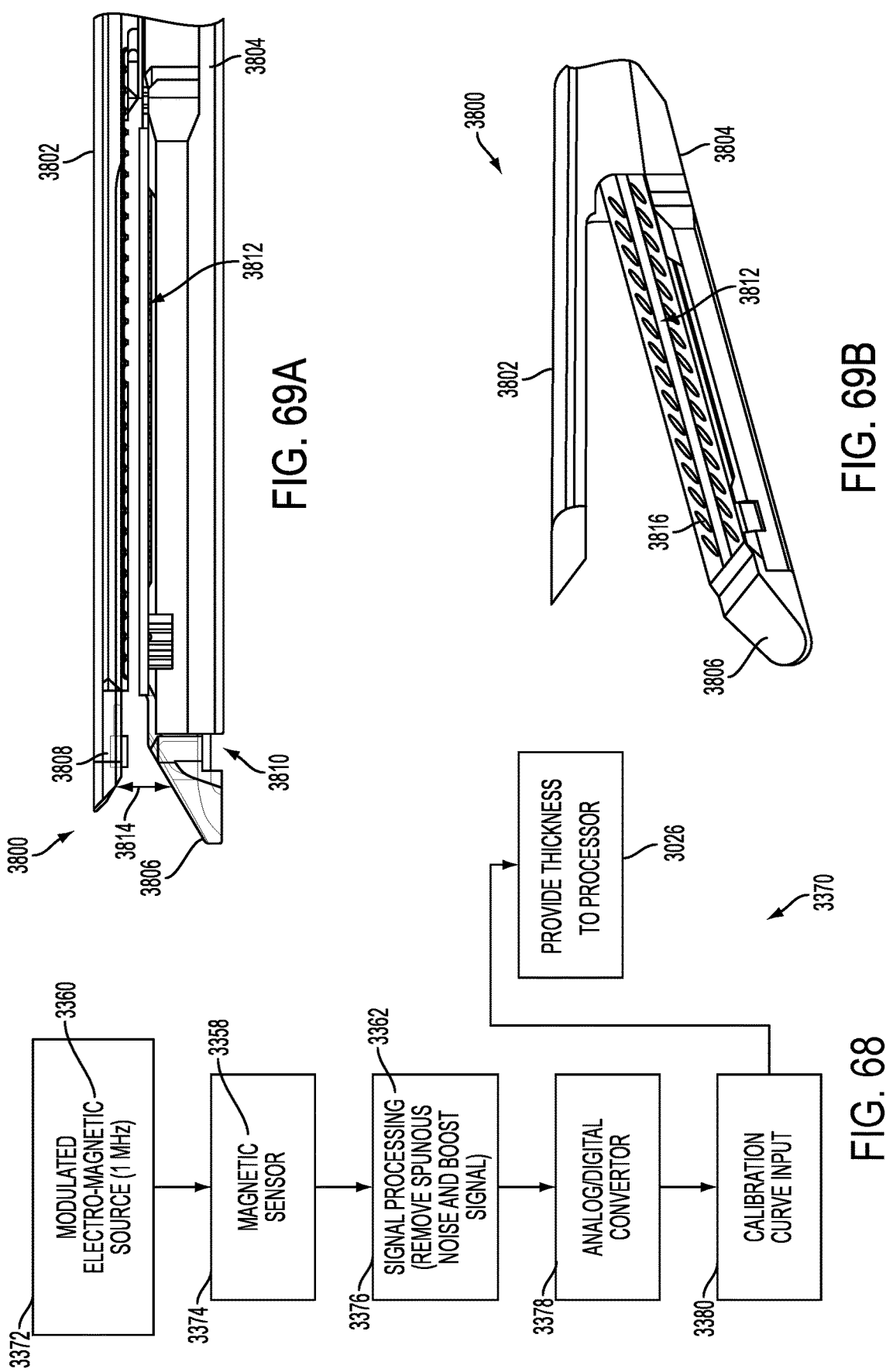

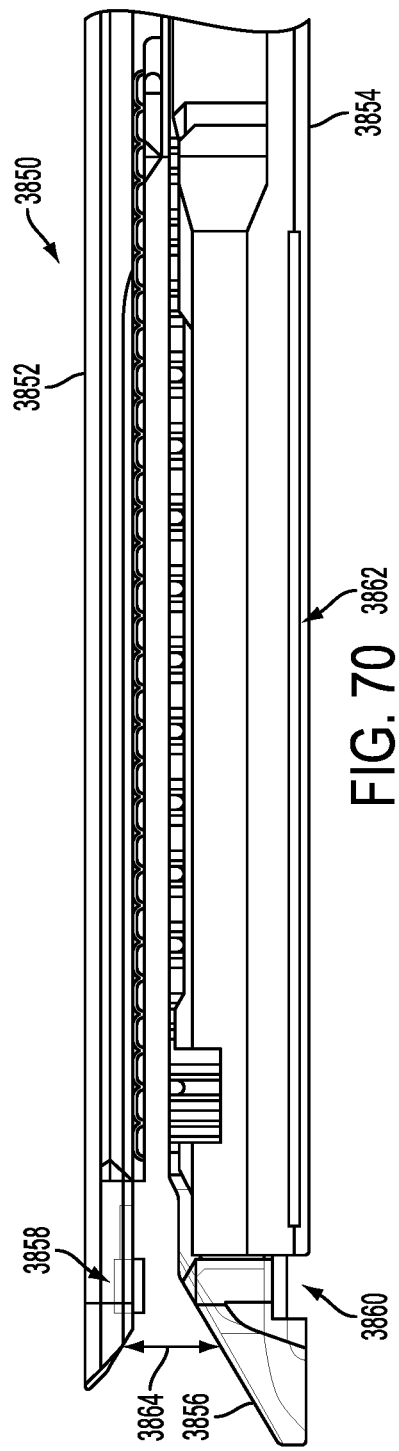
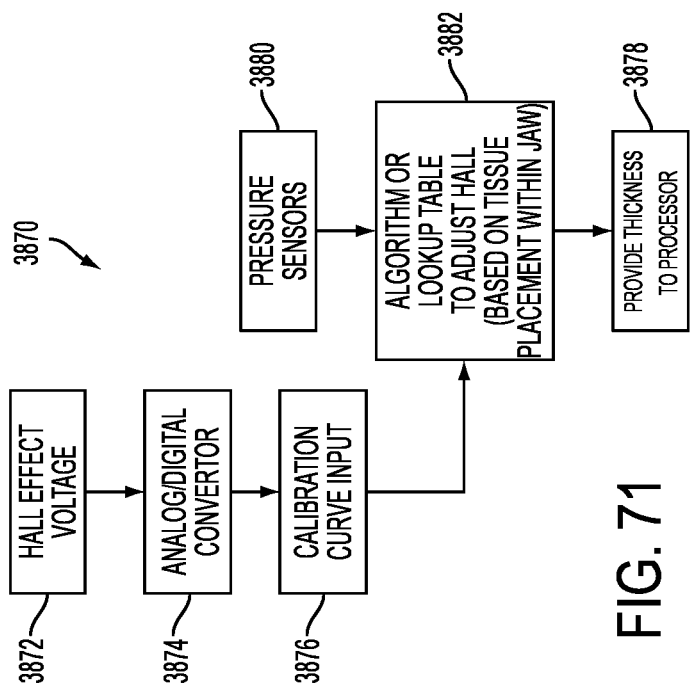
FIG. 70
FIG. 71

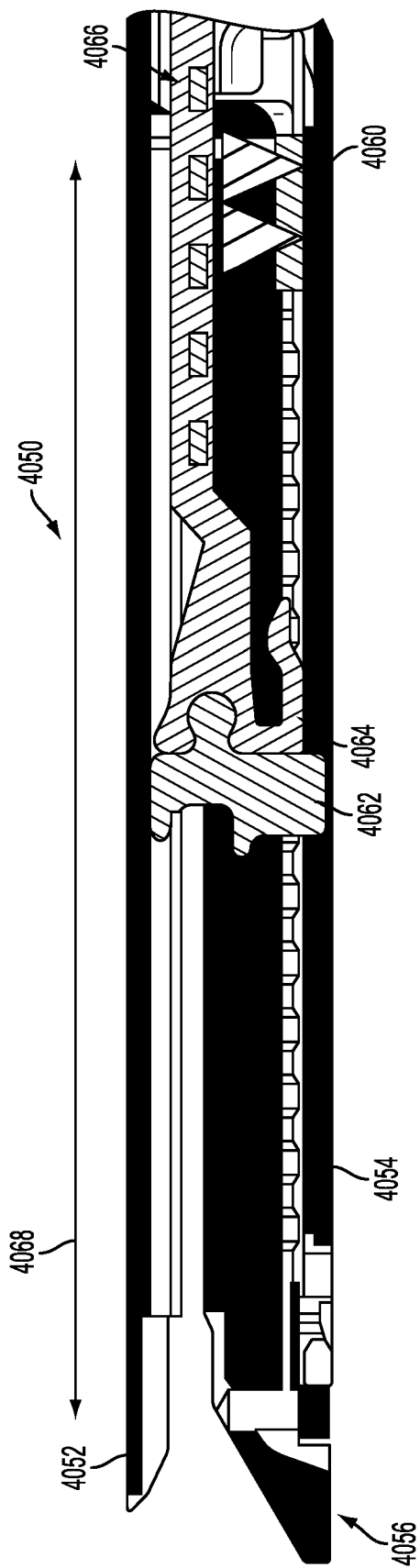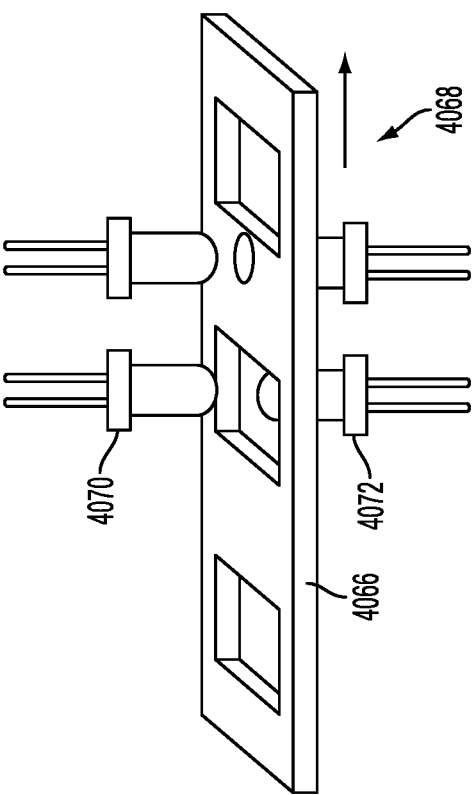

| TISSUE THICKNESS RANGES (T) | THRESHOLD FORCE (F) |
|---|---|
| T1-T2 | F1 |
| T2-T3 | F2 |
| T3-T4 | F3 |
| - | - |
| - | - |
| - | - |
| Tn-1 - Tn | Fn |

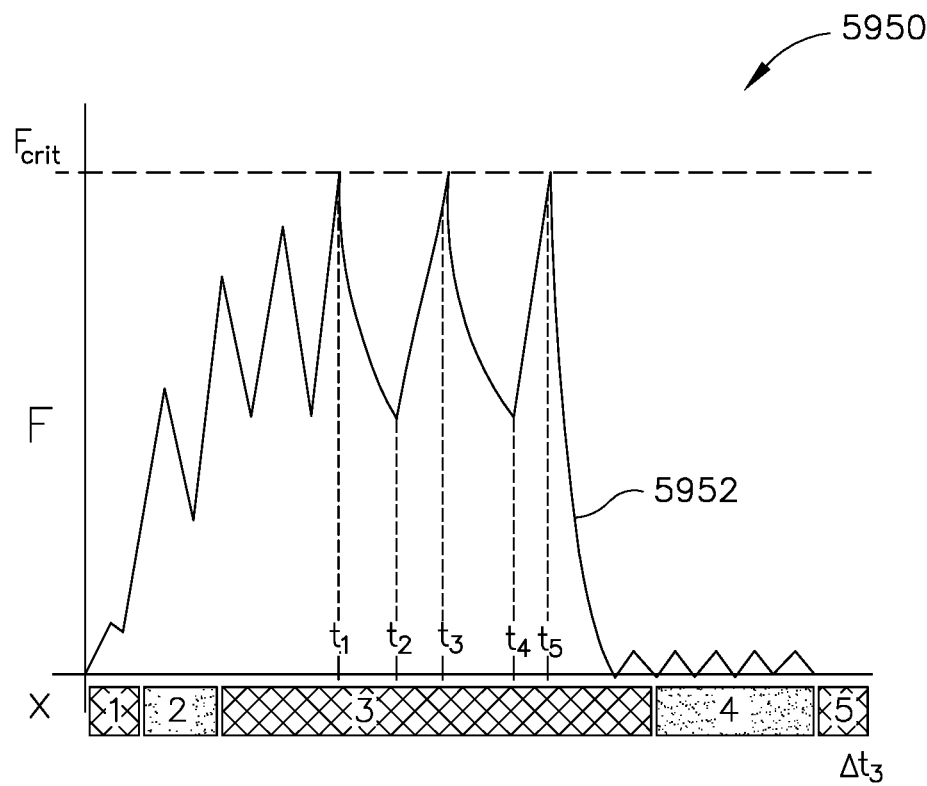
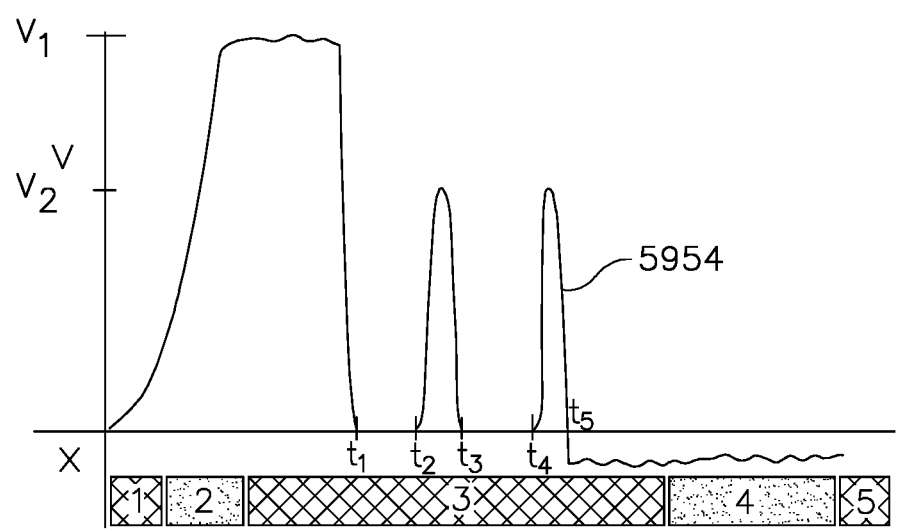
FIG. 127

SURGICAL INSTRUMENT WITH MULTIPLE PROGRAM RESPONSES DURING A FIRING MOTION

CROSS-REFERENCE TO RELATED APPLICATIONS

This application is a continuation application claiming priority under 35 U.S.C. § 120 to U.S. patent application Ser. No. 17/592,197, entitled SURGICAL INSTRUMENT WITH MULTIPLE PROGRAM RESPONSES DURING A FIRING MOTION, filed Feb. 3, 2022, which issued on Mar. 19, 2024 as U.S. Pat. No. 11,931,028, which is a continuation application claiming priority under 35 U.S.C. § 120 to U.S. patent application Ser. No. 16/506,399, entitled SURGICAL INSTRUMENT WITH MULTIPLE PROGRAM RESPONSES DURING A FIRING MOTION, filed Jul. 9, 2019, which issued on Mar. 29, 2022, as U.S. Pat. No. 11,284,891, which is a continuation application claiming priority under 35 U.S.C. § 120 to U.S. patent application Ser. No. 15/130,571, entitled SURGICAL INSTRUMENT WITH MULTIPLE PROGRAM RESPONSES DURING A FIRING MOTION, filed Apr. 15, 2016, which issued on Jul. 23, 2019 as U.S. Pat. No. 10,357,247, the entire disclosures of which are hereby incorporated by reference herein.

TECHNICAL FIELD

The present disclosure relates to surgical instruments and, in various circumstances, to surgical stapling and cutting instruments and staple cartridges therefor that are designed to staple and cut tissue.

BACKGROUND

In a motorized surgical stapling and cutting instrument it would be helpful to have change the firing parameters (speed of firing, timing of a pause in firing, duration of a firing pause, clamp pressure, etc.) to affect staple formation based on real-time (or continuous) determination of defect density. While several devices have been made and used, it is believed that no one prior to the inventors has made or used the device described in the appended claims.

BRIEF SUMMARY

In some aspects, a surgical instrument is provided. The surgical instrument comprises an elongated channel configured to support a staple cartridge; an anvil pivotably connected to the elongated channel; a closure tube mechanically coupled to the anvil; an electric motor; and a control circuit electrically connected to the electric motor, wherein the control circuit is configured to change a closing motion of the surgical instrument based on a combination of events.

The foregoing summary is illustrative only and is not intended to be in any way limiting. In addition to the illustrative aspects and features described above, further aspects and features will become apparent by reference to the drawings and the following detailed description.

BRIEF DESCRIPTION OF THE DRAWINGS

The novel features of the aspects described herein are set forth with particularity in the appended claims. The aspects, however, both as to organization and methods of operation may be better understood by reference to the following description, taken in conjunction with the accompanying drawings as follows.

FIG. 5 is a cross-sectional side view of a portion of the surgical instrument of FIG. 4 with the firing trigger in a fully actuated position in accordance with one or more aspects of the present disclosure.

FIG. 6 is another cross-sectional view of a portion of the surgical instrument of FIG. 5 with the firing trigger in an unactuated position in accordance with one or more aspects of the present disclosure.

FIG. 13 is a right side elevational view of the interchangeable shaft assembly operably coupled to a portion of the surgical instrument of FIG. 1 illustrated with the closure trigger thereof in an actuated position and the firing trigger thereof in an actuated position in accordance with one or more aspects of the present disclosure.

FIG. 45 illustrates one aspect of an exploded view of a staple cartridge that comprises a flex cable connected to a magnetic field sensor and processor in accordance with one or more aspects of the present disclosure.

FIG. 51 illustrates a cutaway view of the distal sensor plug and FIG. 52 further illustrates the magnetic field sensor and the processor operatively coupled to the flex board such that they are capable of communicating in accordance with one or more aspects of the present disclosure.

FIG. 55 is a cross-sectional elevational view of the surgical stapling instrument of FIG. 134 illustrating a sled and a firing member in an unfired position in accordance with one or more aspects of the present disclosure.

FIG. 56 is a detail view depicting the sled of FIG. 55 in a partially advanced position and the firing member in its unfired position in accordance with one or more aspects of the present disclosure.

FIG. 68 is a logic diagram illustrating one aspect of a process for generating a thickness measurement for a tissue section located between an anvil and a staple cartridge of an end effector in accordance with one or more aspects of the present disclosure.

FIGS. 69A-69B illustrate one aspect of an end effector comprising a pressure sensor in accordance with one or more aspects of the present disclosure.

FIG. 70 illustrates one aspect of an end effector comprising a second sensor located between a staple cartridge and a jaw member in accordance with one or more aspects of the present disclosure.

FIG. 71 is a logic diagram illustrating one aspect of a process for determining the thickness of a tissue section clamped in an end effector, according to FIGS. 69A-69B or FIG. 70 in accordance with one or more aspects of the present disclosure.

FIG. 74 illustrates an aspect of an end effector that is configured to determine the location of a cutting member or knife in accordance with one or more aspects of the present disclosure.

FIG. 75 illustrates an example of the code strip in operation with red LEDs and an infrared LED in accordance with one or more aspects of the present disclosure.

FIG. 117 illustrates an example graph showing a curve representative of a firing force signal over time for the surgical instrument of FIG. 115 in accordance with one or more aspects of the present disclosure.

FIG. 118 illustrates another example graph showing a curve representative of a firing force signal over time for the surgical instrument of FIG. 115 in accordance with one or more aspects of the present disclosure.

FIG. 119 illustrates an example graph showing a curve representative of a closing force FC over time t for various aspects of the surgical instrument and a curve representative of a firing force FF over time t for the surgical instrument of FIG. 115 in accordance with one or more aspects of the present disclosure.

FIG. 120 illustrates an example graph showing a curve representative of a firing force signal and a knife position over time and a curve representative of a knife velocity over time for the surgical instrument of FIG. 115 in accordance with one or more aspects of the present disclosure.

FIG. 121 illustrates a perspective view of another surgical instrument in accordance with one or more aspects of the present disclosure.

FIG. 122 illustrates a method of controlling a firing motion of the surgical instrument of FIG. 121 in accordance with one or more aspects of the present disclosure.

FIG. 123 illustrates an example graph showing a curve representative of a firing force signal over time and a knife position over time and a curve representative of a knife velocity over time for the surgical instrument of FIG. 121 in accordance with one or more aspects of the present disclosure.

FIG. 124 illustrates an example graph showing the rate of closure of the jaws for the surgical instrument of FIG. 121 in accordance with one or more aspects of the present disclosure.

FIG. 125 illustrates a perspective view of another surgical instrument in accordance with one or more aspects of the present disclosure.

FIGS. 126A and 126B illustrate a method of controlling a firing motion of the surgical instrument of FIG. 125 in accordance with one or more aspects of the present disclosure.

FIG. 127 illustrates an example graph showing a curve representative of a firing force signal over time and a knife position over time and a curve representative of a knife velocity over time for various aspects of the surgical instrument of FIG. 125 in accordance with one or more aspects of the present disclosure.

DETAILED DESCRIPTION

Figure 1:
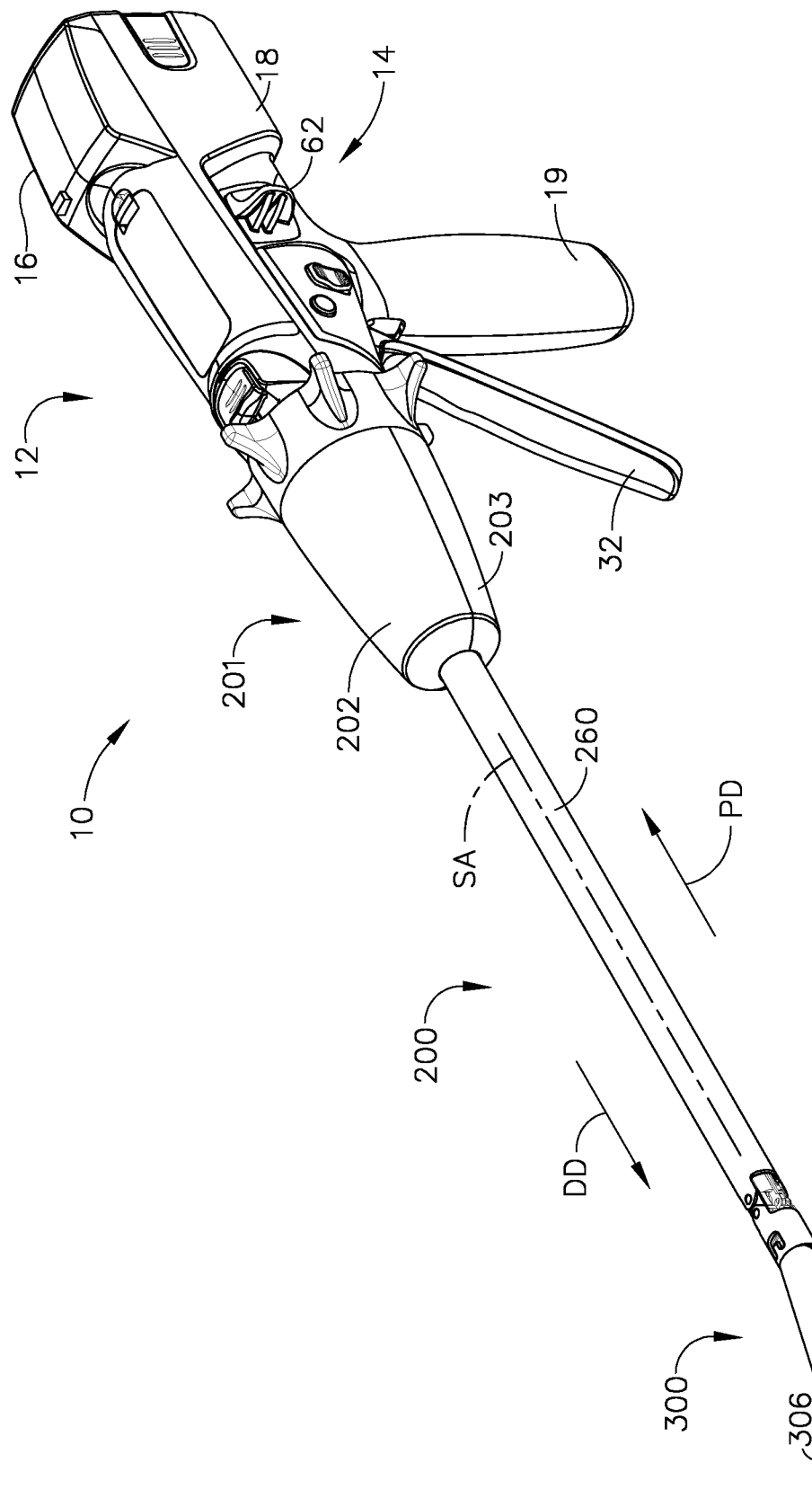
FIG. 1 is a perspective view of a surgical instrument that has an interchangeable shaft assembly operably coupled thereto in accordance with one or more aspects of the present disclosure.

Applicant of the present application owns the following patent applications that were filed on Apr. 15, 2016 and which are each herein incorporated by reference in their respective entireties:

U.S. patent application Ser. No. 15/130,575, entitled STAPLE FORMATION DETECTION MECHANISMS, now U.S. Patent Application Publication No. 2017/0296189;

U.S. patent application Ser. No. 15/130,582, entitled SURGICAL INSTRUMENT WITH DETECTION SENSORS, now U.S. Patent Application Publication No. 2017/0296178;

U.S. patent application Ser. No. 15/130,588, entitled SURGICAL INSTRUMENT WITH IMPROVED STOP/START CONTROL DURING A FIRING MOTION, now U.S. Patent Application Publication No. 2017/0296179;

U.S. patent application Ser. No. 15/130,595, entitled SURGICAL INSTRUMENT WITH ADJUSTABLE STOP/START CONTROL DURING A FIRING MOTION, now U.S. Patent Application Publication No. 2017/0296180;

U.S. patent application Ser. No. 15/130,566, entitled SURGICAL INSTRUMENT WITH MULTIPLE PROGRAM RESPONSES DURING A FIRING MOTION, now U.S. Patent Application Publication No. 2017/0296177;

U.S. patent application Ser. No. 15/130,581, entitled MODULAR SURGICAL INSTRUMENT WITH CONFIGURABLE OPERATING MODE, now U.S. Patent Application Publication No. 2017/0296184;

U.S. patent application Ser. No. 15/130,590, entitled SYSTEMS AND METHODS FOR CONTROLLING A SURGICAL STAPLING AND CUTTING INSTRUMENT, now U.S. Patent Application Publication No. 2017/0296213; and U.S. patent application Ser. No. 15/130,596, entitled SYSTEMS AND METHODS FOR CONTROLLING A SURGICAL STAPLING AND CUTTING INSTRUMENT, now U.S. Patent Application Publication No. 2017/0296169.

The present disclosure provides an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples. The features illustrated or described in connection with one example may be combined with the features of other examples. Such modifications and variations are intended to be included within the scope of the present disclosure.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

In one aspect, the present disclosure provides a motorized surgical stapling and cutting instrument configured to detect staple malformation as a trigger for making firing speed adjustments. In one aspect, the present disclosure provides a motorized surgical stapling and cutting instrument configured to change the firing parameters (speed of firing, timing of a pause in firing, duration of a firing pause, clamp pressure, etc.) to affect staple form based on real-time (or continuous) determination of defect density. In one aspect, the present disclosure provides a motorized surgical stapling and cutting instrument configured to obtain information from sensor arrays and analyze the information by computing the "defect" density at any location along the staple line. "Defect density" can be analyzed as a running number along the entirety of the staple line. Alternatively, the staple line integrity (SLI) may be determined at each opportunity along the length of the staple line. The defect density can be used to inform the surgeon of possible issues prior to unclamping the device. If certain thresholds of defect density are encountered, the device can respond in different ways. If the device detects defect density or rate is above a first decision point, it may slow down to allow more time for tissue flow and presumably better staple form. The detection of malformed staples (lack of detection of good form) also can be used to change the firing parameters in real time to result in better staple formation with the remainder of the staple line. If the device detects defect density or defect rate is above a second decision point, it may display a warning to the surgeon prior to unclamping of where the defects are so that the surgeon can be prepared with additional therapies to treat potential bleeding or stabilize the tissue as appropriate.

Figure 35:
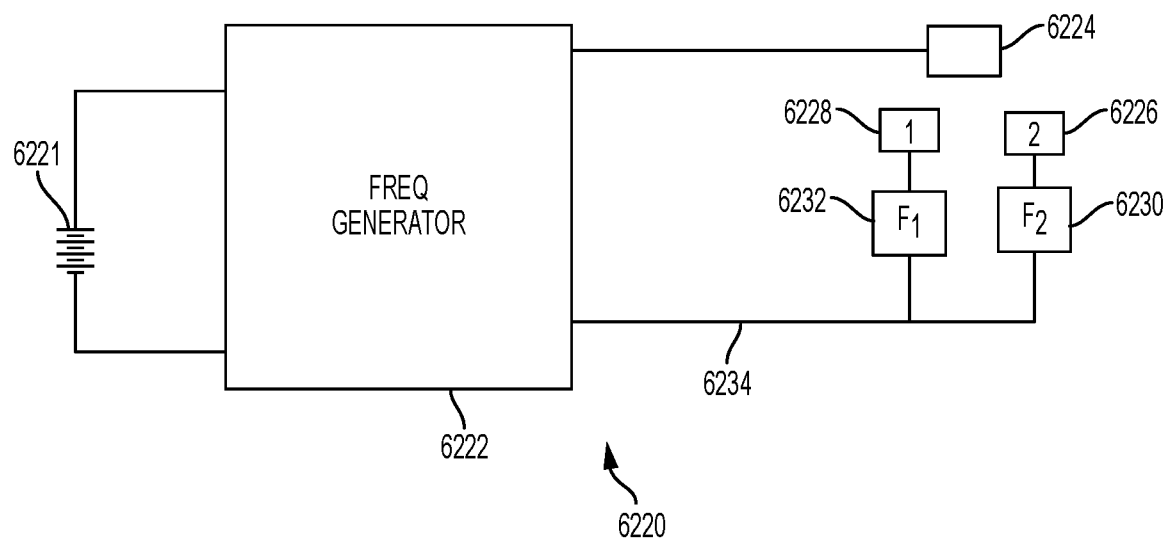
FIG. 35 is an example circuit diagram in accordance with one or more aspects of the present disclosure.
Figure 36:
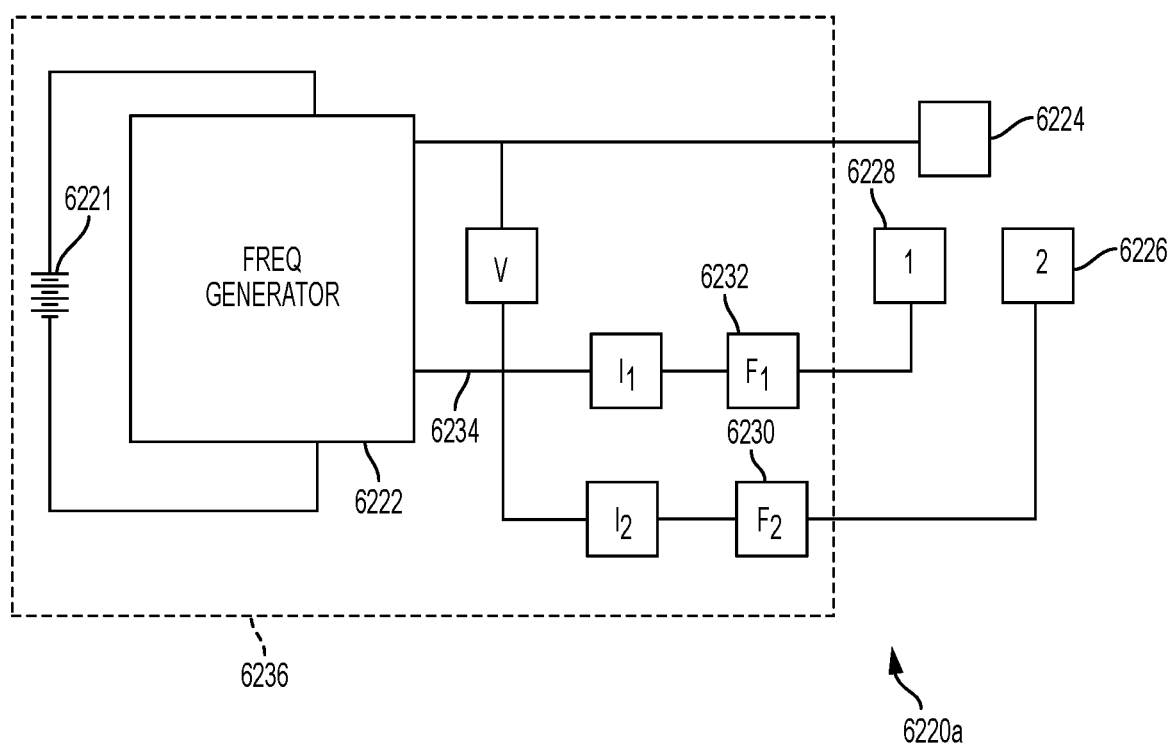
FIG. 36 is also an example circuit diagram in accordance with one or more aspects of the present disclosure.
Figure 37:
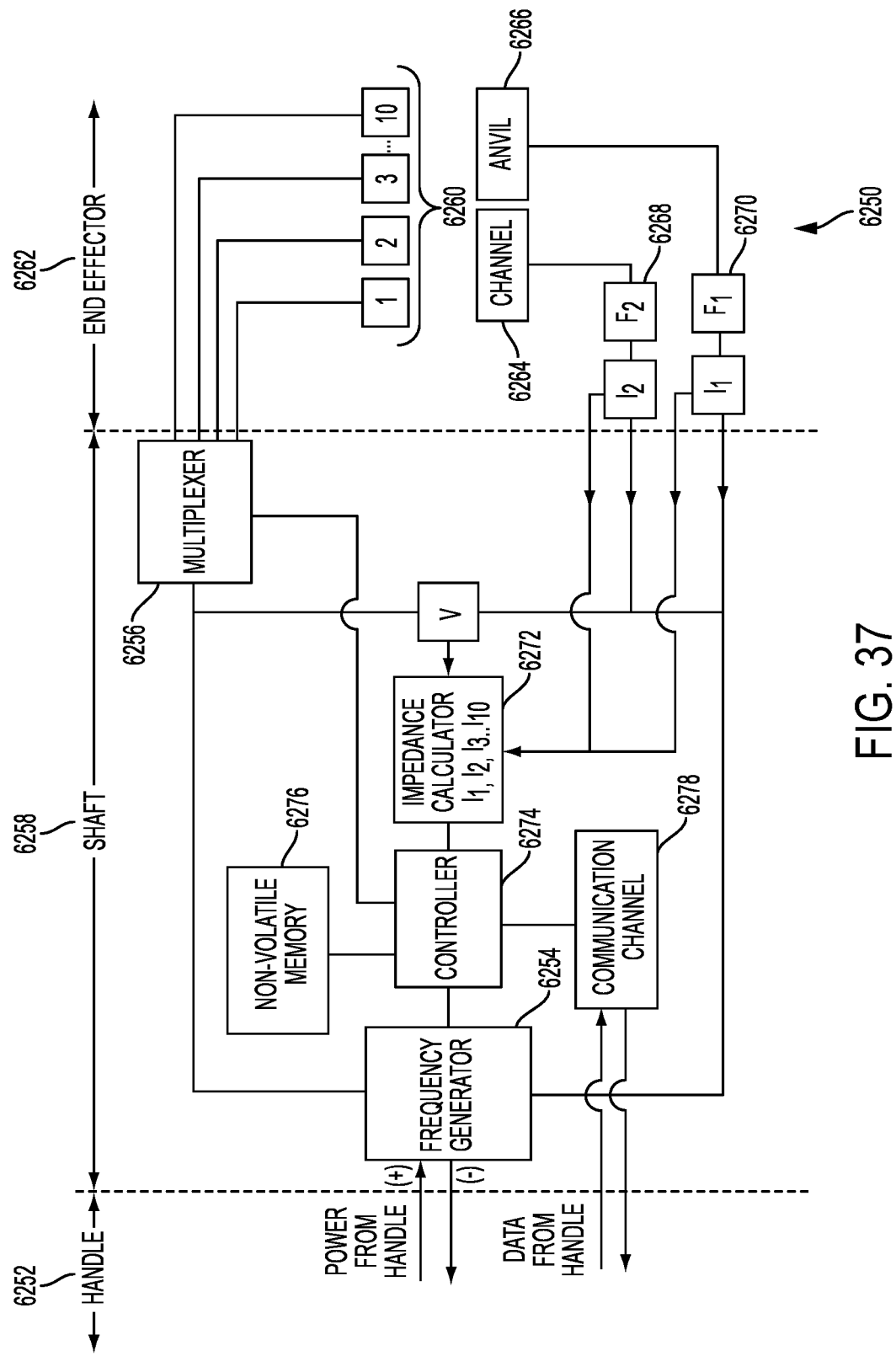
FIG. 37 is also an example circuit diagram in accordance with one or more aspects of the present disclosure.
Figure 38:
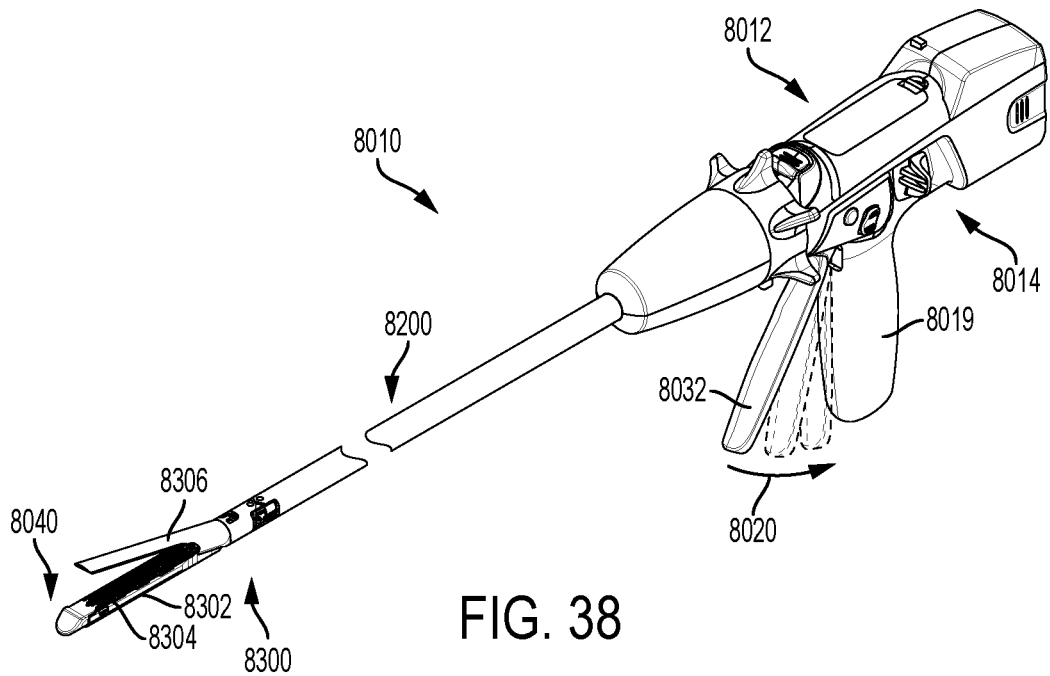
FIG. 38 is a perspective view of a surgical instrument with an articulable, interchangeable shaft in accordance with one or more aspects of the present disclosure.
Figure 97:
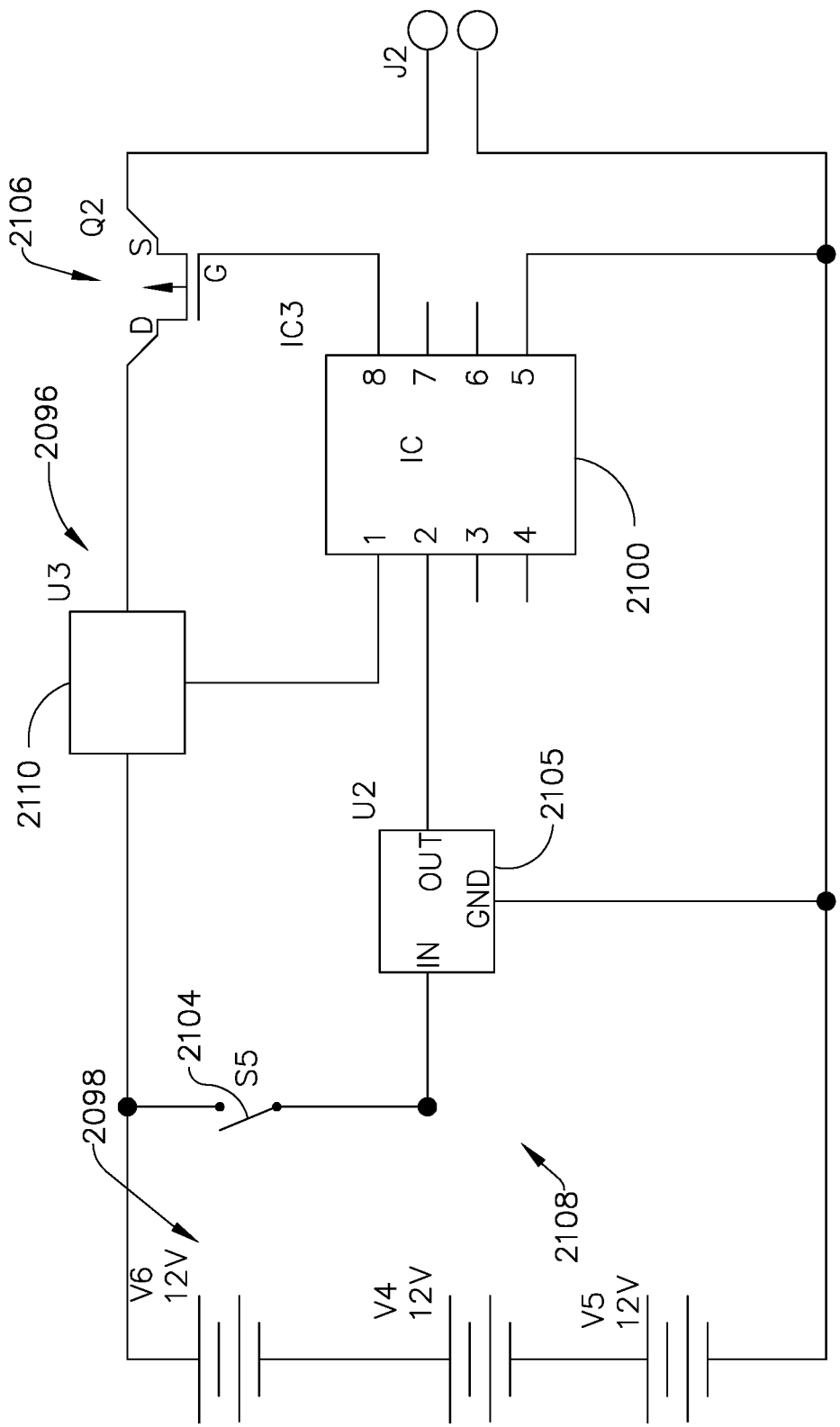
FIG. 97 is a circuit diagram of an example power assembly of a surgical instrument in accordance with one or more aspects of the present disclosure.

Before describing various aspects of a motorized stapling and cutting instrument (surgical instrument) as described in connection with FIGS. 106-127, the present disclosure first turns to FIGS. 1-105 for a general description of the mechanical and electrical platform upon which the present motorized surgical instrument may be implemented and provides the background necessary to appreciate the underlying operation and functionality of the motorized surgical instrument. Accordingly, FIGS. 1-14 provide an example of a general description of the underlying mechanical platform upon which the present motorized stapling and cutting instrument may be implemented. FIGS. 15-21 describe examples of the general underlying microcontroller, motor drive, and electrical interconnection platform upon which the present motorized surgical instrument may be implemented. FIGS. 22-34 describe example end effector channel frames and measuring forces applied to tissue located between the anvil and the staple cartridge of the end effector. FIGS. 35-37 described example circuits for controlling the functionality of the present motorized surgical instrument. FIGS. 38-95 describe example sensors and feedback systems to utilize the sensors outputs to implement the present motorized surgical instrument. FIGS. 97-97 describe example power assemblies for powering the present motorized surgical instrument. FIGS. 98-105 describe example control systems for controlling motor speed and drivable members of the present surgical instrument includes sensors and feedback elements therefor. Upon familiarization with the underlying mechanical and electrical platform upon which the present motorized surgical instrument may be implemented, the reader is directed to the description in connection with FIGS. 106-127 for a description of a motorized surgical stapling and cutting instrument configured to detect staple malformation as a trigger for making firing speed adjustments.

Accordingly, turning now to the figures, FIGS. 1-6 depict a motor-driven surgical instrument 10 for cutting and fastening that may or may not be reused. In the illustrated examples, the surgical instrument 10 includes a housing 12 that comprises a handle assembly 14 that is configured to be grasped, manipulated and actuated by the clinician. The housing 12 is configured for operable attachment to an interchangeable shaft assembly 200 that has an end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" also may represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

Figure 2:
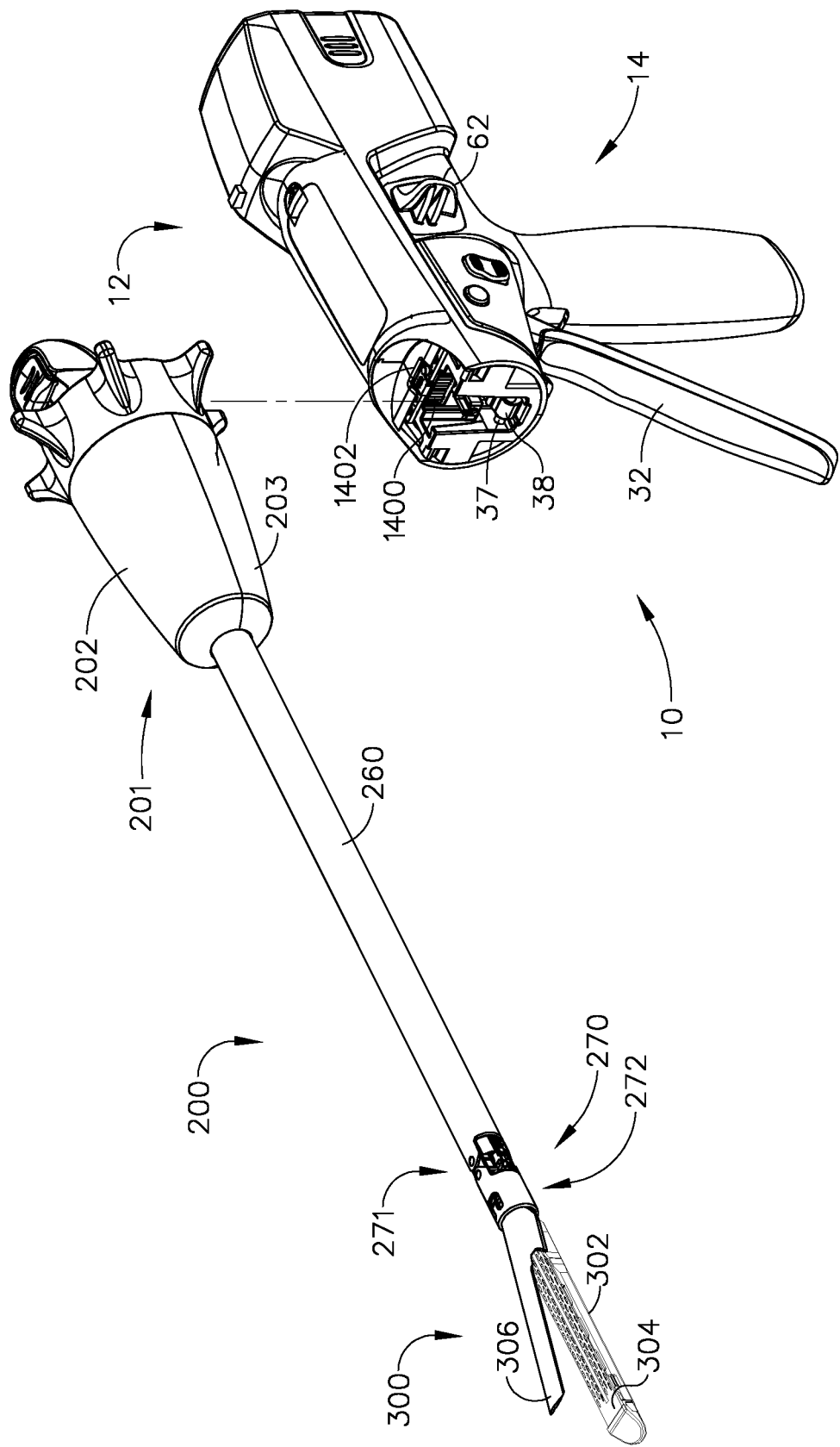
FIG. 2 is an exploded assembly view of the interchangeable shaft assembly and surgical instrument of FIG. 1 in accordance with one or more aspects of the present disclosure.

The housing 12 depicted in FIGS. 1-2 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
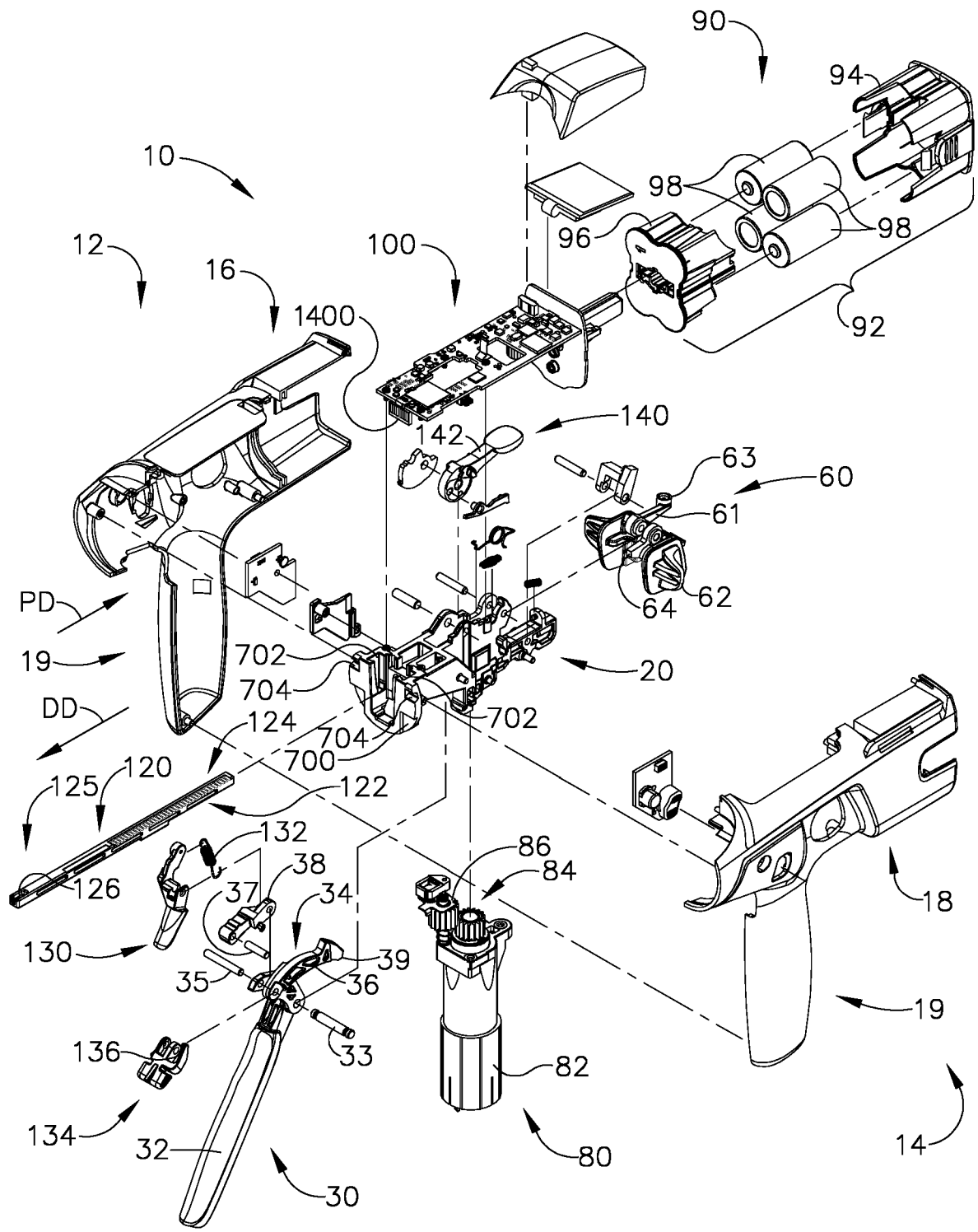
FIG. 4 is an exploded assembly view of a portion of the surgical instrument of FIGS. 1-3 in accordance with one or more aspects of the present disclosure.

FIG. 1 illustrates the surgical instrument 10 with an interchangeable shaft assembly 200 operably coupled thereto. FIG. 2 illustrates attachment of the interchangeable shaft assembly 200 to the housing 12 or handle assembly 14. As shown in FIG. 4, the handle assembly 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle assembly 14 operably supports a plurality of drive systems therein that are configured to generate and apply various control motions to corresponding portions of the interchangeable shaft assembly that is operably attached thereto.

Referring now to FIG. 4, the handle assembly 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the handle assembly 14 by a pivot pin 33. Such arrangement enables the closure trigger 32 to be manipulated by a clinician such that when the clinician grips the pistol grip portion 19 of the handle assembly 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As shown in FIG. 4, the closure linkage assembly 34 may include a first closure link 36 and a second closure link 38 that are pivotally coupled to the closure trigger 32 by a pin 35. The second closure link 38 also may be referred to herein as an "attachment member" and include a transverse attachment pin 37.

Still referring to FIG. 4, it can be observed that the first closure link 36 may have a an end or locking wall 39 thereon that is configured to cooperate with a closure release assembly 60 that is pivotally coupled to the frame 20. In at least one form, the closure release assembly 60 may comprise a closure release button assembly 62 that has a distally protruding locking pawl 64 formed thereon. The closure release button assembly 62 may be pivoted in a counterclockwise direction by a release spring (not shown). As the clinician depresses the closure trigger 32 from its unactuated position towards the pistol grip portion 19 of the handle assembly 14, the first closure link 36 pivots upward to a point wherein the locking pawl 64 drops into retaining engagement with the locking wall 39 on the first closure link 36 thereby preventing the closure trigger 32 from returning to the unactuated position. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements also may be employed.

Figure 10:
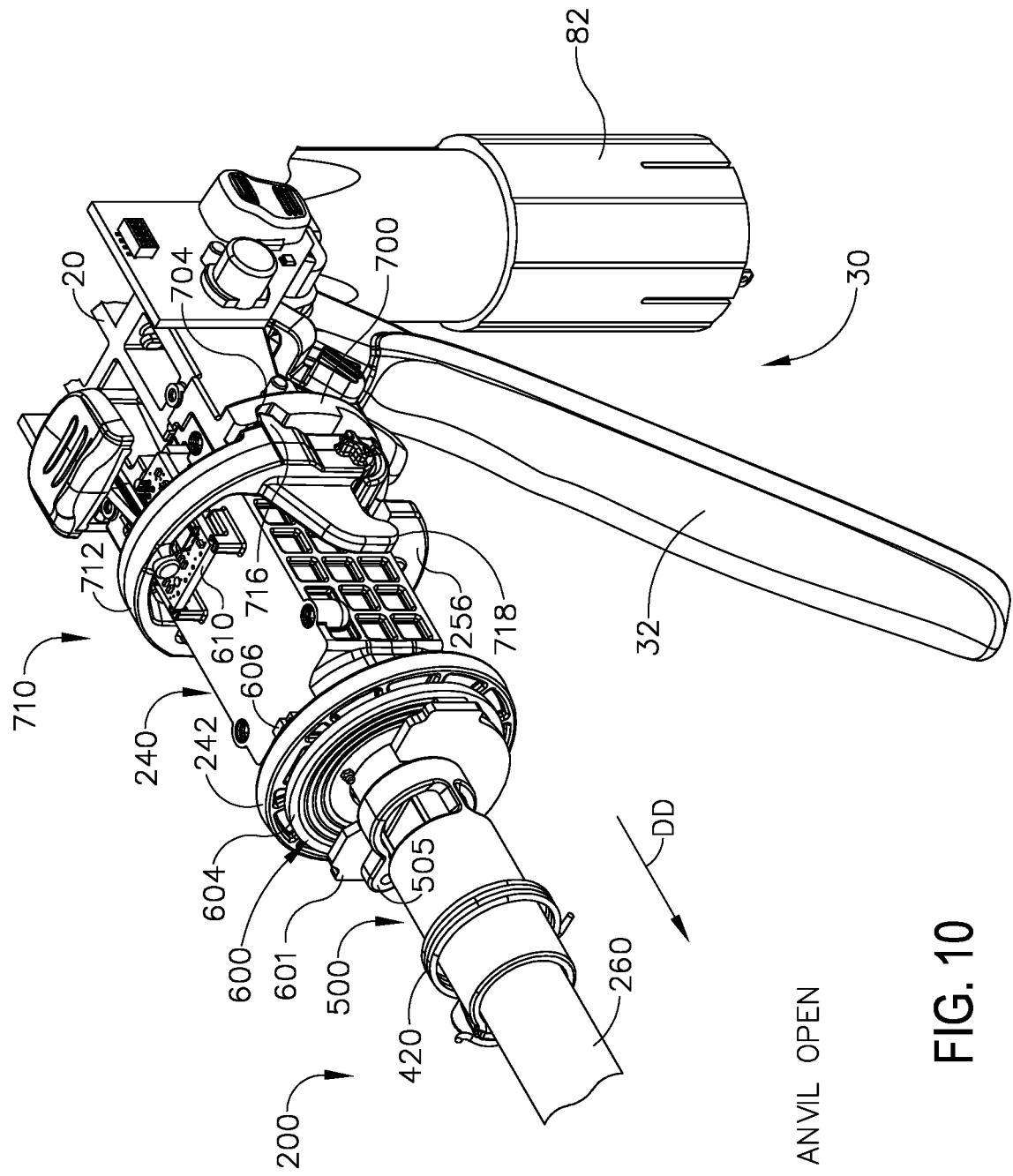
FIG. 10 is a perspective view of a portion of the interchangeable shaft assembly of FIG. 11 operably coupled to a portion of the surgical instrument of FIG. 1 illustrated with the closure trigger thereof in an unactuated position in accordance with one or more aspects of the present disclosure.
Figure 11:
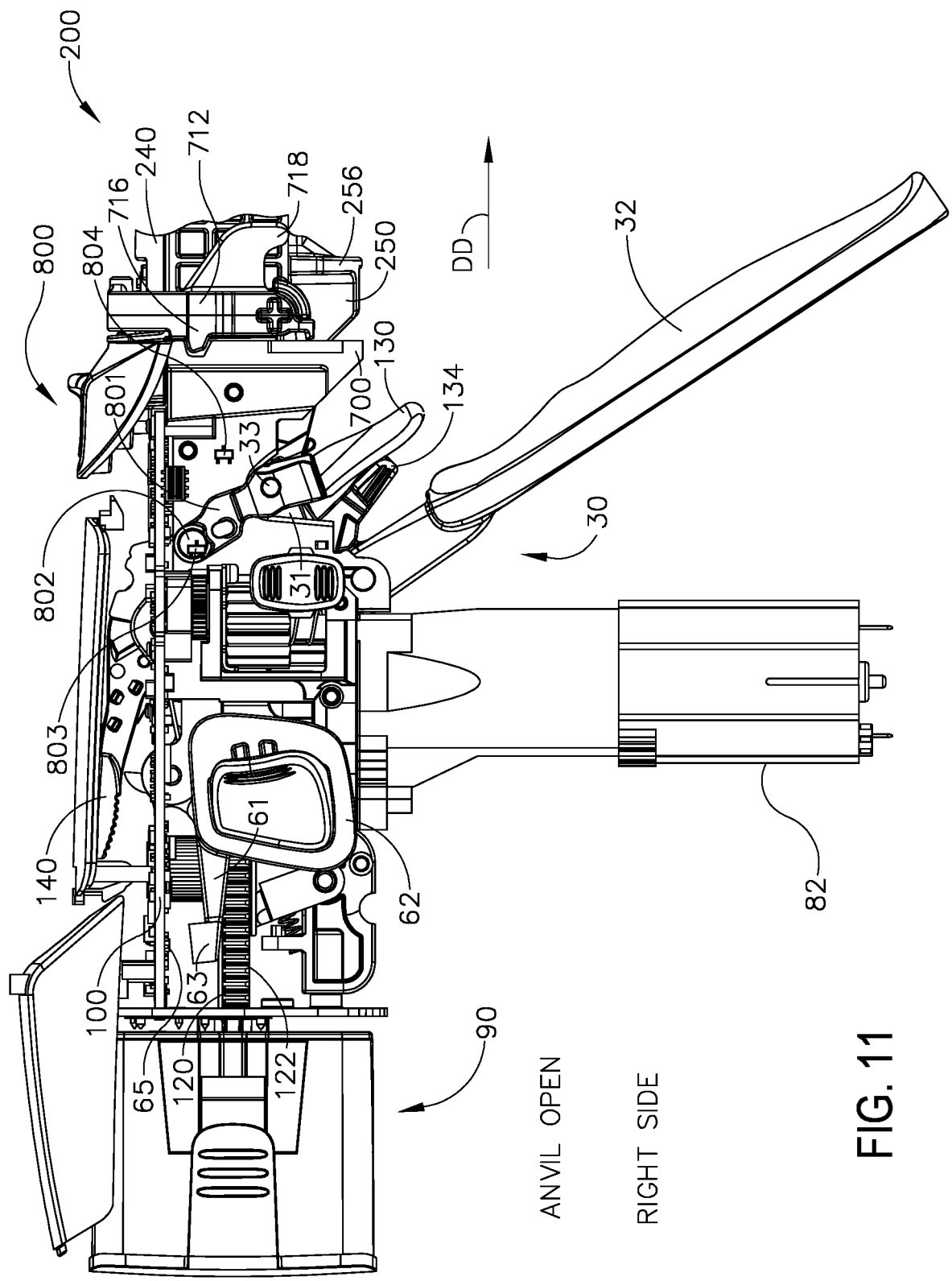
FIG. 11 is a right side elevational view of the interchangeable shaft assembly and surgical instrument of FIG. 10 in accordance with one or more aspects of the present disclosure.
Figure 12:
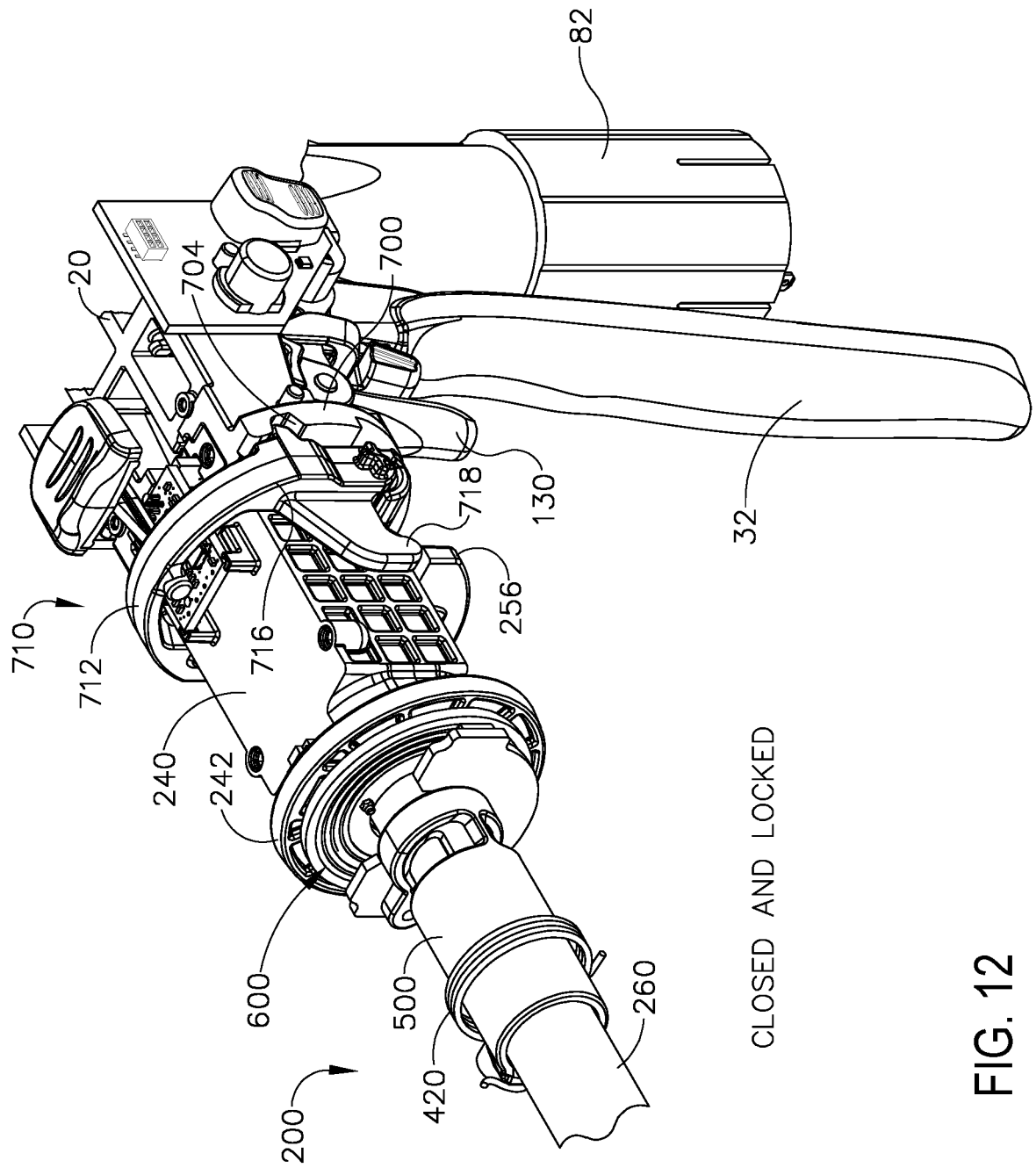
FIG. 12 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position in accordance with one or more aspects of the present disclosure.
Figure 13:
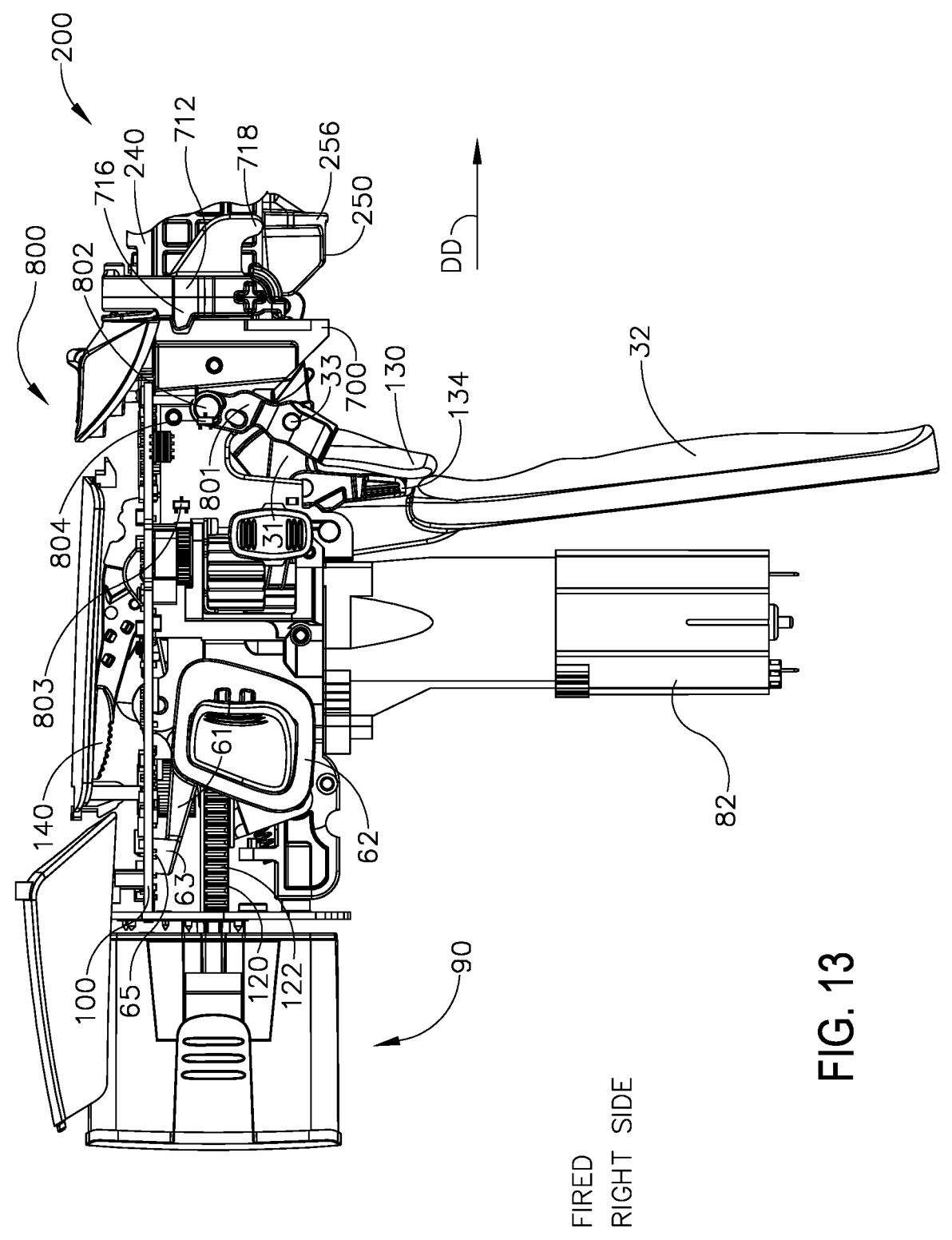

Further to the above, FIGS. 10-11 illustrate the closure trigger 32 in its unactuated position which is associated with an open, or unclamped, configuration of the interchangeable shaft assembly 200 in which tissue can be positioned between the jaws of the interchangeable shaft assembly 200. FIG. 12 illustrates the closure trigger 32 in its actuated position which is associated with a closed, or clamped, configuration of the interchangeable shaft assembly 200 in which tissue is clamped between the jaws of the interchangeable shaft assembly 200. Upon comparing FIGS. 11 and 13, the reader will appreciate that, when the closure trigger 32 is moved from its unactuated position (FIG. 11) to its actuated position (FIG. 13), the closure release button assembly 62 is pivoted between a first position (FIG. 11) and a second position (FIG. 13). The rotation of the closure release button assembly 62 can be referred to as being an upward rotation; however, at least a portion of the closure release button assembly 62 is being rotated toward the circuit board 100. Referring to FIG. 4, the closure release button assembly 62 can include an arm 61 extending therefrom and a magnetic element 63, such as a permanent magnet, for example, mounted to the arm 61. When the closure release button assembly 62 is rotated from its first position to its second position, the magnetic element 63 can move toward the circuit board 100. The circuit board 100 can include at least one sensor configured to detect the movement of the magnetic element 63. In at least one aspect, a magnetic field sensor 65, for example, can be mounted to the bottom surface of the circuit board 100. The magnetic field sensor 65 can be configured to detect changes in a magnetic field surrounding the magnetic field sensor 65 caused by the movement of the magnetic element 63. The magnetic field sensor 65 can be in signal communication with a controller 1500, for example, which can determine whether the closure release button assembly 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

As used throughout the present disclosure, a magnetic field sensor may be a Hall effect sensor, search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In at least one form, the handle assembly 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle assembly 14. In various forms, the electric motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The electric motor 82 may be powered by a power source 90 that in one form may comprise a removable power pack 92. As shown in FIG. 4, for example, the removable power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board 100 which is also operably coupled to the electric motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the longitudinally movable drive member 120 will be axially driven in the distal direction "DD". When the electric motor 82 is driven in the opposite rotary direction, the longitudinally movable drive member 120 will be axially driven in a proximal direction "PD". The handle assembly 14 can include a switch which can be configured to reverse the polarity applied to the electric motor 82 by the power source 90. As with the other forms described herein, the handle assembly 14 can also include a sensor that is configured to detect the position of the longitudinally movable drive member 120 and/or the direction in which the longitudinally movable drive member 120 is being moved.

Actuation of the electric motor 82 can be controlled by a firing trigger 130 that is pivotally supported on the handle assembly 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The firing trigger safety button 134 may be positioned between the firing trigger 130 and the closure trigger 32 and have a pivot arm 136 protruding therefrom. See FIG. 4. When the closure trigger 32 is in the unactuated position, the firing trigger safety button 134 is contained in the handle assembly 14 where the clinician cannot readily access it and move it between a safety position preventing actuation of the firing trigger 130 and a firing position wherein the firing trigger 130 may be fired. As the clinician depresses the closure trigger 32, the firing trigger safety button 134 and the firing trigger 130 pivot down wherein they can then be manipulated by the clinician.

As discussed above, the handle assembly 14 can include a closure trigger 32 and a firing trigger 130. Referring to FIGS. 11-13, the firing trigger 130 can be pivotally mounted to the closure trigger 32. The closure trigger 32 can include an arm 31 extending therefrom and the firing trigger 130 can be pivotally mounted to the arm 31 about a pivot pin 33. When the closure trigger 32 is moved from its unactuated position (FIG. 11) to its actuated position (FIG. 13), the firing trigger 130 can descend downwardly, as outlined above. After the firing trigger safety button 134 has been moved to its firing position, referring primarily to FIG. 18A, the firing trigger 130 can be depressed to operate the motor of the surgical instrument firing system. In various instances, the handle assembly 14 can include a tracking system, such as system 800, for example, configured to determine the position of the closure trigger 32 and/or the position of the firing trigger 130. With primary reference to FIGS. 11 and 13, the tracking system 800 can include a magnetic element, such as magnet 802, for example, which is mounted to an arm 801 extending from the firing trigger 130. The tracking system 800 can comprise one or more sensors, such as a first magnetic field sensor 803 and a second magnetic field sensor 804, for example, which can be configured to track the position of the magnet 802.

Upon comparing FIGS. 11 and 13, the reader will appreciate that, when the closure trigger 32 is moved from its unactuated position to its actuated position, the magnet 802 can move between a first position adjacent the first magnetic field sensor 803 and a second position adjacent the second magnetic field sensor 804.

Upon comparing FIGS. 11 and 13, the reader will further appreciate that, when the firing trigger 130 is moved from an unfired position (FIG. 11) to a fired position (FIG. 13), the magnet 802 can move relative to the second magnetic field sensor 804. The first and second magnetic field sensors 803, 804 can track the movement of the magnet 802 and can be in signal communication with a controller on the circuit board 100. With data from the first magnetic field sensor 803 and/or the second magnetic field sensor 804, the controller can determine the position of the magnet 802 along a predefined path and, based on that position, the controller can determine whether the closure trigger 32 is in its unactuated position, its actuated position, or a position therebetween. Similarly, with data from the first magnetic field sensor 803 and/or the second magnetic field sensor 804, the controller can determine the position of the magnet 802 along a predefined path and, based on that position, the controller can determine whether the firing trigger 130 is in its unfired position, its fully fired position, or a position therebetween.

As indicated above, in at least one form, the longitudinally movable drive member 120 has a rack of drive teeth 122 formed thereon for meshing engagement with a corresponding drive gear 86 of the gear reducer assembly 84. At least one form also includes a manually-actuatable bailout assembly 140 that is configured to enable the clinician to manually retract the longitudinally movable drive member 120 should the electric motor 82 become disabled. The bailout assembly 140 may include a lever or handle assembly 14 that is configured to be manually pivoted into ratcheting engagement with teeth 124 also provided in the longitudinally movable drive member 120. Thus, the clinician can manually retract the longitudinally movable drive member 120 by using the handle assembly 14 to ratchet the longitudinally movable drive member 120 in the proximal direction "PD". U.S. Pat. No. 8,608,045, entitled POWERED SURGICAL CUTTING AND STAPLING APPARATUS WITH MANUALLY RETRACTABLE FIRING SYSTEM discloses bailout arrangements and other components, arrangements and systems that also may be employed with the various instruments disclosed herein. U.S. Pat. No. 8,608,045, is herein incorporated by reference in its entirety.

Figure 7:
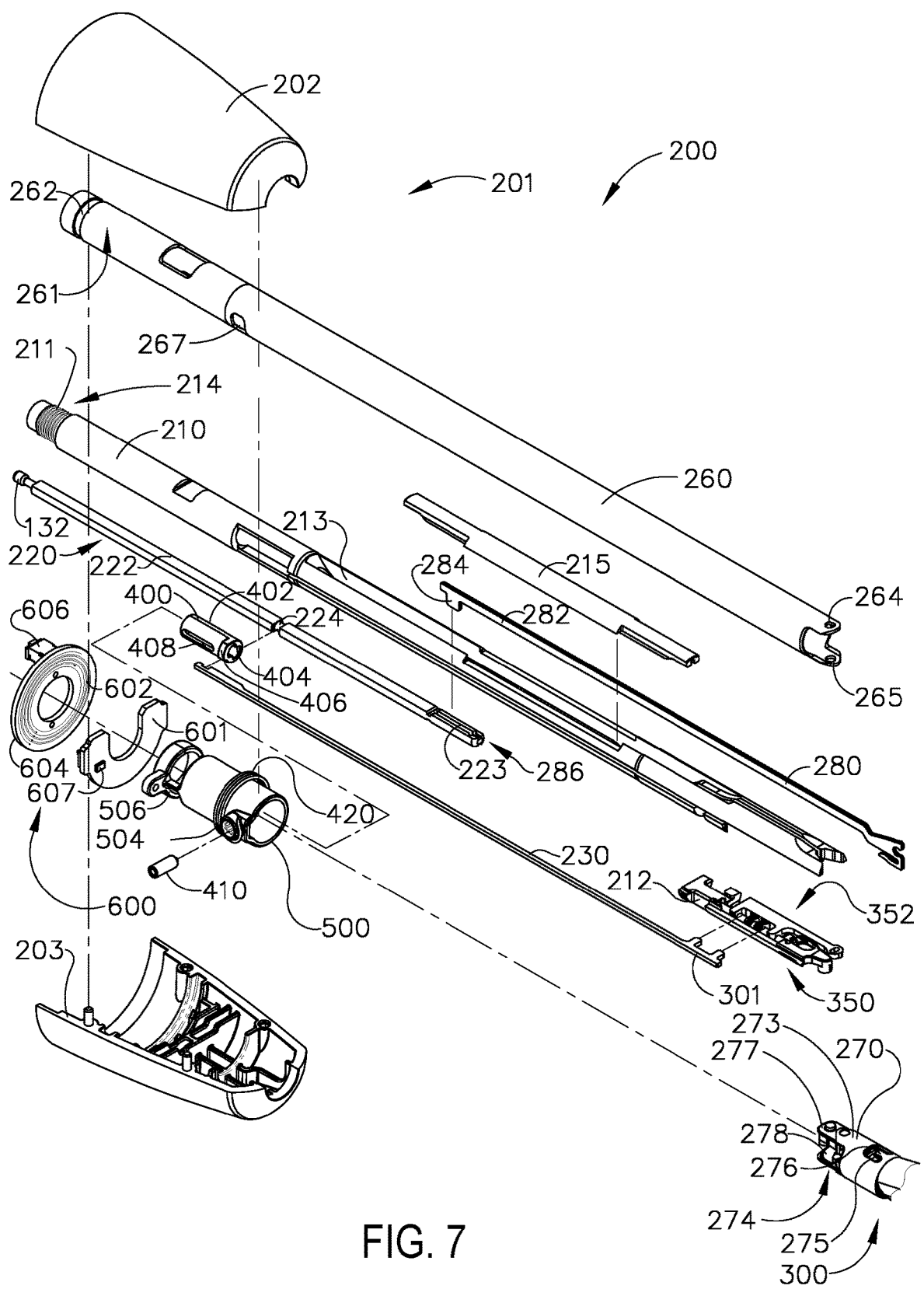
FIG. 7 is another exploded assembly view of portions of the interchangeable shaft assembly of FIG. 7 in accordance with one or more aspects of the present disclosure.

Turning now to FIG. 1, the interchangeable shaft assembly 200 includes an end effector 300 that comprises an elongated channel 302 that is configured to operably support a surgical staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 7) which can be configured to releasably hold the end effector 300 in a desired position relative to a shaft axis SA-SA. Details regarding the construction and operation of the end effector 300, the articulation joint 270 and the articulation lock 350 are set forth in U.S. Patent Application Publication No. 2014/0263541, entitled ARTICULATABLE SURGICAL INSTRUMENT COMPRISING AN ARTICULATION LOCK, which is herein incorporated by reference in its entirety. As shown in FIG. 7, the interchangeable shaft assembly 200 can further include a proximal housing or nozzle 201 comprised of nozzle portions 202, 203. The interchangeable shaft assembly 200 can further include a closure tube 260 which can be utilized to close and/or open the anvil 306 of the end effector 300. Primarily referring now to FIG. 7, the interchangeable shaft assembly 200 can include a spine 210 which can be configured to fixably support a shaft frame 212 of the articulation lock 350. See FIG. 7. The spine 210 can be configured to, one, slidably support a firing member 220 therein and, two, slidably support the closure tube 260 which extends around the spine 210. The spine 210 can also be configured to slidably support an articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. Patent Application Publication No. 2014/0263541. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. Such an arrangement facilitates rotatable attachment of the spine 210 to the chassis 240 such that the spine 210 may be selectively rotated about a shaft axis SA-SA relative to the chassis 240.

Figure 3:
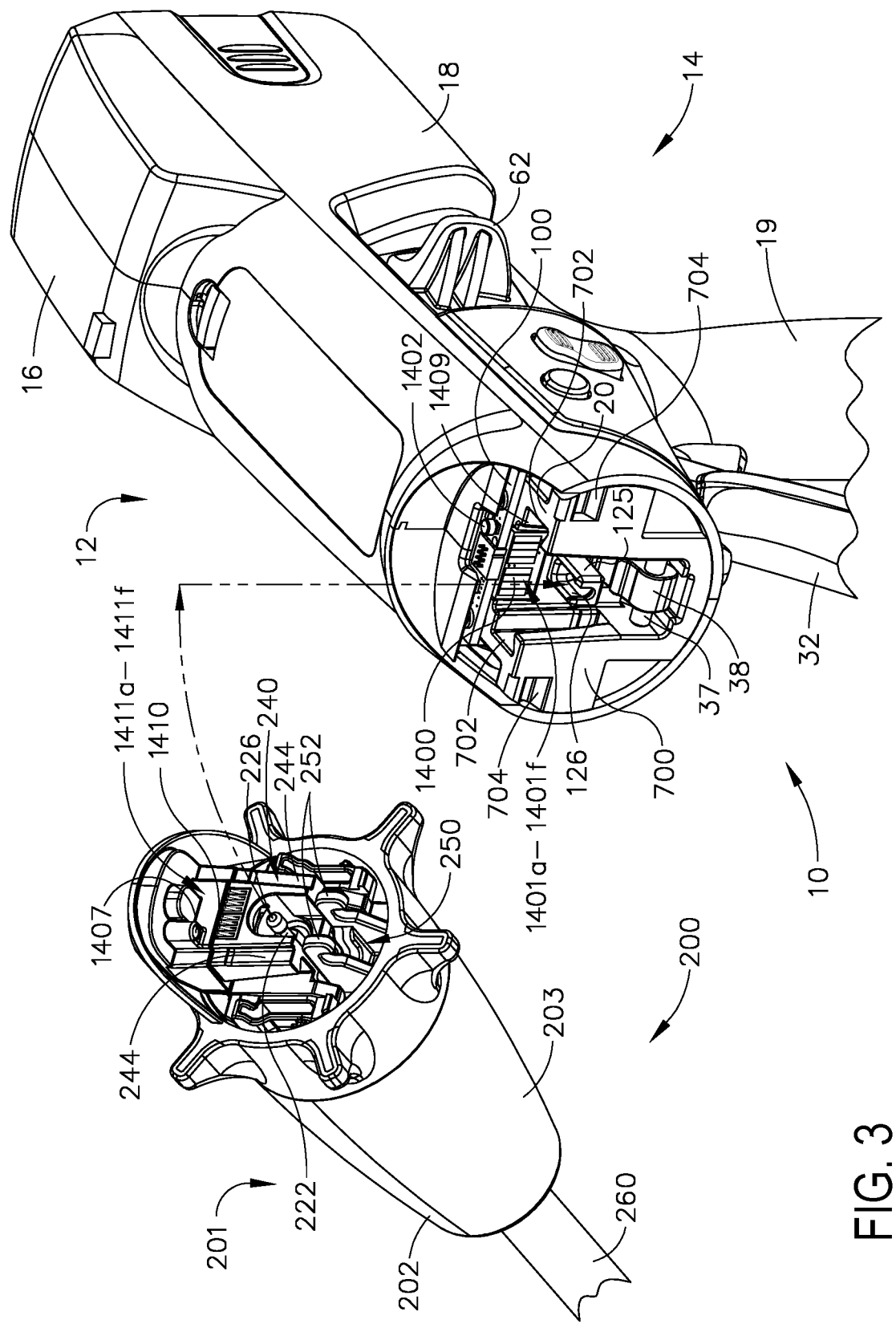
FIG. 3 is another exploded assembly view showing portions of the interchangeable shaft assembly and surgical instrument of FIGS. 1 and 2 in accordance with one or more aspects of the present disclosure.

The interchangeable shaft assembly 200 includes a closure shuttle 250 that is slidably supported within the chassis 240 such that it may be axially moved relative thereto. As shown in FIG. 3, the closure shuttle 250 includes a pair of proximally-protruding hooks 252 that are configured for attachment to the transverse attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle assembly 14.

In at least one form, the interchangeable shaft assembly 200 may further include an articulation joint 270. Other interchangeable shaft assemblies, however, may not be capable of articulation. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. Patent Application Publication No. 2014/0263541. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 7.

In use, the closure tube 260 is translated distally (direction "DD") to close the anvil 306, for example, in response to the actuation of the closure trigger 32. The anvil 306 is closed by distally translating the closure tube 260 and thus the end effector closure sleeve assembly 272, causing it to strike a proximal surface on the anvil 306 in the manner described in the aforementioned reference U.S. Patent Application Publication No. 2014/0263541. As was also described in detail in that reference, the anvil 306 is opened by proximally translating the closure tube 260 and the end effector closure sleeve assembly 272, causing tab 276 and the horseshoe aperture 275 to contact and push against the anvil tab to lift the anvil 306. In the anvil-open position, the closure tube 260 is moved to its proximal position.

As indicated above, the surgical instrument 10 may further include an articulation lock 350 of the types and construction described in further detail in U.S. Patent Application Publication No. 2014/0263541, which can be configured and operated to selectively lock the end effector 300 in position. Such arrangement enables the end effector 300 to be rotated, or articulated, relative to the closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 also may be articulated relative to the closure tube 260 by an articulation driver 230.

As was also indicated above, the interchangeable shaft assembly 200 further includes a firing member 220 that is supported for axial travel within the spine 210. The firing member 220 includes an intermediate firing shaft 222 that is configured for attachment to a distal cutting portion or knife bar 280. The firing member 220 also may be referred to herein as a "second shaft" and/or a "second shaft assembly". As shown in FIG. 7, the intermediate firing shaft 222 may include a longitudinal slot 223 in the distal end thereof which can be configured to receive a tab 284 on the proximal end 282 of the knife bar 280. The longitudinal slot 223 and the proximal end 282 can be sized and configured to permit relative movement therebetween and can comprise a slip joint 286. The slip joint 286 can permit the intermediate firing shaft 222 of the firing member 220 to be moved to articulate the end effector 300 without moving, or at least substantially moving, the knife bar 280. Once the end effector 300 has been suitably oriented, the intermediate firing shaft 222 can be advanced distally until a proximal sidewall of the longitudinal slot 223 comes into contact with the tab 284 in order to advance the knife bar 280 and fire the staple cartridge positioned within the channel 302. As can be further seen in FIG. 7, the spine 210 has an elongated opening or window 213 therein to facilitate assembly and insertion of the intermediate firing shaft 222 into the spine 210. Once the intermediate firing shaft 222 has been inserted therein, a top frame segment 215 may be engaged with the shaft frame 212 to enclose the intermediate firing shaft 222 and knife bar 280 therein. Further description of the operation of the firing member 220 may be found in U.S. Patent Application Publication No. 2014/0263541.

Further to the above, the interchangeable shaft assembly 200 can include a clutch assembly 400 which can be configured to selectively and releasably couple the articulation driver 230 to the firing member 220. In one form, the clutch assembly 400 includes a lock collar, or lock sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 220. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Figure 8:
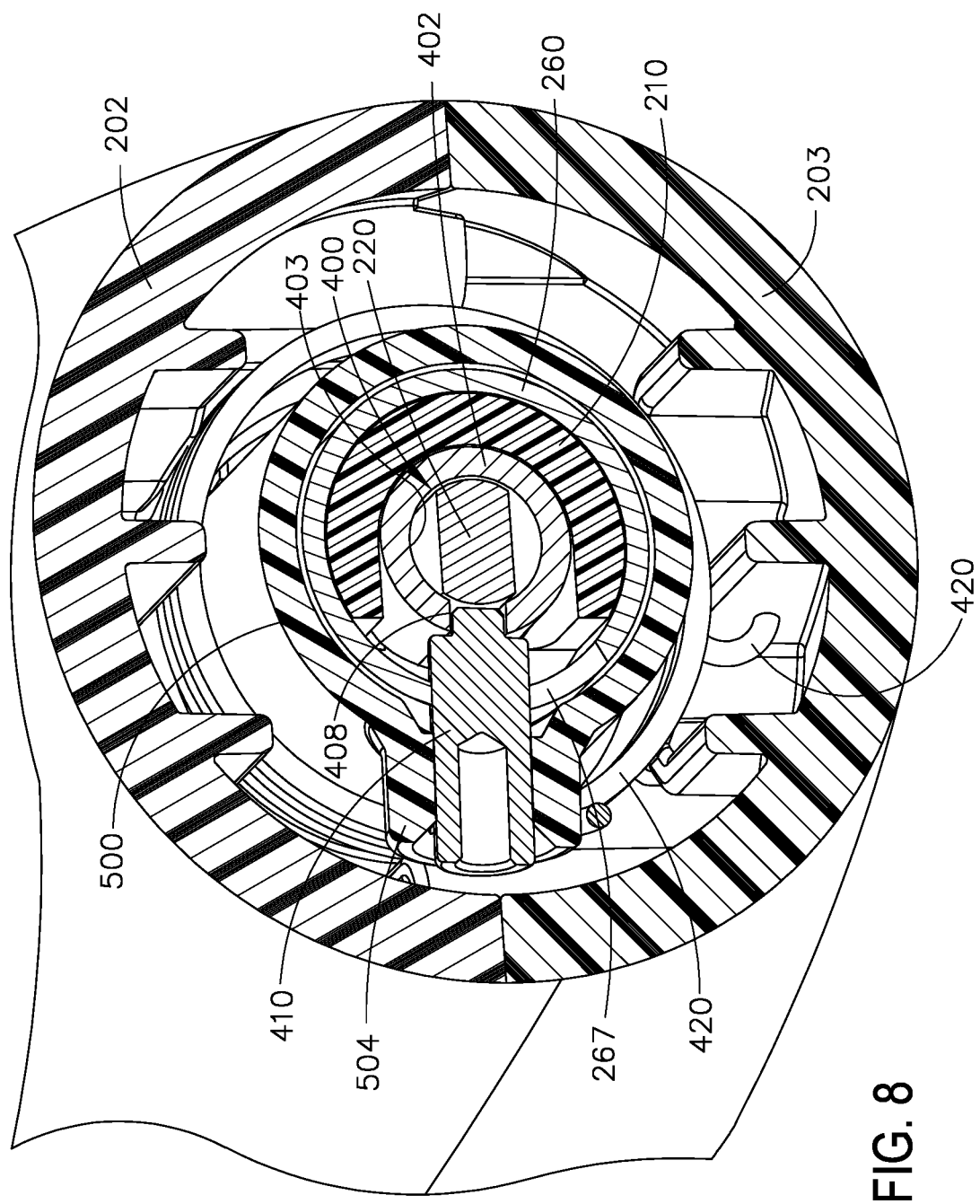
FIG. 8 is a cross-sectional view of a portion of the interchangeable shaft assembly of FIGS. 7-9, in accordance with one or more aspects of the present disclosure.
Figure 9:
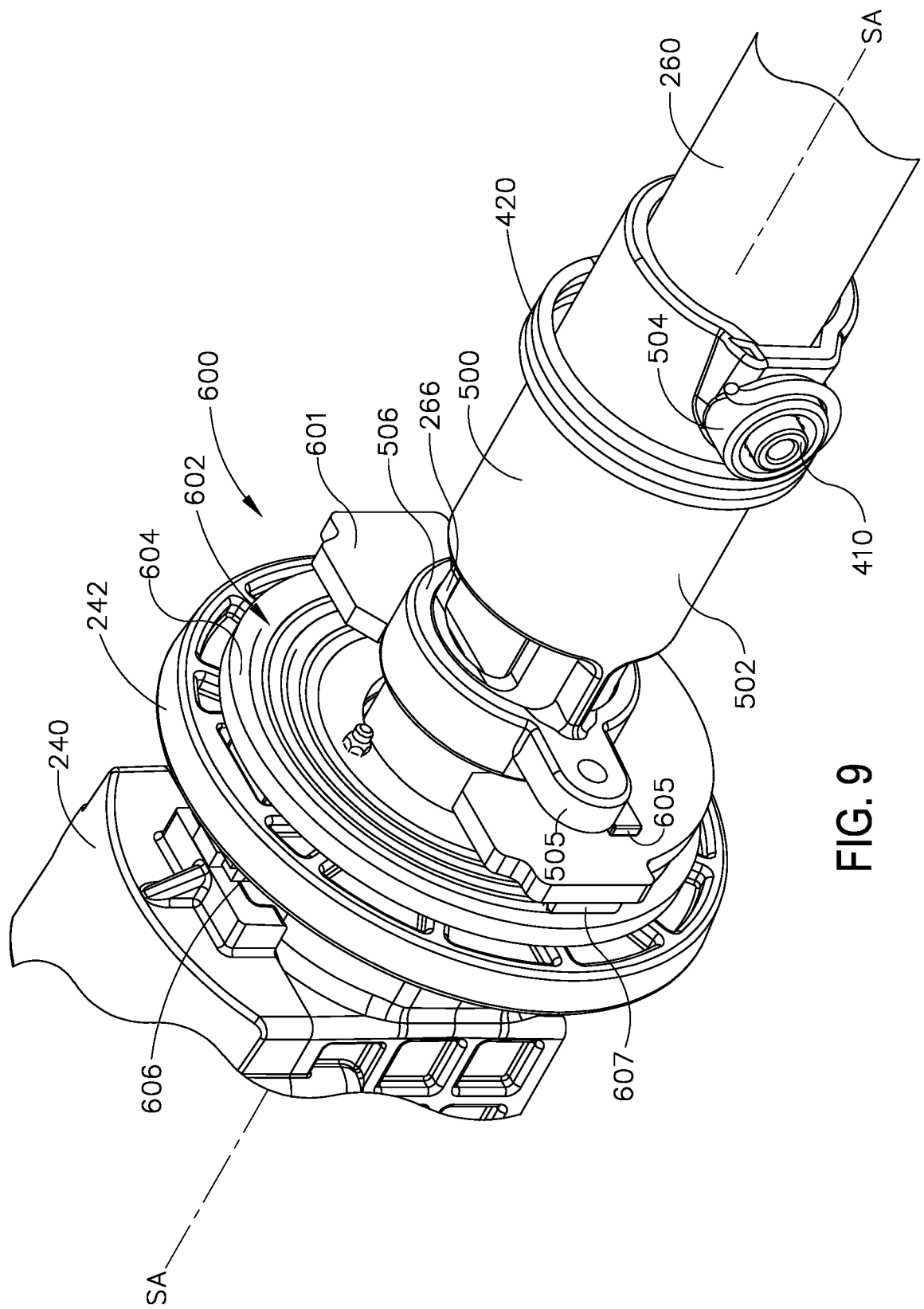
FIG. 9 is another perspective view of the portion of an interchangeable shaft assembly with the switch drum mounted thereon in accordance with one or more aspects of the present disclosure.

As shown in FIGS. 7-9, the interchangeable shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the shaft boss 504 on the switch drum 500 and a portion of the nozzle portion 203 as shown in FIG. 8 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle portions 202, 203 and permit relative rotation, but not translation, between the switch drum 500 and the nozzle 201. As shown in those Figures, the circumferential mounts 204, 205 also extend through openings 266 in the closure tube 260 to be seated in recesses located in the spine 210. However, rotation of the nozzle 201 to a point where the circumferential mounts 204, 205 reach the end of their respective partially circumferential openings 506 in the switch drum 500 will result in rotation of the switch drum 500 about the shaft axis SA-SA. Rotation of the switch drum 500 will ultimately result in the rotation of the actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. Patent Application Publication No. 2014/0263541.

As also illustrated in FIGS. 7-9, the interchangeable shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis mounting flange 242 extending from the chassis 240 and a distal connector flange 601 positioned within a slot defined in the nozzle portions 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the distal connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. U.S. Patent Application Publication No. 2014/0263551, entitled STAPLE CARTRIDGE TISSUE THICKNESS SENSOR SYSTEM, is incorporated herein by reference in its entirety. U.S. Patent Application Publication No. 2014/0263552, entitled STAPLE CARTRIDGE TISSUE THICKNESS SENSOR SYSTEM, is incorporated by reference in its entirety. Further details regarding slip ring assembly 600 may be found in U.S. Patent Application Publication No. 2014/0263541.

As discussed above, the interchangeable shaft assembly 200 can include a proximal portion which is fixably mounted to the handle assembly 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the interchangeable shaft assembly 200. When the switch drum 500 is in its second position, the articulation drive system may be operably engaged with the firing drive system and, thus, the operation of the firing drive system may articulate the end effector 300 of the interchangeable shaft assembly 200. When the switch drum 500 is moved between its first position and its second position, the switch drum 500 is moved relative to distal connector flange 601. In various instances, the interchangeable shaft assembly 200 can comprise at least one sensor configured to detect the position of the switch drum 500. Turning now to FIGS. 9, the distal connector flange 601 can comprise a magnetic field sensor 605, for example, and the switch drum 500 can comprise a magnetic element, such as permanent magnet 505, for example. The magnetic field sensor 605 can be configured to detect the position of the permanent magnet 505. When the switch drum 500 is rotated between its first position and its second position, the permanent magnet 505 can move relative to the magnetic field sensor 605. In various instances, magnetic field sensor 605 can detect changes in a magnetic field created when the permanent magnet 505 is moved. The magnetic field sensor 605 can be in signal communication with the shaft circuit board 610 and/or the circuit board 100 located in the handle, for example. Based on the signal from the magnetic field sensor 605, a controller on the shaft circuit board 610 and/or the circuit board 100 located in the handle can determine whether the articulation drive system is engaged with or disengaged from the firing drive system.

Referring again to FIG. 3, the chassis 240 includes at least one, and preferably two, tapered attachment portions 244 formed thereon that are adapted to be received within corresponding dovetail slots 702 formed within a distal attachment flange 700 of the frame 20. Each dovetail slot 702 may be tapered or, stated another way, be somewhat V-shaped to seatingly receive the tapered attachment portions 244 therein. As can be further seen in FIG. 3, a shaft attachment lug 226 is formed on the proximal end of the intermediate firing shaft 222. As will be discussed in further detail below, when the interchangeable shaft assembly 200 is coupled to the handle assembly 14, the shaft attachment lug 226 is received in a firing shaft attachment cradle 126 formed in the distal end 125 of the longitudinally movable drive member 120 as shown in FIGS. 3 and 6, for example.

Various shaft assemblies employ a latch system 710 for removably coupling the interchangeable shaft assembly 200 to the housing 12 and more specifically to the frame 20. The proximally protruding lock lugs 714 each have a pivot lock lugs 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the pivot lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the interchangeable shaft assembly 200 from the housing 12. One form of the latch system 710 is configured to prevent such inadvertent detachment.

The lock yoke 712 includes at least one, and preferably two, lock hooks 718 that are adapted to contact lock lugs 256 that are formed on the closure shuttle 250. Referring to FIGS. 10 and 11, when the closure shuttle 250 is in an unactuated position (i.e., the first closure drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lugs 256 on the closure shuttle 250. However, when the closure shuttle 250 is moved to an actuated position (i.e., the first closure drive system 30 is actuated and the anvil 306 is in the closed position), the lock yoke 712 is prevented from being pivoted to an unlocked position. See FIGS. 12 and 13. Stated another way, if the clinician were to attempt to pivot the lock yoke 712 to an unlocked position or, for example, the lock yoke 712 was in advertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle assembly 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the interchangeable shaft assembly 200 along an installation axis IA that is perpendicular to the shaft axis SA-SA to seat the tapered attachment portions 244 in "operable engagement" with the corresponding dovetail receiving slots 702. In doing so, the shaft attachment lug 226 on the intermediate firing shaft 222 will also be seated in the firing shaft attachment cradle 126 in the longitudinally movable drive member 120 and the portions of the transverse attachment pin 37 on the second closure link 38 will be seated in the corresponding proximally-protruding hooks 252 in the closure shuttle 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle assembly 14. A first system can comprise a frame system which couples and/or aligns the frame or spine of the interchangeable shaft assembly 200 with the frame 20 of the handle assembly 14. Another system can comprise a closure drive system 30 which can operably connect the closure trigger 32 of the handle assembly 14 and the closure tube 260 and the anvil 306 of the interchangeable shaft assembly 200. As outlined above, the closure shuttle 250 of the interchangeable shaft assembly 200 can be engaged with the transverse attachment pin 37 on the second closure link 38. Another system can comprise the firing drive system 80 which can operably connect the firing trigger 130 of the handle assembly 14 with the intermediate firing shaft 222 of the interchangeable shaft assembly 200.

As outlined above, the shaft attachment lug 226 can be operably connected with the firing shaft attachment cradle 126 of the longitudinally movable drive member 120. Another system can comprise an electrical system which can signal to a controller in the handle assembly 14, such as controller, for example, that a shaft assembly, such as the interchangeable shaft assembly 200, for example, has been operably engaged with the handle assembly 14 and/or, two, conduct power and/or communication signals between the interchangeable shaft assembly 200 and the handle assembly 14. For instance, the interchangeable shaft assembly 200 can include an electrical connector 1410 that is operably mounted to the shaft circuit board 610. The electrical connector 1410 located on the shaft is configured for mating engagement with an electrical connector 1400 on the circuit board 100 located in the handle. Further details regaining the circuitry and control systems may be found in U.S. Patent Application Publication No. 2014/0263541. The fifth system may consist of the latching system for releasably locking the interchangeable shaft assembly 200 to the handle assembly 14.

Figure 14:
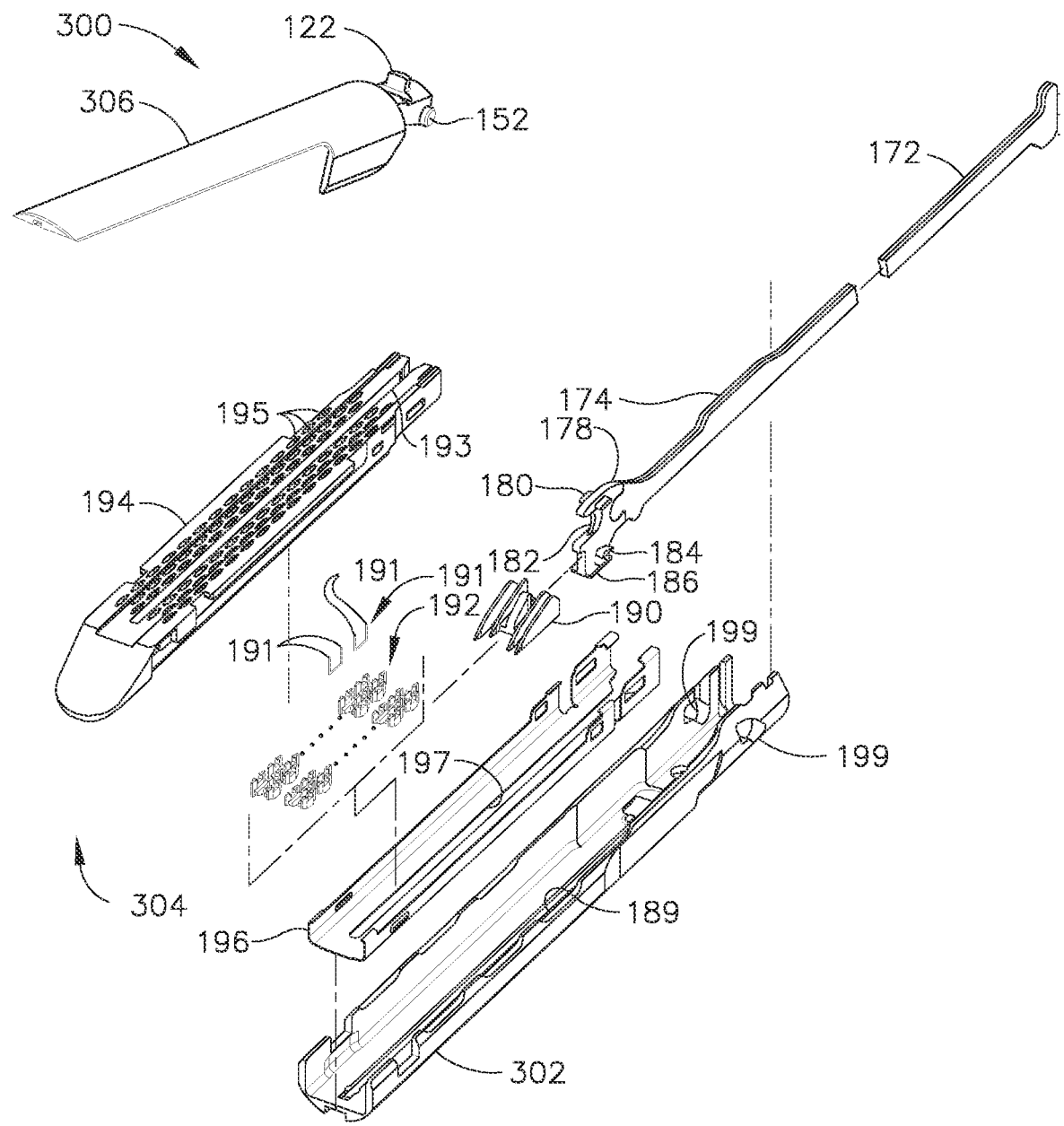
FIG. 14 is an exploded view of one aspect of an end effector of the surgical instrument of FIG. 1 in accordance with one or more aspects of the present disclosure.

Referring to FIG. 14, a non-limiting form of the end effector 300 is illustrated. As described above, the end effector 300 may include the anvil 306 and the surgical staple cartridge 304. In this non-limiting example, the anvil 306 is coupled to an elongated channel 198. For example, apertures 199 can be defined in the elongated channel 198 which can receive pins 152 extending from the anvil 306 and allow the anvil 306 to pivot from an open position to a closed position relative to the elongated channel 198 and surgical staple cartridge 304. In addition, FIG. 14 shows a firing bar 172, configured to longitudinally translate into the end effector 300. The firing bar 172 may be constructed from one solid section, or in various examples, may include a laminate material comprising, for example, a stack of steel plates. A distally projecting end of the firing bar 172 can be attached to an E-beam 178 that can, among other things, assist in spacing the anvil 306 from a surgical staple cartridge 304 positioned in the elongated channel 198 when the anvil 306 is in a closed position. The E-beam 178 can also include a sharpened cutting edge 182 which can be used to sever tissue as the E-beam 178 is advanced distally by the firing bar 172. In operation, the E-beam 178 can also actuate, or fire, the surgical staple cartridge 304. The surgical staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the surgical staple cartridge 304. The wedge sled 190 upwardly cams the staple drivers 192 to force out the staples 191 into deforming contact with the anvil 306 while a cutting edge 182 of the E-beam 178 severs clamped tissue.

Further to the above, the E-beam 178 can include upper pins 180 which engage the anvil 306 during firing. The E-beam 178 can further include middle pins 184 and a bottom foot 186 which can engage various portions of the cartridge body 194, cartridge tray 196 and elongated channel 198. When a surgical staple cartridge 304 is positioned within the elongated channel 198, a slot 193 defined in the cartridge body 194 can be aligned with a longitudinal slot 197 defined in the cartridge tray 196 and a slot 189 defined in the elongated channel 198. In use, the E-beam 178 can slide through the aligned longitudinal slots 193, 197, and 189 wherein, as indicated in FIG. 14, the bottom foot 186 of the E-beam 178 can engage a groove running along the bottom surface of elongated channel 198 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the surgical staple cartridge 304 as the firing bar 172 is moved distally to fire the staples from the surgical staple cartridge 304 and/or incise the tissue captured between the anvil 306 and the surgical staple cartridge 304. Thereafter, the firing bar 172 and the E-beam 178 can be retracted proximally allowing the anvil 306 to be opened to release the two stapled and severed tissue portions (not shown).

Figure 15:
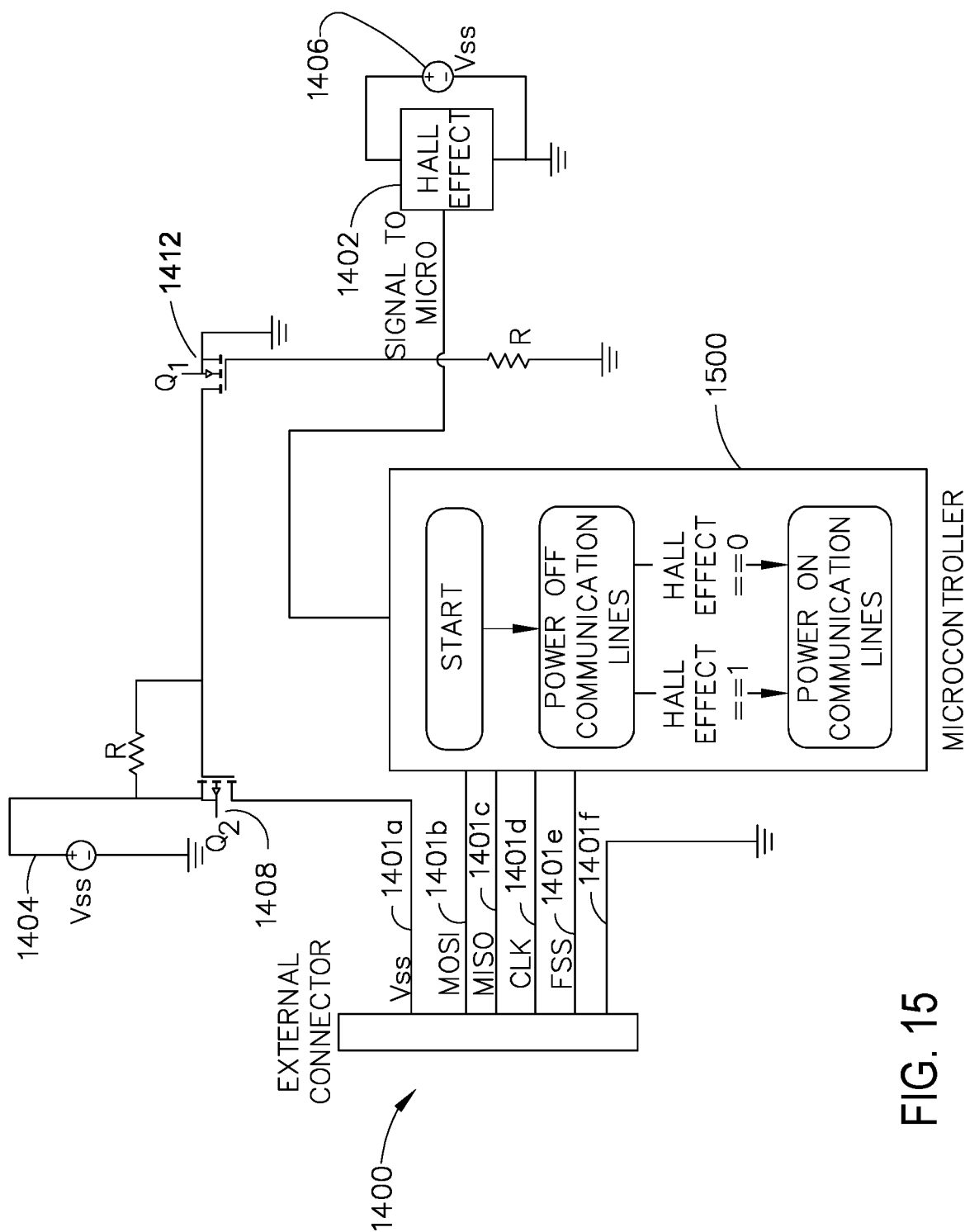
FIG. 15 is a schematic of a system for powering down an electrical connector of a surgical instrument handle when a shaft assembly is not coupled thereto in accordance with one or more aspects of the present disclosure.

Having described a surgical instrument 10 (FIGS. 1-14) in general terms, the description now turns to a detailed description of various electrical/electronic components of the surgical instrument 10. Referring again to FIGS. 2 and 3, the handle assembly 14 can include an electrical connector 1400 comprising a plurality of electrical contacts. Turning now to FIG. 15, the electrical connector 1400 can comprise a first electrical contact 1401*a*, a second electrical contact 1401*b*, a third electrical contact 1401*c*, a fourth electrical contact 1401*d*, a fifth electrical contact 1401*e*, and a sixth electrical contact 1401*f*, for example. While the illustrated example utilizes six contacts, other examples are envisioned which may utilize more than six contacts or less than six contacts.

As illustrated in FIG. 15, the first electrical contact 1401*a* can be in electrical communication with a transistor 1408, electrical contacts 1401*b*-1401*e* can be in electrical communication with a controller 1500, and the sixth electrical contact 1401*f* can be in electrical communication with a ground. In certain circumstances, one or more of the electrical contacts 1401*b*-1401*e* may be in electrical communication with one or more output channels of the controller 1500 and can be energized, or have a voltage potential applied thereto, when the handle 1042 is in a powered state. In some circumstances, one or more of the electrical contacts 1401*b*-1401*e* may be in electrical communication with one or more input channels of the controller 1500 and, when the handle assembly 14 is in a powered state, the controller 1500 can be configured to detect when a voltage potential is applied to such electrical contacts. When a shaft assembly, such as the interchangeable shaft assembly 200, for example, is assembled to the handle assembly 14, the electrical contacts 1401*a*-1401*f* may not communicate with each other. When a shaft assembly is not assembled to the handle assembly 14, however, the electrical contacts 1401*a*-1401*f* of the electrical connector 1400 may be exposed and, in some circumstances, one or more of the electrical contacts 1401*a*-1401*f* may be accidentally placed in electrical communication with each other. Such circumstances can arise when one or more of the electrical contacts 1401*a*-1401*f* come into contact with an electrically conductive material, for example. When this occurs, the controller 1500 can receive an erroneous input and/or the interchangeable shaft assembly 200 can receive an erroneous output, for example. To address this issue, in various circumstances, the handle assembly 14 may be unpowered when a shaft assembly, such as the interchangeable shaft assembly 200, for example, is not attached to the handle assembly 14.

In other circumstances, the handle 1042 can be powered when a shaft assembly, such as the interchangeable shaft assembly 200, for example, is not attached thereto. In such circumstances, the controller 1500 can be configured to ignore inputs, or voltage potentials, applied to the contacts in electrical communication with the controller 1500, i.e., electrical contacts 1401*b*-1401*e*, for example, until a shaft assembly is attached to the handle assembly 14. Even though the controller 1500 may be supplied with power to operate other functionalities of the handle assembly 14 in such circumstances, the handle assembly 14 may be in a powered-down state. In a way, the electrical connector 1400 may be in a powered-down state as voltage potentials applied to the electrical contacts 1401*b*-1401*e* may not affect the operation of the handle assembly 14. The reader will appreciate that, even though electrical contacts 1401*b*-1401*e* may be in a powered-down state, the electrical contacts 1401*a* and 1401*f*, which are not in electrical communication with the controller 1500, may or may not be in a powered-down state. For instance, sixth electrical contact 1401*f* may remain in electrical communication with a ground regardless of whether the handle assembly 14 is in a powered-up or a powered-down state.

Furthermore, the transistor 1408, and/or any other suitable arrangement of transistors, such as transistor 1412, for example, and/or switches may be configured to control the supply of power from a power source 1404, such as a battery, within the handle assembly 14, for example, to the first electrical contact 1401a regardless of whether the handle assembly 14 is in a powered-up or a powered-down state. In various circumstances, the interchangeable shaft assembly 200, for example, can be configured to change the state of the transistor 1408 when the interchangeable shaft assembly 200 is engaged with the handle assembly 14. In certain circumstances, further to the below, a magnetic field sensor 1402 can be configured to switch the state of transistor 1412 which, as a result, can switch the state of transistor 1408 and ultimately supply power from power source 1404 to first electrical contact 1401a. In this way, both the power circuits and the signal circuits to the electrical connector 1400 can be powered down when a shaft assembly is not installed to the handle assembly 14 and powered up when a shaft assembly is installed to the handle assembly 14.

In various circumstances, referring again to FIG. 15, the handle assembly 14 can include the magnetic field sensor 1402, for example, which can be configured to detect a detectable element, such as a magnetic element 1407 (FIG. 3), for example, on a shaft assembly, such as the interchangeable shaft assembly 200, for example, when the shaft assembly is coupled to the handle assembly 14. The magnetic field sensor 1402 can be powered by a power source 1406, such as a battery, for example, which can, in effect, amplify the detection signal of the magnetic field sensor 1402 and communicate with an input channel of the controller 1500 via the circuit illustrated in FIG. 15. Once the controller 1500 has a received an input indicating that a shaft assembly has been at least partially coupled to the handle assembly 14, and that, as a result, the electrical contacts 1401a-1401f are no longer exposed, the controller 1500 can enter into its normal, or powered-up, operating state. In such an operating state, the controller 1500 will evaluate the signals transmitted to one or more of the electrical contacts 1401b-1401e from the shaft assembly and/or transmit signals to the shaft assembly through one or more of the electrical contacts 1401b-1401e in normal use thereof. In various circumstances, the interchangeable shaft assembly 200 may have to be fully seated before the magnetic field sensor 1402 can detect the magnetic element 1407. While a magnetic field sensor 1402 can be utilized to detect the presence of the interchangeable shaft assembly 200, any suitable system of sensors and/or switches can be utilized to detect whether a shaft assembly has been assembled to the handle assembly 14, for example. In this way, further to the above, both the power circuits and the signal circuits to the electrical connector 1400 can be powered down when a shaft assembly is not installed to the handle assembly 14 and powered up when a shaft assembly is installed to the handle assembly 14.

In various examples, as may be used throughout the present disclosure, any suitable magnetic field sensor may be employed to detect whether a shaft assembly has been assembled to the handle assembly 14, for example. For example, the technologies used for magnetic field sensing include Hall effect sensor, search coil, fluxgate, optically pumped, nuclear precession, SQUID (superconducting quantum interference device—a very sensitive magnetometer used to measure extremely subtle magnetic fields, based on superconducting loops containing Josephson junctions), Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 15, the controller 1500 may generally comprise a processor ("microprocessor") and one or more memory units operationally coupled to the processor. By executing instruction code stored in the memory, the processor may control various components of the surgical instrument, such as the motor, various drive systems, and/or a user display, for example. The controller 1500 may be implemented using integrated and/or discrete hardware elements, software elements, and/or a combination of both. Examples of integrated hardware elements may include processors, microprocessors, controllers, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controllers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 1500 may include a hybrid circuit comprising discrete and integrated circuit elements or components on one or more substrates, for example.

Referring to FIG. 15, the controller 1500 may be an LM4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available from the product datasheet. Other controllers may be readily substituted for use with the present disclosure. Accordingly, the present disclosure should not be limited in this context.

As discussed above, the handle assembly 14 and/or the interchangeable shaft assembly 200 can include systems and configurations configured to prevent, or at least reduce the possibility of, the contacts of the electrical connector 1400 located on the handle and/or the contacts of the electrical connector 1410 located on the shaft from becoming shorted out when the interchangeable shaft assembly 200 is not assembled, or completely assembled, to the handle assembly 14. Referring to FIG. 3, the electrical connector 1400 located on the handle can be at least partially recessed within a cavity 1409 defined in the frame 20. The six electrical contacts 1401a-1401f of the electrical connector 1400 can be completely recessed within the cavity 1409. Such arrangements can reduce the possibility of an object accidentally contacting one or more of the electrical contacts 1401a-1401f. Similarly, the electrical connector 1410 located on the shaft can be positioned within a recess defined in the chassis 240 which can reduce the possibility of an object accidentally contacting one or more of the electrical contacts 1411a-1411f of the electrical connector 1410 located on the shaft. With regard to the particular example depicted in FIG.

3, the electrical contacts 1411a-1411f located on the shaft can comprise male contacts. In at least one example, each of the electrical contacts 1411a-1411f located in the shaft can comprise a flexible projection extending therefrom which can be configured to engage an electrical contact 1401a-1401f located on the handle, for example. The electrical contacts 1401a-1401f located on the handle can comprise female contacts. In at least one example, each electrical contact 1401a-1401f located on the handle can comprise a flat surface, for example, against which the male electrical contacts 1401a-1401f located on the shaft can wipe, or slide, against and maintain an electrically conductive interface therebetween. In various instances, the direction in which the interchangeable shaft assembly 200 is assembled to the handle assembly 14 can be parallel to, or at least substantially parallel to, the electrical contacts 1401a-1401f located on the handle such that the electrical contacts 1411a-1411f located on the shaft slide against the electrical contacts 1401a-1401f located on the handle when the interchangeable shaft assembly 200 is assembled to the handle assembly 14. In various alternative examples, the electrical contacts 1401a-1401f located in the handle can comprise male contacts and the electrical contacts 1411a-1411f located on the shaft can comprise female contacts. In certain alternative examples, the electrical contacts 1401a-1401f located on the handle and the electrical contacts 1411a-1411f located on the shaft can comprise any suitable arrangement of contacts.

In various instances, the handle assembly 14 can comprise a connector guard configured to at least partially cover the electrical connector 1400 located on the handle and/or a connector guard configured to at least partially cover the electrical connector 1410 located on the shaft. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one example, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 1400, for example. In various instances, the contacts can be transitioned between an unactivated condition and an activated condition. In certain instances, the contacts can be transitioned between a monitored condition, a deactivated condition, and an activated condition. For instance, the controller 1500, for example, can monitor the electrical contacts 1401a-1401f when a shaft assembly has not been assembled to the handle assembly 14 to determine whether one or more of the electrical contacts 1401a-1401f may have been shorted. The controller 1500 can be configured to apply a low voltage potential to each of the electrical contacts 1401a-1401f and assess whether only a minimal resistance is present at each of the contacts. Such an operating state can comprise the monitored condition. In the event that the resistance detected at a contact is high, or above a threshold resistance, the controller 1500 can deactivate that contact, more than one contact, or, alternatively, all of the contacts. Such an operating state can comprise the deactivated condition. If a shaft assembly is assembled to the handle assembly 14 and it is detected by the controller 1500, as discussed above, the controller 1500 can increase the voltage potential to the electrical contacts 1401a-1401f. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

Figure 16A:
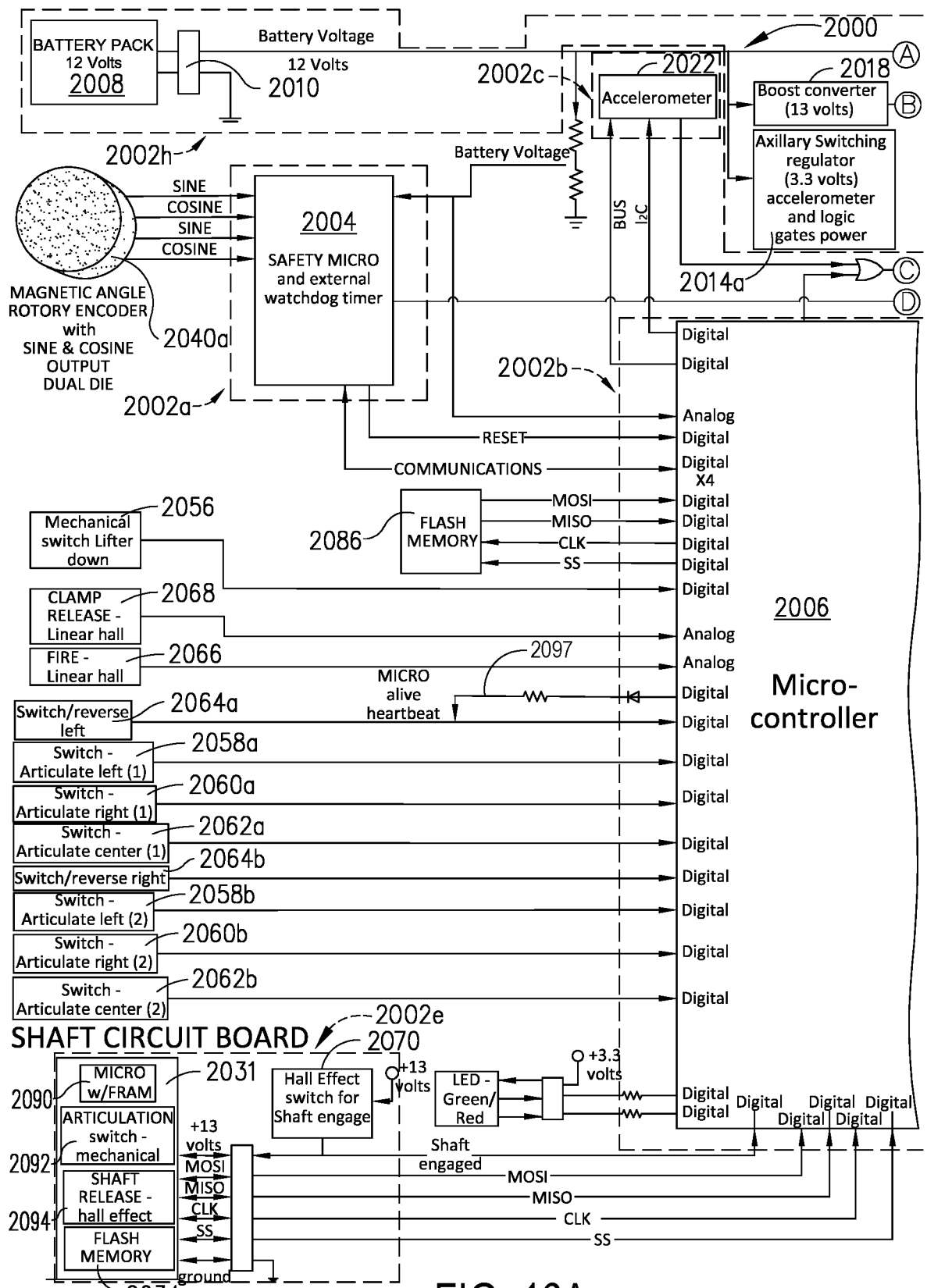
FIGS. 16A-16B is a circuit diagram of the surgical instrument of FIG. 1 spanning two drawings sheets in accordance with one or more aspects of the present disclosure
Figure 16B:
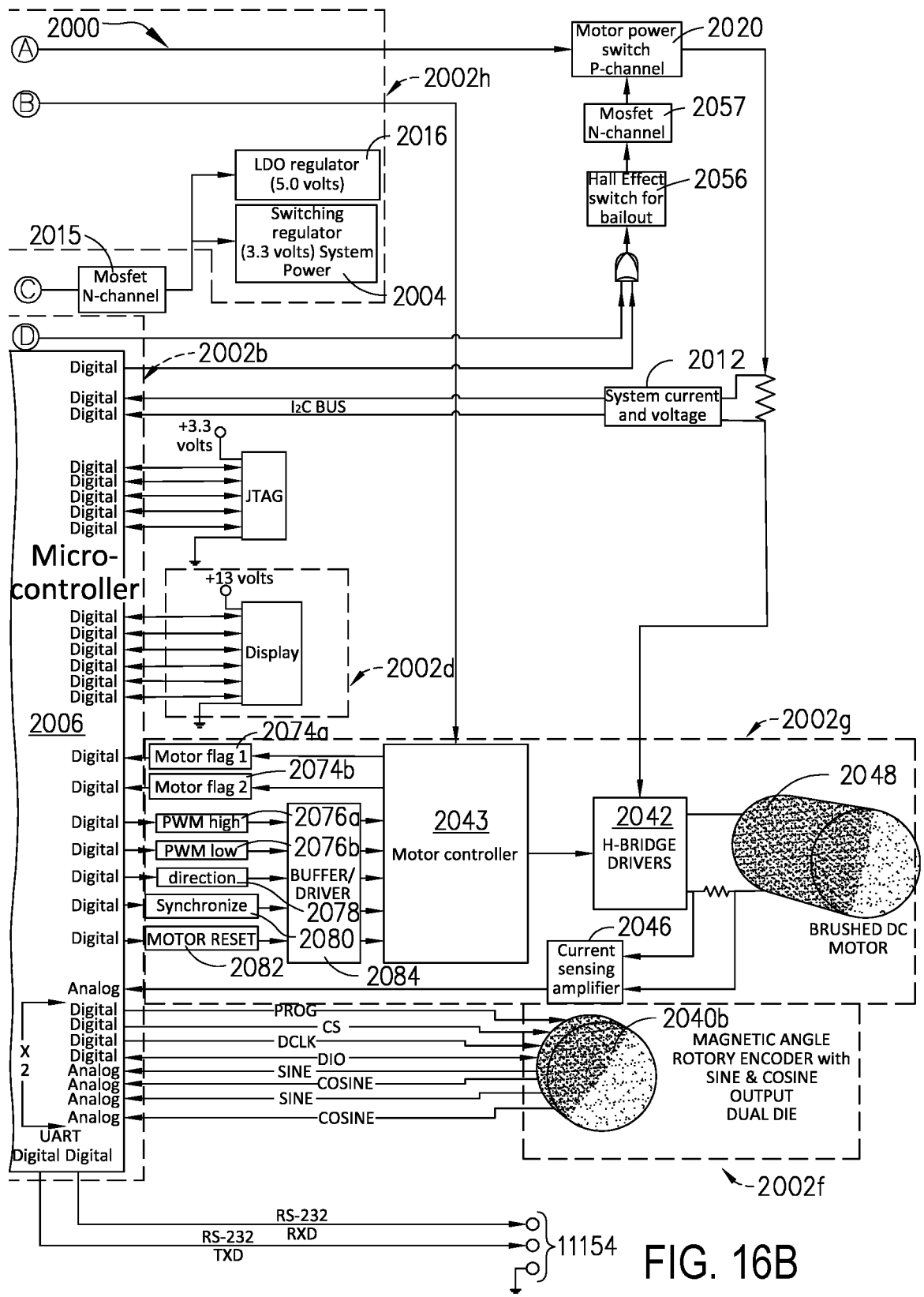

Turning now to FIGS. 16A and 16B, where one example of a segmented circuit 2000 comprising a plurality of circuit segments 2002a-2002g is illustrated. The segmented circuit 2000 comprising the plurality of circuit segments 2002a-2002g is configured to control a powered surgical instrument, such as, for example, the surgical instrument 10 illustrated in FIGS. 1-13, without limitation. The plurality of circuit segments 2002a-2002g is configured to control one or more operations of the powered surgical instrument 10. A safety processor segment 2002a (Segment 1) comprises a safety processor 2004. A primary processor segment 2002b (Segment 2) comprises a primary processor 2006. The safety processor 2004 and/or the primary processor 2006 are configured to interact with one or more additional circuit segments 2002c-2002g to control operation of the powered surgical instrument 10. The primary processor 2006 comprises a plurality of inputs coupled to, for example, one or more circuit segments 2002c-2002g, a battery 2008, and/or a plurality of switches 2058a-2070. The segmented circuit 2000 may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one aspect, the primary processor 2006 may be any single core or multicore processor such as those known under the trade name ARM Cortex by Texas Instruments. In one example, the safety processor 2004 may be a safety controller platform comprising two controller-based families such as TMS570 and RM4x known under the trade name Hercules ARM Cortex R4, also by Texas Instruments. Nevertheless, other suitable substitutes for controllers and safety processor may be employed, without limitation. In one example, the safety processor 2004 may be configured specifically for IEC 61508 and ISO 26262 safety critical applications, among others, to provide advanced integrated safety features while delivering scalable performance, connectivity, and memory options. In certain instances, the primary processor 2006 may be a single core or multicore controller LM4F230H5QR as described in connection with FIGS. 14-17B.

In one aspect, the segmented circuit 2000 comprises an acceleration segment 2002c (Segment 3). The acceleration segment 2002c comprises an accelerometer 2022. The accelerometer 2022 is configured to detect movement or acceleration of the powered surgical instrument 10. In some examples, input from the accelerometer 2022 is used, for example, to transition to and from a sleep mode, identify an orientation of the powered surgical instrument, and/or identify when the surgical instrument has been dropped. In some examples, the acceleration segment 2002c is coupled to the safety processor 2004 and/or the primary processor 2006.

In one aspect, the segmented circuit 2000 comprises a display segment 2002d (Segment 4). The display segment 2002d comprises a display connector 2024 coupled to the primary processor 2006. The display connector 2024 couples the primary processor 2006 to a display 2028 through one or more integrated circuit drivers of the display 2026. The integrated circuit drivers of the display 2026 may be integrated with the display 2028 and/or may be located separately from the display 2028. The display 2028 may comprise any suitable display, such as, for example, an organic light-emitting diode (OLED) display, a liquid-crystal display (LCD), and/or any other suitable display. In some examples, the display segment 2002d is coupled to the safety processor 2004.

In some aspects, the segmented circuit 2000 comprises a shaft segment 2002e (Segment 5). The shaft segment 2002e comprises one or more controls for an interchangeable shaft assembly 200 (FIG. 1) coupled to the surgical instrument 10 and/or one or more controls for an end effector 300 coupled to the interchangeable shaft assembly 200 (FIG. 1). The shaft segment 2002e comprises a shaft connector 2030 configured to couple the primary processor 2006 to a shaft PCBA 2031. The shaft PCBA 2031 comprises a first articulation switch 2036, a second articulation switch 2032, and a shaft PCBA EEPROM 2034. In some examples, the shaft PCBA EEPROM 2034 comprises one or more parameters, routines, and/or programs specific to the interchangeable shaft assembly 200 and/or the shaft PCBA 2031. The shaft PCBA 2031 may be coupled to the interchangeable shaft assembly 200 and/or integral with the surgical instrument 10. In some examples, the shaft segment 2002e comprises a second shaft EEPROM 2038. The second shaft EEPROM 2038 comprises a plurality of algorithms, routines, parameters, and/or other data corresponding to one or more shaft assemblies 200 and/or end effectors 300 which may be interfaced with the powered surgical instrument 10.

In some aspects, the segmented circuit 2000 comprises a position encoder segment 2002f (Segment 6). The position encoder segment 2002f comprises one or more magnetic angle rotary position encoders 2040a-2040b. The one or more magnetic angle rotary position encoders 2040a-2040b are configured to identify the rotational position of a motor 2048, an interchangeable shaft assembly 200 (FIG. 1), and/or an end effector 300 of the surgical instrument 10. In some examples, the magnetic angle rotary position encoders 2040a-2040b may be coupled to the safety processor 2004 and/or the primary processor 2006.

In some aspects, the segmented circuit 2000 comprises a motor circuit segment 2002g (Segment 7). The motor circuit segment 2002g comprises a motor 2048 configured to control one or more movements of the powered surgical instrument 10. The motor 2048 is coupled to the primary processor 2006 by an H-Bridge driver 2042 and one or more H-bridge field-effect transistors 2044 (FETs). The H-bridge FETs 2044 are coupled to the safety processor 2004. A motor current sensor 2046 is coupled in series with the motor 2048 to measure the current draw of the motor 2048. The motor current sensor 2046 is in signal communication with the primary processor 2006 and/or the safety processor 2004. In some examples, the motor 2048 is coupled to a motor electromagnetic interference (EMI) filter 2050.

In some aspects, the segmented circuit 2000 comprises a power segment 2002h (Segment 8). A battery 2008 is coupled to the safety processor 2004, the primary processor 2006, and one or more of the additional circuit segments 2002c-2002g. The battery 2008 is coupled to the segmented circuit 2000 by a battery connector 2010 and a current sensor 2012. The current sensor 2012 is configured to measure the total current draw of the segmented circuit 2000. In some examples, one or more voltage converters 2014a, 2014b, 2016 are configured to provide predetermined voltage values to one or more circuit segments 2002a-2002g. For example, in some examples, the segmented circuit 2000 may comprise 3.3V voltage converters 2014a-2014b and/or 5V voltage converters 2016. A boost converter 2018 is configured to provide a boost voltage up to a predetermined amount, such as, for example, up to 13V. The boost converter 2018 is configured to provide additional voltage and/or current during power intensive operations and prevent brownout or low-power conditions.

In some aspects, the safety processor segment 2002a comprises a motor power switch 2020. The motor power switch 2020 is coupled between the power segment 2002h and the motor circuit segment 2002g. The safety processor segment 2002a is configured to interrupt power to the motor circuit segment 2002g when an error or fault condition is detected by the safety processor 2004 and/or the primary processor 2006 as discussed in more detail herein. Although the circuit segments 2002a-2002g are illustrated with all components of the circuit segments 2002a-2002h located in physical proximity, one skilled in the art will recognize that a circuit segment 2002a-2002h may comprise components physically and/or electrically separate from other components of the same circuit segment 2002a-2002g. In some examples, one or more components may be shared between two or more circuit segments 2002a-2002g.

In some aspects, a plurality of switches 2056-2070 are coupled to the safety processor 2004 and/or the primary processor 2006. The plurality of switches 2056-2070 may be configured to control one or more operations of the surgical instrument 10, control one or more operations of the segmented circuit 2000, and/or indicate a status of the surgical instrument 10. For example, a bail-out door switch 2056 is configured to indicate the status of a bail-out door. A plurality of articulation switches, such as, for example, a left side articulation left switch 2058a, a left side articulation right switch 2060a, a left side articulation center switch 2062a, a right side articulation left switch 2058b, a right side articulation right switch 2060*b*, and a right side articulation center switch 2062*b* are configured to control articulation of a shaft assembly 200 and/or an end effector 300. A left side reverse switch 2064*a* and a right side reverse switch 2064*b* are coupled to the primary processor 2006. In some examples, the left side switches comprising the left side articulation left switch 2058*a*, the left side articulation right switch 2060*a*, the left side articulation center switch 2062*a*, and the left side reverse switch 2064*a* are coupled to the primary processor 2006 by a left flex connector 2072*a*. The right side switches comprising the right side articulation left switch 2058*b*, the right side articulation right switch 2060*b*, the right side articulation center switch 2062*b*, and the right side reverse switch 2064*b* are coupled to the primary processor 2006 by a right flex connector 2072*b*. In some examples, a firing switch 2066, a clamp release switch 2068, and a shaft engaged switch 2070 are coupled to the primary processor 2006.

In some aspects, the plurality of switches 2056-2070 may comprise, for example, a plurality of handle controls mounted to a handle of the surgical instrument 10, a plurality of indicator switches, and/or any combination thereof. In various examples, the plurality of switches 2056-2070 allow a surgeon to manipulate the surgical instrument, provide feedback to the segmented circuit 2000 regarding the position and/or operation of the surgical instrument, and/or indicate unsafe operation of the surgical instrument 10. In some examples, additional or fewer switches may be coupled to the segmented circuit 2000, one or more of the switches 2056-2070 may be combined into a single switch, and/or expanded to multiple switches. For example, in one example, one or more of the left side and/or right side articulation switches 2058*a*-2064*b* may be combined into a single multi-position switch.

In one aspect, the safety processor 2004 is configured to implement a watchdog function, among other safety operations. The safety processor 2004 and the primary processor 2006 of the segmented circuit 2000 are in signal communication. A processor alive heartbeat signal is provided at output 2097. The acceleration segment 2002*c* comprises an accelerometer 2022 configured to monitor movement of the surgical instrument 10. In various examples, the accelerometer 2022 may be a single, double, or triple axis accelerometer. The accelerometer 2022 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 2022. For example, the accelerometer 2022 at rest on the surface of the earth will measure an acceleration g=9.8 m/s² (gravity) straight upwards, due to its weight. Another type of acceleration that accelerometer 2022 can measure is g-force acceleration. In various other examples, the accelerometer 2022 may comprise a single, double, or triple axis accelerometer. Further, the acceleration segment 2002*c* may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

In one aspect, the safety processor 2004 is configured to implement a watchdog function with respect to one or more circuit segments 2002*c*-2002*h*, such as, for example, the motor circuit segment 2002*g*. In this regards, the safety processor 2004 employs the watchdog function to detect and recover from malfunctions of the primary processor 2006. During normal operation, the safety processor 2004 monitors for hardware faults or program errors of the primary processor 2006 and to initiate corrective action or actions. The corrective actions may include placing the primary processor 2006 in a safe state and restoring normal system operation. In one example, the safety processor 2004 is coupled to at least a first sensor. The first sensor measures a first property of the surgical instrument 10 (FIGS. 1-4). In some examples, the safety processor 2004 is configured to compare the measured property of the surgical instrument 10 to a predetermined value. For example, in one example, a magnetic angle rotary position encoder 2040*a* is coupled to the safety processor 2004. The magnetic angle rotary position encoder 2040*a* provides motor speed and position information to the safety processor 2004. The safety processor 2004 monitors the magnetic angle rotary position encoder 2040*a* and compares the value to a maximum speed and/or position value and prevents operation of the motor 2048 above the predetermined values. In some examples, the predetermined values are calculated based on real-time speed and/or position of the motor 2048, calculated from values supplied by a second magnetic angle rotary position encoder 2040*b* in communication with the primary processor 2006, and/or provided to the safety processor 2004 from, for example, a memory module coupled to the safety processor 2004.

In some aspects, a second sensor is coupled to the primary processor 2006. The second sensor is configured to measure the first physical property. The safety processor 2004 and the primary processor 2006 are configured to provide a signal indicative of the value of the first sensor and the second sensor respectively. When either the safety processor 2004 or the primary processor 2006 indicates a value outside of an acceptable range, the segmented circuit 2000 prevents operation of at least one of the circuit segments 2002*c*-2002*h*, such as, for example, the motor circuit segment 2002*g*. For example, in the example illustrated in FIGS. 16A and 16B, the safety processor 2004 is coupled to a first magnetic angle rotary position encoder 2040*a* and the primary processor 2006 is coupled to a second magnetic angle rotary position encoder 2040*b*. The magnetic angle rotary position encoders 2040*a*, 2040*b* may comprise any suitable motor position sensor, such as, for example, a magnetic angle rotary input comprising a sine and cosine output. The magnetic angle rotary position encoders 2040*a*, 2040*b* provide respective signals to the safety processor 2004 and the primary processor 2006 indicative of the position of the motor 2048.

The safety processor 2004 and the primary processor 2006 generate an activation signal when the values of the first magnetic angle rotary position encoder 2040*a* and the second magnetic angle rotary position encoder 2040*b* are within a predetermined range. When either the primary processor 2006 or the safety processor 2004 to detect a value outside of the predetermined range, the activation signal is terminated and operation of at least one of the circuit segments 2002*c*-2002*h*, such as, for example, the motor circuit segment 2002*g*, is interrupted and/or prevented. For example, in some examples, the activation signal from the primary processor 2006 and the activation signal from the safety processor 2004 are coupled to an AND gate. The AND gate is coupled to a motor power switch 2020. The AND gate maintains the motor power switch 2020 in a closed, or on, position when the activation signal from both the safety processor 2004 and the primary processor 2006 are high, indicating a value of the magnetic angle rotary position encoders 2040*a*, 2040*b* within the predetermined range. When either of the magnetic angle rotary position encoders 2040*a*, 2040*b* detect a value outside of the predetermined range, the activation signal from that magnetic angle rotary position encoder 2040*a*, 2040*b* is set low, and the output of the AND gate is set low, opening the motor power switch 2020. In some examples, the value of the first magnetic angle rotary position encoder 2040*a* and the second magnetic angle rotary position encoder 2040*b* is compared, for example, by the safety processor 2004 and/or the primary processor 2006. When the values of the first sensor and the second sensor are different, the safety processor 2004 and/or the primary processor 2006 may prevent operation of the motor circuit segment 2002*g*.

In some aspects, the safety processor 2004 receives a signal indicative of the value of the second magnetic angle rotary position encoder 2040*b* and compares the second sensor value to the first sensor value. For example, in one aspect, the safety processor 2004 is coupled directly to a first magnetic angle rotary position encoder 2040*a*. A second magnetic angle rotary position encoder 2040*b* is coupled to a primary processor 2006, which provides the second magnetic angle rotary position encoder 2040*b* value to the safety processor 2004, and/or coupled directly to the safety processor 2004. The safety processor 2004 compares the value of the first magnetic angle rotary position encoder 2040 to the value of the second magnetic angle rotary position encoder 2040*b*. When the safety processor 2004 detects a mismatch between the first magnetic angle rotary position encoder 2040*a* and the second magnetic angle rotary position encoder 2040*b*, the safety processor 2004 may interrupt operation of the motor circuit segment 2002*g*, for example, by cutting power to the motor circuit segment 2002*g*.

In some aspects, the safety processor 2004 and/or the primary processor 2006 is coupled to a first magnetic angle rotary position encoder 2040*a* configured to measure a first property of a surgical instrument and a second magnetic angle rotary position encoder 2040*b* configured to measure a second property of the surgical instrument. The first property and the second property comprise a predetermined relationship when the surgical instrument is operating normally. The safety processor 2004 monitors the first property and the second property. When a value of the first property and/or the second property inconsistent with the predetermined relationship is detected, a fault occurs. When a fault occurs, the safety processor 2004 takes at least one action, such as, for example, preventing operation of at least one of the circuit segments, executing a predetermined operation, and/or resetting the primary processor 2006. For example, the safety processor 2004 may open the motor power switch 2020 to cut power to the motor circuit segment 2002*g* when a fault is detected.

In one aspect, the safety processor 2004 is configured to execute an independent control algorithm. In operation, the safety processor 2004 monitors the segmented circuit 2000 and is configured to control and/or override signals from other circuit components, such as, for example, the primary processor 2006, independently. The safety processor 2004 may execute a preprogrammed algorithm and/or may be updated or programmed on the fly during operation based on one or more actions and/or positions of the surgical instrument 10. For example, in one example, the safety processor 2004 is reprogrammed with new parameters and/or safety algorithms each time a new shaft and/or end effector is coupled to the surgical instrument 10. In some examples, one or more safety values stored by the safety processor 2004 are duplicated by the primary processor 2006. Two-way error detection is performed to ensure values and/or parameters stored by either of the safety processor 2004 or primary processor 2006 are correct.

In some aspects, the safety processor 2004 and the primary processor 2006 implement a redundant safety check. The safety processor 2004 and the primary processor 2006 provide periodic signals indicating normal operation. For example, during operation, the safety processor 2004 may indicate to the primary processor 2006 that the safety processor 2004 is executing code and operating normally. The primary processor 2006 may, likewise, indicate to the safety processor 2004 that the primary processor 2006 is executing code and operating normally. In some examples, communication between the safety processor 2004 and the primary processor 2006 occurs at a predetermined interval. The predetermined interval may be constant or may be variable based on the circuit state and/or operation of the surgical instrument 10.

Figure 17A:
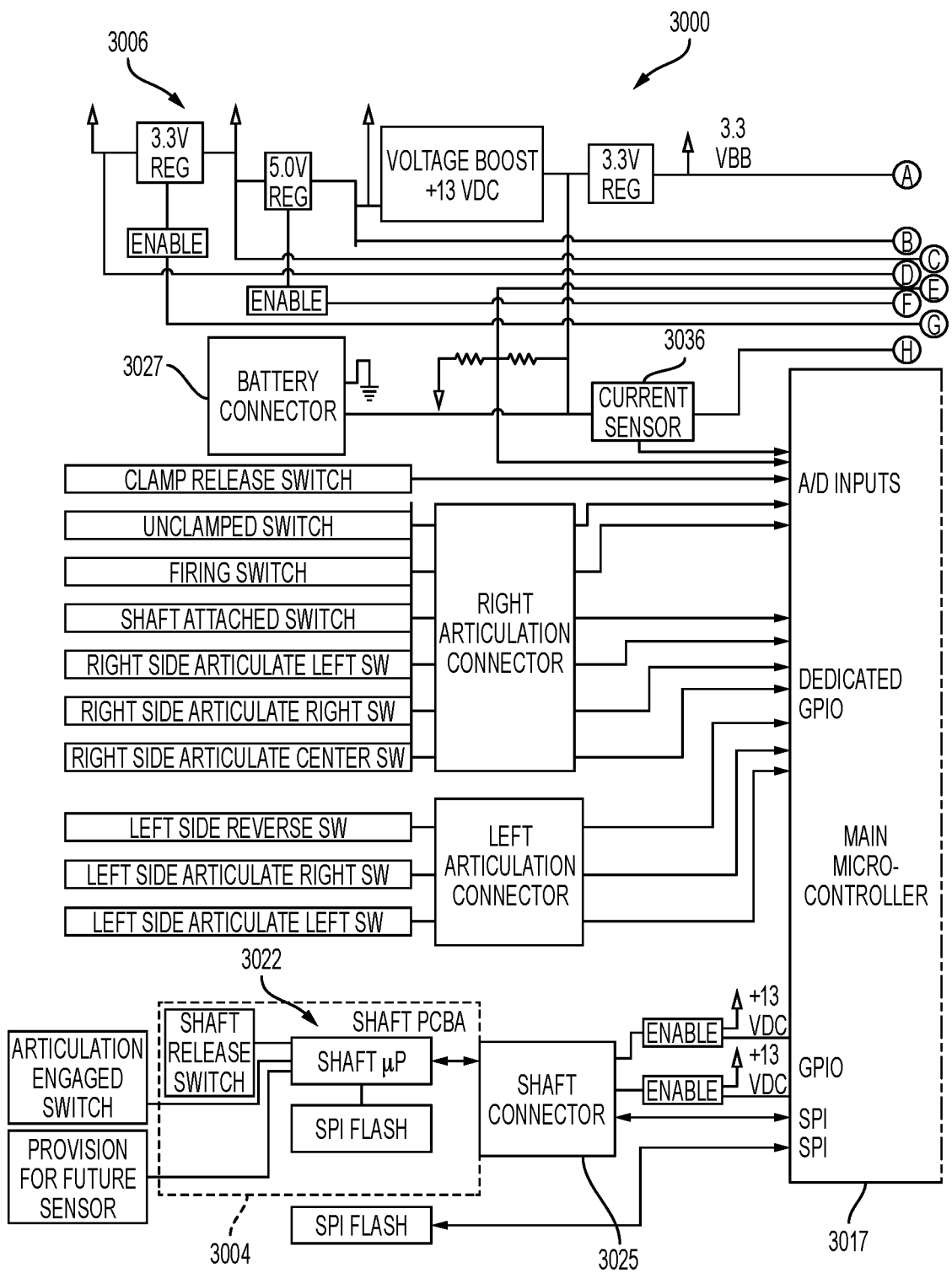
FIGS. 17A-17B, is a circuit diagram of the surgical instrument of FIG. 1 in accordance with one or more aspects of the present disclosure.
Figure 17B:
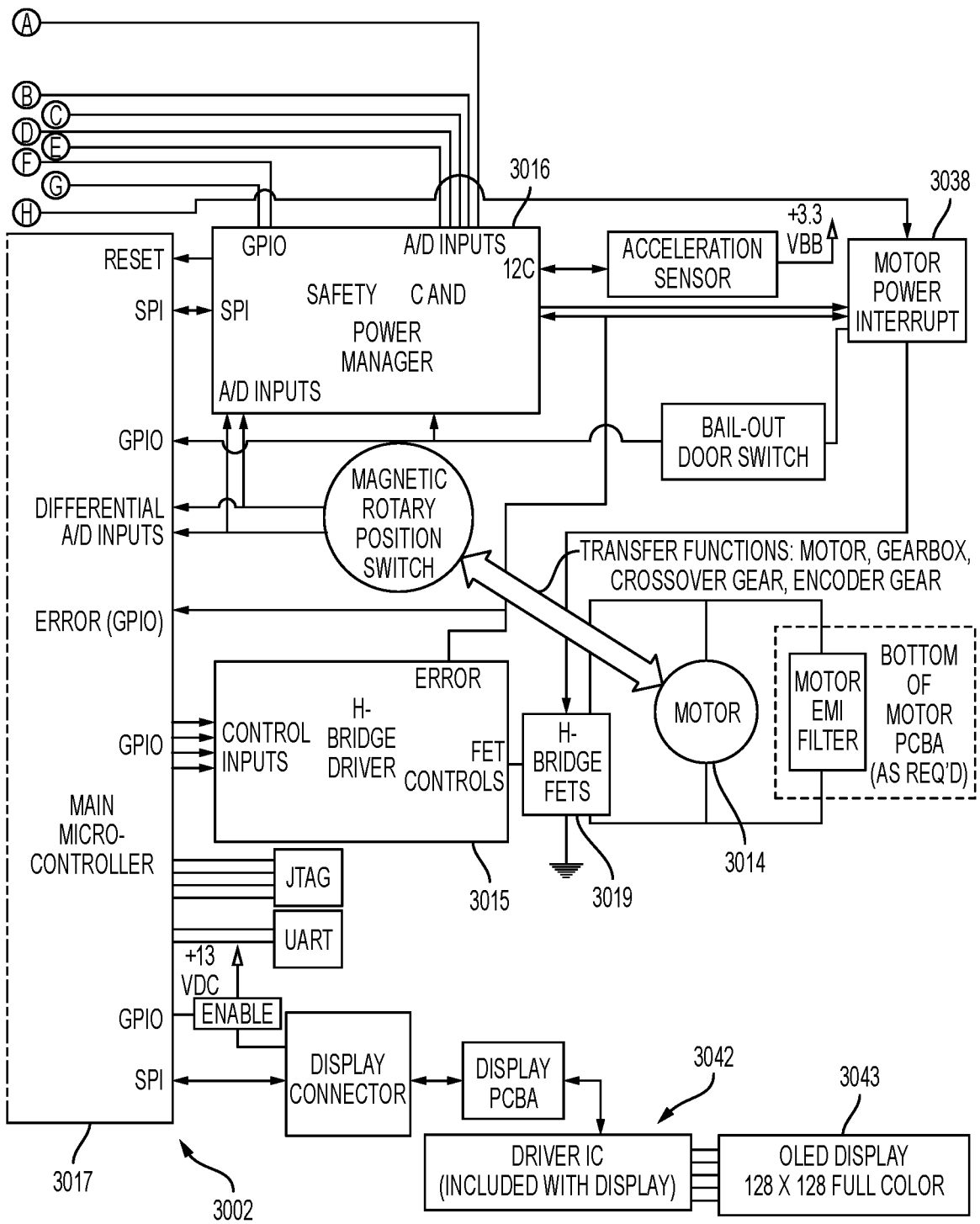

FIGS. 17A and 17B illustrate another aspect of a segmented circuit 3000 configured to control the powered surgical instrument 10, illustrated in FIGS. 1-14. As shown in FIGS. 14, 17B, the handle assembly 14 may include an electric motor 3014 which can be controlled by a motor driver 3015 and can be employed by the firing system of the surgical instrument 10. In various forms, the electric motor 3014 may be a DC brushed driving motor having a maximum rotation of, approximately, 25,000 RPM, for example. In other arrangements, the electric motor 3014 may include a brushless motor, a cordless motor, a synchronous motor, a stepper motor, or any other suitable electric motor. In certain circumstances, the motor driver 3015 may comprise an H-Bridge FETs 3019, as illustrated in FIGS. 17A and 17B, for example. The electric motor 3014 can be powered by a power assembly 3006, which can be releasably mounted to the handle assembly 14. The power assembly 3006 is configured to supply control power to the surgical instrument 10. The power assembly 3006 may comprise a battery which may include a number of battery cells connected in series that can be used as the power source to power the surgical instrument 10. In such configuration, the power assembly 3006 may be referred to as a battery pack. In certain circumstances, the battery cells of the power assembly 3006 may be replaceable and/or rechargeable. In at least one example, the battery cells can be Lithium-Ion batteries which can be separably couplable to the power assembly 3006.

Examples of drive systems and closure systems that are suitable for use with the surgical instrument 10 are disclosed in U.S. Patent Application Publication No. 2014/0263539, entitled CONTROL SYSTEMS FOR SURGICAL INSTRUMENTS, now U.S. Pat. No. 9,629,629, which is incorporated herein by reference herein in its entirety. For example, the electric motor 3014 can include a rotatable shaft (not shown) that may operably interface with a gear reducer assembly that can be mounted in meshing engagement with a set, or rack, of drive teeth on a longitudinally-movable drive member. In use, a voltage polarity provided by the battery can operate the electric motor 3014 to drive the longitudinally-movable drive member to effectuate the end effector 300. For example, the electric motor 3014 can be configured to drive the longitudinally-movable drive member to advance a firing mechanism to fire staples into tissue captured by the end effector 300 from a staple cartridge assembled with the end effector 300 and/or advance a cutting member to cut tissue captured by the end effector 300, for example.

As illustrated in FIGS. 17A and 17B and as described below in greater detail, the power assembly 3006 may include a power management controller which can be configured to modulate the power output of the power assembly 3006 to deliver a first power output to power the electric motor 3014 to advance the cutting member while the interchangeable shaft assembly 200 is coupled to the handle assembly 14 (FIG. 1) and to deliver a second power output to power the electric motor 3014 to advance the cutting member while the interchangeable shaft assembly 200 is coupled to the handle assembly 14, for example. Such modulation can be beneficial in avoiding transmission of excessive power to the electric motor 3014 beyond the requirements of an interchangeable shaft assembly that is coupled to the handle assembly 14.

In certain circumstances, the interface 3024 can facilitate transmission of the one or more communication signals between the power management controller 3016 and the shaft assembly controller 3022 by routing such communication signals through a main controller 3017 residing in the handle assembly 14 (FIG. 1), for example. In other circumstances, the interface 3024 can facilitate a direct line of communication between the power management controller 3016 and the shaft assembly controller 3022 through the handle assembly 14 while the interchangeable shaft assembly 200 (FIG. 1) and the power assembly 3006 are coupled to the handle assembly 14.

In one instance, the main controller 3017 may be any single core or multicore processor such as those known under the trade name ARM Cortex by Texas Instruments. In one instance, the surgical instrument 10 (FIGS. 1-4) may comprise a power management controller 3016 such as, for example, a safety controller platform comprising two controller-based families such as TMS570 and RM4x known under the trade name Hercules ARM Cortex R4, also by Texas Instruments. Nevertheless, other suitable substitutes for controllers and safety processor may be employed, without limitation. In one instance, the safety processor 2004 (FIG. 16a) may be configured specifically for IEC 61508 and ISO 26262 safety critical applications, among others, to provide advanced integrated safety features while delivering scalable performance, connectivity, and memory options.

In certain instances, the main controller 3017 may be a single core or multicore controller LM4F230H5QR as described in connection with FIGS. 15-17B.

Figure 18:
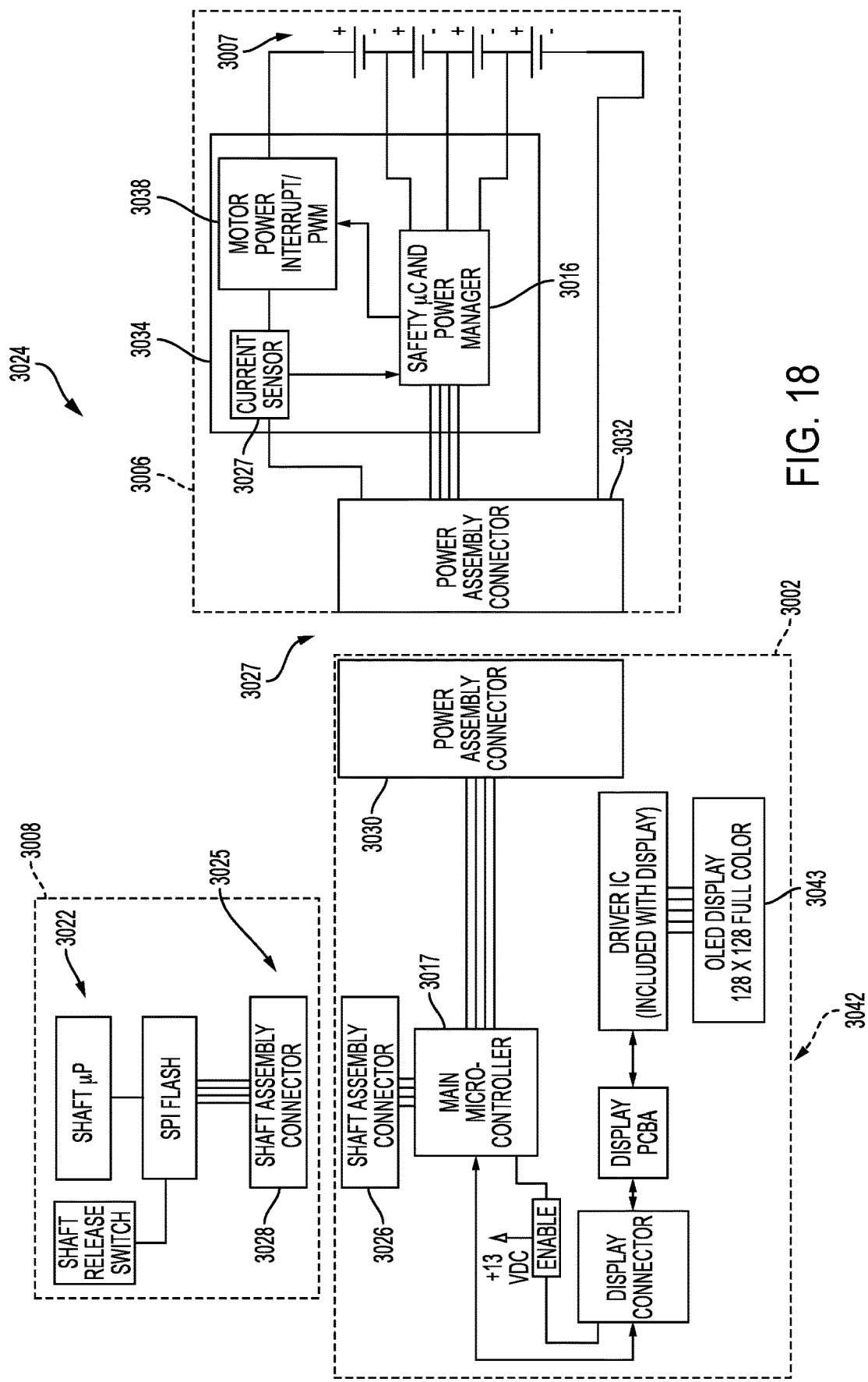
FIG. 18 is a block diagram the surgical instrument of FIG. 1 illustrating interfaces between the handle assembly and the power assembly and between the handle assembly and the interchangeable shaft assembly in accordance with one or more aspects of the present disclosure.

FIG. 18 is a block diagram the surgical instrument of FIG. 1 illustrating interfaces between the handle assembly 14 (FIG. 1) and the power assembly and between the handle assembly 14 and the interchangeable shaft assembly. As shown in FIG. 18, the power assembly 3006 may include a power management circuit 3034 which may comprise the power management controller 3016, a power modulator 3038, and a current sense circuit 3036. The power management circuit 3034 can be configured to modulate power output of the battery 3007 based on the power requirements of the interchangeable shaft assembly 200 (FIG. 1) while the interchangeable shaft assembly 200 and the power assembly 3006 are coupled to the handle assembly 14. For example, the power management controller 3016 can be programmed to control the power modulator 3038 of the power output of the power assembly 3006 and the current sense circuit 3036 can be employed to monitor power output of the power assembly 3006 to provide feedback to the power management controller 3016 about the power output of the battery 3007 so that the power management controller 3016 may adjust the power output of the power assembly 3006 to maintain a desired output.

It is noteworthy that the power management controller 3016 and/or the shaft assembly controller 3022 each may comprise one or more processors and/or memory units which may store a number of software modules. Although certain modules and/or blocks of the surgical instrument 10 (FIG. 1) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 10 (FIGS. 1-4) may comprise an output device 3042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 3042 may comprise a display 3043 which may be included in the handle assembly 14 (FIG. 1). The shaft assembly controller 3022 and/or the power management controller 3016 can provide feedback to a user of the surgical instrument 10 through the output device 3042. The interface 3024 can be configured to connect the shaft assembly controller 3022 and/or the power management controller 3016 to the output device 3042. The reader will appreciate that the output device 3042 can instead be integrated with the power assembly 3006. In such circumstances, communication between the output device 3042 and the shaft assembly controller 3022 may be accomplished through the interface 3024 while the interchangeable shaft assembly 200 is coupled to the handle assembly 14.

Having described a surgical instrument 10 (FIGS. 1-4) and one or more segmented circuit 2000, 3000 for controlling the operation thereof, the disclosure now turns to various specific configurations of the surgical instrument 10 and a segmented circuit 2000 (or 3000).

In various aspects the present disclosure provides techniques for data storage and usage. In one aspect, data storage and usage is based on multiple levels of action thresholds. Such thresholds include upper and lower ultimate threshold limits, ultimate threshold that shuts down motor or activates return is current, pressure, firing load, torque is exceeded, and alternatively, while running within the limits the device automatically compensates for loading of the motor.

In one aspect, the surgical instrument 10 (described in connection with FIGS. 1-18) can be configured to monitor upper and lower ultimate threshold limits to maintain minimum and maximum closure clamp loads within acceptable limits. If a minimum is not achieved the surgical instrument 10 cannot start or if it drops below minimum a user action is required. If the clamp load is at a suitable level but drops under minimum during firing, the surgical instrument 10 can adjust the speed of the motor or warn the user. If the minimum limit is breached during operation the unit could give a warning that the firing may not be completely as anticipated. The surgical instrument 10 also can be configured to monitor when the battery voltage drops below the lower ultimate limit the remaining battery power is only direct able towards returning the device to the I-beam parked state. The opening force on the anvil can be employed to sense jams in the end effector. Alternatively, the surgical instrument 10 can be configured to monitor when the motor current goes up or the related speed goes down, then the motor control increases pulse width or frequency modulation to keep speed constant.

In another aspect, the surgical instrument 10 can (FIG. 1) be configured to detect an ultimate threshold of current draw, pressure, firing load, torque such that when any of these thresholds are exceeded, the surgical instrument 10 shuts down the motor or causes the motor to return the knife to a pre-fired position. A secondary threshold, which is less than the ultimate threshold, may be employed to alter the motor control program to accommodate changes in conditions by changing the motor control parameters. A marginal threshold can be configured as a step function or a ramp function based on a proportionate response to another counter or input. For example, in the case of sterilization, no changes between 0-200 sterilization cycles, slow motor 1% per use from 201-400 sterilization cycles, and prevent use over 400 sterilization cycles. The speed of the motor also can be varied based on tissue gap and current draw.

There are many parameters that could influence the ideal function of a powered reusable stapler device. Most of these parameters have an ultimate maximum and/or minimum threshold beyond which the device should not be operated. Nevertheless, there are also marginal limits that may influence the functional operation of the device. These multiple limits, from multiple parameters may provide an overlying and cumulative effect on the operations program of the device.

Accordingly, the present disclosure relates to surgical instruments and, in various circumstances, to surgical stapling and cutting instruments and staple cartridges therefor that are designed to staple and cut tissue.

Efficient performance of an electromechanical device depends on various factors. One is the operational envelope, i.e., range of parameters, conditions and events in which the device carries out its intended functions. For example, for a device powered by a motor driven by electrical current, there may be an operational region above a certain electrical current threshold where the device runs more inefficiently than desired. Put another way, there may be an upper "speed limit" above which there is decreasing efficiency. Such an upper threshold may have value in preventing substantial inefficiencies or even device degradation.

There may be thresholds within an operational envelope, however, that may form regions exploitable to enhance efficiency within operational states. In other words, there may be regions where the device can adjust and perform better within a defined operational envelope (or sub-envelope). Such a region can be one between a marginal threshold and an ultimate threshold. In addition, these regions may comprise "sweet spots" or a predetermined optional range or point. These regions also may comprise a large range within which performance is judged to be adequate.

An ultimate threshold can be defined, above which or below which an action or actions could be taken (or refrained from being taken) such as stopping the device. In addition, a marginal threshold or thresholds can be defined, above which or below which an action or actions could be taken (or refrained from being taken). By way of non-limiting example, a marginal threshold can be set to define where the current draw of the motor exceeds 75% of an ultimate threshold. Exceeding the marginal threshold can result, for example, in the device's beginning to slow motor speed at an increasing rate as it continues to climb toward the ultimate threshold.

Various mechanisms can be employed to carry out the adjustment(s) taken as a result of exceeding a threshold. For example, the adjustment can reflect a step function. It can also reflect a ramped function. Other functions can be utilized.

In various aspects, to enhance performance by additional mechanisms, an overlaying threshold can be defined. An overlaying threshold can comprise one or more thresholds defined by multiple parameters. An overlaying threshold can result in one or more thresholds being an input into the generation of another threshold or thresholds. An overlaying threshold can be predetermined or dynamically generated such as at runtime. The overlaying threshold may come into effect when you the threshold is defined by multiple inputs. For example, as the number of sterilization cycles exceeds 300 (the marginal threshold) but not 500 (the ultimate threshold) the device runs the motor slower. Then as the current draw exceeds its 75% marginal threshold it multiples the slow down going even slower.

Figure 19:
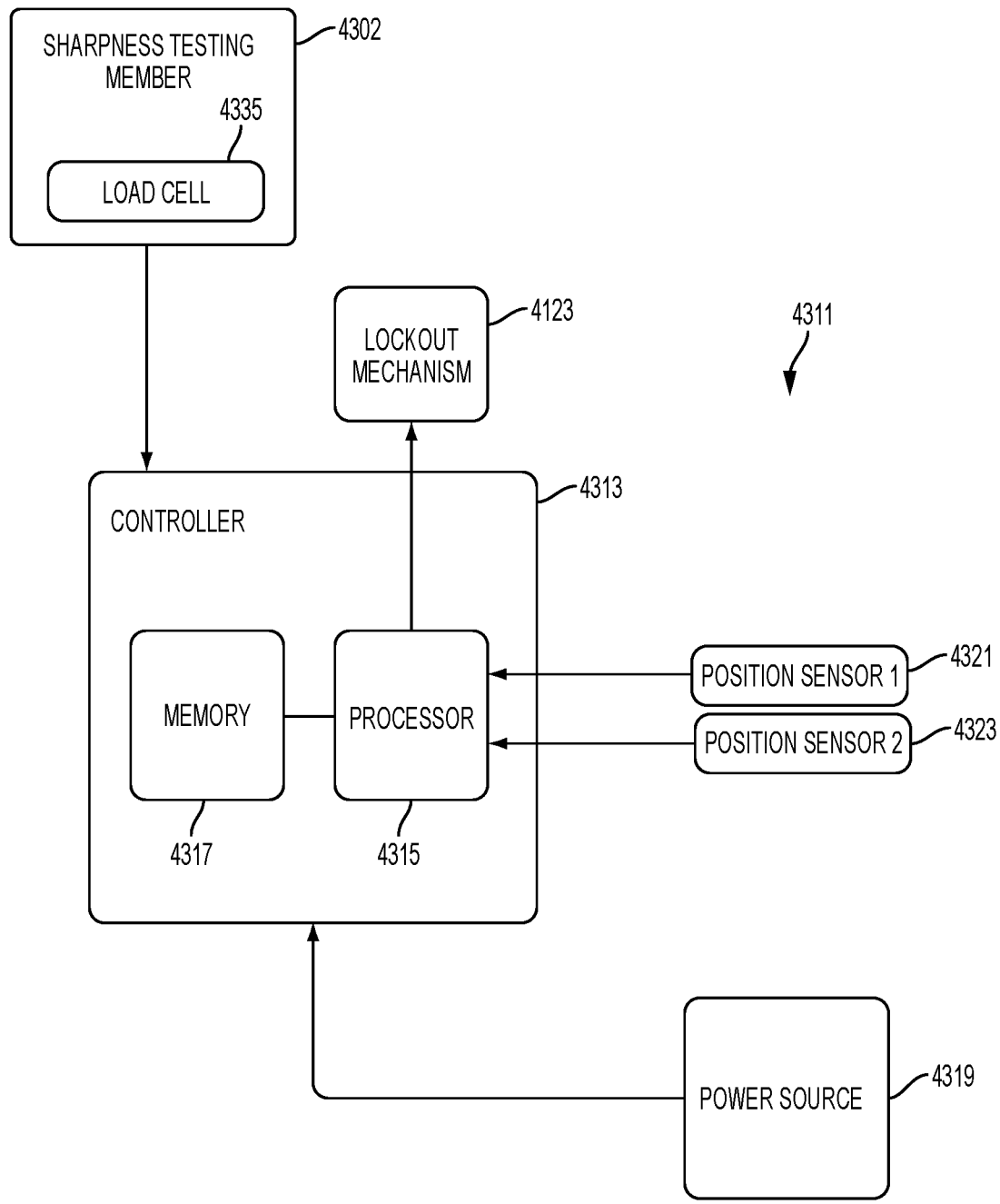
FIG. 19 illustrates a logic diagram of a system for evaluating sharpness of a cutting edge of a surgical instrument in accordance with one or more aspects of the present disclosure.

FIG. 19 illustrates a logic diagram of a system 4311 for evaluating sharpness of a cutting edge 182 (FIG. 14) of a surgical instrument 10 (FIGS. 1-4) according to various examples. In certain instances, the system 4311 can evaluate the sharpness of the cutting edge 182 by testing the ability of the cutting edge 182 to be advanced through a sharpness testing member 4302. For example, the system 4311 can be configured to observe the time period the cutting edge 182 takes to fully transect and/or completely pass through at least a predetermined portion of a sharpness testing member 4302. If the observed time period exceeds a predetermined threshold, the circuit 4310 may conclude that the sharpness of the cutting edge 182 has dropped below an acceptable level, for example.

In one aspect, the sharpness testing member 4302 can be employed to test the sharpness of the cutting edge 182 (FIG. 14). In certain instances, the sharpness testing member 4302 can be attached to and/or integrated with the cartridge body 194 (FIG. 14) of the surgical staple cartridge 304 (FIGS. 1, 2, and 15), for example. In certain instances, the sharpness testing member 4302 can be disposed in the proximal portion of the surgical staple cartridge 304, for example. In certain instances, the sharpness testing member 4302 can be disposed onto a cartridge deck or cartridge body 194 of the surgical staple cartridge 304, for example.

In certain instances, a load cell 4335 can be configured to monitor the force (Fx) applied to the cutting edge 182 (FIG. 14) while the cutting edge 182 is engaged and/or in contact with the sharpness testing member 4302, for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. The load cell 4335 of the sharpness testing member 4302 may be employed to measure the force (Fx) applied to the cutting edge 182 while the cutting edge 182 travels a predefined distance (D) through the sharpness testing member 4302 may be employed to determine the sharpness of the cutting edge 182.

In certain instances, the system 4311 may include a controller 4313 ("microcontroller") which may include a processor 4315 ("microprocessor") and one or more computer readable mediums or memory 4317 units ("memory"). In certain instances, the memory 4317 may store various program instructions, which when executed may cause the processor 4315 to perform a plurality of functions and/or calculations described herein. In certain instances, the memory 4317 may be coupled to the processor 4315, for example. A power source 4319 can be configured to supply power to the controller 4313, for example. In certain instances, the power source 4319 may comprise a battery (or "battery pack" or "power pack"), such as a Li ion battery, for example. In certain instances, the battery pack may be configured to be releasably mounted to the handle assembly 14. A number of battery cells connected in series may be used as the power source 4319. In certain instances, the power source 4319 may be replaceable and/or rechargeable, for example.

In certain instances, the controller 4313 can be operably coupled to the feedback system and/or the lockout mechanism 4123, for example.

The system 4311 may comprise one or more position sensors. Example position sensors and positioning systems suitable for use with the present disclosure are described in U.S. Patent Application Publication No. 2014/0263538, entitled SENSOR ARRANGEMENTS FOR ABSOLUTE POSITIONING SYSTEM FOR SURGICAL INSTRUMENTS, now U.S. Pat. No. 9,808,244, which is herein incorporated by reference in its entirety. In certain instances, the system 4311 may include a first position sensor 4321 and a second position sensor 4323. In certain instances, the first position sensor 4321 can be employed to detect a first position of the cutting edge 182 (FIG. 14) at a proximal end of a sharpness testing member 4302, for example; and the second position sensor 4323 can be employed to detect a second position of the cutting edge 182 at a distal end of a sharpness testing member 4302, for example.

In certain instances, the first and second position sensors 4321, 4323 can be employed to provide first and second position signals, respectively, to the controller 4313. It will be appreciated that the position signals may be analog signals or digital values based on the interface between the controller 4313 and the first and second position sensors 4321, 4323. In one example, the interface between the controller 4313 and the first and second position sensors 4321, 4323 can be a standard serial peripheral interface (SPI), and the position signals can be digital values representing the first and second positions of the cutting edge 182, as described above.

Further to the above, the processor 4315 may determine the time period between receiving the first position signal and receiving the second position signal. The determined time period may correspond to the time it takes the cutting edge 182 (FIG. 14) to advance through a sharpness testing member 4302 from the first position at a proximal end of the sharpness testing member 4302, for example, to a second position at a distal end of the sharpness testing member 4302, for example. In at least one example, the controller 4313 may include a time element which can be activated by the processor 4315 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4313 can compare the time period it takes the cutting edge 182 (FIG. 14) to advance from the first position to the second position to a predefined threshold value to assess whether the sharpness of the cutting edge 182 has dropped below an acceptable level, for example. In certain instances, the controller 4313 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 20:
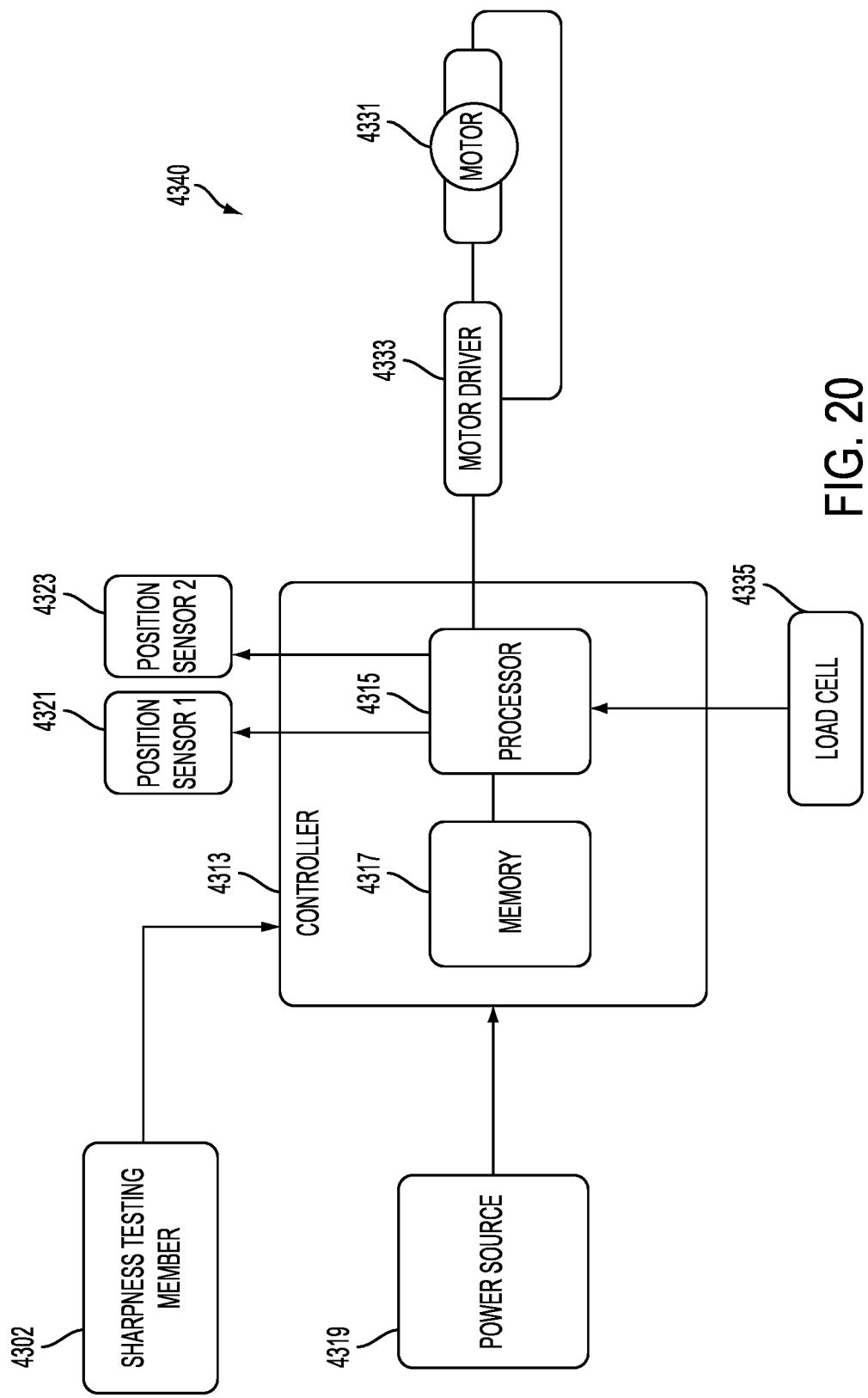
FIG. 20 illustrates a logic diagram of a system for determining the forces applied against a cutting edge of a surgical instrument by a sharpness testing member at various sharpness levels in accordance with one or more aspects of the present disclosure.

FIG. 20 illustrates a logic diagram of a system 4340 for determining the forces applied against a cutting edge of a surgical instrument 10 (FIGS. 1-4) by a sharpness testing member 4302 at various sharpness levels according to various aspects. Referring to FIG. 20, in various instances, an electric motor 4331 can drive the firing bar 172 (FIG. 20) to advance the cutting edge 182 (FIG. 14) during a firing stroke and/or to retract the cutting edge 182 during a return stroke, for example. A motor driver 4333 can control the electric motor 4331; and a controller such as, for example, the controller 4313 can be in signal communication with the motor driver 4333. As the electric motor 4331 advances the cutting edge 182, the controller 4313 can determine the current drawn by the electric motor 4331, for example. In such instances, the force required to advance the cutting edge 182 can correspond to the current drawn by the electric motor 4331, for example. Referring still to FIG. 20, the controller 4313 of the surgical instrument 10 can determine if the current drawn by the electric motor 4331 increases during advancement of the cutting edge 182 and, if so, can calculate the percentage increase of the current.

In certain instances, the current drawn by the electric motor 4331 may increase significantly while the cutting edge 182 (FIG. 14) is in contact with the sharpness testing member 4302 due to the resistance of the sharpness testing member 4302 to the cutting edge 182. For example, the current drawn by the electric motor 4331 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the electric motor 4331 while the cutting edge is in contact with the sharpness testing member 4302 can increase as the sharpness of the cutting edge 182 decreases from repetitive use, for example.

In certain instances, the determined value of the percentage increase of the current drawn by the electric motor 4331 can be the maximum detected percentage increase of the current drawn by the electric motor 4331. In various instances, the controller 4313 can compare the determined value of the percentage increase of the current drawn by the electric motor 4331 to a predefined threshold value of the percentage increase of the current drawn by the electric motor 4331. If the determined value exceeds the predefined threshold value, the controller 4313 may conclude that the sharpness of the cutting edge 182 has dropped below an acceptable level, for example.

In certain instances, as illustrated in FIG. 20, the processor 4315 can be in communication with the feedback system and/or the lockout mechanism for example. In certain instances, the processor 4315 can employ the feedback system to alert a user if the determined value of the percentage increase of the current drawn by the electric motor 4331 exceeds the predefined threshold value, for example. In certain instances, the processor 4315 may employ the lockout mechanism to prevent advancement of the cutting edge 182 (FIG. 14) if the determined value of the percentage increase of the current drawn by the electric motor 4331 exceeds the predefined threshold value, for example. In certain instances, the system 4311 may include first and second position sensors 4321, 4323. The surgical instrument 10 (FIGS. 1-4) may include a load cell 4335.

In various instances, the controller 4313 can utilize an algorithm to determine the change in current drawn by the electric motor 4331. For example, a current sensor can detect the current drawn by the electric motor 4331 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

In certain instances, the load cell 4335 (FIGS. 19, 20) can be configured to monitor the force (Fx) applied to the cutting edge 182 (FIG. 14) while the cutting edge 182 is engaged and/or in contact with the sharpness testing member 4302 (FIGS. 19, 20), for example. The reader will appreciate that the force (Fx) applied by the sharpness testing member 4302 to the cutting edge 182 while the cutting edge 182 is engaged and/or in contact with the sharpness testing member 4302 may depend, at least in part, on the sharpness of the cutting edge 182. In certain instances, a decrease in the sharpness of the cutting edge 182 can result in an increase in the force (Fx) required for the cutting edge 182 to cut or pass through the sharpness testing member 4302. In certain instances, the controller 4313 (FIGS. 19, 20) may compare a maximum value of the monitored force (Fx) applied to the cutting edge 182 (FIG. 14) to one or more predefined threshold values.

In certain instances, the cutting edge 182 (FIG. 14) may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example. In certain instances, the memory 4317 (FIGS. 19, 20) can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, when the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

In various aspects, the present disclosure provides techniques for determining tissue compression and additional techniques to control the operation of the surgical instrument 10 (described in connection with FIGS. 1-18) in response to the tissue compression. In one example, the cartridges may be configured to define variable compression algorithm which drives the surgical instrument 10 to close differently based on intended tissue type and thickness. In another example, the surgical instrument 10 learns from surgeon use and original tissue compression profile to adapt closure based on load experienced during firing. When the surgical instrument 10 experiences tissue compression loads that are dramatically different that those experienced for this cartridge type the instrument highlights this to the user.

Active adjustment of a motor control algorithm over time as the instrument become acclimated to the hospital's usage can improve the life expectancy of a rechargeable battery as well as adjust to tissue/procedure requirements of minimizing tissue flow, thus improving staple formation in the tissue seal.

Accordingly, the present disclosure relates to surgical instruments and, in various circumstances, to surgical stapling and cutting instruments and staple cartridges therefor that are designed to staple and cut tissue. For example, in various aspects the present disclosure provides an endosurgical instrument configured to sense the cartridge type or tissue gap to enable the handle to adjust the closure and firing algorithms to adjust for intended tissue properties. This adaptive algorithm adjustment can "learn" from the user's operations allowing the device to react and benefit two different systems. The first benefit provided by the disclosed adaptive algorithm includes tissue flow and staple formation. As the device learns the users' basic habits and step timings, the device can adjust the closure speed and firing speed to provide a more consistent and reliable output. The second benefit provided by the disclosed adaptive algorithm is related to the battery pack. As the device learns how many firings and what conditions the instrument was used, the device can adjust motor current needs/speed in a predefined manner to prolong battery life. There is a substantially small likelihood that a device used in a hospital that performs predominantly bariatric procedures would be operated in a manner similar to a device used in a hospital that performs mostly colorectal or thoracic procedures. Thus, when the device is used to perform substantially similar procedure, over time, the device is configured to learn and adjust its operational algorithm to maintain within the "ideal" discharge and tissue flow envelopes.

Safe and effective surgery requires due knowledge of, and respect for, the tissue involved. Clinicians are mindful that adjustments made during surgery may be beneficial. These adjustments include mechanisms to detect and promote desirable staple formation.

Endosurgical instruments can generate, monitor and process a substantial amount of data during their use in connection with a surgical procedure. Such data can be obtained from the surgical instrument itself, including battery usage. Additionally, data can be obtained from the properties of the tissue with which the surgical instrument interacts, including properties such as tissue compression. Further, data can be obtained from the clinician's interaction with the surgical instrument itself. The repository of data so obtained can be processed and, where desired, the surgical instrument can be designed to adapt to circumstances so as to promote a safe and effective outcome to the current surgical procedure, as well as lay the foundation for more generalized productive use by multiple clinicians. Such adaptive adjustments—both during a surgical procedure, and wherein the instrument "learns" based on usage patterns drawn from multiple surgical procedures—can provide numerous mechanisms to enhance the overall patient-care environment.

Figure 21:
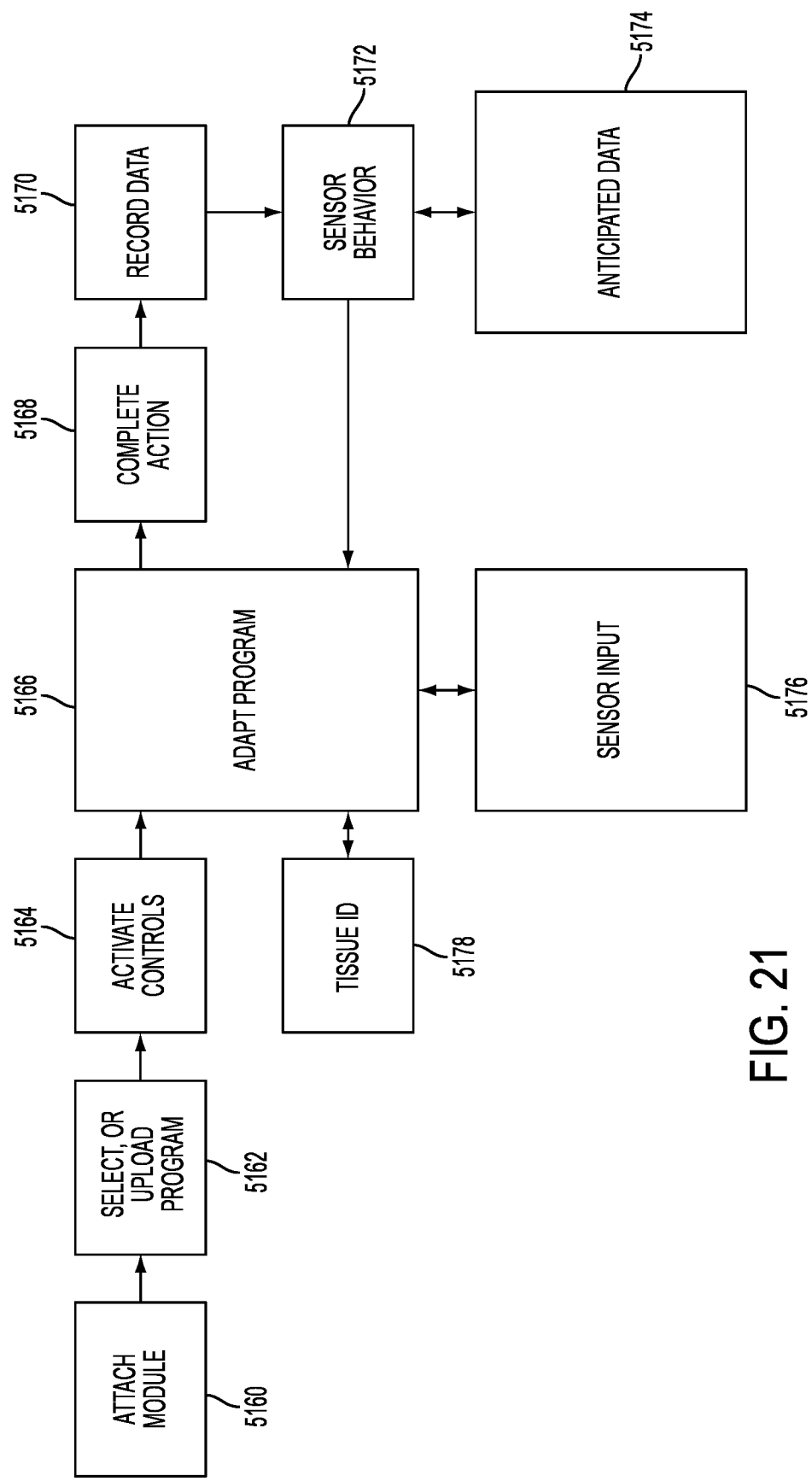
FIG. 21 illustrates one aspect of a process for adapting operations of a surgical instrument in accordance with one or more aspects of the present disclosure.
Figure 22A:
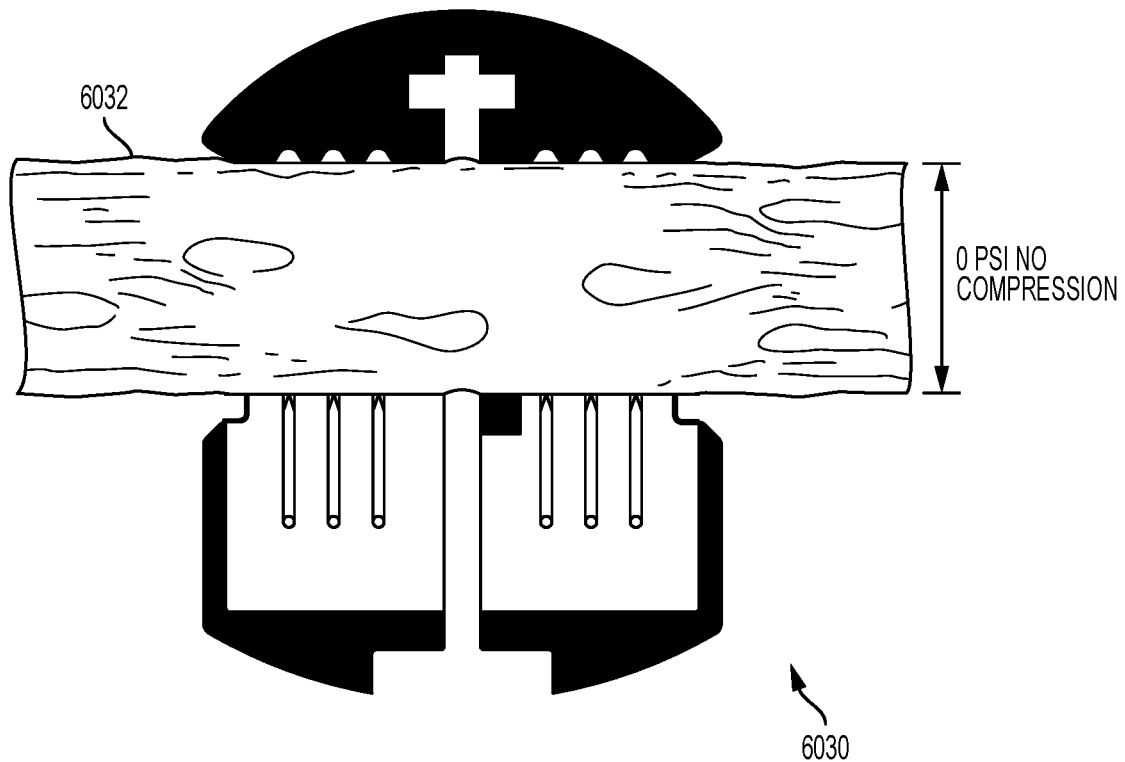
FIG. 22A depicts an example end-effector of a medical device surrounding tissue in accordance with one or more aspects of the present disclosure.
Figure 22B:
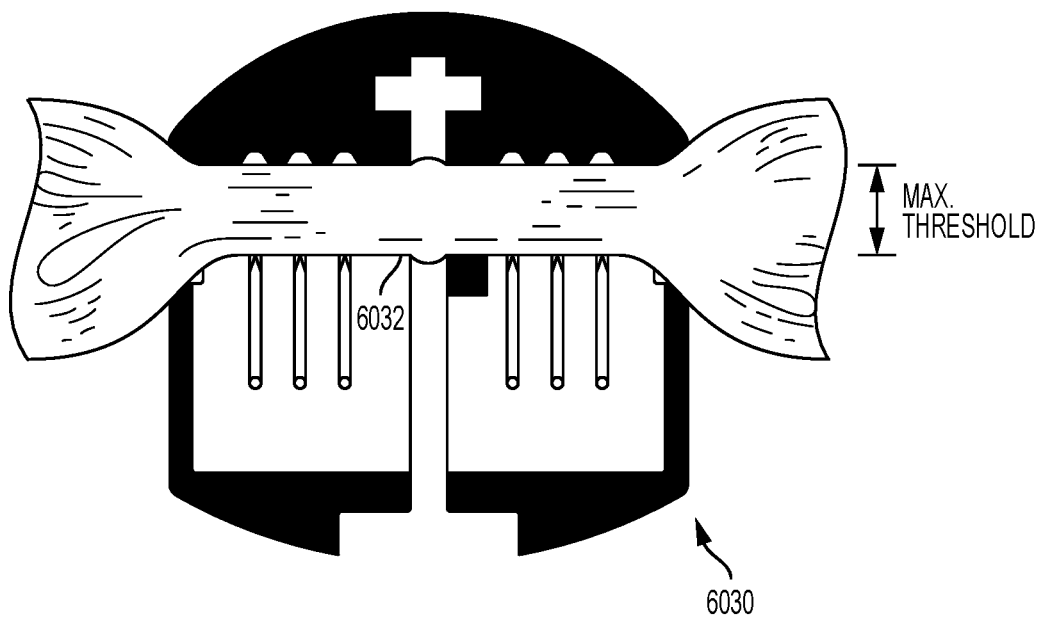
FIG. 22B depicts an example end-effector of a medical device compressing tissue in accordance with one or more aspects of the present disclosure.

FIG. 21 illustrates one aspect of a process for adapting operations of a surgical instrument. As depicted in FIG. 21, a module can be attached 5160 or otherwise loaded to the surgical instrument 10 (FIGS. 1-4). The module can contain a program that is selected or uploaded 5162. Controls can be activated 5164 such that they can be ready to operate the surgical instrument 10. During or after usage of the surgical instrument 10, control measures can be included to adapt 5166 a program. For example, this can include adjusting the data rate within the surgical instrument 10 or with respect to remote operation of the surgical instrument 10. This can include adjusting speed, such as speed by which anvil 306 (FIG. 1) and surgical staple cartridge 304 (FIG. 1) engage in a closure motion. This can also include a pulse from an emitter and sensor or to apply a pulse of electrical current to tissue, and the timing of such pulse. This can include adjusting a program to adapt to acceleration, such as acceleration of the surgical instrument 10 if dropped, or transition from a sleep mode. A program can be adapted to handle an actual and/or expected load based on clamping force.

The surgical instrument 10 (FIGS. 1-4) can be employed to complete an action 5168, for example to carry out a stapling procedure. Data can be recorded 5170 in appropriate memory locations of the surgical instrument 10. Sensor behavior 5172 can be assessed, such as to what extent a sensor accurately measured and/or measures a parameter. Anticipated data can be assessed 5174, including but not limited to tissue properties, wait period and firing speed. Foregoing mechanisms disclosed herein can provide an input to adapt 5166 a program further. In addition, a tissue identification 5178 can be performed, based on historical, actual or expected tissue properties, and this can provide an input to further adapt 5166 a program. In addition, tissue identification 5178 properties can be updated. Moreover, measured sensor input 5176 during a procedure can be used as an additional input to further adapt 5166 a program; such sensor measurements can include those of the gap between anvil 306 and surgical staple cartridge 304, obtaining a derivative measurement including a derivative of a function, current, or torque.

Figure 23A:
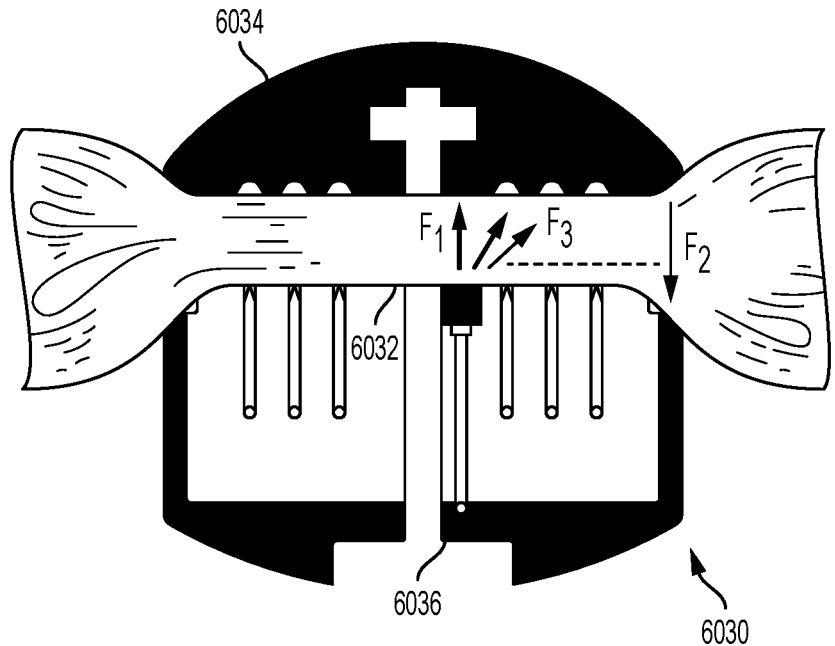
FIG. 23A depicts example forces exerted by an end-effector of a medical device compressing tissue in accordance with one or more aspects of the present disclosure.
Figure 23B:
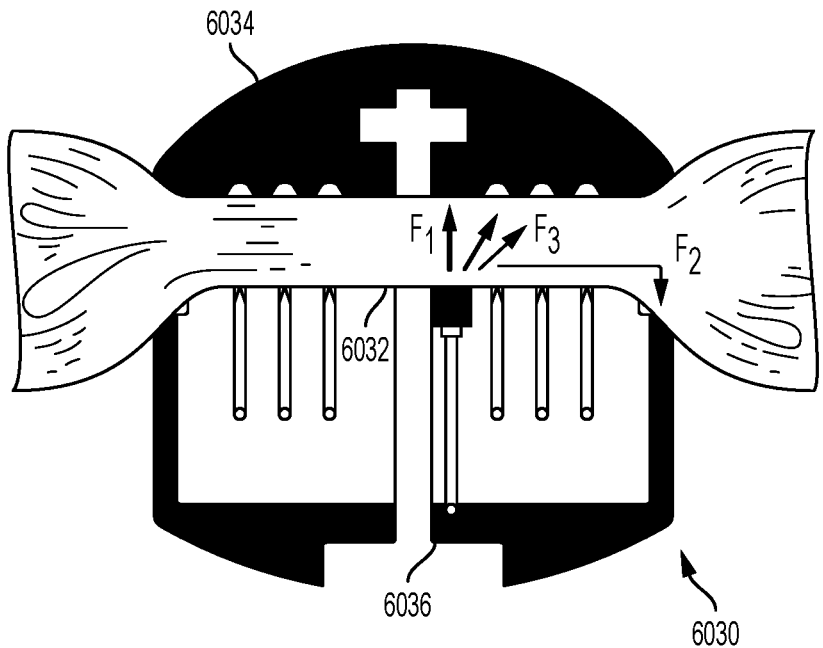
FIG. 23B also depicts example forces exerted by an end-effector of a medical device compressing tissue in accordance with one or more aspects of the present disclosure.

The end-effector 6006 may be used to compress, cut, or staple tissue. Referring now to FIG. 23A, an end-effector 6030 may be positioned by a physician to surround tissue 6032 prior to compression, cutting, or stapling. As shown in FIG. 23A, no compression may be applied to the tissue while preparing to use the end-effector. Referring now to FIG. 23B, by engaging the handle (e.g., handle 6002) of the endocutter, the physician may use the end-effector 6030 to compress the tissue 6032. In one aspect, the tissue 6032 may be compressed to its maximum threshold, as shown in FIG. 23B.

Referring to FIG. 23A, various forces may be applied to the tissue 6032 by the end-effector 6030. For example, vertical forces F1 and F2 may be applied by the anvil 6034 and the channel frame 6036 of the end-effector 6030 as tissue 6032 is compressed between the two. Referring now to FIG. 23B, various diagonal and/or lateral forces also may be applied to the tissue 6032 when compressed by the end-effector 6030. For example, force F3 may be applied. For the purposes of operating a medical device such as endocutter 6000, it may be desirable to sense or calculate the various forms of compression being applied to the tissue by the end-effector. For example, knowledge of vertical or lateral compression may allow the end-effector to more precisely or accurately apply a staple operation or may inform the operator of the endocutter such that the endocutter can be used more properly or safely.

The compression through tissue 6032 may be determined from an impedance of tissue 6032. At various levels of compression, the impedance Z of tissue 6032 may increase or decrease. By applying a voltage V and a current I to the tissue 6032, the impedance Z of the tissue 6032 may be determined at various levels of compression. For example, impedance Z may be calculated by dividing the applied voltage V by the current I.

Figure 24:
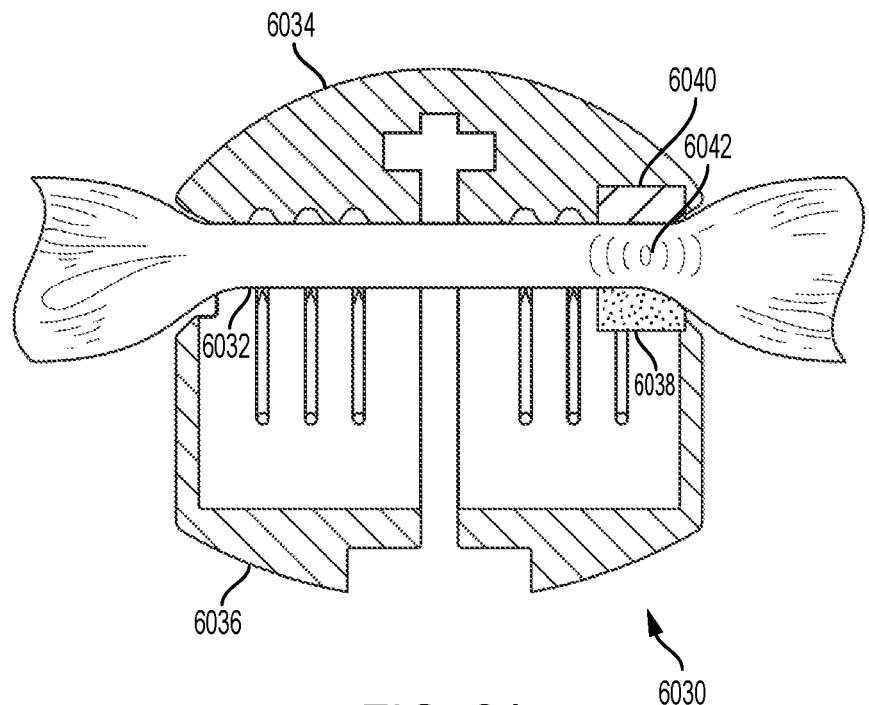
FIG. 24 depicts an example tissue compression sensor system in accordance with one or more aspects of the present disclosure.

Referring now to FIG. 24, in one aspect, an RF electrode 6038 may be positioned on the end-effector 6030 (e.g., on a staple cartridge, knife, or channel frame of the end-effector 6030). Further, an electrical contact 6040 may be positioned on the anvil 6034 of the end-effector 6030. In one aspect, the electrical contact may be positioned on the channel frame of the end-effector. As the tissue 6032 is compressed between the anvil 6034 and, for example, the channel frame 6036 of the end-effector 6030, an impedance Z of the tissue 6032 changes. The vertical tissue compression 6042 caused by the end-effector 6030 may be measured as a function of the impedance Z of the tissue 6032.

Figure 25:
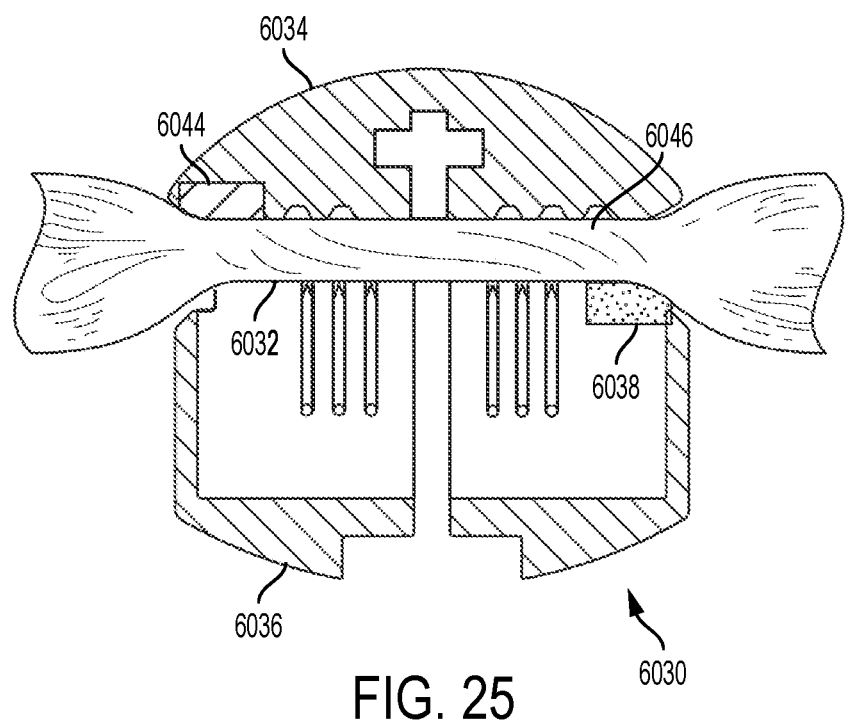
FIG. 25 also depicts an example tissue compression sensor system in accordance with one or more aspects of the present disclosure.

Referring now to FIG. 25, in one aspect, an electrical contact 6044 may be positioned on an opposite end of the anvil 6034 of the end-effector 6030 as the RF electrode 6038 is positioned. As the tissue 6032 is compressed between the anvil 6034 and, for example, the channel frame 6036 of the end-effector 6030, an impedance Z of the tissue 6032 changes. The lateral tissue compression 6046 caused by the end-effector 6030 may be measured as a function of the impedance Z of the tissue 6032.

Figure 26:
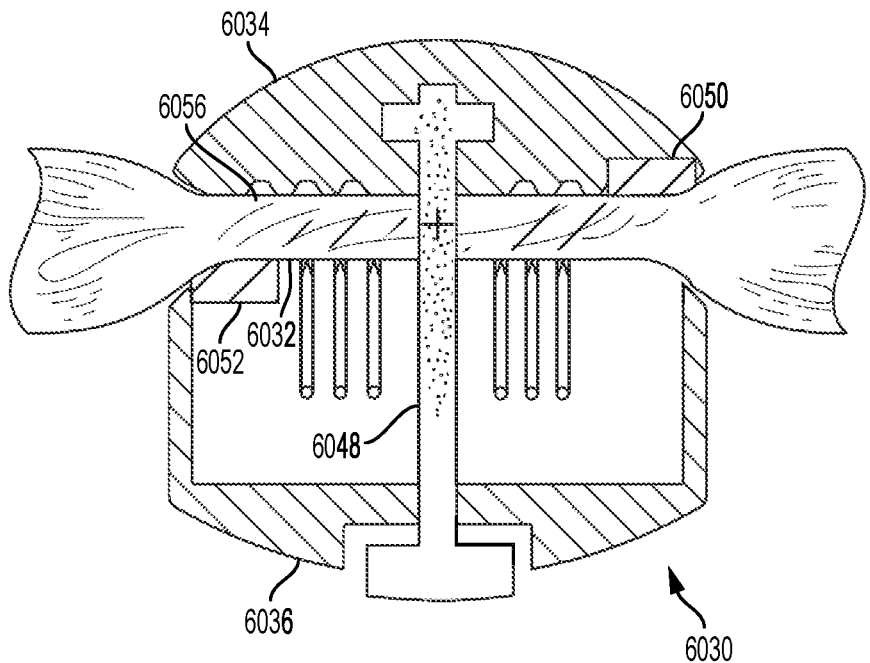
FIG. 26 also depicts an example tissue compression sensor system in accordance with one or more aspects of the present disclosure.

Referring now to FIG. 26, in one aspect, electrical contact 6050 may be positioned on the anvil 6034 and electrical contact 6052 may be positioned on an opposite end of the end-effector 6030 at channel frame 6036. RF electrode 6048 may be positioned laterally to the central to the end-effector 6030. As the tissue 6032 is compressed between the anvil 6034 and, for example, the channel frame 6036 of the end-effector 6030, an impedance Z of the tissue 6032 changes. The lateral compression or angular compressions 6054 and 6056 on either side of the RF electrode 6048 may be caused by the end-effector 6030 and may be measured as a function of different impedances Z of the tissue 6032, based on the relative positioning of the RF electrode 6048 and electrical contacts 6050 and 6052.

Figure 27:
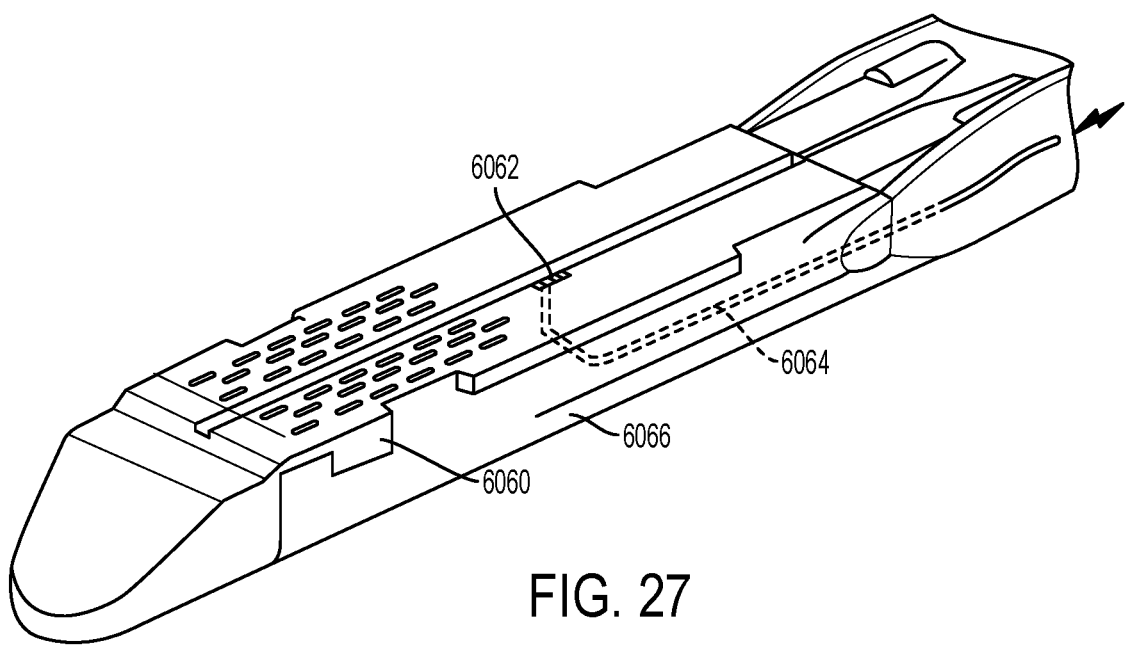
FIG. 27 depicts an example end-effector channel frame in accordance with one or more aspects of the present disclosure.

In accordance with one or more of the techniques and features described in the present disclosure, and as discussed above, an RF electrode may be used as an RF sensor. Referring now to FIG. 27, in one aspect, an RF sensor 6062 may be positioned on a staple cartridge 6060 inserted into a channel frame 6066 an end-effector. The RF electrode may run from a power line 6064 which may be powered by a power source in a handle (e.g., handle 6002) of an endocutter.

Figure 28:
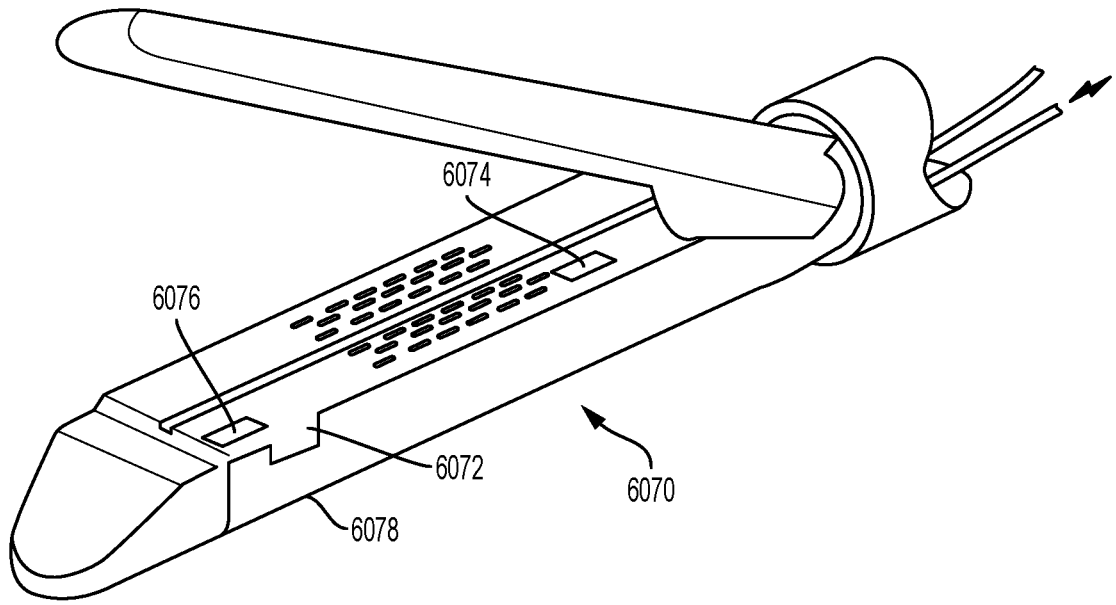
FIG. 28 depicts an example end-effector in accordance with one or more aspects of the present disclosure.

Referring now to FIG. 28, in one aspect, RF electrodes 6074 and 6076 may be positioned on a staple cartridge 6072 inserted into a channel frame 6078 of end-effector 6070. As shown, RF electrode 6074 may be placed in a proximal position of the end-effector relative to an endocutter handle. Further, RF electrode 6076 may be placed in a distal position of the end-effector relative to the endocutter handle. RF electrodes 6074 and 6076 may be utilized to measure vertical, lateral, proximal, or distal compression at different points in a tissue based on the position of one or more electrical contacts on the end-effector.

Figure 29:
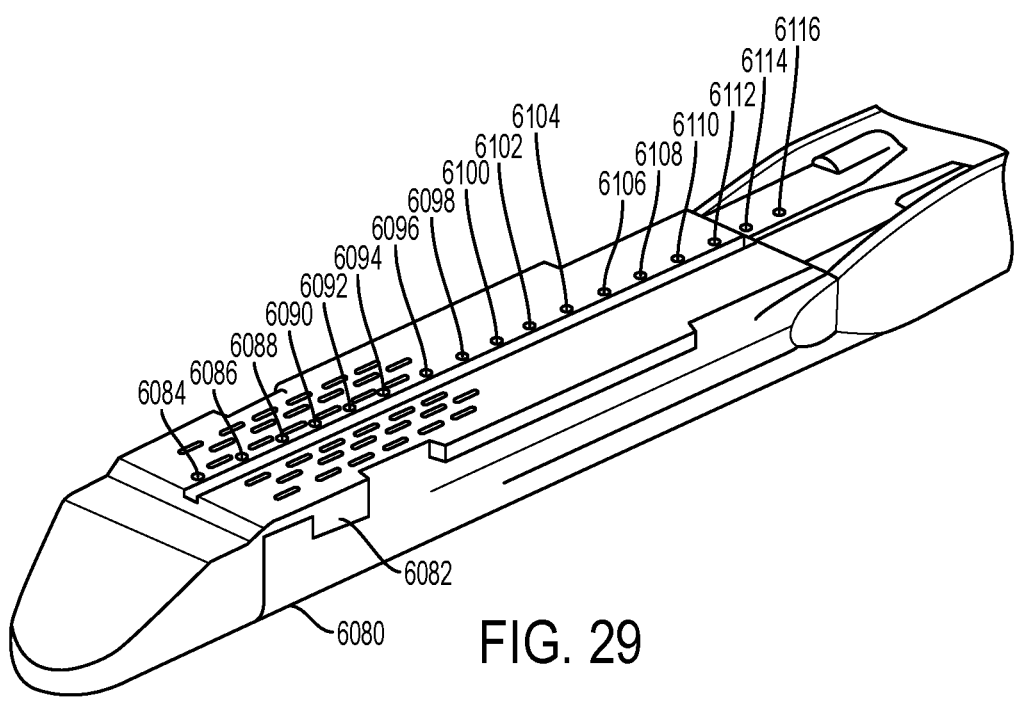
FIG. 29 also depicts an example end-effector channel frame in accordance with one or more aspects of the present disclosure.
Figure 30:
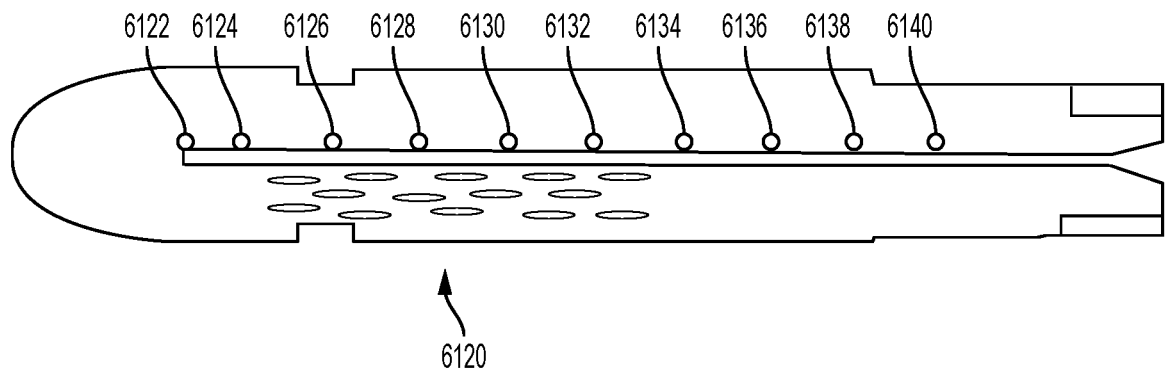
FIG. 30 also depicts an example end-effector channel frame in accordance with one or more aspects of the present disclosure.
Figure 31:
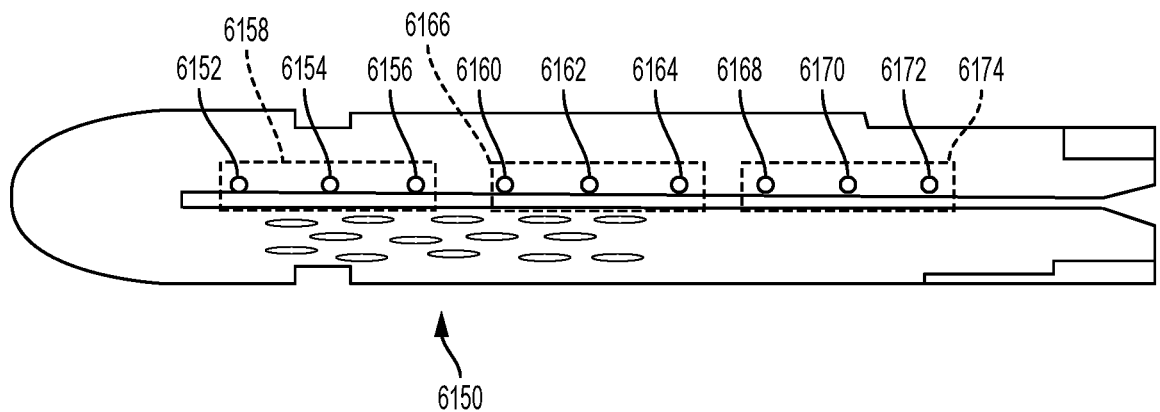
FIG. 31 also depicts an example end-effector channel frame in accordance with one or more aspects of the present disclosure.

Referring now to FIG. 29, in one aspect, RF electrodes 6084-6116 may be positioned on staple cartridge 6082 inserted into the channel frame 6080 (or other component of an end-effector) based on various points for which compression information is desired. Referring now to FIG. 30, in one aspect, RF electrodes 6122-6140 may be positioned on staple cartridge 6120 at discrete points for which compression information is desired. Referring now to FIG. 31, RF electrodes 6152-6172 may be positioned at different points in multiple zones of a staple cartridge based on how accurate or precise the compression measurements should be. For example, RF electrodes 6152-6156 may be positioned in zone 6158 of staple cartridge 6150 depending on how accurate or precise the compression measurements in zone 6158 should be. Further, RF electrodes 6160-6164 may be positioned in zone 6166 of staple cartridge 6150 depending on how accurate or precise the compression measurements in zone 6166 should be. Additionally, RF electrodes 6168-6172 may be positioned in zone 6174 of staple cartridge 6150 depending on how accurate or precise the compression measurements in zone 6174 should be.

Figure 32:
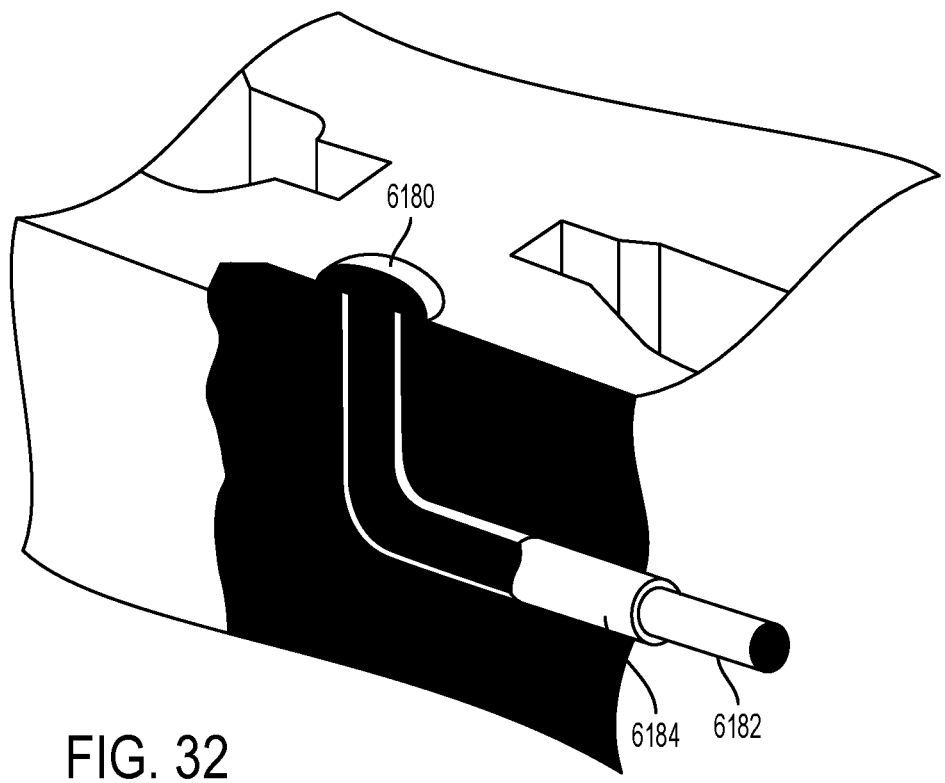
FIG. 32 depicts an example electrode in accordance with one or more aspects of the present disclosure.

The RF electrodes discussed herein may be wired through a staple cartridge inserted in the channel frame. Referring now to FIG. 32, in one aspect, an RF electrode may have a stamped "mushroom head" 6180 of about 1.0 mm in diameter. While the RF electrode may have the stamped "mushroom head" of about 1.0 mm in diameter, this is intended to be a non-limiting example and the RF electrode may be differently shaped and sized depending on each particular application or design. The RF electrode may be connected to, fastened to, or may form, a conductive wire 6182. The conductive wire 6182 may be about 0.5 mm in diameter, or may have a larger or smaller diameter based on a particular application or design. Further, the conductive wire may have an insulative coating 6184. In one example, the RF electrode may protrude through a staple cartridge, channel frame, knife, or other component of an end-effector.

Figure 33:
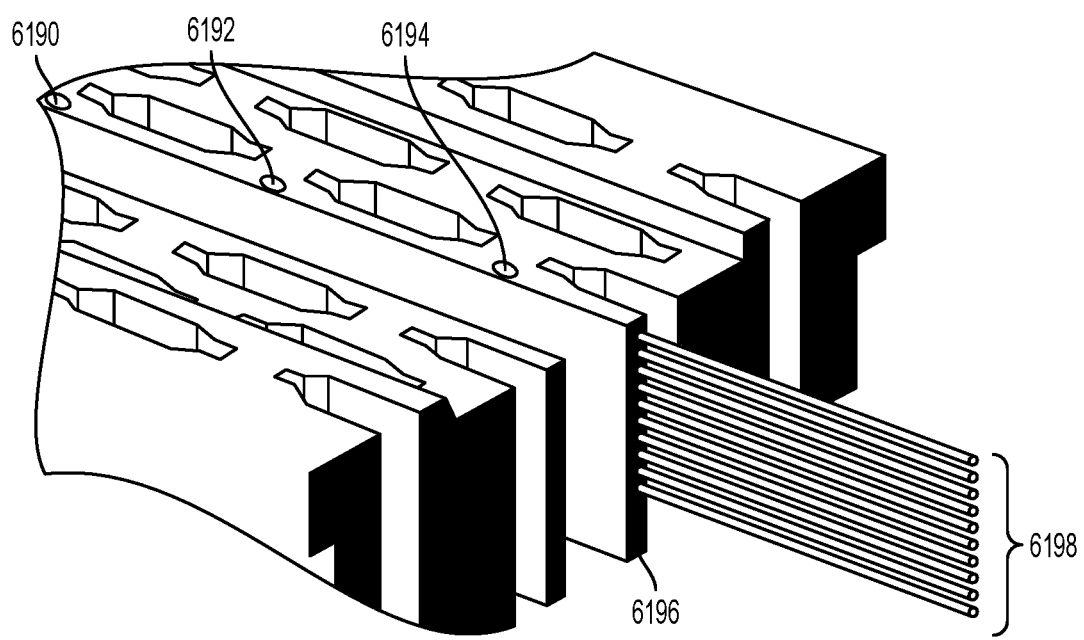
FIG. 33 depicts an example electrode wiring system in accordance with one or more aspects of the present disclosure.

Referring now to FIG. 33, the RF electrodes may be wired through a single wall or through multiple walls of a staple cartridge or channel frame of an end-effector. For example, RF electrodes 6190-6194 may be wired through wall 6196 of the staple cartridge or channel frame of an end-effector. One or more of wires 6198 may be connected to, fastened to, or be part of, RF electrodes 6190-6194 and may run through wall 6196 from a power source in, e.g., a handle of an endocutter.

Figure 34:
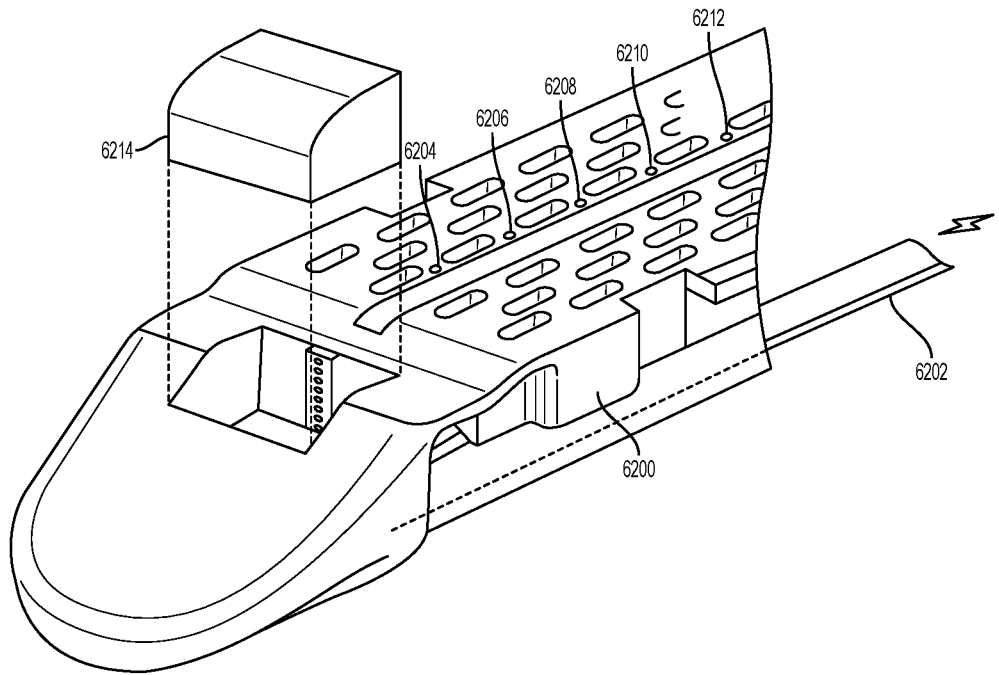
FIG. 34 also depicts an example end-effector channel frame in accordance with one or more aspects of the present disclosure.

Referring now to FIG. 34, the power source may be in communication with the RF electrodes or may provide power to the RF electrodes through a wire or cable. The wire or cable may join each individual wire and lead to the power source. For example, RF electrodes 6204-6212 may receive power from a power source through wire or cable 6202, which may run through staple cartridge 6200 or a channel frame of an end-effector. In one example, each of RF electrodes 6204-6212 may have its own wire that runs to or through wire or cable 6202. The staple cartridge 6200 or channel frame also may include a controller 6214, such as the primary processor 2006 shown in connection with FIGS. 16A and 16B, or the main controller 3017 shown in connection with FIGS. 17A, 17B, and 18, for example. It will be appreciated that the controller 6214 should be suitably sized to fit in the staple cartridge 6200 or channel frame form factor.

In various aspects, the tissue compression sensor system described herein for use with medical devices may include a frequency generator. The frequency generator may be located on a circuit board of the medical device, such as an endocutter. For example the frequency generator may be located on a circuit board in a shaft or handle of the endocutter. Referring now to FIG. 35, an example circuit diagram 6220 in accordance with one example of the present disclosure is shown. As shown, frequency generator 6222 may receive power or current from a power source 6221 and may supply one or more RF signals to one or more RF electrodes 6224. As discussed above, the one or more RF electrodes may be positioned at various locations or components on an end-effector or endocutter, such as a staple cartridge or channel frame. One or more electrical contacts, such as electrical contacts 6226 or 6228 may be positioned on a channel frame or an anvil of an end-effector. Further, one or more filters, such as filters 6230 or 6232 may be communicatively coupled to the electrical contacts 6226 or 6228 as shown in FIG. 35. The filters 6230 and 6232 may filter one or more RF signals supplied by the frequency generator 6222 before joining a single return path 6234. A voltage V and a current I associated with the one or more RF signals may be used to calculate an impedance Z associated with a tissue that may be compressed and/or communicatively coupled between the one or more RF electrodes 6224 and the electrical contacts 6226 or 6228.

Referring now to FIG. 36, various components of the tissue compression sensor system described herein may be located in a handle 6236 of an endocutter. For example, as shown in circuit diagram 6220a, frequency generator 6222 may be located in the handle 6236 and receives power from power source 6221. Also, current I1 and current I2 may be measured on a return path corresponding to electrical contacts 6228 and 6226. Using a voltage V applied between the supply and return paths, impedances Z1 and Z2 may be calculated. Z1 may correspond to an impedance of a tissue compressed and/or communicatively coupled between one or more of RF electrodes 6224 and electrical contact 6228. Further, Z2 may correspond to an impedance of a tissue compressed and/or communicatively coupled between one or more of RF electrodes 6224 and electrical contact 6226. Applying the formulas Z1=V/I1 and Z2=V/I2, impedances Z1 and Z2 corresponding to different compression levels of a tissue compressed by an end-effector may be calculated.

Referring now to FIG. 37, one or more aspects of the present disclosure are described in circuit diagram 6250. In an implementation, a power source at a handle 6252 of an endocutter may provide power to a frequency generator 6254. The frequency generator 6254 may generate one or more RF signals. The one or more RF signals may be multiplexed or overlaid at a multiplexer 6256, which may be in a shaft 6258 of the endocutter. In this way, two or more RF signals may be overlaid (or, e.g., nested or modulated together) and transmitted to the end-effector. The one or more RF signals may energize one or more RF electrodes 6260 at an end-effector 6262 (e.g., positioned in a staple cartridge) of the endocutter. A tissue (not shown) may be compressed and/or communicatively coupled between the one or more of RF electrodes 6260 and one or more electrical contacts. For example, the tissue may be compressed and/or communicatively coupled between the one or more RF electrodes 6260 and the electrical contact 6264 positioned in a channel frame of the end-effector 6262 or the electrical contact 6266 positioned in an anvil of the end-effector 6262. A filter 6268 may be communicatively coupled to the electrical contact 6264 and a filter 6270 may be communicatively coupled to the electrical contact 6266.

A voltage V and a current I associated with the one or more RF signals may be used to calculate an impedance Z associated with a tissue that may be compressed between the staple cartridge (and communicatively coupled to one or more RF electrodes 6260) and the channel frame or anvil (and communicatively coupled to one or more of electrical contacts 6264 or 6266).

In one aspect, various components of the tissue compression sensor system described herein may be located in a shaft 6258 of the endocutter. For example, as shown in circuit diagram 6250 (and in addition to the frequency generator 6254), an impedance calculator 6272, a controller 6274, a non-volatile memory 6276, and a communication channel 6278 may be located in the shaft 6258. In one example, the frequency generator 6254, impedance calculator 6272, controller 6274, non-volatile memory 6276, and communication channel 6278 may be positioned on a circuit board in the shaft 6258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 6264 and 6266. Using a voltage V applied between the supply and return paths, impedances Z1 and Z2 may be calculated. Z1 may correspond to an impedance of a tissue compressed and/or communicatively coupled between one or more of RF electrodes 6260 and electrical contact 6264. Further, Z2 may correspond to an impedance of the tissue compressed and/or communicatively coupled between one or more of RF electrodes 6260 and electrical contact 6266. Applying the formulas $Z1=V/I1$ and $Z2=V/I2$, impedances Z1 and Z2 corresponding to different compressions of a tissue compressed by an end-effector 6262 may be calculated. In example, the impedances Z1 and Z2 may be calculated by the impedance calculator 6272. The impedances Z1 and Z2 may be used to calculate various compression levels of the tissue.

In one aspect, filters 6268 and 6270 may be High Q filters such that the filter range may be narrow (e.g., Q=10). Q may be defined by the Center frequency (Wo)/Bandwidth (BW) where Q=Wo/BW. In one example, Frequency 1 may be 150 kHz and Frequency 2 may be 300 KHz. A viable impedance measurement range may be 100 kHz-20 MHz. In various examples, other sophisticated techniques, such as correlation, quadrature detection, etc., may be used to separate the RF signals.

Using one or more of the techniques and features described herein, a single energized electrode on a staple cartridge or an isolated knife of an end-effector may be used to make multiple tissue compression measurements simultaneously. If two or more RF signals are overlaid or multiplexed (or nested or modulated), they may be transmitted down a single power side of the end-effector and may return on either the channel frame or the anvil of the end-effector. If a filter were built into the anvil and channel contacts before they join a common return path, the tissue impedance represented by both paths could be differentiated. This may provide a measure of vertical tissue vs lateral tissue compression. This approach also may provide proximal and distal tissue compression depending on placement of the filters and location of the metallic return paths. A frequency generator and signal processor may be located on one or more chips on a circuit board or a sub board (which may already exist in an endocutter).

In various aspects, the present disclosure provides techniques for monitoring the speed and precision incrementing of the drive motor in the surgical instrument 10 (described in connection with FIGS. 1-18). In one example, a magnet can be placed on a planet frame of one of the stages of gear reduction with an inductance sensor on the gear housing. In another example, placing the magnet and magnetic field sensor on the last stage would provide the most precise incremental movement monitoring.

Conventional motor control systems employ encoders to detect the location and speed of the motor in hand held battery powered endosurgical instruments such as powered endocutter/stapler devices. Precision operation of endocutter/stapler devices relies in part on the ability to verify the motor operation under load. Simple sensor implementations may be employed to achieve verify the motor operation under load.

Accordingly, the present disclosure includes a magnetic body on one of the planetary carriers of a gear reduction system or employ brushless motor technology. Both approaches involve the placement of an inductance sensor on the outside housing of the motor or planetary gear system. In the case of a brushless motor there are electromagnetic field coils (windings, inductors, etc.) arrayed radially around the center magnetic shaft of the motor. The coils are sequentially activated and deactivated to drive the central motor shaft. One or more inductance sensors can be placed outside of the motor and adjacent to at least some of the coils to sense the activation/deactivation cycles of the motor windings to determine the number times the shaft has been rotated. Alternatively, a permanent magnet can be placed on one of the planetary carriers and the inductance sensor can be placed adjacent to the radial path of the planetary carrier to measure the number of times that stage of the gear train is rotated. This implementation can be applied to any rotational components in the system with increasingly more resolution possible in regions with a relatively large number of rotations during function, or as the rotational components become closer (in terms of number of connections) to the end effector depending on the design. The gear train sensing method may be preferred since it actually measures rotation of one of the stages whereas the motor sensing method senses the number of times the motor has been commanded to energize, rather than the actual shaft rotation. For example, if the motor is stalled under high load, the motor sensing method would not be able to detect the lack of rotation because it senses only the energizing cycles not shaft rotation. Nevertheless, both techniques can be employed in a cost effective manner to sense motor rotation.

During stapling, for example, tissue is firmly clamped between opposing jaws before a staple is driven into the clamped tissue. Tissue compression during clamping can cause fluid to be displaced from the compressed tissue, and the rate or amount of displacement varies depending on tissue type, tissue thickness, the surgical operation (e.g., clamping pressure and clamping time). In various instances, fluid displacement between the opposing jaws of an end effector may contribute to malformation (e.g., bending) of staples between the opposing jaws. Accordingly, in various instances, it may be desirable to control the firing stroke, e.g., to control the firing speed, in relationship to the detected fluid flow, or lack thereof, intermediate opposing jaws of a surgical end effector.

Accordingly, also provided herein are methods, devices, and systems for monitoring speed and incremental movement of a surgical instrument drive train, which in turn provides information about the operational velocity of the device (e.g., jaw closure, stapling). In accordance with the present examples, the surgical instrument 10 (FIGS. 1-4) does not include a motor encoder. Rather, the surgical instrument 10 may be equipped with a motor comprising a speed sensor assembly for a power train of the motor, in accordance with an illustrative example. The speed sensor assembly can include a motor having an output shaft that is coupled directly or indirectly to a drive shaft. In some examples, the output shaft is connected to a gear reduction assembly, such as a planetary gear train comprising a sensor that detects the rotational speed of any suitable component of the system. For example, the sensor may be a proximity sensor, such as an induction sensor, which detects movement of one or more detectable elements affixed to any rotating part of the gear reduction assembly. The detectable element is affixed to the last stage annular gear and the sensor is positioned adjacent the radial path of the detectable element so as to detect movement of the detectable element. Rotating components may vary depending on design—and the sensor(s) can be affixed to any rotating component of the gear reduction assembly. For example, in another example, a detectable element is associated with the carrier gear of the final stage or even the drive gear. In some examples, a detectable element is located outside of the gear reduction assembly, such as on the driveshaft between gear reduction assembly and the end effector. In some example, a detectable element is located on a rotating component in the final gear reduction at the end effector.

Various functions may be implemented utilizing the circuitry previously described, For example, the motor may be controlled with a motor controller similar those described in connection with FIGS. 16A, 16B, 17A, 17B, and 18, where the encoder is replaced with the monitoring speed control and precision incrementing of motor systems for powered surgical instruments described herein.

In one aspect, the present disclosure provides a surgical instrument 10 (described in connection with FIGS. 1-18) configured with various sensing systems. Accordingly, for conciseness and clarity the details of operation and construction will not be repeated here. In one aspect, the sensing system includes a viscoelasticity/rate of change sensing system to monitor knife acceleration, rate of change of impedance, and rate of change of tissue contact. In one example, the rate of change of knife acceleration can be used as a measure of for tissue type. In another example, the rate of change of impedance can be measures with a pulse sensor ad can be employed as a measure for compressibility. Finally, the rate of change of tissue contact can be measured with a sensor based on knife firing rate to measure tissue flow.

The rate of change of a sensed parameter or stated otherwise, how much time is necessary for a tissue parameter to reach an asymptotic steady state value, is a separate measurement in itself and may be more valuable than the sensed parameter it was derived from. To enhance measurement of tissue parameters such as waiting a predetermined amount of time before making a measurement, the present disclosure provides a novel technique for employing the derivate of the measure such as the rate of change of the tissue parameter.

The derivative technique or rate of change measure becomes most useful with the understanding that there is no single measurement that can be employed alone to dramatically improve staple formation. It is the combination of multiple measurements that make the measurements valid. In the case of tissue gap it is helpful to know how much of the jaw is covered with tissue to make the gap measure relevant. Rate of change measures of impedance may be combined with strain measurements in the anvil to relate force and compression applied to the tissue grasped between the jaw members of the end effector such as the anvil and the staple cartridge. The rate of change measure can be employed by the endosurgical device to determine the tissue type and not merely the tissue compression. Although stomach and lung tissue sometimes have similar thicknesses, and even similar compressive properties when the lung tissue is calcified, an instrument may be able to distinguish these tissue types by employing a combination of measurements such as gap, compression, force applied, tissue contact area, and rate of change of compression or rate of change of gap. If any of these measurements were used alone, the endosurgical it may be difficult for the endosurgical device to distinguish one tissue type form another. Rate of change of compression also may be helpful to enable the device to determine if the tissue is "normal" or if some abnormality exists. Measuring not only how much time has passed but the variation of the sensor signals and determining the derivative of the signal would provide another measurement to enable the endosurgical device to measure the signal. Rate of change information also may be employed in determining when a steady state has been achieved to signal the next step in a process. For example, after clamping the tissue between the jaw members of the end effector such as the anvil and the staple cartridge, when tissue compression reaches a steady state (e.g., about 15 seconds), an indicator or trigger to start firing the device can be enabled.

Also provided herein are methods, devices, and systems for time dependent evaluation of sensor data to determine stability, creep, and viscoelastic characteristics of tissue during surgical instrument operation. A surgical instrument 10, such as the stapler illustrated in FIG. 1, can include a variety of sensors for measuring operational parameters, such as jaw gap size or distance, firing current, tissue compression, the amount of the jaw that is covered by tissue, anvil strain, and trigger force, to name a few. These sensed measurements are important for automatic control of the surgical instrument and for providing feedback to the clinician.

The examples shown in connection with FIGS. 22A-37 may be employed to measure the various derived parameters such as gap distance versus time, tissue compression versus time, and anvil strain versus time. Motor current may be monitored employing the current sensor 2312 in series with the battery 2308 as described herein, the current sensor 2412 in series with the battery 2408 or the current sensor 3027 in FIG. 18.

FIG. 38 illustrates a motor-driven surgical instrument 8010 for cutting and fastening that may or may not be reused. The surgical instrument 8010 is similarly constructed and equipped as the surgical instrument 10 for cutting and fastening described in connection with FIGS. 1-18. In the example illustrated in FIG. 38, the surgical instrument 8010 includes a housing 8012 that comprises a handle assembly 8014 that is configured to be grasped, manipulated and actuated by the clinician. The housing 8012 is configured for operable attachment to an interchangeable shaft assembly 8200 that has an end effector 8300 operably coupled thereto that is configured to perform one or more surgical tasks or procedures. Since the surgical instrument 8010 is similarly constructed and equipped as the surgical instrument 10 for cutting and fastening described in connection with FIGS. 1-18, for conciseness and clarity the details of operation and construction will not be repeated here.

The housing 8012 depicted in FIG. 38 is shown in connection with an interchangeable shaft assembly 8200 that includes an end effector 8300 that comprises a surgical cutting and fastening device that is configured to operably support a surgical staple cartridge 8304 therein. The housing 8012 may be configured for use in connection with interchangeable shaft assemblies that include end effectors that are adapted to support different sizes and types of staple cartridges, have different shaft lengths, sizes, and types, etc. In addition, the housing 8012 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Turning now to FIG. 38, the surgical instrument 8010 is depicted that may or may not be reused. The surgical instrument 8010 is similarly constructed and equipped as the surgical instrument 10 for cutting and fastening described herein. In the example illustrated in FIG. 38, the surgical instrument 8010 includes a housing 8012 that comprises a handle assembly 8014 that is configured to be grasped, manipulated and actuated by the clinician. The housing 8012 is configured for operable attachment to an interchangeable shaft assembly 8200 that has an end effector 8300 operably coupled thereto that is configured to perform one or more surgical tasks or procedures. Since the surgical instrument 8010 is similarly constructed and equipped as the surgical instrument 10 for cutting and fastening described herein in connection with FIGS. 1-18, for conciseness and clarity the details of operation and construction will not be repeated here.

The housing 8012 depicted in FIG. 38 is shown in connection with an interchangeable shaft assembly 8200 that includes an end effector 8300 that comprises a surgical cutting and fastening device that is configured to operably support a surgical staple cartridge 8304 therein. The housing 8012 may be configured for use in connection with interchangeable shaft assemblies that include end effectors that are adapted to support different sizes and types of staple cartridges, have different shaft lengths, sizes, and types, etc. In addition, the housing 8012 also may be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 38 illustrates the surgical instrument 8010 with an interchangeable shaft assembly 8200 operably coupled thereto. In the illustrated arrangement, the handle housing forms a pistol grip portion 8019 that can be gripped and manipulated by the clinician. The handle assembly 8014 operably supports a plurality of drive systems therein that are configured to generate and apply various control motions to corresponding portions of the interchangeable shaft assembly that is operably attached thereto. Trigger 8032 is operably associated with the pistol grip for controlling various of these control motions.

With continued reference to FIG. 38, the interchangeable shaft assembly 8200 includes an end effector 8300 that comprises an elongated channel 8302 that is configured to operably support a surgical staple cartridge 8304 therein. The end effector 8300 may further include an anvil 8306 that is pivotally supported relative to the elongated channel 8302.

The inventors have discovered that derived parameters can be even more useful for controlling a surgical instrument, such as the instrument illustrated in FIG. 38, than the sensed parameter(s) upon which the derived parameter is based. Non-limiting examples of derived parameters include the rate of change of a sensed parameter (e.g., jaw gap distance) and how much time elapses before a tissue parameter reaches an asymptotic steady state value (e.g., 15 seconds). Derived parameters, such as rate of change, are particularly useful because they dramatically improve measurement accuracy and also provide information not otherwise evident directly from sensed parameters. For example, impedance (i.e., tissue compression) rate of change can be combined with strain in the anvil to relate compression and force, which enables the controller to determine the tissue type and not merely the amount of tissue compression. This example is illustrative only, and any derived parameters can be combined with one or more sensed parameters to provide more accurate information about tissue types (e.g., stomach vs. lung), tissue health (calcified vs. normal), and operational status of the surgical device (e.g., clamping complete). Different tissues have unique viscoelastic properties and unique rates of change, making these and other parameters discussed herein useful indicia for monitoring and automatically adjusting a surgical procedure.

Figure 39:
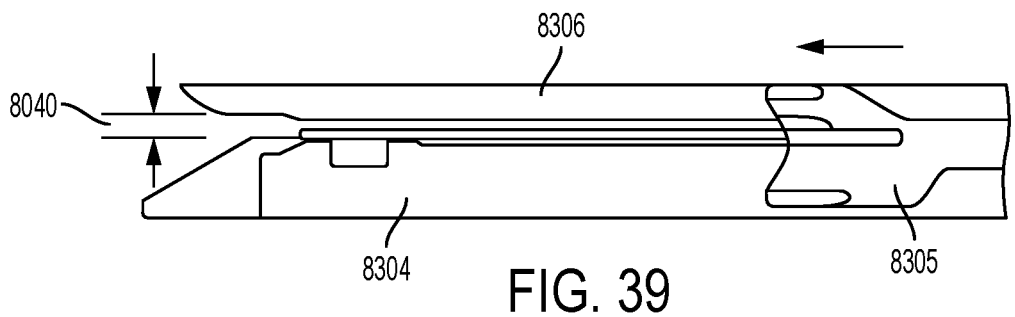
FIG. 39 is a side view of the tip of the surgical instrument shown in FIG. 38 in accordance with one or more aspects of the present disclosure.

Specifically, referring to FIGS. 38 and 39, the gap 8040 is the distance between the anvil 8306 and the elongated channel 8302 of the end effector 8300. In the open jaw position, at time zero, the gap 8040 between the anvil 8306 and the elongated member is at its maximum distance. The width of the gap 8040 decreases as the anvil 8306 closes, such as during tissue clamping. The gap distance rate of change can vary because tissue has non-uniform resiliency. For example, certain tissue types may initially show rapid compression, resulting in a faster rate of change. However, as tissue is continually compressed, the viscoelastic properties of the tissue can cause the rate of change to decrease until the tissue cannot be compressed further, at which point the gap distance will remain substantially constant. The gap decreases over time as the tissue is squeezed between the anvil 8306 and the surgical staple cartridge 8304 of the end effector 8300. The one or more sensors described in connection with FIGS. 22A-37 and FIG. 40 may be adapted and configured to measure the gap distance "d" between the anvil 8306 and the surgical staple cartridge 8304 over time t and the rate of change of the gap distance "d" over time t is the Slope of the curve, where Slope=Δd/Δt. In addition, the rate of change of firing current is can be used as an indicator that the tissue is transitioning from one state to another state. Accordingly, firing current and, in particular, the rate of change of firing current can be used to monitor device operation. The firing current decreases over time as the knife cuts through the tissue. The rate of change of firing current can vary if the tissue being cut provides more or less resistance due to tissue properties or sharpness of the knife 8305 (FIG. 39). For example, the motor current may be monitored employing the current sensor 2312 in series with the battery 2308 as described herein, the current sensor 2412 in series with the battery 2408 shown herein, or the current sensor 3027 shown in FIG. 18. The current sensors 2312, 2314, 3027 may be adapted and configured to measure the motor firing current "i" over time t and the rate of change of the firing current "i" over time t is the Slope of the curve, where Slope=Δi/Δt. The sensors described in connection with FIGS. 22A-37 and 40 may be adapted and configured to measure tissue compression/impedance. The sensors may be adapted and configured to measure tissue impedance "Z" over time t and the rate of change of the tissue impedance "Z" over time t is the Slope, where Slope=ΔZ/Δt. The rate of change of anvil 8306 strain can be measured by a pressure sensor or strain gauge positioned on either or both the anvil 8306 and the surgical staple cartridge 8304 (FIGS. 38, 39) to measure the pressure or strain applied to the tissue grasped between the anvil 8306 and the surgical staple cartridge 8304. Thus, at time zero, trigger 8020 (FIG. 38) pressure may be at its lowest and trigger pressure may increase until completion of an operation (e.g., clamping, cutting, or stapling). The rate of change trigger force can be measured by a pressure sensor or strain gauge positioned on the trigger 8032 of the pistol grip portion 8019 of the handle of the surgical instrument 8010 (FIG. 38) to measure the force required to drive the knife 8305 (FIG. 39) through the tissue grasped between the anvil 8306 and the surgical staple cartridge 8304.

Figure 40:
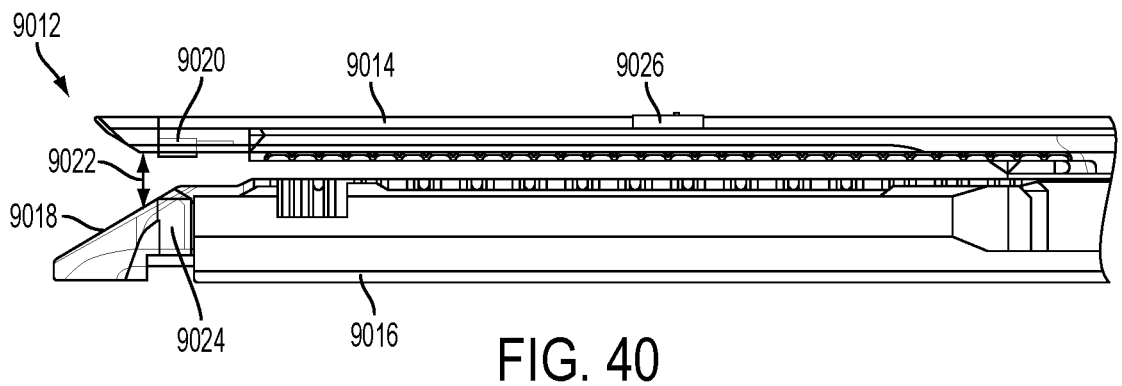
FIG. 40 illustrates a cross-sectional view of an end effector of a surgical instrument in accordance with one or more aspects of the present disclosure.

Turning briefly to FIG. 40, the end effector 9012 is one aspect of the end effector 8300 (FIG. 38) that may be adapted to operate with surgical instrument 8010 (FIG. 38) to measure the various derived parameters such as gap distance versus time, tissue compression versus time, and anvil strain versus time. Accordingly, the end effector 9012 shown in FIG. 40 may include one or more sensors configured to measure one or more parameters or characteristics associated with the end effector 9012 and/or a tissue section captured by the end effector 9012. In the example illustrated in FIG. 40, the end effector 9012 comprises a first sensor 9020 and a second sensor 9026. In various examples, the first sensor 9020 and/or the second sensor 9026 may comprise, for example, a magnetic sensor such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 9012.

In certain instances, the first sensor 9020 and/or the second sensor 9026 may comprise, for example, a magnetic field sensor embedded in an anvil 9014 and configured to detect a magnetic field generated by a magnet 9024 embedded in a jaw member 9016 and/or the staple cartridge 9018. The anvil 9014 is pivotally rotatable between open and closed positions. The strength of the detected magnetic field may correspond to, for example, the thickness and/or fullness of a bite of tissue located between the anvil 9014 and the jaw member 9016. In certain instances, the first sensor 9020 and/or the second sensor 9026 may comprise a strain gauge, such as, for example, a micro-strain gauge, configured to measure the magnitude of the strain in the anvil 9014 during a clamped condition. The strain gauge provides an electrical signal whose amplitude varies with the magnitude of the strain.

In some aspects, one or more sensors of the end effector 9012 such as, for example, the first sensor 9020 and/or the second sensor 9026 may comprise a pressure sensor configured to detect a pressure generated by the presence of compressed tissue between the anvil 9014 and the jaw member 9016. In some examples, one or more sensors of the end effector 9012 such as, for example, the first sensor 9020 and/or the second sensor 9026 are configured to detect the impedance of a tissue section located between the anvil 9014 and the jaw member 9016. The detected impedance may be indicative of the thickness and/or fullness of tissue located between the anvil 9014 and the jaw member 9016.

In one aspect, one or more of the sensors of the end effector 9012 such as, for example, the first sensor 9020 is configured to measure the gap 9022 between the anvil 9014 and the jaw member 9016. In certain instances, the gap 9022 can be representative of the thickness and/or compressibility of a tissue section clamped between the anvil 9014 and the jaw member 9016. In at least one example, the gap 9022 can be equal, or substantially equal, to the thickness of the tissue section clamped between the anvil 9014 and the jaw member 9016. In one example, one or more of the sensors of the end effector 9012 such as, for example, the first sensor 9020 is configured to measure one or more forces exerted on the anvil 9014 by the jaw member 9016 and/or tissue clamped between the anvil 9014 and the jaw member 9016. The forces exerted on the anvil 9014 can be representative of the tissue compression experienced by the tissue section captured between the anvil 9014 and the jaw member 9016. In one aspect, the gap 9022 between the anvil 9014 and the jaw member 9016 can be measured by positioning a magnetic field sensor on the anvil 9014 and positioning a magnet on the jaw member 9016 such that the gap 9022 is proportional to the signal detected by the magnetic field sensor and the signal is proportional to the distance between the magnet and the magnetic field sensor. It will be appreciated that the location of the magnetic field sensor and the magnet may be swapped such that the magnetic field sensor is positioned on the jaw member 9016 and the magnet is placed on the anvil 9014.

One or more of the sensors such as, for example, the first sensor 9020 and/or the second sensor 9026 may be measured in real-time during a clamping operation. Real-time measurement allows time based information to be analyzed, for example, by a processor, and used to select one or more algorithms and/or look-up tables for the purpose of assessing, in real-time, a manual input of an operator of the surgical instrument 9010. Furthermore, real-time feedback can be provided to the operator to assist the operator in calibrating the manual input to yield a desired output.

Figure 41:
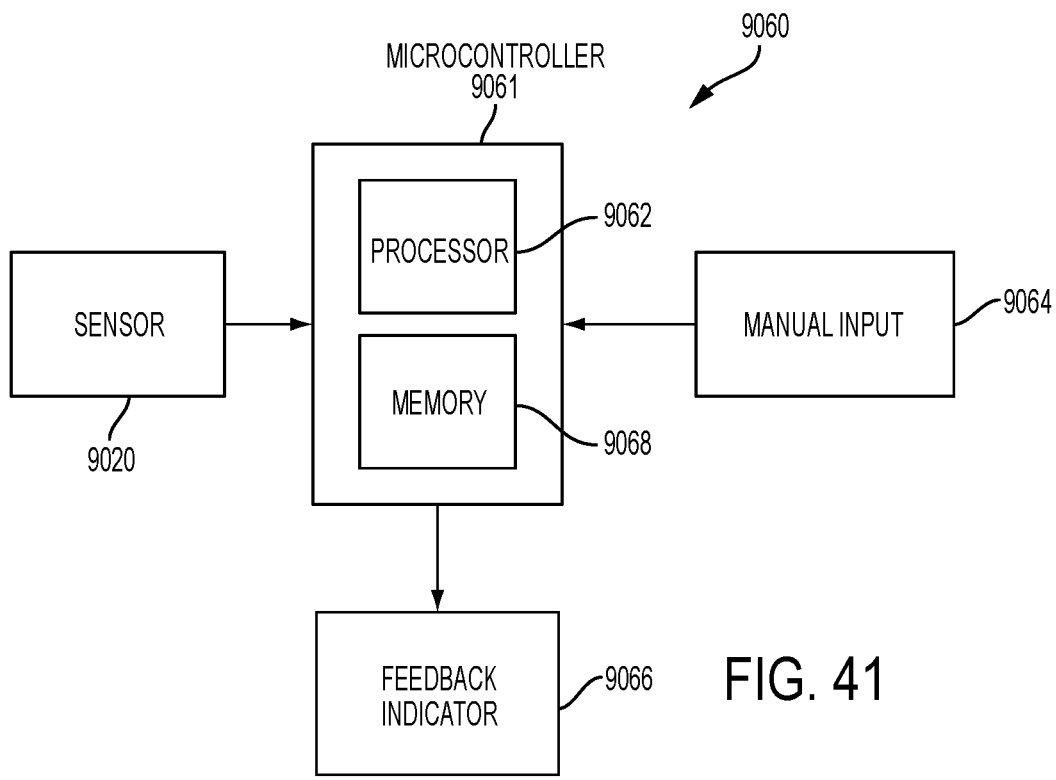
FIG. 41 illustrates a logic diagram of a feedback system in accordance with one or more aspects of the present disclosure.

FIG. 41 is a logic diagram illustrating one aspect of a real-time feedback system 9060 for assessing, in real-time, a manual input 9064 of an operator of the surgical instrument 9010 and providing to the operator real-time feedback as to the adequacy of the manual input 9064. With reference to FIGS. 40 and 41, in the example illustrated in FIG. 41, the real-time feedback system 9060 is comprised of a circuit. The circuit includes a controller 9061 comprising a processor 9062. A sensor such as, for example, the first sensor 9020 is employed by the processor 9062 to measure a parameter of the end effector 9012. In addition, the processor 9062 can be configured to determine or receive a value representative of a manual input 9064 of an operator of the surgical instrument 9010. The manual input 9064 can be continuously assessed by the processor 9062 for as long as the manual input 9064 is being provided by the operator. The processor 9062 can be configured to monitor a value representative of the manual input 9064. Furthermore, the processor 9062 is configured to assign, select, or determine a position, rank, and/or status for the determined value with respect to a desired zone or range. The measurement of the parameter of the end effector 9012 and the determined value can be employed by the processor 9062 to select or determine the position, rank, and/or status associated with the determined value, as described in greater detail below. A change in the manual input 9064 yields a change in the determined value which, in turn, yields a change in the position, rank, and/or status assigned to the determined value with respect to the desired zone or range.

As illustrated in FIG. 41, the real-time feedback system 9060 may further include a feedback indicator 9066 which can be adjusted between a plurality of positions, ranks, and/or statuses inside and outside a desired zone or range. In one example, the processor 9062 may select a first position (P1), rank, and/or status that characterizes the manual input 9064 based on a measurement (M1) of a parameter of the end effector 9012 and a first determined value (V1) representing a first manual input (I1). In certain instances, the first position (P1), rank, and/or status may fall outside the desired zone or range. In such instances, the operator may change the manual input 9064 from the first manual input (I1) to a second manual input (I2) by increasing or decreasing the manual input 9064, for example. In response, the processor 9062 may adjust the feedback indicator 9066 from the first position (P1), rank, and/or status to a second position (P2), rank, and/or status, which characterizes the change to the manual input 9064. The processor 9062 may select the second position (P2), rank, and/or status based on the measurement (M1) of the parameter of the end effector 9012 and a second determined value (V2) representing a second manual input (I2). In certain instances, the second position (P2), rank, and/or status may fall inside the desired zone or range. In such instances, the operator may maintain the second manual input (I2) for a remainder of a treatment cycle or procedure, for example.

In the aspect illustrated in FIG. 41, the controller 9061 includes a storage medium such as, for example, a memory 9068. The memory 9068 may be configured to store correlations between measurements of one or more parameters of the end effector 9012, values representing manual inputs, and corresponding positions, ranks, and/or statuses characterizing the manual input 9064 with respect to a desired zone or range. In one example, the memory 9068 may store the correlation between the measurement (M1), the first determined value (V1), and the first manual input (I1), and the correlation between the measurement (M1), the second determined value (V2), and the second manual input (I2). In one example, the memory 9068 may store an algorism, an equation, or a look-up table for determining correlations between measurements of one or more parameters of the end effector 9012, values representing manual inputs, and corresponding positions, ranks, or statuses with respect to a desired zone or range. The processor 9062 may employ such algorism, equation, and/or look-up table to characterize a manual input 9064 provided by an operator of the surgical instrument 9010 and provide feedback to the operator as to the adequacy of the manual input 9064.

Figure 42:
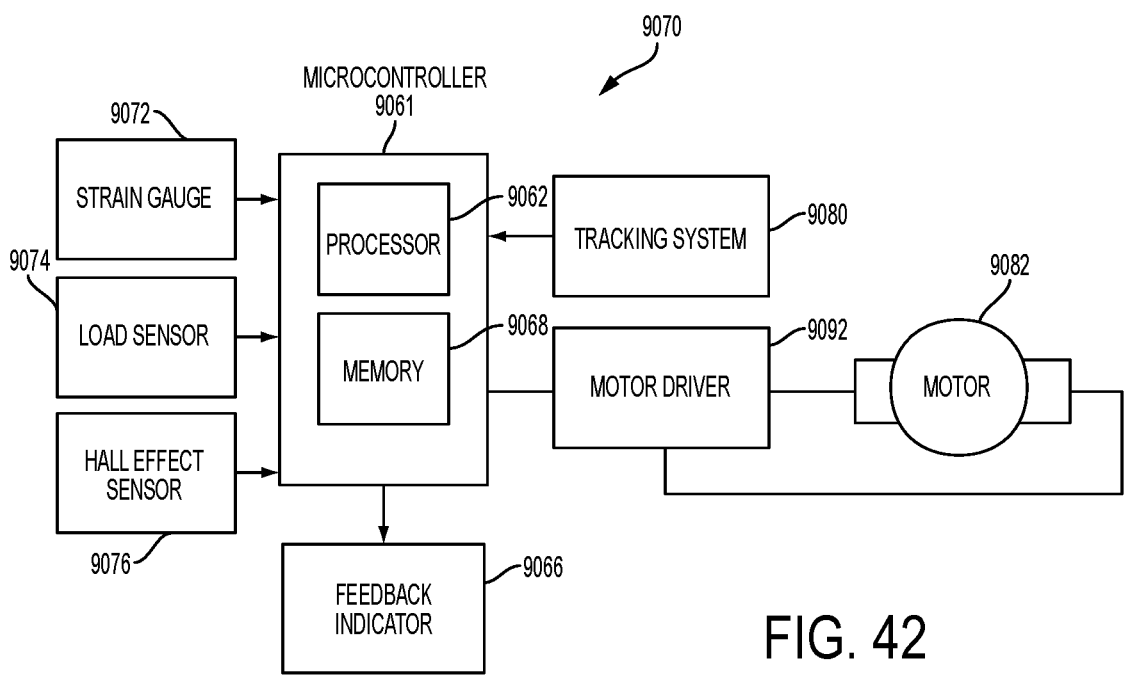
FIG. 42 illustrates a logic diagram of a feedback system in accordance with one or more aspects of the present disclosure.

FIG. 42 is a logic diagram illustrating one aspect of a real-time feedback system 9070. The real-time feedback system 9070 is similar in many respects to the real-time feedback system 9060. For example, like the real-time feedback system 9060, the real-time feedback system 9070 is configured for assessing, in real-time, a manual input of an operator of the surgical instrument 9010 and providing to the operator real-time feedback as to the adequacy of the manual input. Furthermore, like the real-time feedback system 9060, the real-time feedback system 9070 is comprised of a circuit that may include the controller 9061.

In the aspect illustrated in FIG. 42, a sensor 9072, such as, for example, a strain gauge or a micro-strain gauge, is configured to measure one or more parameters of the end effector 9012, such as, for example, the amplitude of the strain exerted on the anvil 9014 during a clamping operation, which can be indicative of the tissue compression. The measured strain is converted to a digital signal and provided to the processor 9062. A sensor 9074, such as, for example, a load sensor, can measure the force to advance the cutting member 9040 to cut tissue captured between the anvil 9014 and the staple cartridge 9018. Alternatively, a current sensor (not shown) can be employed to measure the current drawn by the motor 9082. The force required to advance the firing bar 9036 can correspond to the current drawn by the motor 9082, for example. The measured force is converted to a digital signal and provided to the processor 9062. A sensor 9076, such as, for example, a magnetic field sensor, can be employed to measure the thickness of the captured tissue, as described above. The measurement of the magnetic field sensor 9076 is also converted to a digital signal and provided to the processor 9062.

In the aspect illustrated in FIG. 42, the real-time feedback system 9070 further includes the tracking system 9080 which can be configured to determine the position of the firing trigger. As described above, the firing trigger 9094 can be depressed or actuated by moving the firing trigger 9094 between a plurality of positions, each corresponding to one of a plurality of values of a characteristic of motion of the firing bar 9036 and/or the cutting member 9040 during a firing stroke. As describe above, a characteristic of motion can be a speed of advancement of the firing bar 9036 and/or the cutting member 9040 during the firing stroke. In certain instances, a motor driver 9092 can be in communication with the controller 9061, and can be configured to drive the motor 9082 in accordance with an operator's manual input as detected by the tracking system 9080.

Further to the above, the real-time feedback system 9070 may include a feedback indicator 9066. In one aspect, the feedback indicator 9066 can be disposed in the handle 9030. Alternatively, the feedback indicator can be disposed in the shaft assembly 9032, for example. In any event, the controller 9061 may employ the feedback indicator 9066 to provide feedback to an operator of the surgical instrument 9010 with regard to the adequacy of a manual input such as, for example, a selected position of the firing trigger 9094. To do so, the controller 9061 may assess the selected position of the firing trigger 9094 and/or the corresponding value of the speed of the firing bar 9036 and/or the cutting member 9040. The measurements of the tissue compression, the tissue thickness, and/or the force required to advance the firing bar 9036, as respectively measured by the sensors 9072, 9074, and 9076, can be used by the controller 9061 to characterize the selected position of the firing trigger 9094 and/or the corresponding value of the speed of the firing bar 9036 and/or the cutting member 9040. In one instance, the memory 9068 may store an algorism, an equation, and/or a look-up table which can be employed by the controller 9061 in the assessment. In one example, the measurements of the sensors 9072, 9074, and/or 9076 can be used to select or determine a position, rank, and/or a status that characterizes the selected position of the firing trigger 9094 and/or the corresponding value of the speed of the firing bar 9036 and/or the cutting member 9040. The determined position, rank, and/or status can be communicated to the operator via the feedback indicator 9066.

The reader will appreciate that an optimal speed of the firing bar 9036 and/or the cutting member 9040 during a firing stroke can depend on several parameters of the end effector 9012 such as, for example, the thickness of the tissue captured by the end effector 9012, the tissue compression, and/or the force required to advance the firing bar 9036 and, in turn, the cutting member 9040. As such, measurements of these parameters can be leveraged by the controller 9061 in assessing whether a current speed of advancement of the cutting member 9040 through the captured tissue is within an optimal zone or range.

Figure 43:
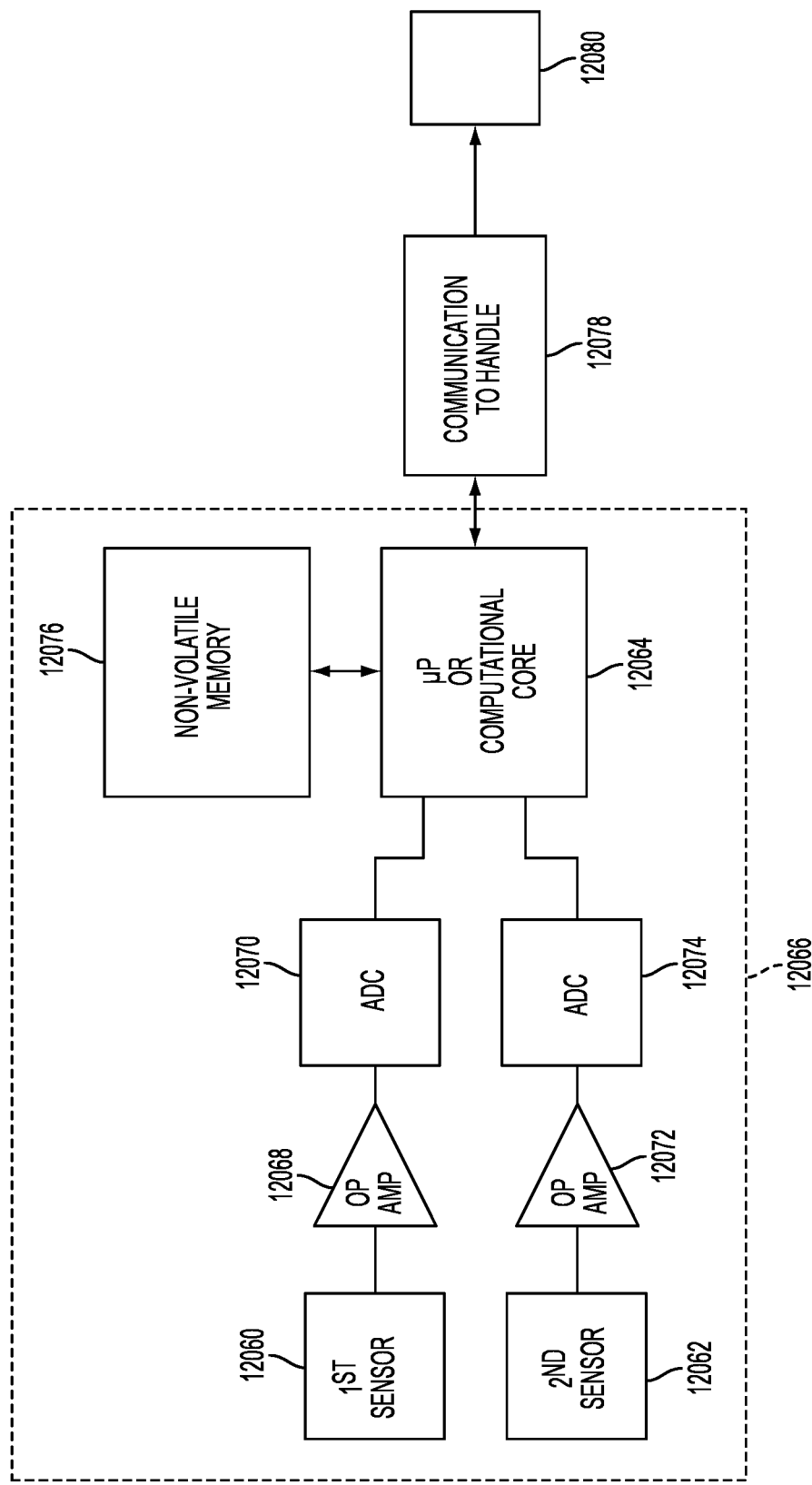
FIG. 43 is a diagram of a smart sensor component in accordance with an aspect the present disclosure.

In one aspect, a plurality of smart sensors may be positioned on a power line of an end-effector and may be communicatively coupled to a handle of an endocutter. The smart sensors may be positioned in series or parallel with respect to the power line. Referring now to FIG. 43, smart sensors 12060 and 12062 may be in communication with a signal processing component or a processor 12064 which may be local to the smart sensors. Both the smart sensors 12060 and 12062 and the processor 12064 may be located at the end-effector (represented by dashed-box 12066). For example, smart sensor 12060 may output signals or data to an operational amplifier 12068 and an ADC converter 12070, which may condition the signals or data for input into processor 12064. Similarly, smart sensor 12062 may output signals or data to an operational amplifier 12072 and an ADC converter 12074, which may condition the signals or data for input into processor 12064.

Smart sensors 12060 and/or 12062 may be different types of sensors or the same type of sensor, which may be, for example, magnetic field sensors, magnetic sensors, inductive sensors, capacitive sensors, or other types of sensors used in medical devices or endocutters. Component 12064, previously referred to as a processor, also may be a computational core, FPGA (field programmable gate array), logic unit (e.g., logic processor or logic controller), signal processing unit, or other type of processor. The processor 12064 may be in communication with a memory, such as non-volatile memory 12076, which may store calculation data, equipment information such as a type of cartridge inserted in the end-effector 12066, tabular data, or other reference data that may enable the processor 12064 to process signals or data received from one or more of the smart sensors 12060 or 12062 for use in operating the end-effector 12066 or an endocutter.

Further, a shaft 12078 may include a return path through which at least one of the plurality of smart sensors (e.g., smart sensors 12060 or 12062) and the handle 12080 are communicatively coupled. The shaft may include one or more wires which may transfer information from the processor 12064 to the handle 12080 for operation of the end-effector 12066 or endocutter. In one example, the information from the processor 12064 may be communicated to the handle 12080 (by way of shaft 12078 or directly without use of shaft 12078) over one or more of: a wired-line, a single-wired line, a multi-wired line, a wireless communication protocol such as Bluetooth, an optical line, or an acoustic line.

In one aspect, at least one of a plurality of smart sensors positioned at an end-effector may include a signal processing component. For example, the signal processing component may be built into the smart sensor or may be locally coupled to the smart sensor as a single module. The signal processing component may be configured to process data received from a sensor component (e.g., sensor component 12020) of at least one of the plurality of smart sensors. A controller 12024 (e.g., a controller) at the handle may be communicatively coupled to at least one of the plurality of smart sensors.

In one aspect, a smart sensor may be configured for local signal processing in a medical device. The smart sensor may include at least one sensor component (e.g., sensor component 12020) and at least one processing component (e.g., processing component 12022). The processing component may be configured to receive data from the at least one sensor component and to process the data into information for use by the medical device. The medical device may be, for example, an endocutter, however this is not intended to be a limitation of the present disclosure. It should be understood that the techniques and features discussed herein for smart sensors with local signal processing may be used in any medical device where processing of sensor signals or data is used for operation of the medical device.

Further, a controller (e.g., controller 12024, controller) in the medical device may be configured to receive the information (i.e., processed signals or data) from the at least one processing component (e.g., processing component 12022). As discussed above, the medical device may be a surgical instrument such as an endocutter and the smart sensor may be configured for local signal processing in the surgical instrument. Local signal processing may refer to, for example, processing signals or data from a sensor component at a processing component coupled to the sensor, where the resulting processed information may be used by a separate component. For example, the controller 12024 may be positioned in the handle 12012 of the surgical instrument (i.e., the endocutter 12010) and the smart sensor may be configured to be positioned in a separate component (i.e., the end-effector 12016) of the surgical instrument (i.e., the endocutter 12010), separate from the handle 12012. Thus, the controller 12024 may be positioned at the handle 12012 of the surgical instrument and the signal processing component 12022 and the sensor 12020 may be located in a component separate from the handle 12012 (e.g., end-effector 12016).

In this way, the handle or controller 12024 need not have information about the smart sensor, knowledge of what the smart sensor is doing, or capability to interpret data feed back from the smart sensor. This is because the processing component 12022 may transform or condition the data from the smart sensor and generate information from the data directly usable by the handle or controller 12024. The information generated by the processing component may be used directly, without the data from the smart sensor needing to be processed in another part of the medical device (e.g., near the handle 12012 or controller 12024). Thus, the surgical instrument may be controlled based on the (processed) information from the signal processing component local to the sensor.

In one aspect, a current draw on a power line communicatively coupled to the signal processing component 12022 (i.e., local to the sensor 12020) may be monitored. The current draw may be monitored by a processor, controller, or other monitoring device at the shaft 12014 or the handle 12012, or at another processor, controller or other monitoring device separate from the signal processing component 12022. For example, the monitoring may be a standard Morse Code type monitoring of the current draw on the power line. An issue with the surgical instrument based on the current draw and a particular sensor may be determined by the separate processor at, e.g., the handle 12012. In this way, the monitoring may allow the handle (or a processor or controller therein) to be informed of various issues related to signals or data received by one or more sensor and which particular sensor identified the issue, without a further communication requirement (e.g., pairing, or other coupled communication).

Figure 44:
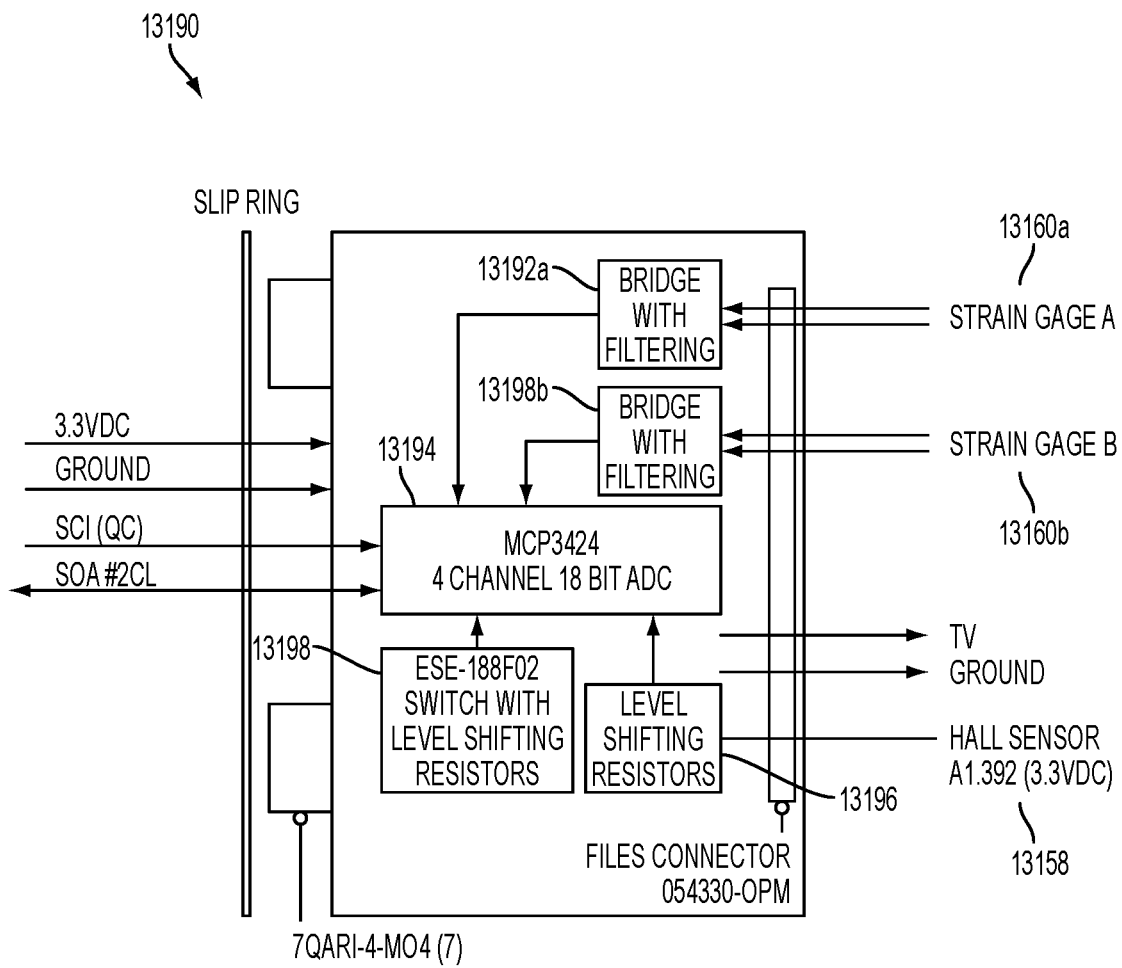
FIG. 44 illustrates one aspect of a circuit configured to convert signals from a first sensor and a plurality of secondary sensors into digital signals receivable by a processor in accordance with one or more aspects of the present disclosure.

FIG. 44 illustrates one aspect of a circuit 13190 configured to convert signals from the first sensor 13158 and the plurality of secondary sensors 13160*a*, 13160*b* into digital signals receivable by a processor, such as, for example, the primary processor 2006 (FIGS. 16A-16B). The circuit 13190 comprises an analog-to-digital convertor 13194. In some examples, the analog-to-digital convertor 13194 comprises a 4-channel, 18-bit analog to digital convertor. Those skilled in the art will recognize that the analog-to-digital convertor 13194 may comprise any suitable number of channels and/or bits to convert one or more inputs from analog to digital signals. The circuit 13190 comprises one or more level shifting resistors 13196 configured to receive an input from the first sensor 13158, such as, for example, a magnetic field sensor. The level shifting resistors 13196 adjust the input from the first sensor, shifting the value to a higher or lower voltage depending on the input. The level shifting resistors 13196 provide the level-shifted input from the first sensor 13158 to the analog-to-digital convertor.

In some aspects, a plurality of secondary sensors 13160*a*, 13160*b* are coupled to a plurality of bridges 13192*a*, 13192*b* within the circuit 13190. The plurality of bridges 13192*a*, 13192*b* may provide filtering of the input from the plurality of secondary sensors 13160*a*, 13160*b*. After filtering the input signals, the plurality of bridges 13192*a*, 13192*b* provide the inputs from the plurality of secondary sensors 13160*a*, 13160*b* to the analog-to-digital convertor 13194. In some examples, a switch 13198 coupled to one or more level shifting resistors may be coupled to the analog-to-digital convertor 13194. The switch 13198 is configured to calibrate one or more of the input signals, such as, for example, an input from a magnetic field sensor. The switch 13198 may be engaged to provide one or more level shifting signals to adjust the input of one or more of the sensors, such as, for example, to calibrate the input of a magnetic field sensor. In some examples, the adjustment is not necessary, and the switch 13198 is left in the open position to decouple the level shifting resistors. The switch 13198 is coupled to the analog-to-digital convertor 13194. The analog-to-digital convertor 13194 provides an output to one or more processors, such as, for example, the primary processor 2006 (FIGS. 16A-16B). The primary processor 2006 calculates one or more parameters of the end effector 13150 based on the input from the analog-to-digital convertor 13194. For example, in one example, the primary processor 2006 calculates a thickness of tissue located between the anvil 13152 and the staple cartridge 13156 based on inputs from the first sensor 13158 and the plurality of secondary sensors 13160*a*, 13160*b*.

Figure 112:
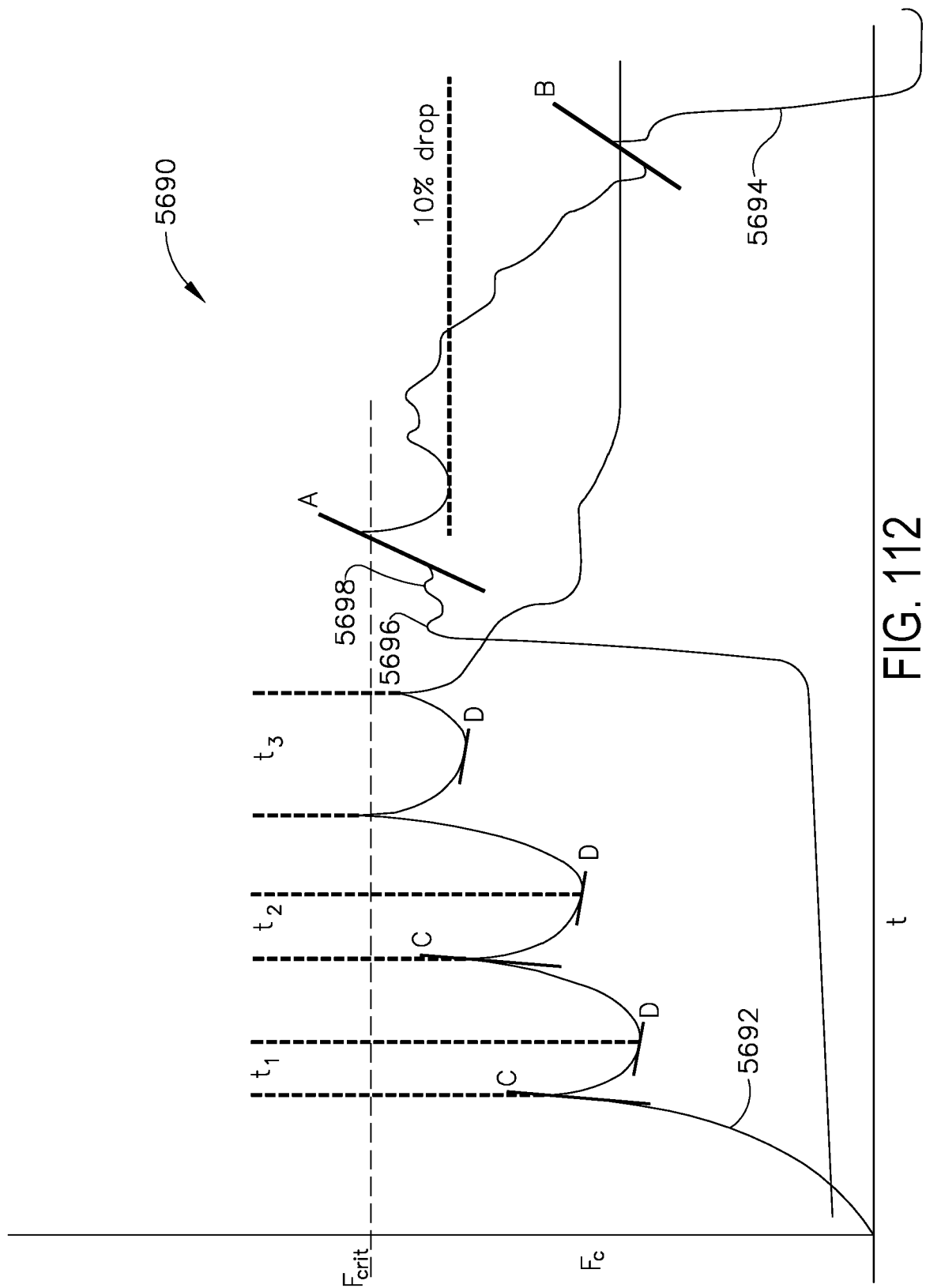
FIG. 112 illustrates an example graph showing a curve representative of a closing force FC over time t for various aspects of the surgical instrument of FIG. 106 and a curve representative of a firing force FF over time t of the surgical instrument of FIG. 106 in accordance with one or more aspects of the present disclosure.

FIG. 45 illustrates one aspect of a staple cartridge 13606 that comprises a flex cable 13630 connected to a magnetic field sensor 13610 and processor 13612. The staple cartridge 13606 is similar to the staple cartridge 13606 is similar to the surgical staple cartridge 304 (FIG. 1) described above in connection with surgical instrument 10 (FIGS. 1-6). FIG. 112 is an exploded view of the staple cartridge 13606. The staple cartridge comprises 13606 a cartridge body 13620, a wedge sled 13618, a cartridge tray 13622, and a flex cable 13630. The flex cable 13630 further comprises electrical contacts 13632 at the proximal end of the staple cartridge 13606, placed to make an electrical connection when the staple cartridge 13606 is operatively coupled with an end effector, such as end effector 13800 described below. The electrical contacts 13632 are integrated with cable traces 13634, which extend along some of the length of the staple cartridge 13606. The cable traces 13634 connect 13636 near the distal end of the staple cartridge 13606 and this connection 13636 joins with a conductive coupling 13614. A magnetic field sensor 13610 and a processor 13612 are operatively coupled to the conductive coupling 13614 such that the magnetic field sensor 13610 and the processor 13612 are able to communicate.

Figure 46:
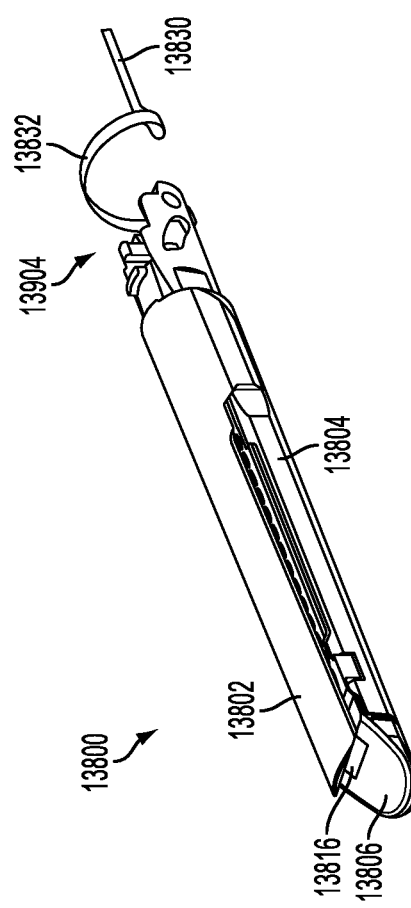
FIG. 46 illustrates the end effector shown in FIG. 46 with a flex cable and without the shaft assembly in accordance with one or more aspects of the present disclosure.

FIG. 46 illustrates one aspect of an end effector 13800 with a flex cable 13830 operable to provide power to a staple cartridge 13806 that comprises a distal sensor plug 13816. The end effector 13800 is similar to the end effector 300 (FIG. 1) described above in connection with surgical instrument 10 (FIGS. 1-6). The end effector 13800 comprises an anvil 13802, a jaw member or elongated channel 13804, and a staple cartridge 13806 operatively coupled to the elongated channel 13804. The end effector 13800 is operatively coupled to a shaft assembly. The shaft assembly is similar to interchangeable shaft assembly 200 (FIG. 1) described above in connection with surgical instrument 10 (FIGS. 1-6). The shaft assembly further comprises a closure tube that encloses the exterior of the shaft assembly. In some examples the shaft assembly further comprises an articulation joint 13904, which includes a double pivot closure sleeve assembly. The double pivot closure sleeve assembly includes an end effector closure sleeve assembly that is operable to couple with the end effector 13800.

Figure 47:
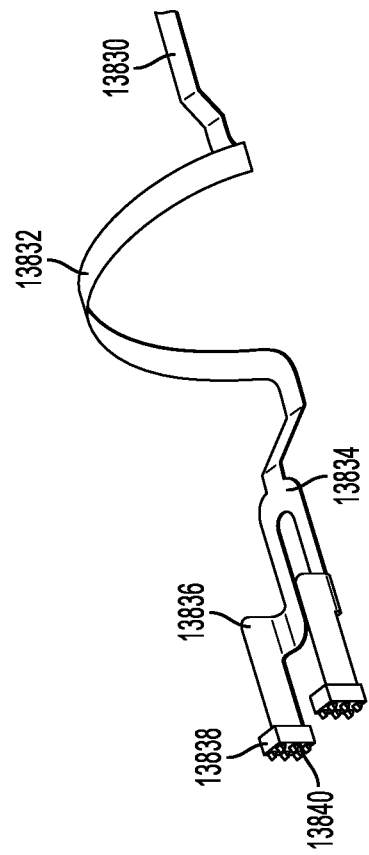
FIGS. 47 and 48 illustrate an elongated channel portion of an end effector without the anvil or the staple cartridge, to illustrate how the flex cable shown in FIG. 46 can be seated within the elongated channel in accordance with one or more aspects of the present disclosure.
Figure 48:
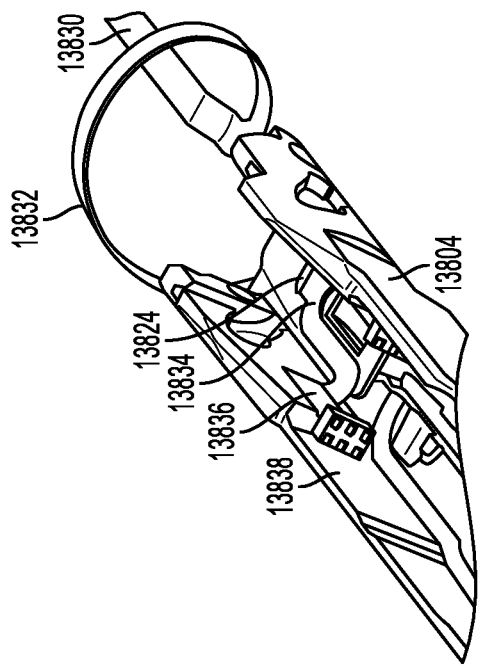

FIGS. 47 and 48 illustrate the elongated channel 13804 portion of the end effector 13800 without the anvil 13802 or the staple cartridge, to illustrate how the flex cable 13830 can be seated within the elongated channel 13804. In some examples, the elongated channel 13804 further comprises a third aperture 13824 for receiving the flex cable 13830. Within the body of the elongated channel 13804 the flex cable splits 13834 to form extensions 13836 on either side of the elongated channel 13804. FIG. 48 further illustrates that connectors 13838 can be operatively coupled to the flex cable extensions 13836.

Figure 49:
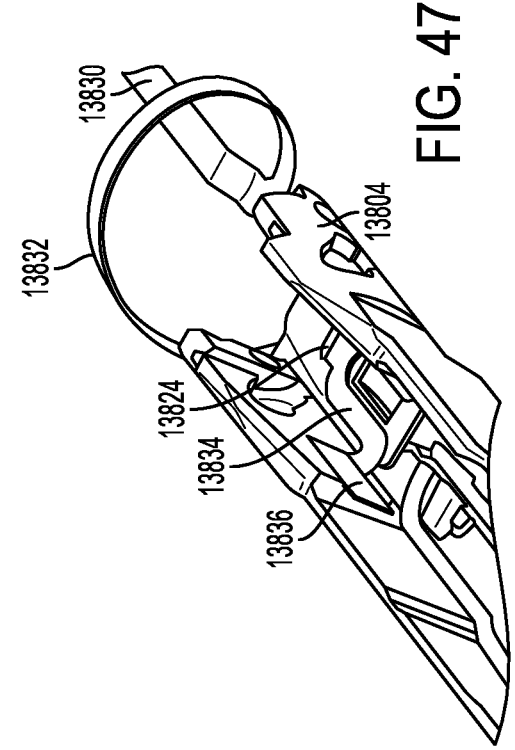
FIG. 49 illustrates a flex cable, shown in FIGS. 46-48, alone in accordance with one or more aspects of the present disclosure.

FIG. 49 illustrates the flex cable 13830 alone. As illustrated, the flex cable 13830 comprises a single coil 13832 operative to wrap around the articulation joint 13904 (FIG. 46), and a split 13834 that attaches to extensions 13836. The extensions can be coupled to connectors 13838 that have on their distal facing surfaces prongs 13840 for coupling to the staple cartridge 13806, as described below.

Figure 50:
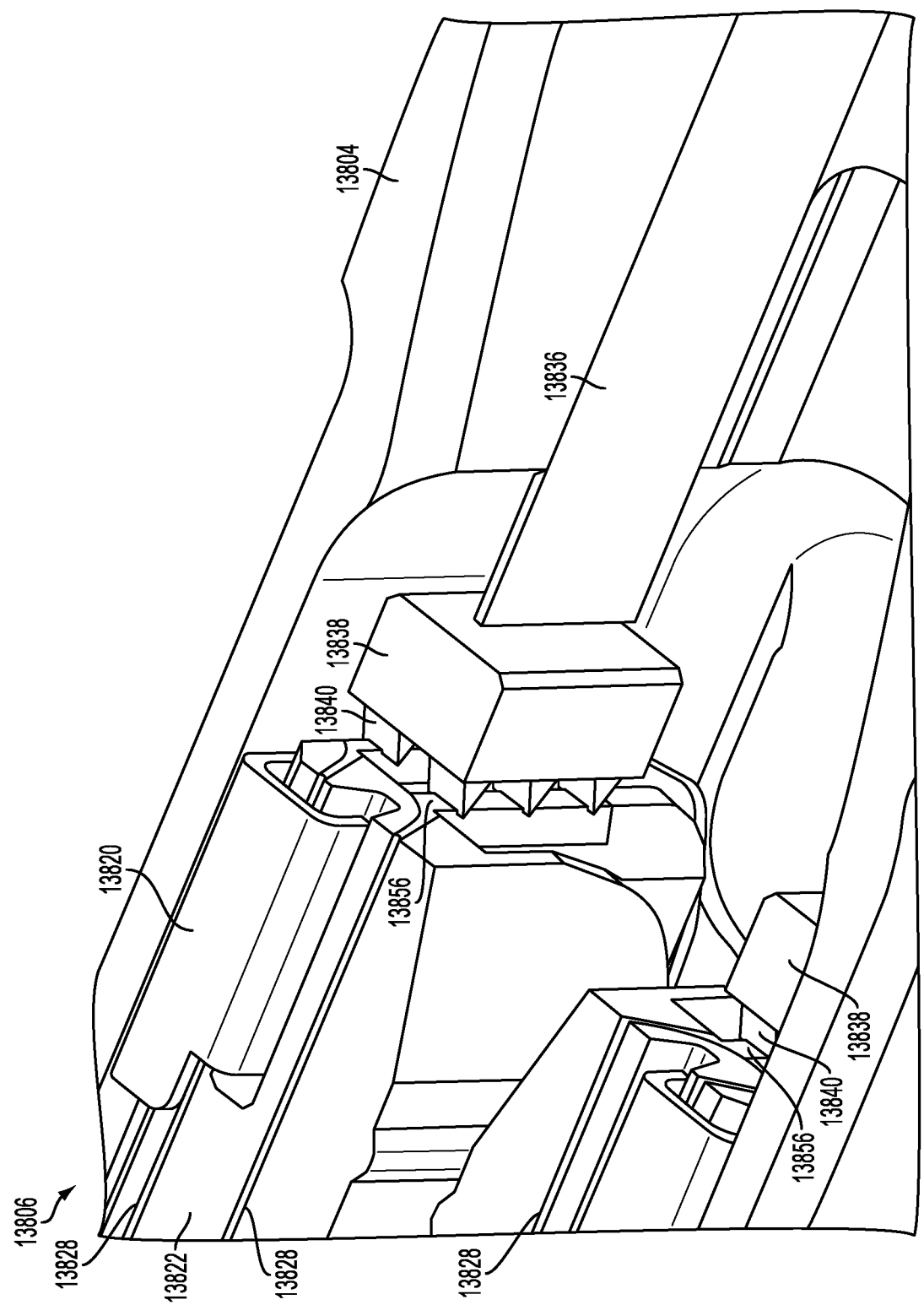
FIG. 50 illustrates a close up view of the elongated channel shown in FIGS. 114 and 115 with a staple cartridge coupled thereto in accordance with one or more aspects of the present disclosure.

FIG. 50 illustrates a close up view of the elongated channel 13804 shown in FIGS. 47 and 48 with a staple cartridge 13804 coupled thereto. The staple cartridge 13804 comprises a cartridge body 13822 and a cartridge tray 13820. In some examples the staple cartridge 13806 further comprises electrical traces 13828 that are coupled to proximal contacts 13856 at the proximal end of the staple cartridge 13806. The proximal contacts 13856 can be positioned to form a conductive connection with the prongs 13840 of the connectors 13838 that are coupled to the flex cable extensions 13836. Thus, when the staple cartridge 13806 is operatively coupled with the elongated channel 13804, the flex cable 13830, through the connectors 13838 and the connector prongs 13840, can provide power to the staple cartridge 13806.

Figure 52:
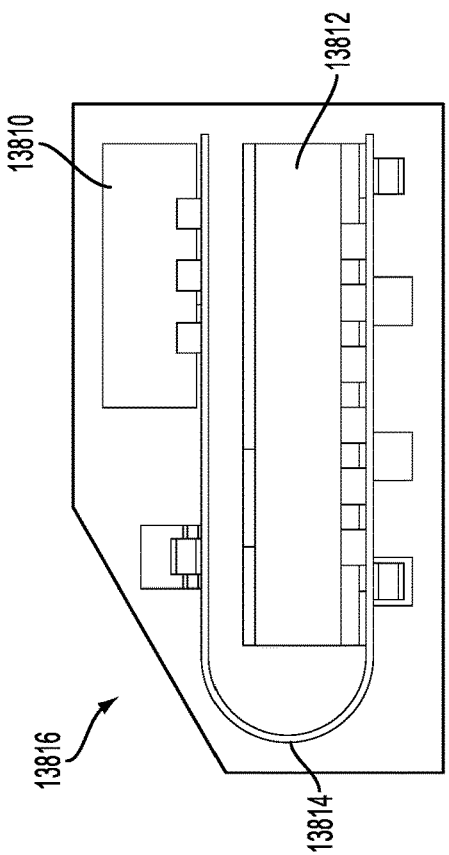
FIGS. 51 and 52 illustrate one aspect of a distal sensor plug where
Figure 51:
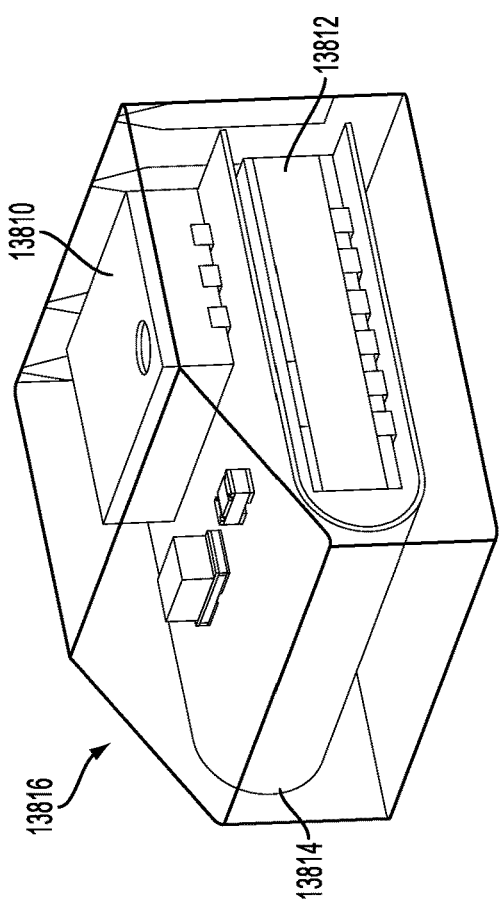

FIGS. 51 and 52 illustrate one aspect of a distal sensor plug 13816. FIG. 51 illustrates a cutaway view of the distal sensor plug 13816. As illustrated, the distal sensor plug 13816 comprises a magnetic field sensor 13810 and a processor 13812. The distal sensor plug 13816 further comprises a flex board 13814. As further illustrated in FIG. 52, the magnetic field sensor 13810 and the processor 13812 are operatively coupled to the flex board 13814 such that they are capable of communicating.

Figure 53:
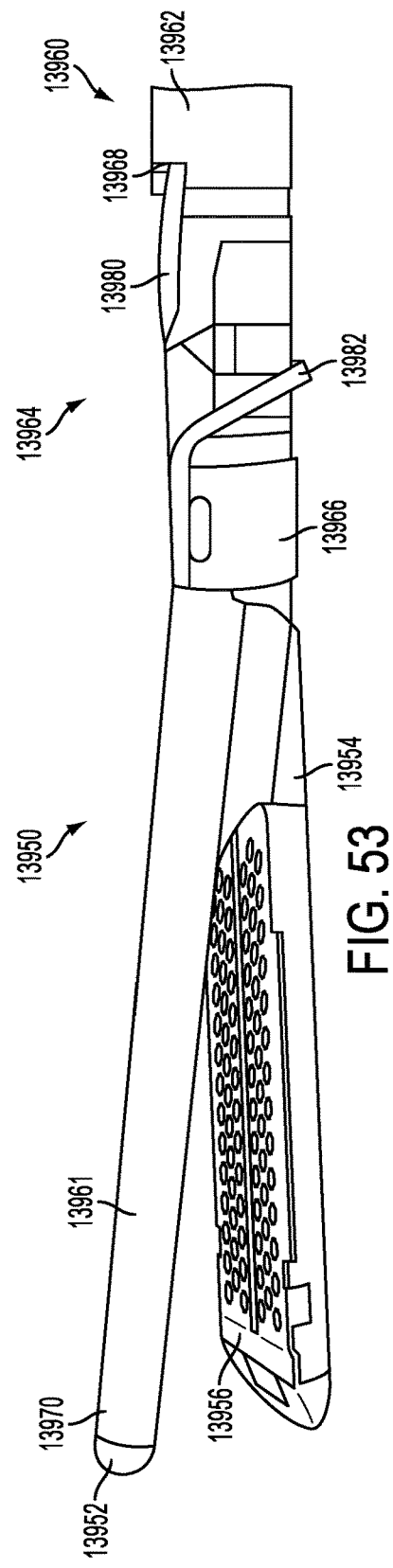
FIG. 53 illustrates an aspect of an end effector with a flex cable operable to provide power to sensors and electronics in the distal tip of the anvil portion in accordance with one or more aspects of the present disclosure.

FIG. 53 illustrates one aspect of an end effector 13950 with a flex cable 13980 operable to provide power to sensors and electronics in the distal tip 13952 of the anvil 13961 portion. The end effector 13950 comprises an anvil 13961, a jaw member or elongated channel 13954, and a staple cartridge 13956 operatively coupled to the elongated channel. The end effector 13950 is operatively coupled to a shaft assembly 13960. The shaft assembly 13960 further comprises a closure tube 13962 that encloses the shaft assembly 13960. In some examples the shaft assembly 13960 further comprises an articulation joint 13964, which includes a double pivot closure sleeve assembly 13966.

In various aspects, the end effector 13950 further comprises a flex cable 13980 that is configured to not interfere with the function of the articulation joint 13964. In some examples, the closure tube 13962 comprises a first aperture 13968 through which the flex cable 13980 can extend. In some examples, flex cable 13980 further comprises a loop or coil 13982 that wraps around the articulation joint 13964 such that the flex cable 13980 does not interfere with the operation of the articulation joint 13964, as further described below. In some examples, the flex cable 13980 extends along the length of the anvil 13961 to a second aperture 13970 in the distal tip of the anvil 13961.

Figure 54:
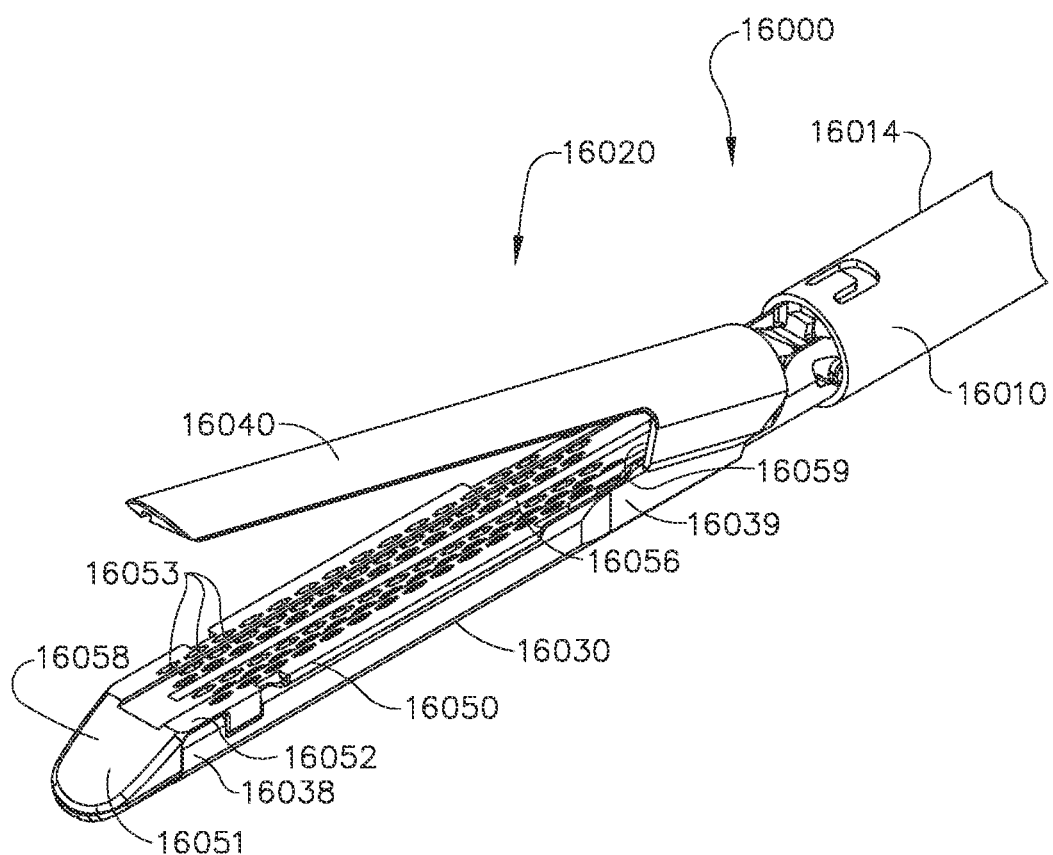
FIG. 54 is a perspective view of an end effector of a surgical stapling instrument including a cartridge channel, a staple cartridge positioned in the cartridge channel, and an anvil in accordance with one or more aspects of the present disclosure.

A portion of a surgical stapling instrument 16000 is illustrated in FIGS. 54-56. The stapling instrument 16000 is usable with a manually-operated system and/or a robotically-controlled system, for example. The stapling instrument 16000 comprises a shaft 16010 and an end effector 16020 extending from the shaft 16010. The end effector 16020 comprises a cartridge channel 16030 and a staple cartridge 16050 positioned in the cartridge channel 16030. The staple cartridge 16050 comprises a cartridge body 16051 and a retainer 16057 attached to the cartridge body 16051. The cartridge body 16051 is comprised of a plastic material, for example, and the retainer 16057 is comprised of metal, for example; however, the cartridge body 16051 and the retainer 16057 can be comprised of any suitable material. The cartridge body 16051 comprises a deck 16052 configured to support tissue, a longitudinal slot 16056, and a plurality of staple cavities 16053 defined in the deck 16052.

Referring primarily to FIGS. 55 and 56, staples 16055 are removably positioned in the staple cavities 16053 and are supported by staple drivers 16054 which are also movably positioned in the staple cavities 16053. The retainer 16057 extends around the bottom of the cartridge body 16051 to keep the staple drivers 16054 and/or the staples 16055 from falling out of the bottom of the staple cavities 16053. The staple drivers 16054 and the staples 16055 are movable between an unfired position (FIG. 55) and a fired position by a sled 16060. The sled 16060 is movable between a proximal, unfired position (FIG. 55) toward a distal, fired position to eject the staples 16055 from the staple cartridge 16050, as illustrated in FIG. 56. The sled 16060 comprises one or more ramped surfaces 16064 which are configured to slide under the staple drivers 16054. The end effector 16020 further comprises an anvil 16040 configured to deform the staples 16055 when the staples 16055 are ejected from the staple cartridge 16050. In various instances, the anvil 16040 can comprise forming pockets 16045 defined therein which are configured to deform the staples 16055.

The shaft 16010 comprises a frame 16012 and an outer sleeve 16014 which is movable relative to the frame 16012. The cartridge channel 16030 is mounted to and extends from the shaft frame 16012. The outer sleeve 16014 is operably engaged with the anvil 16040 and is configured to move the anvil 16040 between an open position (FIG. 54) and a closed position (FIG. 55). In use, the anvil 16040 is movable toward a staple cartridge 16050 positioned in the cartridge channel 16030 to clamp tissue against the deck 16052 of the staple cartridge 16050. In various alternative aspects, the cartridge channel 16030 and the staple cartridge 16050 are movable relative to the anvil 16040 to clamp tissue therebetween. In either event, the shaft 16010 further comprises a firing member 16070 configured to push the sled 16060 distally. The firing member 16070 comprises a knife edge 16076 which is movable within the longitudinal slot 16056 and is configured to incise the tissue positioned intermediate the anvil 16040 and the staple cartridge 16050 as the firing member 16070 is advanced distally to eject the staples 16055 from the staple cartridge 16050. The firing member 16070 further comprises a first cam 16071 configured to engage the cartridge channel 16030 and a second cam 16079 configured to engage the anvil 16040 and hold the anvil 16040 in position relative to the staple cartridge 16050. The first cam 16071 is configured to slide under the cartridge channel 16030 and the second cam 16079 is configured to slide within an elongated slot 16049 defined in the anvil 16040.

Figure 57:
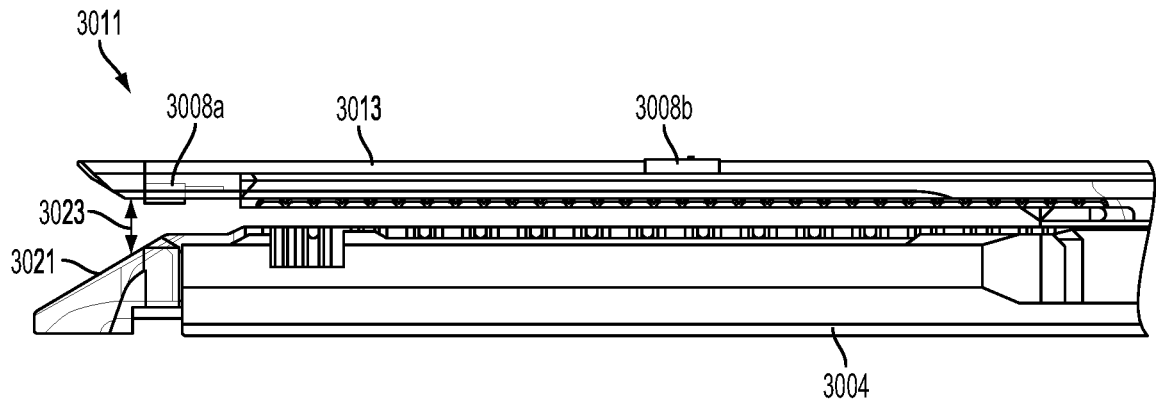
FIG. 57 illustrates one aspect of an end effector comprising a first sensor and a second sensor in accordance with one or more aspects of the present disclosure.

FIG. 57 illustrates one aspect of an end effector 3011 comprising a first sensor 3008a and a second sensor 3008b. The end effector 3011 is similar to the end effector 300 described above. The end effector 3011 comprises an anvil 3013 pivotally coupled to a jaw member 3004. The jaw member 3004 is configured to receive a staple cartridge 3021 therein. The staple cartridge 3021 comprises a plurality of staples (not shown). The plurality of staples is deployable from the staple cartridge 3021 during a surgical operation. The end effector 3011 comprises a first sensor 3008a configured to measure one or more parameters of the end effector 3011. For example, in one aspect, the first sensor 3008a is configured to measure the gap 3023 between the anvil 3013 and the jaw member 3004. The first sensor 3008a may comprise, for example, a Hall effect sensor configured to detect a magnetic field generated by a magnet 3012 embedded in the second jaw member 3004 and/or the staple cartridge 3021. As another example, in one aspect, the first sensor 3008a is configured to measure one or more forces exerted on the anvil 3013 by the second jaw member 3004 and/or tissue clamped between the anvil 3013 and the second jaw member 3004.

The end effector 3011 comprises a second sensor 3008b. The second sensor 3008b is configured to measure one or more parameters of the end effector 3011. For example, in various aspects, the second sensor 3008b may comprise a strain gauge configured to measure the magnitude of the strain in the anvil 3013 during a clamped condition. The strain gauge provides an electrical signal whose amplitude varies with the magnitude of the strain. In various aspects, the first sensor 3008a and/or the second sensor 3008b may comprise, for example, a magnetic sensor such as, for example, a Hall effect sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 3011. The first sensor 3008a and the second sensor 3008b may be arranged in a series configuration and/or a parallel configuration. In a series configuration, the second sensor 3008b may be configured to directly affect the output of the first sensor 3008a. In a parallel configuration, the second sensor 3008b may be configured to indirectly affect the output of the first sensor 3008a.

In one aspect, the one or more parameters measured by the first sensor 3008a are related to the one or more parameters measured by the second sensor 3008b. For example, in one aspect, the first sensor 3008a is configured to measure the gap 3023 between the anvil 3013 and the jaw member 3004. The gap 3023 is representative of the thickness and/or compressibility of a tissue section clamped between the anvil 3013 and the staple cartridge 3021 located in the jaw member 3004. The first sensor 3008a may comprise, for example, a Hall effect sensor configured to detect a magnetic field generated by a magnet 3012 coupled to the second jaw member 3004 and/or the staple cartridge 3021. Measuring at a single location accurately describes the compressed tissue thickness for a calibrated full bit of tissue, but may provide inaccurate results when a partial bite of tissue is placed between the anvil 3013 and the second jaw member 3004. A partial bite of tissue, either a proximal partial bite or a distal partial bite, changes the clamping geometry of the anvil 3013.

In some aspects, the second sensor 3008b is configured to detect one or more parameters indicative of a type of tissue bite, for example, a full bite, a partial proximal bite, and/or a partial distal bite. The measurement of the second sensor 3008b may be used to adjust the measurement of the first sensor 3008a to accurately represent a proximal or distal positioned partial bite's true compressed tissue thickness. For example, in one aspect, the second sensor 3008b comprises a strain gauge, such as, for example, a micro-strain gauge, configured to monitor the amplitude of the strain in the anvil during a clamped condition. The amplitude of the strain of the anvil 3013 is used to modify the output of the first sensor 3008a, for example, a Hall effect sensor, to accurately represent a proximal or distal positioned partial bite's true compressed tissue thickness. The first sensor 3008a and the second sensor 3008b may be measured in real-time during a clamping operation. Real-time measurement allows time based information to be analyzed, for example, by the primary processor 2006, and used to select one or more algorithms and/or look-up tables to recognize tissue characteristics and clamping positioning to dynamically adjust tissue thickness measurements.

In some aspects, the thickness measurement of the first sensor 3008a may be provided to an output device of a surgical instrument 10 coupled to the end effector 3011. For example, in one aspect, the end effector 3011 is coupled to the surgical instrument 10 comprising a display 2028. The measurement of the first sensor 3008a is provided to a processor, for example, the primary processor 2006. The primary processor 2006 adjusts the measurement of the first sensor 3008a based on the measurement of the second sensor 3008b to reflect the true tissue thickness of a tissue section clamped between the anvil 3013 and the staple cartridge 3021. The primary processor 2006 outputs the adjusted tissue thickness measurement and an indication of full or partial bite to the display 2028. An operator may determine whether or not to deploy the staples in the staple cartridge 3021 based on the displayed values.

In some aspects, the first sensor 3008a and the second sensor 3008b may be located in different environments, such as, for example, the first sensor 3008a being located within a patient at a treatment site and the second sensor 3008b being located externally to the patient. The second sensor 3008b may be configured to calibrate and/or modify the output of the first sensor 3008a. The first sensor 3008a and/or the second sensor 3008b may comprise, for example, an environmental sensor. Environmental sensors may comprise, for example, temperature sensors, humidity sensors, pressure sensors, and/or any other suitable environmental sensor.

Figure 58:
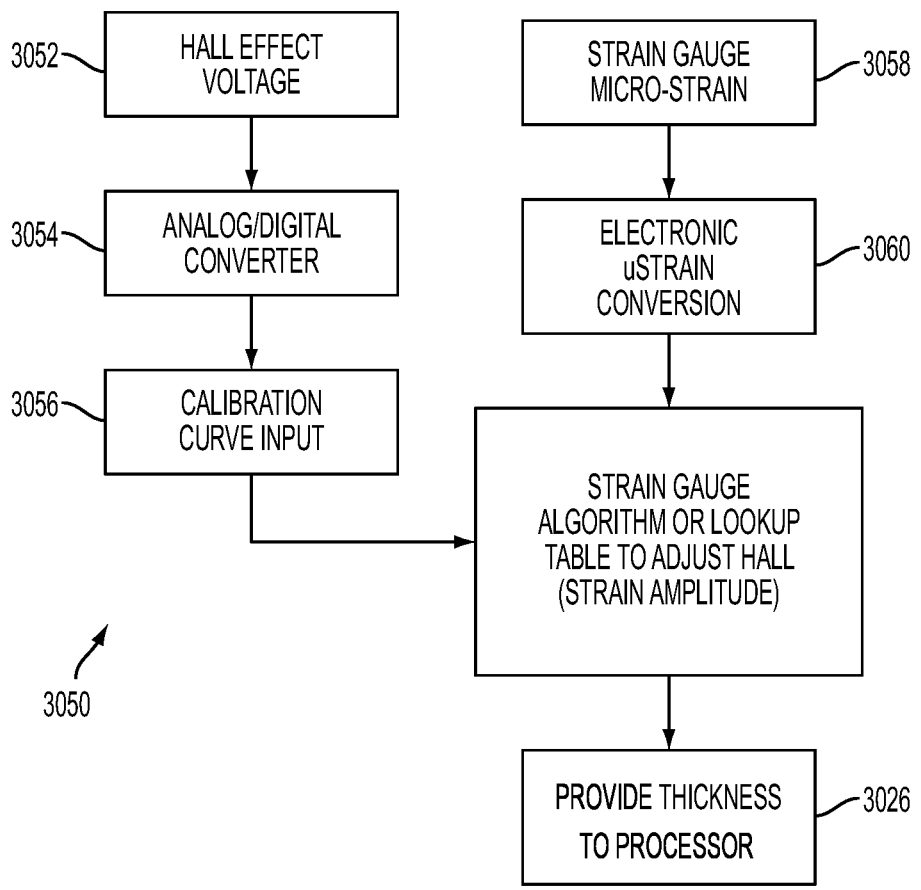
FIG. 58 is a logic diagram illustrating one aspect of a process for determining the thickness of a tissue section clamped between an anvil and a staple cartridge of an end effector in accordance with one or more aspects of the present disclosure.

FIG. 58 is a logic diagram illustrating one aspect of a process 3050 for determining and displaying the thickness of a tissue section clamped between the anvil 3013 and the staple cartridge 3021 of the end effector 3011. The process 3050 comprises obtaining a Hall effect voltage 3052, for example, through a Hall effect sensor located at the distal tip of the anvil 3013. The Hall effect voltage 3052 is provided to an analog to digital convertor 3054 and converted into a digital signal. The digital signal is provided to a processor, such as, for example, the primary processor 2006. The primary processor 2006 calibrates 3056 the curve input of the Hall effect voltage 3052 signal. A strain gauge 3058, such as, for example, a micro-strain gauge, is configured to measure one or more parameters of the end effector 3011, such as, for example, the amplitude of the strain exerted on the anvil 3013 during a clamping operation. The measured strain is converted 3060 to a digital signal and provided to the processor, such as, for example, the primary processor 2006. The primary processor 2006 uses one or more algorithms and/or lookup tables to adjust the Hall effect voltage 3052 in response to the strain measured by the strain gauge 3058 to reflect the true thickness and fullness of the bite of tissue clamped by the anvil 3013 and the staple cartridge 3021. The adjusted thickness is displayed 3026 to an operator by, for example, a display 2026 embedded in the surgical instrument 10.

In some aspects, the surgical instrument can further comprise a load sensor 3082 or load cell. The load sensor 3082 can be located, for instance, in the interchangeable shaft assembly 200, described above, or in the housing 12, also described above.

Figure 59:
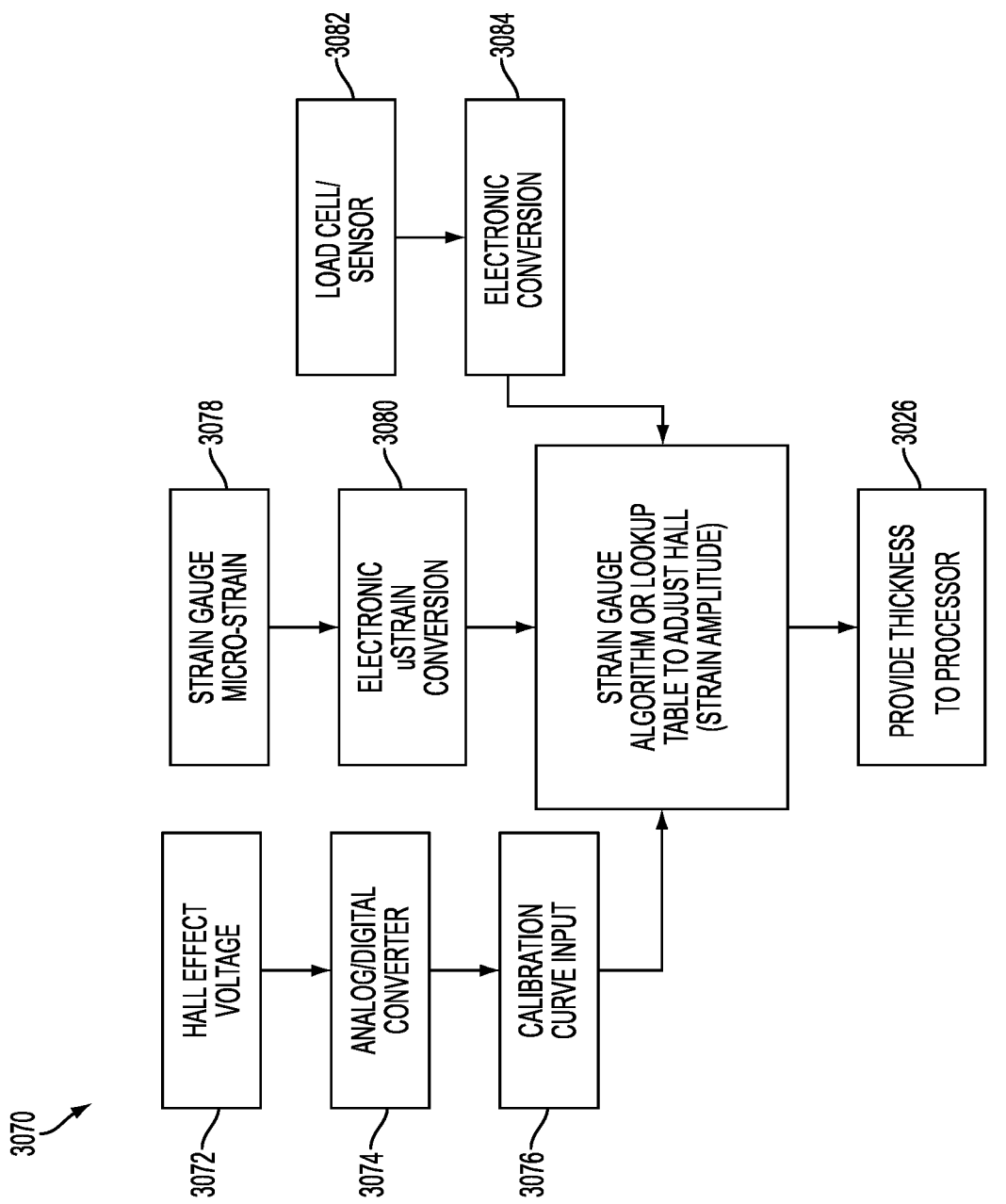
FIG. 59 is a logic diagram illustrating one aspect of a process for determining the thickness of a tissue section clamped between the anvil and the staple cartridge of the end effector in accordance with one or more aspects of the present disclosure.

FIG. 59 is a logic diagram illustrating one aspect of a process 3070 for determining and displaying the thickness of a tissue section clamped between the anvil 3013 and the staple cartridge 3021 of the end effector 3011. The process comprises obtaining a Hall effect voltage 3072, for example, through a Hall effect sensor located at the distal tip of the anvil 3013. The Hall effect voltage 3072 is provided to an analog to digital convertor 3074 and converted into a digital signal. The digital signal is provided to a processor, such as, for example, the primary processor 2006. The primary processor 2006 applies calibrates 3076 the curve input of the Hall effect voltage 3072 signal. A strain gauge 3078, such as, for example, a micro-strain gauge, is configured to measure one or more parameters of the end effector 3011, such as, for example, the amplitude of the strain exerted on the anvil 3013 during a clamping operation. The measured strain is converted 3080 to a digital signal and provided to the processor, such as, for example, the primary processor 2006. The load sensor 3082 measures the clamping force of the anvil 3013 against the staple cartridge 3021. The measured clamping force is converted 3084 to a digital signal and provided to the processor, such as for example, the primary processor 2006. The primary processor 2006 uses one or more algorithms and/or lookup tables to adjust the Hall effect voltage 3072 in response to the strain measured by the strain gauge 3078 and the clamping force measured by the load sensor 3082 to reflect the true thickness and fullness of the bite of tissue clamped by the anvil 3013 and the staple cartridge 3021. The adjusted thickness is displayed 3026 to an operator by, for example, a display 2026 embedded in the surgical instrument 10.

Figure 60:
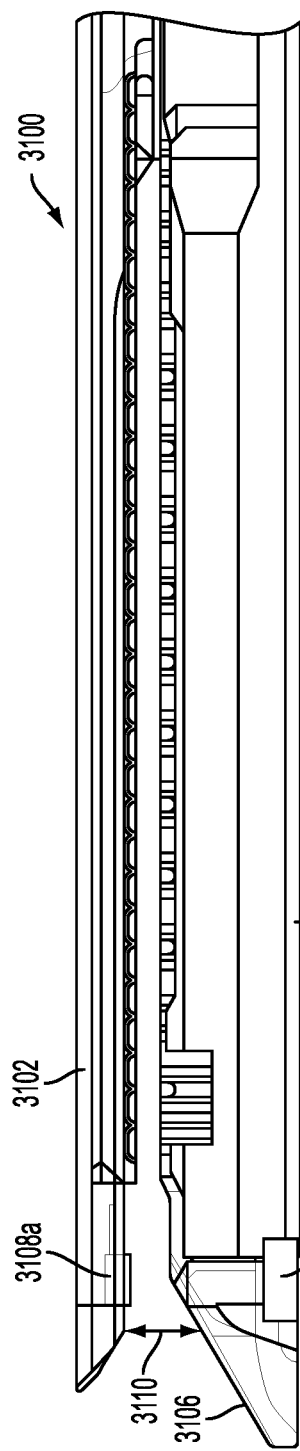
FIG. 60 illustrates one aspect of an end effector comprising a first sensor and a second sensor in accordance with one or more aspects of the present disclosure.

FIG. 60 illustrates one aspect of an end effector 3100 comprising a first sensor 3108*a* and a second sensor 3108*b*. The end effector 3100 is similar to the end effector 3011. The end effector 3100 comprises a anvil, or anvil, 3102 pivotally coupled to a jaw member 3104. The jaw member 3104 is configured to receive a staple cartridge 3106 therein. The end effector 3100 comprises a first sensor 3108*a* coupled to the anvil 3102. The first sensor 3108*a* is configured to measure one or more parameters of the end effector 3100, such as, for example, the gap 3110 between the anvil 3102 and the staple cartridge 3106. The gap 3110 may correspond to, for example, a thickness of tissue clamped between the anvil 3102 and the staple cartridge 3106. The first sensor 3108*a* may comprise any suitable sensor for measuring one or more parameters of the end effector. For example, in various aspects, the first sensor 3108*a* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some aspects, the end effector 3100 comprises a second sensor 3108*b*. The second sensor 3108*b* is coupled to jaw member 3104 and/or the staple cartridge 3106. The second sensor 3108*b* is configured to detect one or more parameters of the end effector 3100. For example, in some aspects, the second sensor 3108*b* is configured to detect one or more instrument conditions such as, for example, a color of the staple cartridge 3106 coupled to the jaw member 3104, a length of the staple cartridge 3106, a clamping condition of the end effector 3100, the number of uses/number of remaining uses of the end effector 3100 and/or the staple cartridge 3106, and/or any other suitable instrument condition. The second sensor 3108*b* may comprise any suitable sensor for detecting one or more instrument conditions, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In one aspect, input from the second sensor 3108*b* may be used to calibrate the input of the first sensor 3108*a*. The second sensor 3108*b* may be configured to detect one or more parameters of the staple cartridge 3106, such as, for example, the color and/or length of the staple cartridge 3106. The detected parameters, such as the color and/or the length of the staple cartridge 3106, may correspond to one or more properties of the cartridge, such as, for example, the height of the cartridge deck, the thickness of tissue useable/optimal for the staple cartridge, and/or the pattern of the staples in the staple cartridge 3106. The known parameters of the staple cartridge 3106 may be used to adjust the thickness measurement provided by the first sensor 3108*a*. For example, if the staple cartridge 3106 has a higher deck height, the thickness measurement provided by the first sensor 3108*a* may be reduced to compensate for the added deck height. The adjusted thickness may be displayed to an operator, for example, through a display 2026 coupled to the surgical instrument 10.

Figure 61:
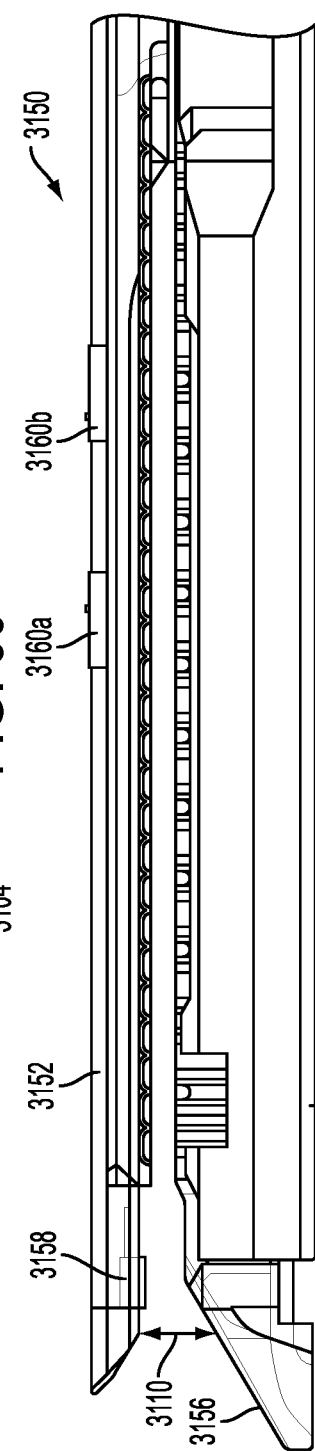
FIG. 61 illustrates one aspect of an end effector comprising a first sensor and a plurality of second sensors in accordance with one or more aspects of the present disclosure.

FIG. 61 illustrates one aspect of an end effector 3150 comprising a first sensor 3158 and a plurality of secondary sensors 3160*a*, 3160*b*. The end effector 3150 comprises a anvil, or anvil, 3152 and a jaw member 3154. The jaw member 3154 is configured to receive a staple cartridge 3156. The anvil 3152 is pivotally moveable with respect to the jaw member 3154 to clamp tissue between the anvil 3152 and the staple cartridge 3156. The anvil comprises a first sensor 3158. The first sensor 3158 is configured to detect one or more parameters of the end effector 3150, such as, for example, the gap 3110 between the anvil 3152 and the staple cartridge 3156. The gap 3110 may correspond to, for example, a thickness of tissue clamped between the anvil 3152 and the staple cartridge 3156. The first sensor 3158 may comprise any suitable sensor for measuring one or more parameters of the end effector. For example, in various aspects, the first sensor 3158 may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In some aspects, the end effector 3150 comprises a plurality of secondary sensors 3160*a*, 3160*b*. The secondary sensors 3160*a*, 3160*b* are configured to detect one or more parameters of the end effector 3150. For example, in some aspects, the secondary sensors 3160*a*, 3160*b* are configured to measure an amplitude of strain exerted on the anvil 3152 during a clamping procedure. In various aspects, the secondary sensors 3160*a*, 3160*b* may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor. The secondary sensors 3160*a*, 3160*b* may be configured to measure one or more identical parameters at different locations of the anvil 3152, different parameters at identical locations on the anvil 3152, and/or different parameters at different locations on the anvil 3152.

Figure 62:
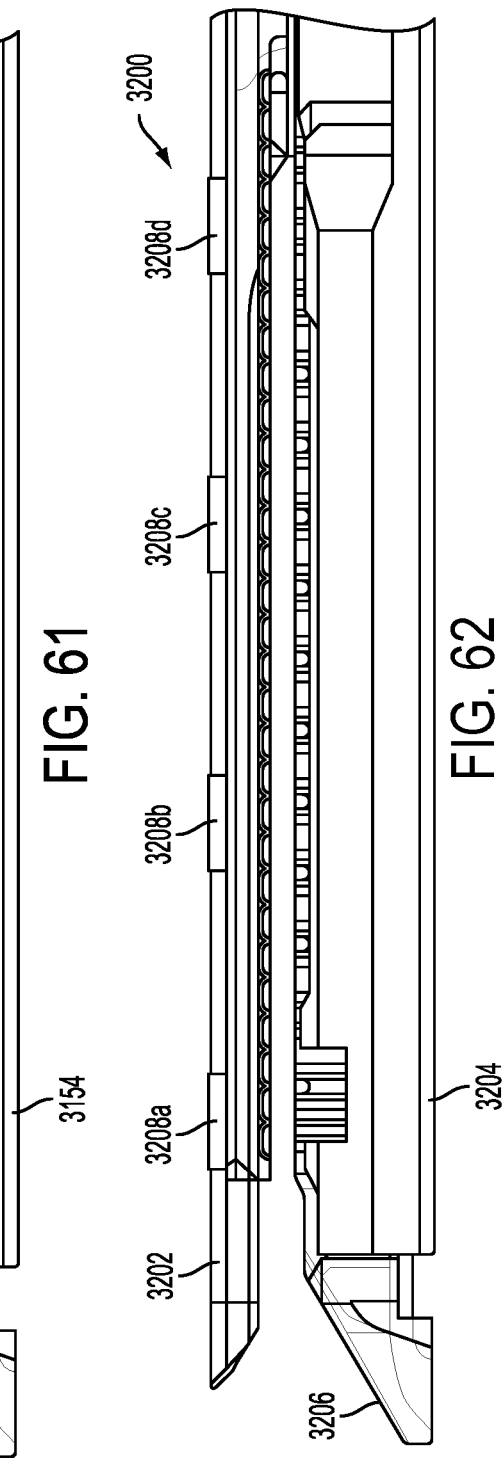
FIG. 62 illustrates one aspect of an end effector comprising a plurality of sensors in accordance with one or more aspects of the present disclosure.

FIG. 62 illustrates one aspect of an end effector 3200 comprising a plurality of sensors 3208*a*-3208*d*. The end effector 3200 comprises an anvil 3202 pivotally coupled to a jaw member 3204. The jaw member 3204 is configured to receive a staple cartridge 3206 therein. The anvil 3202 comprises a plurality of sensors 3208*a*-3208*d* thereon. The plurality of sensors 3208*a*-3208*d* is configured to detect one or more parameters of the end effector 3200, such as, for example, the anvil 3202. The plurality of sensors 3208*a*-3208*d* may comprise one or more identical sensors and/or different sensors. The plurality of sensors 3208*a*-3208*d* may comprise, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. For example, in one aspect, the plurality of sensors 3208*a*-3208*d* may comprise a plurality of strain gauges.

In one aspect, the plurality of sensors 3208*a*-3208*d* allows a robust tissue thickness sensing process to be implemented. By detecting various parameters along the length of the anvil 3202, the plurality of sensors 3208*a*-3208*d* allow a surgical instrument, such as, for example, the surgical instrument 10, to calculate the tissue thickness in the jaws regardless of the bite, for example, a partial or full bite. In some aspects, the plurality of sensors 3208*a*-3208*d* comprises a plurality of strain gauges. The plurality of strain gauges is configured to measure the strain at various points on the anvil 3202. The amplitude and/or the slope of the strain at each of the various points on the anvil 3202 can be used to determine the thickness of tissue in between the anvil 3202 and the staple cartridge 3206. The plurality of strain gauges may be configured to optimize maximum amplitude and/or slope differences based on clamping dynamics to determine thickness, tissue placement, and/or material properties of the tissue. Time based monitoring of the plurality of sensors 3208a-3208d during clamping allows a processor, such as, for example, the primary processor 2006, to utilize algorithms and look-up tables to recognize tissue characteristics and clamping positions and dynamically adjust the end effector 3200 and/or tissue clamped between the anvil 3202 and the staple cartridge 3206.

Figure 63:
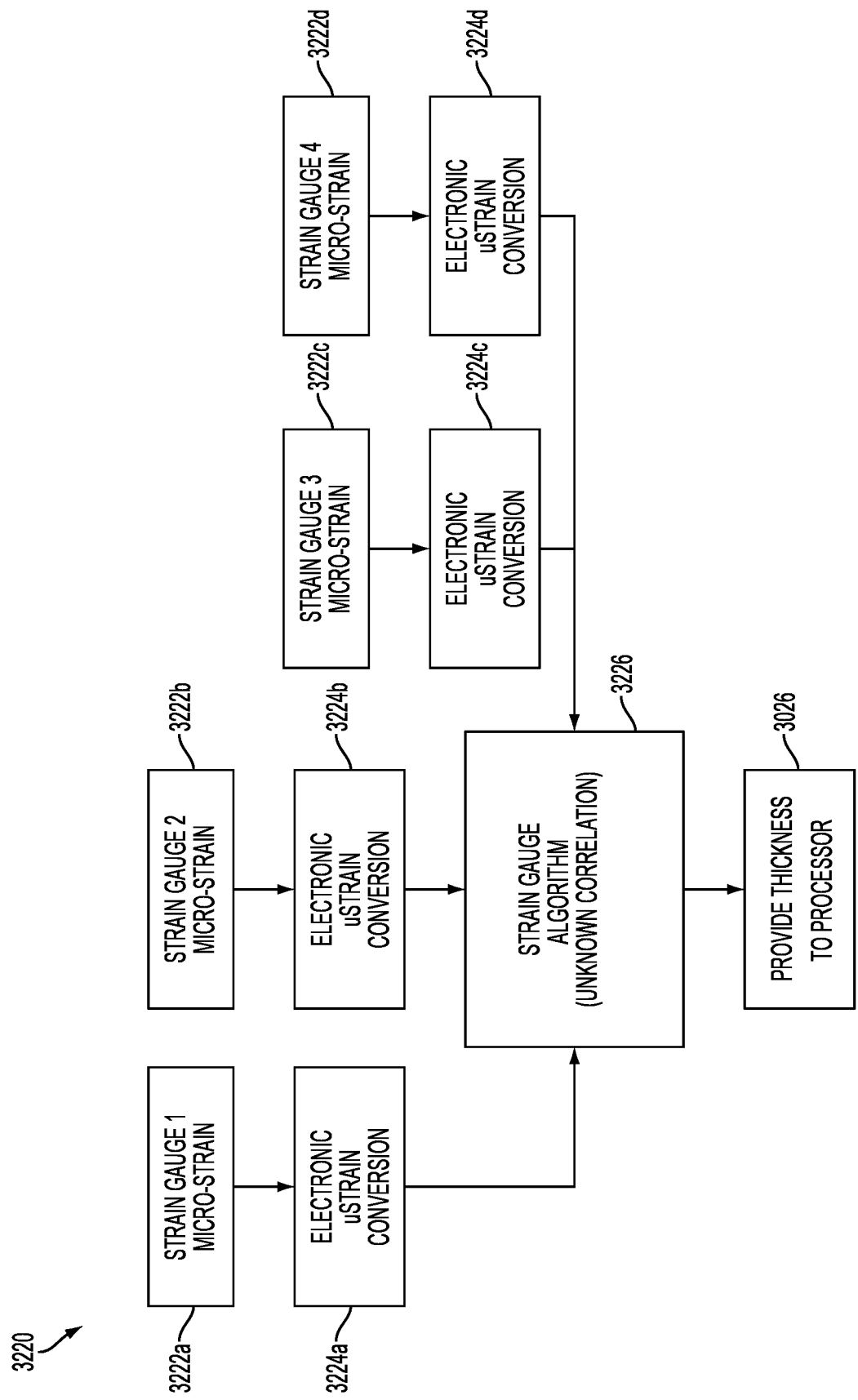
FIG. 63 is a logic diagram illustrating one aspect of a process for determining one or more tissue properties based on a plurality of sensors in accordance with one or more aspects of the present disclosure.

FIG. 63 is a logic diagram illustrating one aspect of a process 3220 for determining one or more tissue properties based on a plurality of sensors 3208a-3208d. In one aspect, a plurality of sensors 3208a-3208d generate 3222a-3222d a plurality of signals indicative of one or more parameters of the end effector 3200. The plurality of generated signals is converted 3224a-3224d to digital signals and provided to a processor. For example, in one aspect comprising a plurality of strain gauges, a plurality of electronic μStrain (microstrain) conversion circuits convert 3224a-3224d the strain gauge signals to digital signals. The digital signals are provided to a processor, such as, for example, the primary processor 2006. The primary processor 2006 determines 3226 one or more tissue characteristics based on the plurality of signals. The primary processor 2006 may determine the one or more tissue characteristics by applying an algorithm and/or a look-up table. The one or more tissue characteristics are displayed 3026 to an operator, for example, by a display 2026 embedded in the surgical instrument 10.

Figure 64:
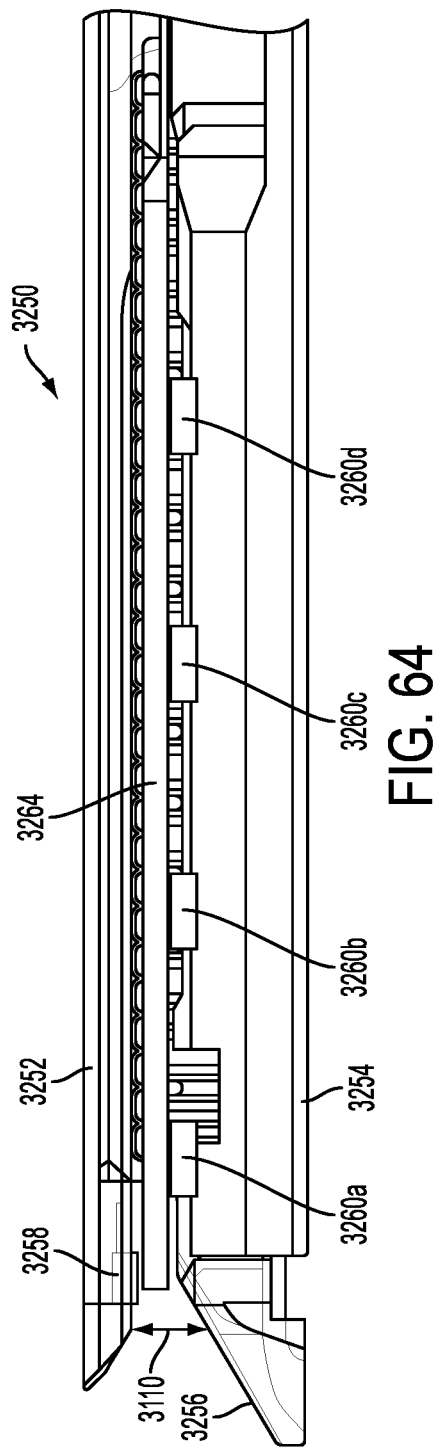
FIG. 64 illustrates one aspect of an end effector comprising a plurality of sensors coupled to a jaw member in accordance with one or more aspects of the present disclosure.

FIG. 64 illustrates one aspect of an end effector 3250 comprising a plurality of secondary sensors 3260a-3260d coupled to a jaw member 3254. The end effector 3250 comprises an anvil 3252 pivotally coupled to a jaw member 3254. The anvil 3252 is moveable relative to the jaw member 3254 to clamp one or more materials, such as, for example, a tissue section 3264, therebetween. The jaw member 3254 is configured to receive a staple cartridge 3256. A first sensor 3258 is coupled to the anvil 3252. The first sensor is configured to detect one or more parameters of the end effector 3150, such as, for example, the gap 3110 between the anvil 3252 and the staple cartridge 3256. The gap 3110 may correspond to, for example, a thickness of tissue clamped between the anvil 3252 and the staple cartridge 3256. The first sensor 3258 may comprise any suitable sensor for measuring one or more parameters of the end effector. For example, in various aspects, the first sensor 3258 may comprise a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

A plurality of secondary sensors 3260a-3260d is coupled to the jaw member 3254. The plurality of secondary sensors 3260a-3260d may be formed integrally with the jaw member 3254 and/or the staple cartridge 3256. For example, in one aspect, the plurality of secondary sensors 3260a-3260d is disposed on an outer row of the staple cartridge 3256 (see FIG. 63). The plurality of secondary sensors 3260a-3260d are configured to detect one or more parameters of the end effector 3250 and/or a tissue section 3264 clamped between the anvil 3252 and the staple cartridge 3256. The plurality of secondary sensors 3260a-3260d may comprise any suitable sensors for detecting one or more parameters of the end effector 3250 and/or the tissue section 3264, such as, for example, magnetic sensors, such as a Hall effect sensor, strain gauges, pressure sensors, inductive sensors, such as an eddy current sensor, resistive sensors, capacitive sensors, optical sensors, and/or any other suitable sensors or combination thereof. The plurality of secondary sensors 3260a-3260d may comprise identical sensors and/or different sensors.

In some aspects, the plurality of secondary sensors 3260a-3260d comprises dual purpose sensors and tissue stabilizing elements. The plurality of secondary sensors 3260a-3260d comprise electrodes and/or sensing geometries configured to create a stabilized tissue condition when the plurality of secondary sensors 3260a-3260d are engaged with a tissue section 3264, such as, for example, during a clamping operation. In some aspects, one or more of the plurality of secondary sensors 3260a-3260d may be replaced with non-sensing tissue stabilizing elements. The secondary sensors 3260a-3260d create a stabilized tissue condition by controlling tissue flow, staple formation, and/or other tissue conditions during a clamping, stapling, and/or other treatment process.

Figure 65:
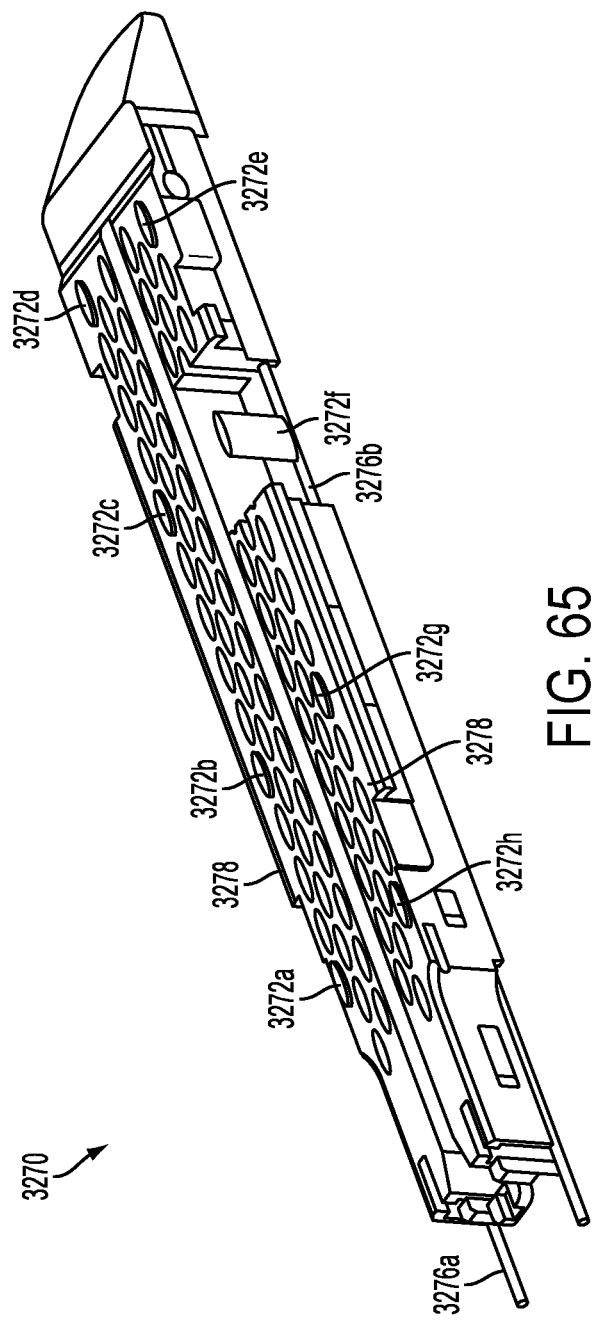
FIG. 65 illustrates one aspect of a staple cartridge comprising a plurality of sensors formed integrally therein in accordance with one or more aspects of the present disclosure.

FIG. 65 illustrates one aspect of a staple cartridge 3270 comprising a plurality of sensors 3272a-3272h formed integrally therein. The staple cartridge 3270 comprises a plurality of rows containing a plurality of holes for storing staples therein. One or more of the holes in the outer row 3278 are replaced with one of the plurality of sensors 3272a-3272h. A cut-away section 3274 is shown to illustrate a sensor 3272f coupled to a sensor wire 3276b. The sensor wires 3276a, 3276b may comprise a plurality of wires for coupling the plurality of sensors 3272a-3272h to one or more circuits of a surgical instrument, such as, for example, the surgical instrument 10. In some aspects, one or more of the plurality of sensors 3272a-3272h comprise dual purpose sensor and tissue stabilizing elements having electrodes and/or sensing geometries configured to provide tissue stabilization. In some aspects, the plurality of sensors 3272a-3272h may be replaced with and/or co-populated with a plurality of tissue stabilizing elements. Tissue stabilization may be provided by, for example, controlling tissue flow and/or staple formation during a clamping and/or stapling process. The plurality of sensors 3272a-3272h provide signals to one or more circuits of the surgical instrument 10 to enhance feedback of stapling performance and/or tissue thickness sensing.

Figure 66:
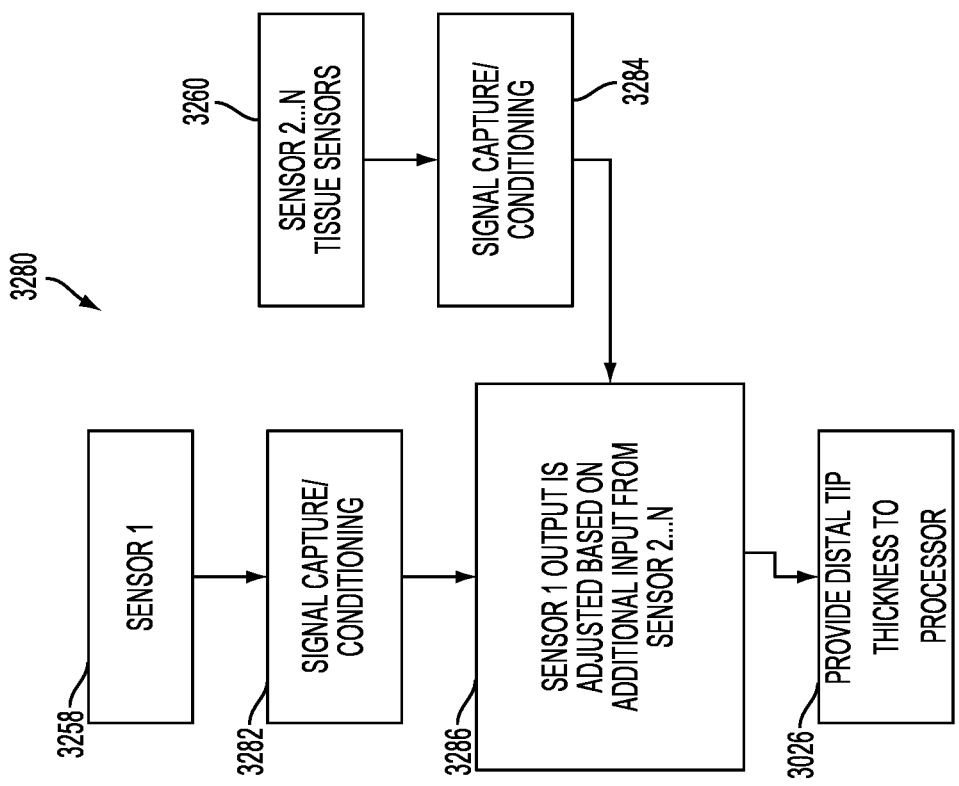
FIG. 66 is a logic diagram illustrating one aspect of a process for determining one or more parameters of a tissue section clamped within an end effector in accordance with one or more aspects of the present disclosure.

FIG. 66 is a logic diagram illustrating one aspect of a process 3280 for determining one or more parameters of a tissue section 3264 clamped within an end effector, such as, for example, the end effector 3250 illustrated in FIG. 64. In one aspect, a first sensor 3258 is configured to detect one or more parameters of the end effector 3250 and/or a tissue section 3264 located between the anvil 3252 and the staple cartridge 3256. A first signal is generated 3282 by the first sensors 3258. The first signal is indicative of the one or more parameters detected by the first sensor 3258. One or more secondary sensors 3260 are configured to detect one or more parameters of the end effector 3250 and/or the tissue section 3264. The secondary sensors 3260 may be configured to detect the same parameters, additional parameters, or different parameters as the first sensor 3258. Secondary signals 3284 are generated by the secondary sensors 3260. The secondary signals 3284 are indicative of the one or more parameters detected by the secondary sensors 3260. The first signal and the secondary signals are provided to a processor, such as, for example, a primary processor 2006. The primary processor 2006 adjusts 3286 the first signal generated by the first sensor 3258 based on input generated by the secondary sensors 3260. The adjusted signal may be indicative of, for example, the true thickness of a tissue section 3264 and the fullness of the bite. The adjusted signal is displayed 3026 to an operator by, for example, a display 2026 embedded in the surgical instrument 10.

Figure 67:
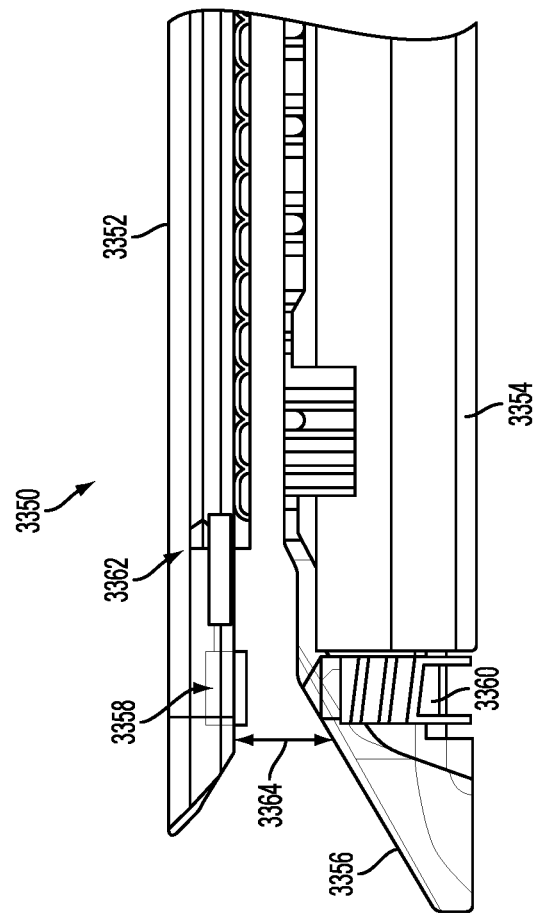
FIG. 67 illustrates one aspect of an end effector comprising a sensor comprising a specific sampling rate to limit or eliminate false signals in accordance with one or more aspects of the present disclosure.

FIG. 67 illustrates one aspect of an end effector 3350 comprising a magnetic sensor 3358 comprising a specific sampling rate to limit or eliminate false signals. The end effector 3350 comprises a anvil, or anvil, 3352 pivotably coupled to a jaw member 3354. The jaw member 3354 is configured to receive a staple cartridge 3356 therein. The staple cartridge 3356 contains a plurality of staples that may be delivered to a tissue section located between the anvil 3352 and the staple cartridge 3356. A magnetic sensor 3358 is coupled to the anvil 3352. The magnetic sensor 3358 is configured to detect one or more parameters of the end effector 3350, such as, for example, the gap 3364 between the anvil 3352 and the staple cartridge 3356. The gap 3364 may correspond to the thickness of a material, such as, for example, a tissue section, and/or the fullness of a bite of material located between the anvil 3352 and the staple cartridge 3356. The magnetic sensor 3358 may comprise any suitable sensor for detecting one or more parameters of the end effector 3350, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

In one aspect, the magnetic sensor 3358 comprises a magnetic sensor configured to detect a magnetic field generated by an electromagnetic source 3360 coupled to the jaw member 3354 and/or the staple cartridge 3356. The electromagnetic source 3360 generates a magnetic field detected by the magnetic sensor 3358. The strength of the detected magnetic field may correspond to, for example, the thickness and/or fullness of a bite of tissue located between the anvil 3352 and the staple cartridge 3356. In some aspects, the electromagnetic source 3360 generates a signal at a known frequency, such as, for example, 1 MHz. In other aspects, the signal generated by the electromagnetic source 3360 may be adjustable based on, for example, the type of staple cartridge 3356 installed in the jaw member 3354, one or more additional sensor, an algorithm, and/or one or more parameters.

In one aspect, a signal processor 3362 is coupled to the end effector 3350, such as, for example, the anvil 3352. The signal processor 3362 is configured to process the signal generated by the magnetic sensor 3358 to eliminate false signals and to boost the input from the magnetic sensor 3358. In some aspects, the signal processor 3362 may be located separately from the end effector 3350, such as, for example, in the handle assembly 14 of a surgical instrument 10. In some aspects, the signal processor 3362 is formed integrally with and/or comprises an algorithm executed by a general processor, such as, for example, the primary processor 2006. The signal processor 3362 is configured to process the signal from the magnetic sensor 3358 at a frequency substantially equal to the frequency of the signal generated by the electromagnetic source 3360. For example, in one aspect, the electromagnetic source 3360 generates a signal at a frequency of 1 MHz. The signal is detected by the magnetic sensor 3358. The magnetic sensor 3358 generates a signal indicative of the detected magnetic field which is provided to the signal processor 3362. The signal is processed by the signal processor 3362 at a frequency of 1 MHz to eliminate false signals. The processed signal is provided to a processor, such as, for example, the primary processor 2006. The primary processor 2006 correlates the received signal to one or more parameters of the end effector 3350, such as, for example, the gap 3364 between the anvil 3352 and the staple cartridge 3356.

FIG. 68 is a logic diagram illustrating one aspect of a process 3370 for generating a thickness measurement for a tissue section located between an anvil and a staple cartridge of an end effector, such as, for example, the end effector 3350 illustrated in FIG. 45. In one aspect of the process 3370, a signal is generated 3372 by a modulated electromagnetic source 3360. The generated signal may comprise, for example, a 1 MHz signal. A magnetic sensor 3358 is configured to detect 3374 the signal generated by the electromagnetic source 3360. The magnetic sensor 3358 generates a signal indicative of the detected magnetic field and provides the signal to a signal processor 3362. The signal processor 3362 processes 3376 the signal to remove noise, false signals, and/or to boost the signal. The processed signal is provided to an analog-to-digital convertor for conversion 3378 to a digital signal. Calibration 3380 of the digital signal may be performed, for example, by application of a calibration curve input algorithm and/or look-up table. The processes 3376, conversion 3378, and calibration 3380 may be performed by one or more circuits. The calibrated signal is displayed 3026 to a user by, for example, a display 2026 formed integrally with the surgical instrument 10.

FIGS. 69A and 69B illustrate one aspect of an end effector 3800 comprising a pressure sensor. The end effector 3800 comprises a anvil, or anvil, 3802 pivotally coupled to a jaw member 3804. The jaw member 3804 is configured to receive a staple cartridge 3806 therein. The staple cartridge 3806 comprises a plurality of staples. A first sensor 3808 is coupled to the anvil 3802 at a distal tip. The first sensor 3808 is configured to detect one or more parameters of the end effector, such as, for example, the distance, or gap 3814, between the anvil 3802 and the staple cartridge 3806. The first sensor 3808 may comprise any suitable sensor, such as, for example, a magnetic sensor. A magnet 3810 may be coupled to the jaw member 3804 and/or the staple cartridge 3806 to provide a magnetic signal to the magnetic sensor.

In some aspects, the end effector 3800 comprises a second sensor 3812. The second sensor 3812 is configured to detect one or more parameters of the end effector 3800 and/or a tissue section located therebetween. The second sensor 3812 may comprise any suitable sensor, such as, for example, one or more pressure sensors. The second sensor 3812 may be coupled to the anvil 3802, the jaw member 3804, and/or the staple cartridge 3806. A signal from the second sensor 3812 may be used to adjust the measurement of the first sensor 3808 to adjust the reading of the first sensor to accurately represent proximal and/or distal positioned partial bites true compressed tissue thickness. In some aspects, the second sensor 3812 may be surrogate with respect to the first sensor 3808.

In some aspects, the second sensor 3812 may comprise, for example, a single continuous pressure sensing film and/or an array of pressure sensing films. The second sensor 3812 is coupled to the deck of the staple cartridge 3806 along the central axis covering, for example, a slot 3816 configured to receive a cutting and/or staple deployment member. The second sensor 3812 provides signals indicate of the amplitude of pressure applied by the tissue during a clamping procedure. During firing of the cutting and/or deployment member, the signal from the second sensor 3812 may be severed, for example, by cutting electrical connections between the second sensor 3812 and one or more circuits. In some aspects, a severed circuit of the second sensor 3812 may be indicative of a spent staple cartridge 3806. In other aspects, the second sensor 3812 may be positioned such that deployment of a cutting and/or deployment member does not sever the connection to the second sensor 3812.

FIG. 70 illustrates one aspect of an end effector 3850 comprising a second sensor 3862 located between a staple cartridge 3806 and a jaw member 3804. The end effector 3850 comprises a anvil, or anvil, 3852 pivotally coupled to a jaw member 3854. The jaw member 3854 is configured to receive a staple cartridge 3856 therein. A first sensor 3858 is coupled to the anvil 3852 at a distal tip. The first sensor 3858 is configured to detect one or more parameters of the end effector 3850, such as, for example, the distance, or gap 3864, between the anvil 3852 and the staple cartridge 3856. The first sensor 3858 may comprise any suitable sensor, such as, for example, a magnetic sensor. A magnet 3860 may be coupled to the jaw member 3854 and/or the staple cartridge 3856 to provide a magnetic signal to the magnetic sensor. In some aspects, the end effector 3850 comprises a second sensor 3862 similar in all respect to the second sensor 3812 of FIGS. 69A-69B, except that it is located between the staple cartridge 3856 and the jaw member 3854.

FIG. 71 is a logic diagram illustrating one aspect of a process 3870 for determining and displaying the thickness of a tissue section clamped in an end effector 3800 or 3850, according to FIGS. 69A-69B or FIG. 70. The process comprises obtaining a Hall effect voltage 3872, for example, through a Hall effect sensor located at the distal tip of the anvil 3802. The Hall effect voltage 3872 is proved to an analog to digital converter 3876 and converted into a digital signal. The digital signal is provided to a process, such as for example the primary processor 2006. The primary processor 2006 calibrates 3874 the curve input of the Hall effect voltage 3872 signal. Pressure sensors, such as for example, second sensor 3812, is configured to measure 3880 one or more parameters of, for example, the end effector 3800, such as for example the amount of pressure being exerted by the anvil 3802 on the tissue clamped in the end effector 3800. In some aspects the pressure sensors may comprise a single continuous pressure sensing film and/or array of pressure sensing films. The pressure sensors may thus be operable determine variations in the measure pressure at different locations between the proximal and distal ends of the end effector 3800. The measured pressure is provided to the processor, such as for example the primary processor 2006. The primary processor 2006 uses one or more algorithms and/or lookup tables to adjust 3882 the Hall effect voltage 3872 in response to the pressure measured 3880 by the pressure sensors to more accurately reflect the thickness of the tissue clamped between, for example, the anvil 3802 and the staple cartridge 3806. The adjusted thickness is displayed 3878 to an operator by, for example, a display 2026 embedded in the surgical instrument 10.

Figure 72:
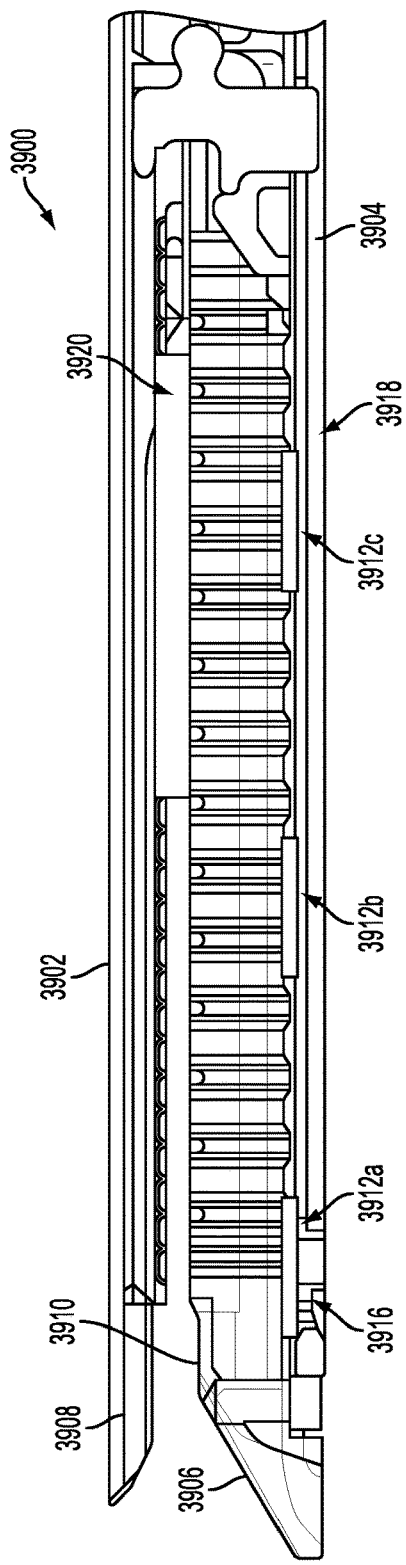
FIG. 72 illustrates one aspect of an end effector comprising a plurality of second sensors located between a staple cartridge and an elongated channel in accordance with one or more aspects of the present disclosure.

FIG. 72 illustrates one aspect of an end effector 3900 comprising a plurality of second sensors 3192a-3192b located between a staple cartridge 3906 and an elongated channel 3904. The end effector 3900 comprises an anvil 3902 pivotally coupled to a jaw member or elongated channel 3904. The elongated channel 3904 is configured to receive a staple cartridge 3906 therein. The anvil 3902 further comprises a first sensor 3908 located in the distal tip. The first sensor 3908 is configured to detect one or more parameters of the end effector 3900, such as, for example, the distance, or gap, between the anvil 3902 and the staple cartridge 3906. The first sensor 3908 may comprise any suitable sensor, such as, for example, a magnetic sensor. A magnet 3910 may be coupled to the elongated channel 3904 and/or the staple cartridge 3906 to provide a magnetic signal to the first sensor 3908. In some aspects, the end effector 3900 comprises a plurality of second sensors 3912a-3912c located between the staple cartridge 3906 and the elongated channel 3904. The second sensors 3912a-3912c may comprise any suitable sensors, such as for instance piezoresistive pressure film strips. In some aspects, the second sensors 3912a-3912c may be uniformly distributed between the distal and proximal ends of the end effector 3900.

In some aspects, signals from the second sensors 3912a-3912c may be used to adjust the measurement of the first sensor 3908. For instance, the signals from the second sensors 3912a-3912c may be used to adjust the reading of the first sensor 3908 to accurately represent the gap between the anvil 3902 and the staple cartridge 3906, which may vary between the distal and proximal ends of the end effector 3900, depending on the location and/or density of tissue 3920 between the anvil 3902 and the staple cartridge 3906. FIG. 11 illustrates an example of a partial bite of tissue 3920. As illustrated for purposes of this example, the tissue is located only in the proximal area of the end effector 3900, creating a high pressure 3918 area near the proximal area of the end effector 3900 and a corresponding low pressure 3916 area near the distal end of the end effector.

Figure 73B:
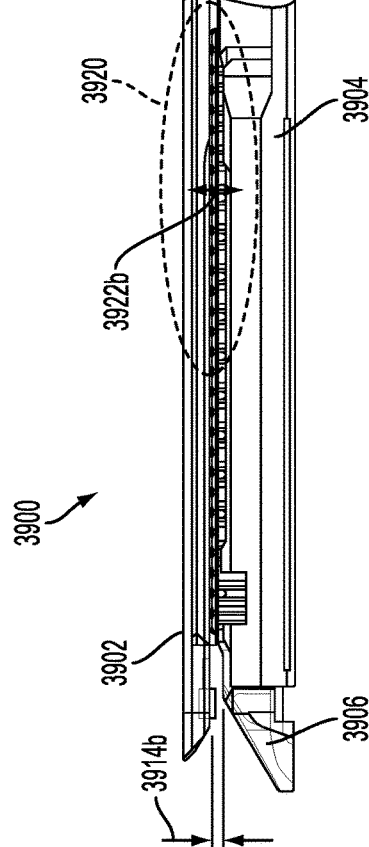
FIGS. 73A and 73B further illustrate the effect of a full versus partial bite of tissue in accordance with one or more aspects of the present disclosure.
Figure 73A:
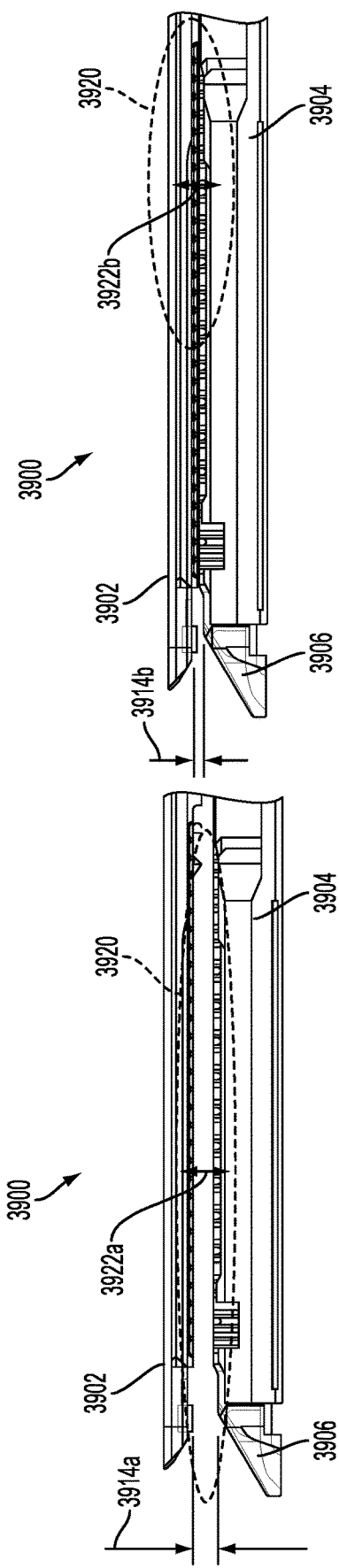

FIGS. 73A and 73B further illustrate the effect of a full versus partial bite of tissue 3920. FIG. 73A illustrates the end effector 3900 with a full bite of tissue 3920, where the tissue 3920 is of uniform density. With a full bite of tissue 3920 of uniform density, the measured first gap 3914a at the distal tip of the end effector 3900 may be approximately the same as the measured second gap 3922a in the middle or proximal end of the end effector 3900. For example, the first gap 3914a may measure 2.4 mm, and the second gap may measure 2.3 mm. FIG. 73B illustrates an end effector 3900 with a partial bite of tissue 3920, or alternatively a full bit of tissue 3920 of non-uniform density. In this case, the first gap 3914b will measure less than the second gap 3922b measured at the thickest or densest portion of the tissue 3920. For example, the first gap may measure 1.0 mm, while the second gap may measure 1.9 mm. In the conditions illustrated in FIGS. 73A-73B, signals from the second sensors 3912a-3912c, such as for instance measured pressure at different points along the length of the end effector 3900, may be employed by the instrument to determine tissue 3920 placement and/or material properties of the tissue 3920. The instrument may further be operable to use measured pressure over time to recognize tissue characteristics and tissue position, and dynamically adjust tissue thickness measurements.

FIG. 74 illustrates an aspect of an end effector 4050 that is configured to determine the location of a cutting member or knife 4062. The end effector 4050 comprises an anvil 4052 pivotally coupled to a jaw member or elongated channel 4054. The elongated channel 4054 is configured to receive a staple cartridge 4056 therein. The staple cartridge 4056 further comprises a slot (not shown) and a cutting member or knife 4062 located therein. The knife 4062 is operably coupled to a knife bar 4064. The knife bar 4064 is operable to move the knife 4062 from the proximal end of the slot to the distal end. The end effector 4050 may further comprise an optical sensor 4060 located near the proximal end of the slot. The optical sensor may be coupled to a processor, such as for instance the primary processor 2006. The optical sensor 4060 may be operable to emit an optical signal towards the knife bar 4064. The knife bar 4064 may further comprise a code strip 4066 along its length. The code strip 4066 may comprise cut-outs, notches, reflective pieces, or any other configuration that is optically readable. The code strip 4066 is placed such that the optical signal from the optical sensor 4060 will reflect off or through the code strip 4066. As the knife 4062 moves and knife bar 4064 moves 4068 along the slot 4058, the optical sensor 4060 will detect the reflection of the emitted optical signal coupled to the code strip 4066. The optical sensor 4060 may be operable to communicate the detected signal to the primary processor 2006. The primary processor 2006 may be configured to use the detected signal to determine the position of the knife 4062. The position of the knife 4062 may be sensed more precisely by designing the code strip 4066 such that the detected optical signal has a gradual rise and fall.

FIG. 75 illustrates an example of the code strip 4066 in operation with red LEDs 4070 and infrared LEDs 4072. For purposes of this example only, the code strip 4066 comprises cut-outs. As the code strip 4066 moves 4068, the light emitted by the red LEDs 4070 will be interrupted as the cut-outs passed before it. The infrared LEDs 4072 will therefore detect the motion of the code strip 4066, and therefore, by extension, the motion of the knife 4062.

Figure 76:
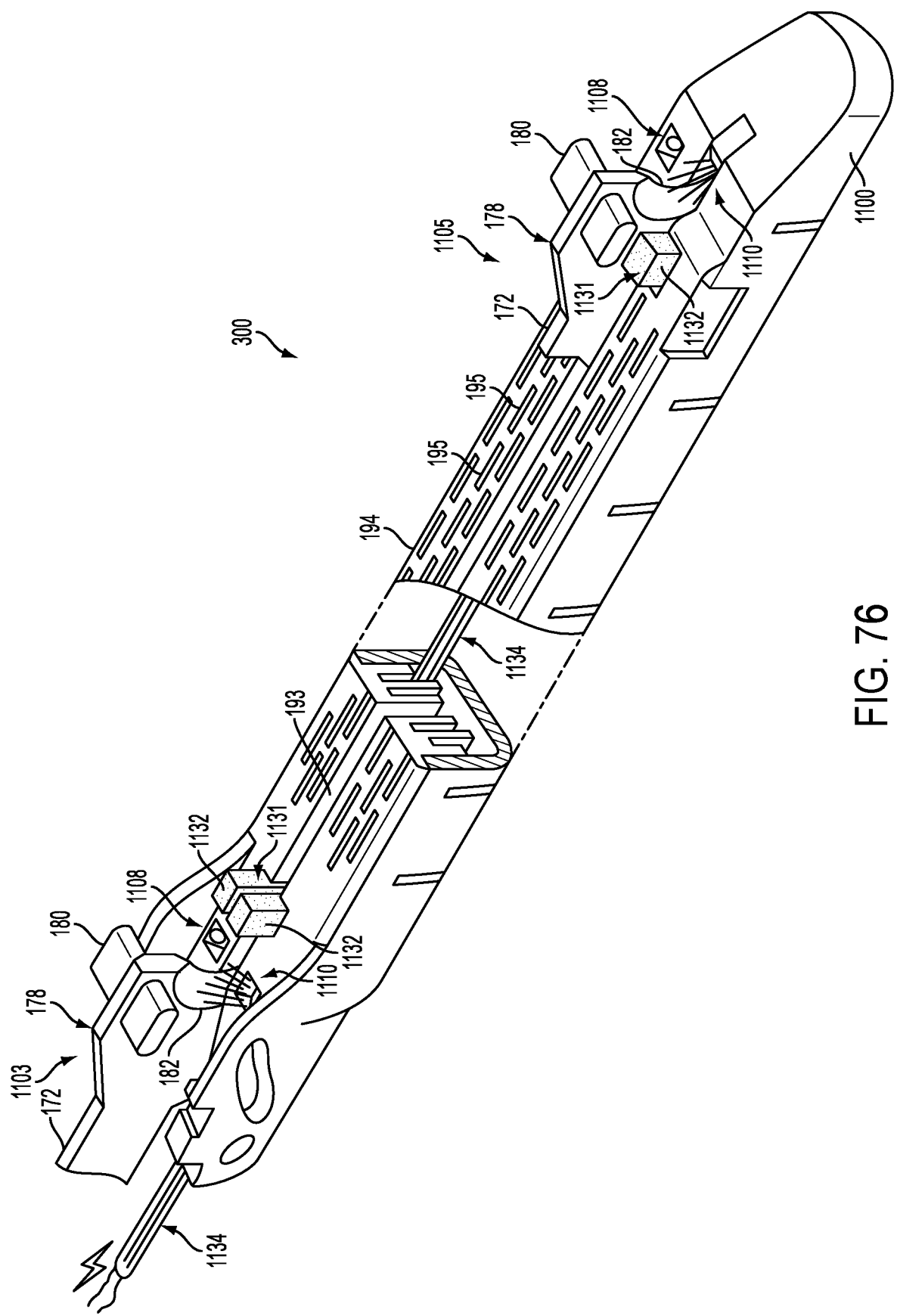
FIG. 76 illustrates a partial perspective view of an end effector of a surgical instrument comprising a staple cartridge in accordance with one or more aspects of the present disclosure.

FIG. 76 depicts a partial view of the end effector 300 of the surgical instrument 10. In the example form depicted in FIG. 76, the end effector 300 comprises a staple cartridge 1100 which is similar in many respects to the surgical staple cartridge 304 (FIG. 15). Several parts of the end effector 300 are omitted to enable a clearer understanding of the present disclosure. In certain instances, the end effector 300 may include a first jaw such as, for example, the anvil 306 (FIG. 20) and a second jaw such as, for example, the elongated channel 198 (FIG. 14). In certain instances, as described above, the elongated channel 198 may accommodate a staple cartridge such as, for example, the surgical staple cartridge 304 or the staple cartridge 1100, for example. At least one of the elongated channel 198 and the anvil 306 may be movable relative to the other one of the elongated channel 198 and the anvil 306 to capture tissue between the staple cartridge 1100 and the anvil 306. Various actuation assemblies are described herein to facilitation motion of the elongated channel 198 and/or the anvil 306 between an open configuration (FIG. 1) and a closed configuration (FIG. 77), for example.

In certain instances, as described above, the E-beam 178 can be advanced distally to deploy the staples 191 into the captured tissue and/or advance the cutting edge 182 between a plurality of positions to engage and cut the captured tissue. As illustrated in FIG. 76, the cutting edge 182 can be advanced distally along a path defined by the slot 193, for example. In certain instances, the cutting edge 182 can be advanced from a proximal portion 1103 of the staple cartridge 1100 to a distal portion 1105 of the staple cartridge 1100 to cut the captured tissue. In certain instances, the cutting edge 182 can be retracted proximally from the distal portion 1105 to the proximal portion 1103 by retraction of the E-beam 178 proximally, for example.

In certain instances, the cutting edge 182 can be employed to cut tissue captured by the end effector 300 in multiple procedures. The reader will appreciate that repetitive use of the cutting edge 182 may affect the sharpness of the cutting edge 182. The reader will also appreciate that as the sharpness of the cutting edge 182 decreases, the force required to cut the captured tissue with the cutting edge 182 may increase. Referring to FIGS. 78-83, in certain instances, the surgical instrument 10 may comprise a circuit 1106 (FIG. 78) for monitoring the sharpness of the cutting edge 182 during, before, and/or after operation of the surgical instrument 10 in a surgical procedure, for example. In certain instances, the circuit 1106 can be employed to test the sharpness of the cutting edge 182 prior to utilizing the cutting edge 182 to cut the captured tissue. In certain instances, the circuit 1106 can be employed to test the sharpness of the cutting edge 182 after the cutting edge 182 has been used to cut the captured tissue. In certain instances, the circuit 1106 can be employed to test the sharpness of the cutting edge 182 prior to and after the cutting edge 182 is used to cut the captured tissue. In certain instances, the circuit 1106 can be employed to test the sharpness of the cutting edge 182 at the proximal portion 1103 and/or at the distal portion 1105.

Referring to FIGS. 78-83, the circuit 1106 may include one or more sensors such as, for example, an optical sensor 1108; the optical sensor 1108 of the circuit 1106 can be employed to test the reflective ability of the cutting edge 182, for example. In certain instances, the ability of the cutting edge 182 to reflect light may correlate with the sharpness of the cutting edge 182. In other words, a decrease in the sharpness of the cutting edge 182 may result in a decrease in the ability of the cutting edge 182 to reflect the light. Accordingly, in certain instances, the dullness of the cutting edge 182 can be evaluated by monitoring the intensity of the light reflected from the cutting edge 182, for example. In certain instances, the optical sensor 1108 may define a light sensing region. The optical sensor 1108 can be oriented such that the optical sensing region is disposed in the path of the cutting edge 182, for example. The optical sensor 1108 may be employed to sense the light reflected from the cutting edge 182 while the cutting edge 182 is in the optical sensing region, for example. A decrease in intensity of the reflected light beyond a threshold can indicate that the sharpness of the cutting edge 182 has decreased beyond an acceptable level.

Referring again to FIGS. 78-83, the circuit 1106 may include one or more lights sources such as, for example, a light source 1110. In certain instances, the circuit 1106 may include a controller 1112 ("microcontroller") which may be operably coupled to the optical sensor 1108, as illustrated in FIGS. 78-83. In certain instances, the controller 1112 may include a processor 1114 ("microprocessor") and one or more computer readable mediums or memory 1116 ("memory units"). In certain instances, the memory 1116 may store various program instructions, which when executed may cause the processor 1114 to perform a plurality of functions and/or calculations described herein. In certain instances, the memory 1116 may be coupled to the processor 1114, for example. A power source 1118 can be configured to supply power to the controller 1112, the optical sensors 1108, and/or the light sources 1110, for example. In certain instances, the power source 1118 may comprise a battery (or "battery pack" or "power pack"), such as a Li ion battery, for example. In certain instances, the battery pack may be configured to be releasably mounted to the handle assembly 14 for supplying power to the surgical instrument 10. A number of battery cells connected in series may be used as the power source 4428. In certain instances, the power source 1118 may be replaceable and/or rechargeable, for example.

The controller 1112 and/or other controllers of the present disclosure may be implemented using integrated and/or discrete hardware elements, software elements, and/or a combination of both. Examples of integrated hardware elements may include processors, microprocessors, controllers, integrated circuits, ASICs, PLDs, DSPs, FPGAs, logic gates, registers, semiconductor devices, chips, microchips, chip sets, controllers, SoC, and/or SIP. Examples of discrete hardware elements may include circuits and/or circuit elements such as logic gates, field effect transistors, bipolar transistors, resistors, capacitors, inductors, and/or relays. In certain instances, the controller 1112 may include a hybrid circuit comprising discrete and integrated circuit elements or components on one or more substrates, for example. In certain instances, the controller 1112 and/or other controllers of the present disclosure may be a single core or multicore controller LM4F230H5QR as described in connection with FIGS. 14-17B.

In certain instances, the light source 1110 can be employed to emit light which can be directed at the cutting edge 182 in the optical sensing region, for example. The optical sensor 1108 may be employed to measure the intensity of the light reflected from the cutting edge 182 while in the optical sensing region in response to exposure to the light emitted by the light source 1110. In certain instances, the processor 1114 may receive one or more values of the measured intensity of the reflected light and may store the one or more values of the measured intensity of the reflected light on the memory 1116, for example. The stored values can be detected and/or recorded before, after, and/or during a plurality of surgical procedures performed by the surgical instrument 10, for example.

In certain instances, the processor 1114 may compare the measured intensity of the reflected light to a predefined threshold values that may be stored on the memory 1116, for example. In certain instances, the controller 1112 may conclude that the sharpness of the cutting edge 182 has dropped below an acceptable level if the measured light intensity exceeds the predefined threshold value by 1%, 5%, 10%, 25%, 50%, 100% and/or more than 100%, for example. In certain instances, the processor 1114 can be employed to detect a decreasing trend in the stored values of the measured intensity of the light reflected from the cutting edge 182 while in the optical sensing region.

In certain instances, the surgical instrument 10 may include one or more feedback systems such as, for example, the feedback system 1120. In certain instances, the processor 1114 can employ the feedback system 1120 to alert a user if the measured light intensity of the light reflected from cutting edge 182 while in the optical sensing region is beyond the stored threshold value, for example. In certain instances, the feedback system 1120 may comprise one or more visual feedback systems such as display screens, backlights, and/or LEDs, for example. In certain instances, the feedback system 1120 may comprise one or more audio feedback systems such as speakers and/or buzzers, for example. In certain instances, the feedback system 1120 may comprise one or more haptic feedback systems, for example. In certain instances, the feedback system 1120 may comprise combinations of visual, audio, and/or tactile feedback systems, for example.

Figure 78:
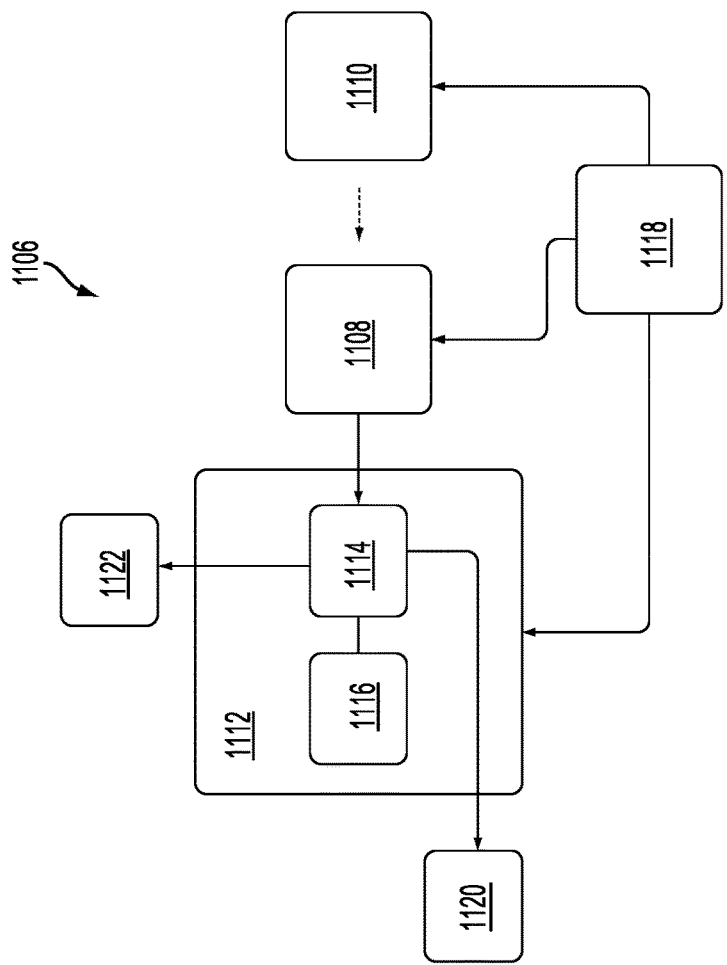
FIG. 78 illustrates a logic diagram of a module of the surgical instrument of FIG. 76 in accordance with one or more aspects of the present disclosure.

In certain instances, the surgical instrument 10 may comprise a firing lockout mechanism 1122 which can be employed to prevent advancement of the cutting edge 182. Various suitable firing lockout mechanisms are described in greater detail in U.S. Patent Application Publication No. 2014/0001231, entitled FIRING SYSTEM LOCKOUT ARRANGEMENTS FOR SURGICAL INSTRUMENTS, which is herein incorporated by reference in its entirety. In certain instances, as illustrated in FIG. 78, the processor 1114 can be operably coupled to the firing lockout mechanism 1122; the processor 1114 may employ the firing lockout mechanism 1122 to prevent advancement of the cutting edge 182 in the event it is determined that the measured intensity of the light reflected from the cutting edge 182 is beyond the stored threshold, for example. In other words, the processor 1114 may activate the firing lockout mechanism 1122 if the cutting edge is not sufficiently sharp to cut the tissue captured by the end effector 300.

In certain instances, the optical sensor 1108 and the light source 1110 can be housed at a distal portion of the interchangeable shaft assembly 200. In certain instances, the sharpness of cutting edge 182 can be evaluated by the optical sensor 1108, as described above, prior to transitioning the cutting edge 182 into the end effector 300. The firing bar 172 (FIG. 14) may advance the cutting edge 182 through the optical sensing region defined by the optical sensor 1108 while the cutting edge 182 is in the interchangeable shaft assembly 200 and prior to entering the end effector 300, for example. In certain instances, the sharpness of cutting edge 182 can be evaluated by the optical sensor 1108 after retracting the cutting edge 182 proximally from the end effector 300. The firing bar 172 (FIG. 14) may retract the cutting edge 182 through the optical sensing region defined by the optical sensor 1108 after retracting the cutting edge 182 from the end effector 300 into the interchangeable shaft assembly 200, for example.

In certain instances, the optical sensor 1108 and the light source 1110 can be housed at a proximal portion of the end effector 300 which can be proximal to the staple cartridge 1100, for example. The sharpness of cutting edge 182 can be evaluated by the optical sensor 1108 after transitioning the cutting edge 182 into the end effector 300 but prior to engaging the staple cartridge 1100, for example. In certain instances, the firing bar 172 (FIG. 14) may advance the cutting edge 182 through the optical sensing region defined by the optical sensor 1108 while the cutting edge 182 is in the end effector 300 but prior to engaging the staple cartridge 1100, for example.

In various instances, the sharpness of cutting edge 182 can be evaluated by the optical sensor 1108 as the cutting edge 182 is advanced by the firing bar 172 through the slot 193. As illustrated in FIGS. 78-83, the optical sensor 1108 and the light source 1110 can be housed at the proximal portion 1103 of the staple cartridge 1100, for example; and the sharpness of cutting edge 182 can be evaluated by the optical sensor 1108 at the proximal portion 1103, for example. The firing bar 172 (FIG. 14) may advance the cutting edge 182 through the optical sensing region defined by the optical sensor 1108 at the proximal portion 1103 before the cutting edge 182 engages tissue captured between the staple cartridge 1100 and the anvil 306, for example. In certain instances, as illustrated in FIGS. 78-83, the optical sensor 1108 and the light source 1110 can be housed at the distal portion 1105 of the staple cartridge 1100, for example. The sharpness of cutting edge 182 can be evaluated by the optical sensor 1108 at the distal portion 1105. In certain instances, the firing bar 172 (FIG. 14) may advance the cutting edge 182 through the optical sensing region defined by the optical sensor 1108 at the distal portion 1105 after the cutting edge 182 has passed through the tissue captured between the staple cartridge 1100 and the anvil 306, for example.

Referring again to FIG. 76, the staple cartridge 1100 may comprise a plurality of optical sensors 1108 and a plurality of corresponding light sources 1110, for example. In certain instances, a pair of the optical sensor 1108 and the light source 1110 can be housed at the proximal portion 1103 of the staple cartridge 1100, for example; and a pair of the optical sensor 1108 and the light source 1110 can be housed at the distal portion 1105 of the staple cartridge 1100, for example. In such instances, the sharpness of the cutting edge 182 can be evaluated a first time at the proximal portion 1103 prior to engaging the tissue, for example, and a second time at the distal portion 1105 after passing through the captured tissue, for example.

The reader will appreciate that an optical sensor 1108 may evaluate the sharpness of the cutting edge 182 a plurality of times during a surgical procedure. For example, the sharpness of the cutting edge can be evaluated a first time during advancement of the cutting edge 182 through the slot 193 in a firing stroke, and a second time during retraction of the cutting edge 182 through the slot 193 in a return stroke, for example. In other words, the light reflected from the cutting edge 182 can be measured by the optical sensor 1108 once as the cutting edge is advanced through the optical sensing region, and once as the cutting edge 182 is retracted through the optical sensing region, for example.

The reader will appreciate that the processor 1114 may receive a plurality of readings of the intensity of the light reflected from the cutting edge 182 from one or more of the optical sensors 1108. In certain instances, the processor 1114 may be configured to discard outliers and calculate an average reading from the plurality of readings, for example. In certain instances, the average reading can be compared to a threshold stored in the memory 1116, for example. In certain instances, the processor 1114 may be configured to alert a user through the feedback system 1120 and/or activate the firing lockout mechanism 1122 if it is determined that the calculated average reading is beyond the threshold stored in the memory 1116, for example.

Figure 77:
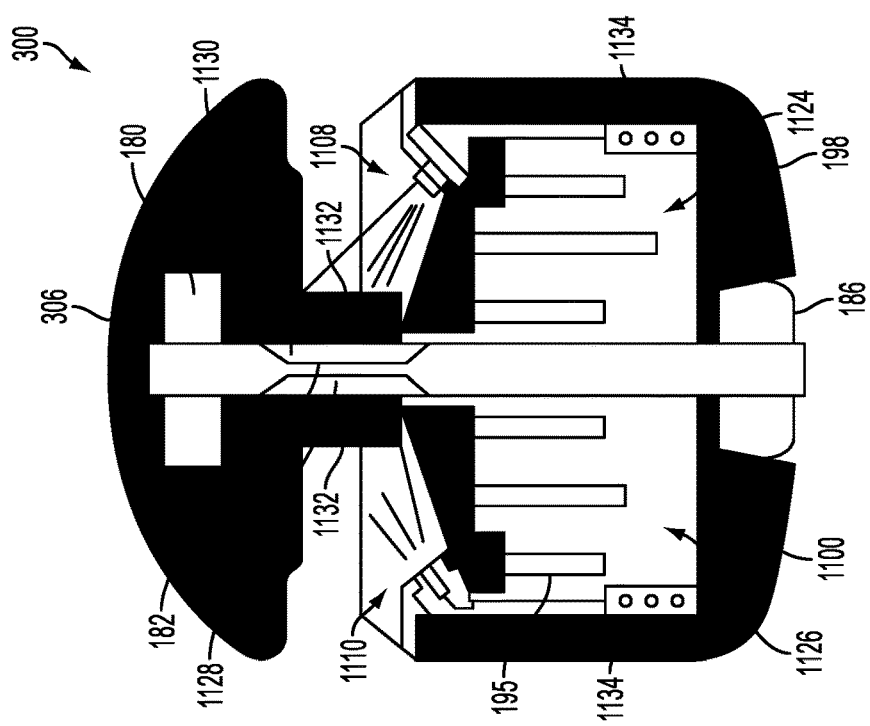
FIG. 77 illustrates an elevational view of a portion of the end effector of FIG. 76 in accordance with one or more aspects of the present disclosure.
Figure 79:
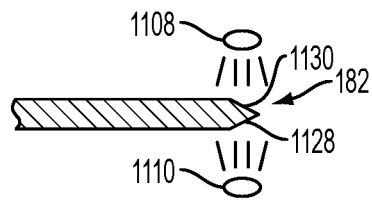
FIG. 79 illustrates a partial view of a cutting edge, an optical sensor, and a light source of the surgical instrument of FIG. 76 in accordance with one or more aspects of the present disclosure.
Figure 80:
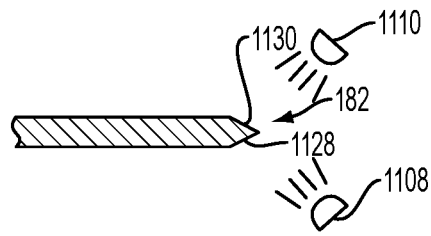
FIG. 80 illustrates a partial view of a cutting edge, an optical sensor, and a light source of the surgical instrument of FIG. 76 in accordance with one or more aspects of the present disclosure.

In certain instances, as illustrated in FIGS. 77, 79, and 80, a pair of the optical sensor 1108 and the light source 1110 can be positioned on opposite sides of the staple cartridge 1100. In other words, the optical sensor 1108 can be positioned on a first side 1124 of the slot 193, for example, and the light source 1110 can be positioned on a second side 1126, opposite the first side 1124, of the slot 193, for example. In certain instances, the pair of the optical sensor 1108 and the light source 1110 can be substantially disposed in a plane transecting the staple cartridge 1100, as illustrated in FIG. 77. The pair of the optical sensor 1108 and the light source 1110 can be oriented to define an optical sensing region that is positioned, or at least substantially positioned, on the plane transecting the staple cartridge 1100, for example. Alternatively, the pair of the optical sensor 1108 and the light source 1110 can be oriented to define an optical sensing region that is positioned proximal to the plane transecting the staple cartridge 1100, for example, as illustrated in FIG. 80.

Figure 81:
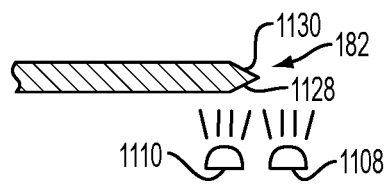
FIG. 81 illustrates a partial view of a cutting edge, an optical sensor, and a light source of the surgical instrument of FIG. 76 in accordance with one or more aspects of the present disclosure.

In certain instances, a pair of the optical sensor 1108 and the light source 1110 can be positioned on a same side of the staple cartridge 1100. In other words, as illustrated in FIG. 81, the pair of the optical sensor 1108 and the light source 1110 can be positioned on a first side of the cutting edge 182, e.g. the side 1128, as the cutting edge 182 is advanced through the slot 193. In such instances, the light source 1110 can be oriented to direct light at the side 1128 of the cutting edge 182; and the intensity of the light reflected from the side 1128, as measured by the optical sensor 1108, may represent the sharpness of the side 1128.

Figure 82:
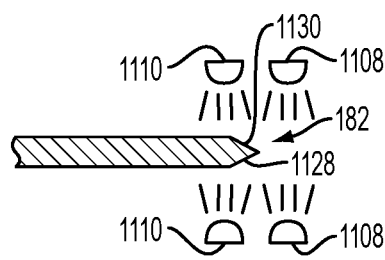
FIG. 82 illustrates a partial view of a cutting edge, optical sensors, and light sources of the surgical instrument of FIG. 76 in accordance with one or more aspects of the present disclosure.
Figure 83:
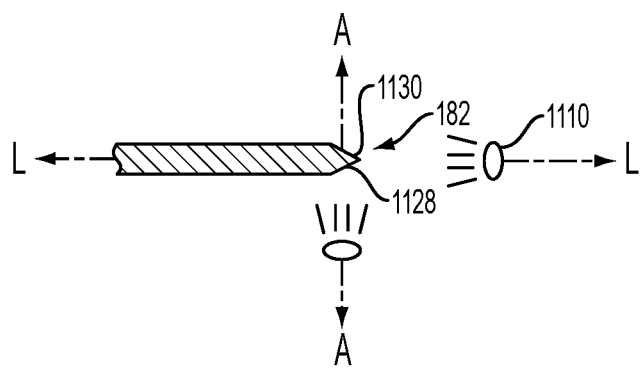
FIG. 83 illustrates a partial view of a cutting edge, an optical sensor, and a light source of the surgical instrument of FIG. 76 in accordance with one or more aspects of the present disclosure.

In certain instances, as illustrated in FIG. 82, a second pair of the optical sensor 1108 and the light source 1110 can be positioned on a second side of the cutting edge 182, e.g. the side 1130, for example. The second pair can be employed to evaluate the sharpness of the side 1130. For example, the light source 1110 of the second pair can be oriented to direct light at the side 1130 of the cutting edge 182; and the intensity of the light reflected from the side 1130, as measured by the optical sensor 1108 of the second pair, may represent the sharpness of the side 1130. In certain instances, the processor can be configured to assess the sharpness of the cutting edge 182 based upon the measured intensities of the light reflected from the sides 1128 and 1130 of the cutting edge 182, for example.

In certain instances, as illustrated in FIG. 77, a pair of the optical sensor 1108 and the light source 1110 can be housed at the distal portion 1105 of the staple cartridge 1100. As illustrated in FIG. 81, the optical sensor 1108 can be positioned, or at least substantially positioned, on an axis LL which extends longitudinally along the path of the cutting edge 182 through the slot 193, for example. In addition, the light source 1110 can be positioned distal to the cutting edge 182 and oriented to direct light at the cutting edge 182 as the cutting edge is advanced toward the light source 1110, for example. Furthermore, the optical sensor 1108 can be positioned, or at least substantially positioned, along an axis AA that intersects the axis LL, as illustrated in FIG. 81. In certain instances, the axis AA may be perpendicular to the axis LL, for example. In any event, the optical sensor 1108 can be oriented to define an optical sensing region at the intersection of the axis LL and the axis AA, for example.

The reader will appreciate that the position, orientation and/or number of optical sensors and corresponding light sources described herein in connection with the surgical instrument 10 are example aspects intended for illustration purposes. Various other arrangements of optical sensors and light sources can be employed by the present disclosure to evaluate the sharpness of the cutting edge 182.

The reader will appreciate that advancement of the cutting edge 182 through the tissue captured by the end effector 300 may cause the cutting edge to collect tissue debris and/or bodily fluids during each firing of the surgical instrument 10. Such debris may interfere with the ability of the circuit 1106 to accurately evaluate the sharpness of the cutting edge 182. In certain instances, the surgical instrument 10 can be equipped with one or more cleaning mechanisms which can be employed to clean the cutting edge 182 prior to evaluating the sharpness of the cutting edge 182, for example.

Referring to FIG. 76, in certain instances, the staple cartridge 1100 may include a first pair of the optical sensor 1108 and the light source 1110, which can be housed in the proximal portion 1103 of the staple cartridge 1100, for example. Furthermore, as illustrated in FIG. 76, the staple cartridge 1100 may include a first pair of the cleaning members 1132, which can be housed in the proximal portion 1103 on opposite sides of the slot 193. The first pair of the cleaning members 1132 can be positioned distal to the first pair of the optical sensor 1108 and the light source 1110, for example. As illustrated in FIG. 76, the staple cartridge 1100 may include a second pair of the optical sensor 1108 and the light source 1110, which can be housed in the distal portion 1105 of the staple cartridge 1100, for example. As illustrated in FIG. 76, the staple cartridge 1100 may include a second pair of the cleaning members 1132, which can be housed in the distal portion 1105 on opposite sides of the slot 193. The second pair of the cleaning members 1132 can be positioned proximal to the second pair of the optical sensor 1108 and the light source 1110.

Further to the above, as illustrated in FIG. 76, the cutting edge 182 may be advanced distally in a firing stroke to cut tissue captured by the end effector 300. As the cutting edge is advanced, a first evaluation of the sharpness of the cutting edge 182 can be performed by the first pair of the optical sensor 1108 and the light source 1110 prior to tissue engagement by the cutting edge 182, for example. A second evaluation of the sharpness of the cutting edge 182 can be performed by the second pair of the optical sensor 1108 and the light source 1110 after the cutting edge 182 has transected the captured tissue, for example. The cutting edge 182 may be advanced through the second pair of the cleaning members 1132 prior to the second evaluation of the sharpness of the cutting edge 182 to remove any debris collected by the cutting edge 182 during the transection of the captured tissue.

Further to the above, as illustrated in FIG. 76, the cutting edge 182 may be retracted proximally in a return stroke. As the cutting edge is retracted, a third evaluation of the sharpness of the cutting edge 182 can be performed by the first pair of the optical sensor 1108 and the light source 1110 during the return stroke. The cutting edge 182 may be retracted through the first pair of the cleaning members 1132 prior to the third evaluation of the sharpness of the cutting edge 182 to remove any debris collected by the cutting edge 182 during the transection of the captured tissue, for example.

In certain instances, one or more of the lights sources 1110 may comprise one or more optical fiber cables. In certain instances, one or more flex circuits 1134 can be employed to transmit energy from the power source 1118 to the optical sensors 1108 and/or the light sources 1110. In certain instances, the flex circuits 1134 may be configured to transmit one or more of the readings of the optical sensors 1108 to the controller 1112, for example.

Figure 84:
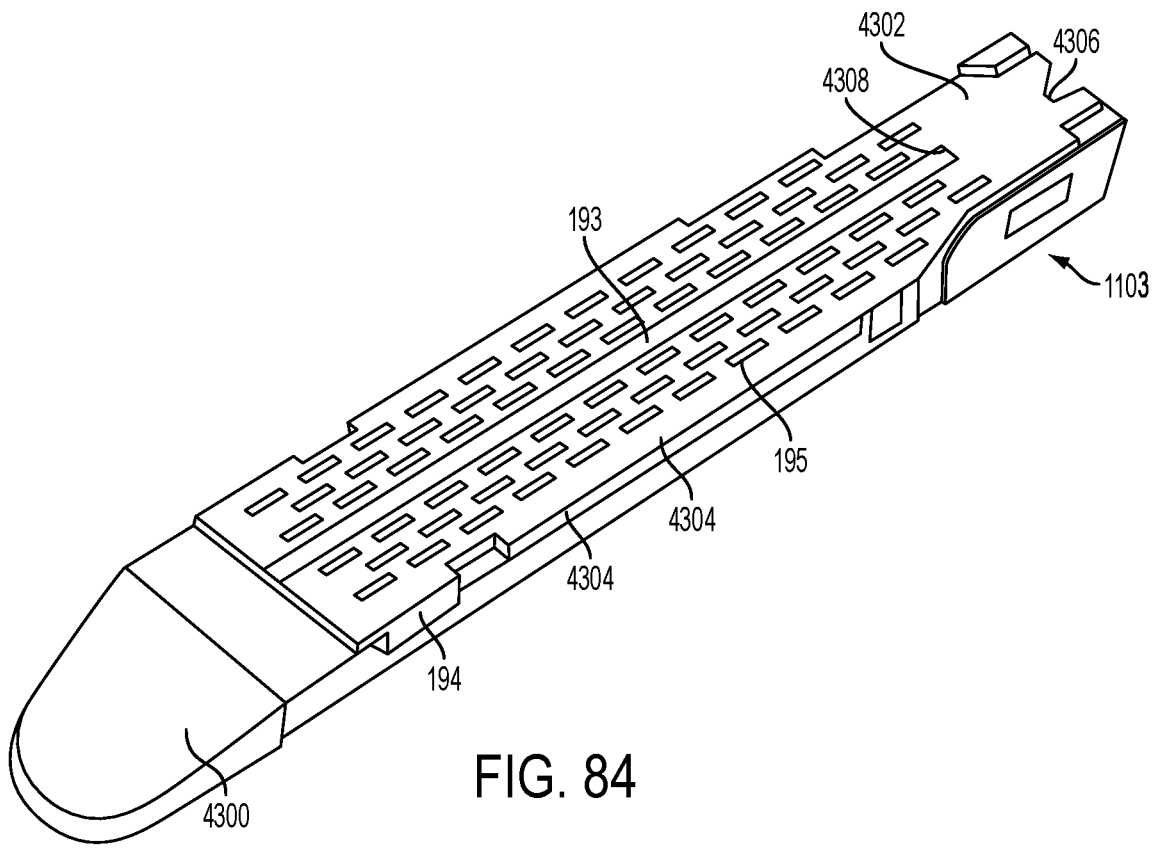
FIG. 84 illustrates a perspective view of a staple cartridge including a sharpness testing member in accordance with one or more aspects of the present disclosure.

Referring now to FIG. 84, a staple cartridge 4300 is depicted; the staple cartridge 4300 is similar in many respects to the surgical staple cartridge 304 (FIG. 14). For example, the staple cartridge 4300 can be employed with the end effector 300. In certain instances, as illustrated in FIG. 84, the staple cartridge 4300 may comprise a sharpness testing member 4302 which can be employed to test the sharpness of the cutting edge 182. In certain instances, the sharpness testing member 4302 can be attached to and/or integrated with the cartridge body 194 of the staple cartridge 4300, for example. In certain instances, the sharpness testing member 4302 can be disposed in the proximal portion 1103 of the staple cartridge 4300, for example. In certain instances, as illustrated in FIG. 84, the sharpness testing member 4302 can be disposed onto a cartridge deck 4304 of the staple cartridge 4300, for example.

In certain instances, as illustrated in FIG. 84, the sharpness testing member 4302 can extend across the slot 193 of the staple cartridge 4300 to bridge, or at least partially bridge, the gap defined by the slot 193, for example. In certain instances, the sharpness testing member 4302 may interrupt, or at least partially interrupt, the path of the cutting edge 182. The cutting edge 182 may engage, cut, and/or pass through the sharpness testing member 4302 as the cutting edge 182 is advanced during a firing stroke, for example. In certain instances, the cutting edge 182 may be configured to engage, cut, and/or pass through the sharpness testing member 4302 prior to engaging tissue captured by the end effector 300 in a firing stroke, for example. In certain instances, the cutting edge 182 may be configured to engage the sharpness testing member 4302 at a proximal end 4306 of the sharpness testing member 4302, and exit and/or disengage the sharpness testing member 4302 at a distal end 4308 of the sharpness testing member 4302, for example. In certain instances, the cutting edge 182 can travel and/or cut through the sharpness testing member 4302 a distance (D) between the proximal end 4306 and the distal end 4308, for example, as the cutting edge 182 is advanced during a firing stroke.

Figure 85:
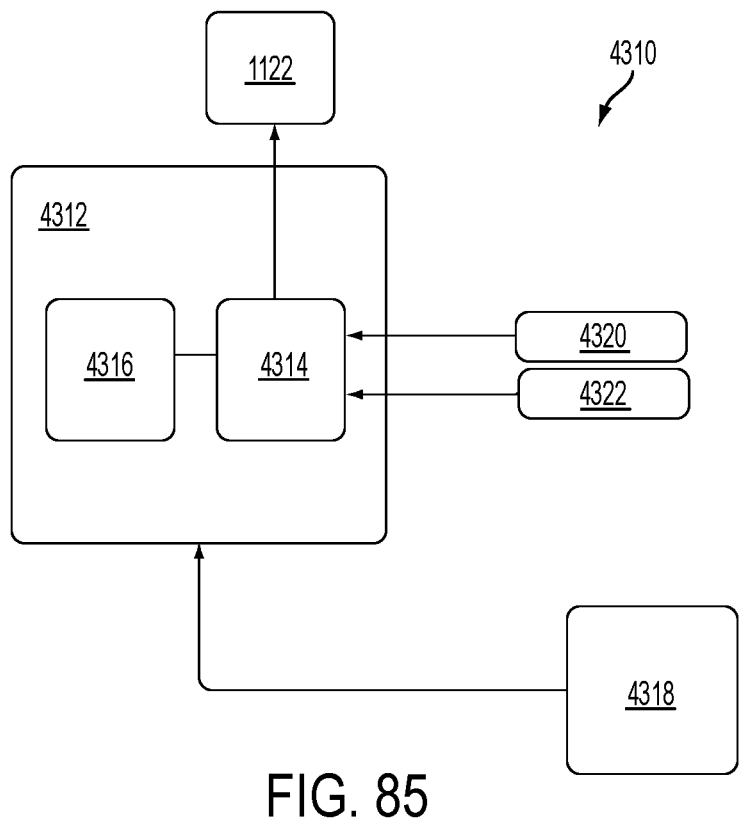
FIG. 85 illustrates a logic diagram of a module of a surgical instrument in accordance with one or more aspects of the present disclosure.

Referring primarily to FIGS. 84 and 85, the surgical instrument 10 may comprise a circuit 4310 for testing the sharpness of the cutting edge 182, for example. In certain instances, the circuit 4310 can evaluate the sharpness of the cutting edge 182 by testing the ability of the cutting edge 182 to be advanced through the sharpness testing member 4302. For example, the circuit 4310 can be configured to observe the time period the cutting edge 182 takes to fully transect and/or completely pass through at least a predetermined portion of the sharpness testing member 4302. If the observed time period exceeds a predetermined threshold, the circuit 4310 may conclude that the sharpness of the cutting edge 182 has dropped below an acceptable level, for example.

In certain instances, the circuit 4310 may include a controller 4312 ("microcontroller") which may include a processor 4314 ("microprocessor") and one or more computer readable mediums or memory 4316 units ("memory"). In certain instances, the memory 4316 may store various program instructions, which when executed may cause the processor 4314 to perform a plurality of functions and/or calculations described herein. In certain instances, the memory 4316 may be coupled to the processor 4314, for example. A power source 4318 can be configured to supply power to the controller 4312, for example. In certain instances, the power source 4138 may comprise a battery (or "battery pack" or "power pack"), such as a Li ion battery, for example. In certain instances, the battery pack may be configured to be releasably mounted to the handle assembly 14. A number of battery cells connected in series may be used as the power source 4318. In certain instances, the power source 4318 may be replaceable and/or rechargeable, for example.

In certain instances, the controller 4313 can be operably coupled to the feedback system 1120 and/or the firing lockout mechanism 1122, for example.

Referring to FIGS. 84 and 85, the circuit 4310 may comprise one or more position sensors. Example position sensors and positioning systems suitable for use with the present disclosure are described in U.S. Patent Application Publication No. 2014/0263538, entitled SENSOR ARRANGEMENTS FOR ABSOLUTE POSITIONING SYSTEM FOR SURGICAL INSTRUMENTS, now U.S. Pat. No. 9,808,244, which is herein incorporated by reference in its entirety. In certain instances, the circuit 4310 may include a first position sensor 4320 and a second position sensor 4322. In certain instances, the first position sensor 4320 can be employed to detect a first position of the cutting edge 182 at the proximal end 4306 of the sharpness testing member 4302, for example; and the second position sensor 4322 can be employed to detect a second position of the cutting edge 182 at the distal end 4308 of the sharpness testing member 4302, for example.

In certain instances, the first and second position sensors 4320, 4322 can be employed to provide first and second position signals, respectively, to the controller 4312. It will be appreciated that the position signals may be analog signals or digital values based on the interface between the controller 4312 and the first and second position sensors 4320, 4322. In one aspect, the interface between the controller 4312 and the first and second position sensors 4320, 4322 can be a standard serial peripheral interface (SPI), and the position signals can be digital values representing the first and second positions of the cutting edge 182, as described above.

Further to the above, the processor 4314 may determine the time period between receiving the first position signal and receiving the second position signal. The determined time period may correspond to the time it takes the cutting edge 182 to advance through the sharpness testing member 4302 from the first position at the proximal end 4306 of the sharpness testing member 4302, for example, to the second position at the distal end 4308 of the sharpness testing member 4302, for example. In at least one example, the controller 4312 may include a time element which can be activated by the processor 4314 upon receipt of the first position signal, and deactivated upon receipt of the second position signal. The time period between the activation and deactivation of the time element may correspond to the time it takes the cutting edge 182 to advance from the first position to the second position, for example. The time element may comprise a real time clock, a processor configured to implement a time function, or any other suitable timing circuit.

In various instances, the controller 4312 can compare the time period it takes the cutting edge 182 to advance from the first position to the second position to a predefined threshold value to assess whether the sharpness of the cutting edge 182 has dropped below an acceptable level, for example. In certain instances, the controller 4312 may conclude that the sharpness of the cutting edge 182 has dropped below an acceptable level if the measured time period exceeds the predefined threshold value by 1%, 5%, 10%, 25%, 50%, 100% and/or more than 100%, for example.

Figure 86:
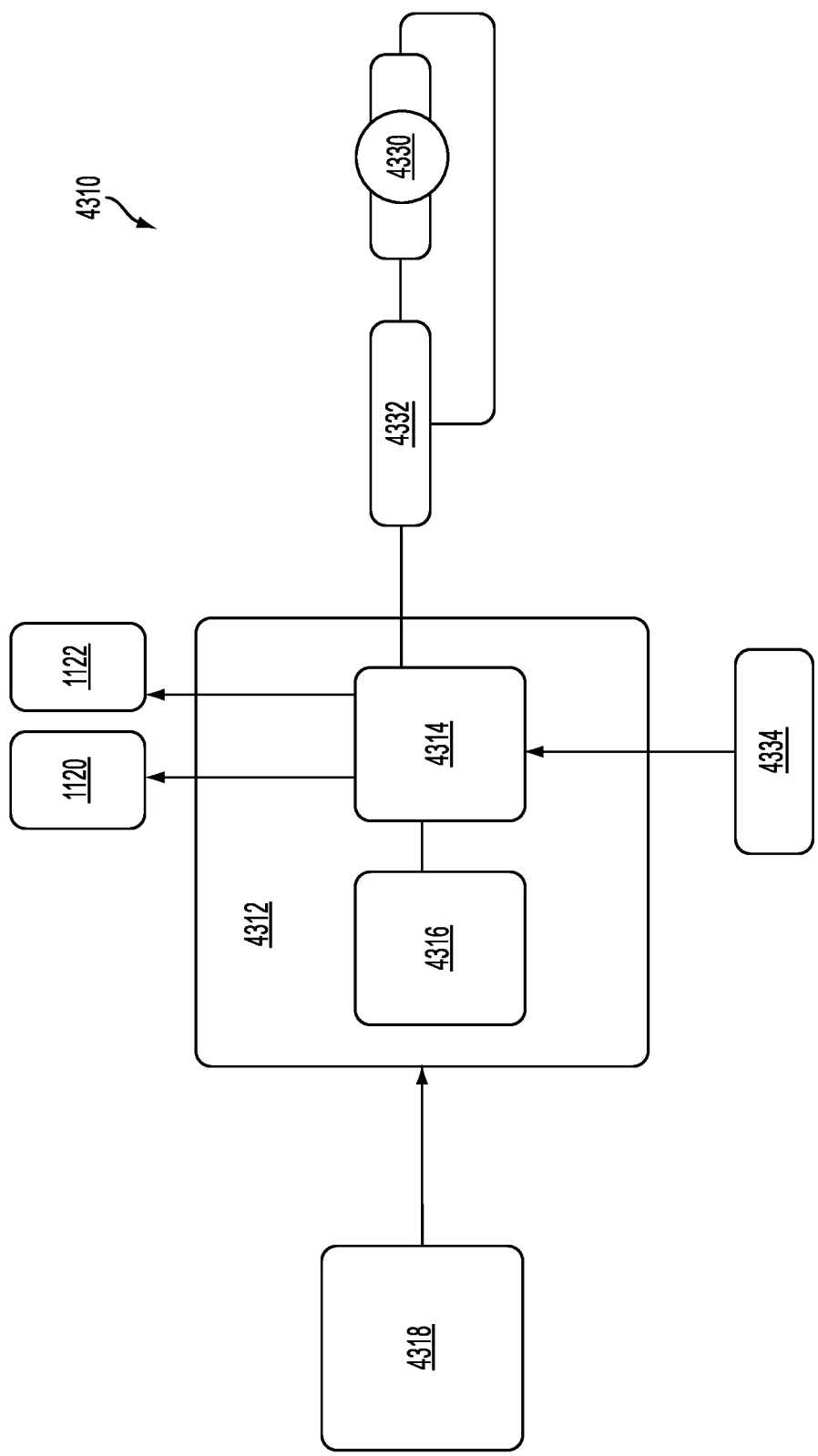
FIG. 86 illustrates a logic diagram of a module of a surgical instrument in accordance with one or more aspects of the present disclosure.

Referring to FIG. 86, in various instances, an electric motor 4330 can drive the firing bar 172 (FIG. 14) to advance the cutting edge 182 during a firing stroke and/or to retract the cutting edge 182 during a return stroke, for example. A motor driver 4332 can control the electric motor 4330; and a controller such as, for example, the controller 4312 can be in signal communication with the motor driver 4332. As the electric motor 4330 advances the cutting edge 182, the controller 4312 can determine the current drawn by the electric motor 4330, for example. In such instances, the force required to advance the cutting edge 182 can correspond to the current drawn by the electric motor 4330, for example. Referring still to FIG. 86, the controller 4312 of the surgical instrument 10 can determine if the current drawn by the electric motor 4330 increases during advancement of the cutting edge 182 and, if so, can calculate the percentage increase of the current.

In certain instances, the current drawn by the electric motor 4330 may increase significantly while the cutting edge 182 is in contact with the sharpness testing member 4302 due to the resistance of the sharpness testing member 4302 to the cutting edge 182. For example, the current drawn by the electric motor 4330 may increase significantly as the cutting edge 182 engages, passes and/or cuts through the sharpness testing member 4302. The reader will appreciate that the resistance of the sharpness testing member 4302 to the cutting edge 182 depends, in part, on the sharpness of the cutting edge 182; and as the sharpness of the cutting edge 182 decreases from repetitive use, the resistance of the sharpness testing member 4302 to the cutting edge 182 will increase. Accordingly, the value of the percentage increase of the current drawn by the electric motor 4330 while the cutting edge is in contact with the sharpness testing member 4302 can increase as the sharpness of the cutting edge 182 decreases from repetitive use, for example.

In certain instances, the determined value of the percentage increase of the current drawn by the electric motor 4330 can be the maximum detected percentage increase of the current drawn by the electric motor 4330. In various instances, the controller 4312 can compare the determined value of the percentage increase of the current drawn by the electric motor 4330 to a predefined threshold value of the percentage increase of the current drawn by the electric motor 4330. If the determined value exceeds the predefined threshold value, the controller 4312 may conclude that the sharpness of the cutting edge 182 has dropped below an acceptable level, for example.

In certain instances, as illustrated in FIG. 86, the processor 4314 can be in communication with the feedback system 1120 and/or the firing lockout mechanism 1122, for example. In certain instances, the processor 4314 can employ the feedback system 1120 to alert a user if the determined value of the percentage increase of the current drawn by the electric motor 4330 exceeds the predefined threshold value, for example. In certain instances, the processor 4314 may employ the firing lockout mechanism 1122 to prevent advancement of the cutting edge 182 if the determined value of the percentage increase of the current drawn by the electric motor 4330 exceeds the predefined threshold value, for example.

In various instances, the controller 4312 can utilize an algorithm to determine the change in current drawn by the electric motor 4330. For example, a current sensor can detect the current drawn by the electric motor 4330 during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Figure 87:
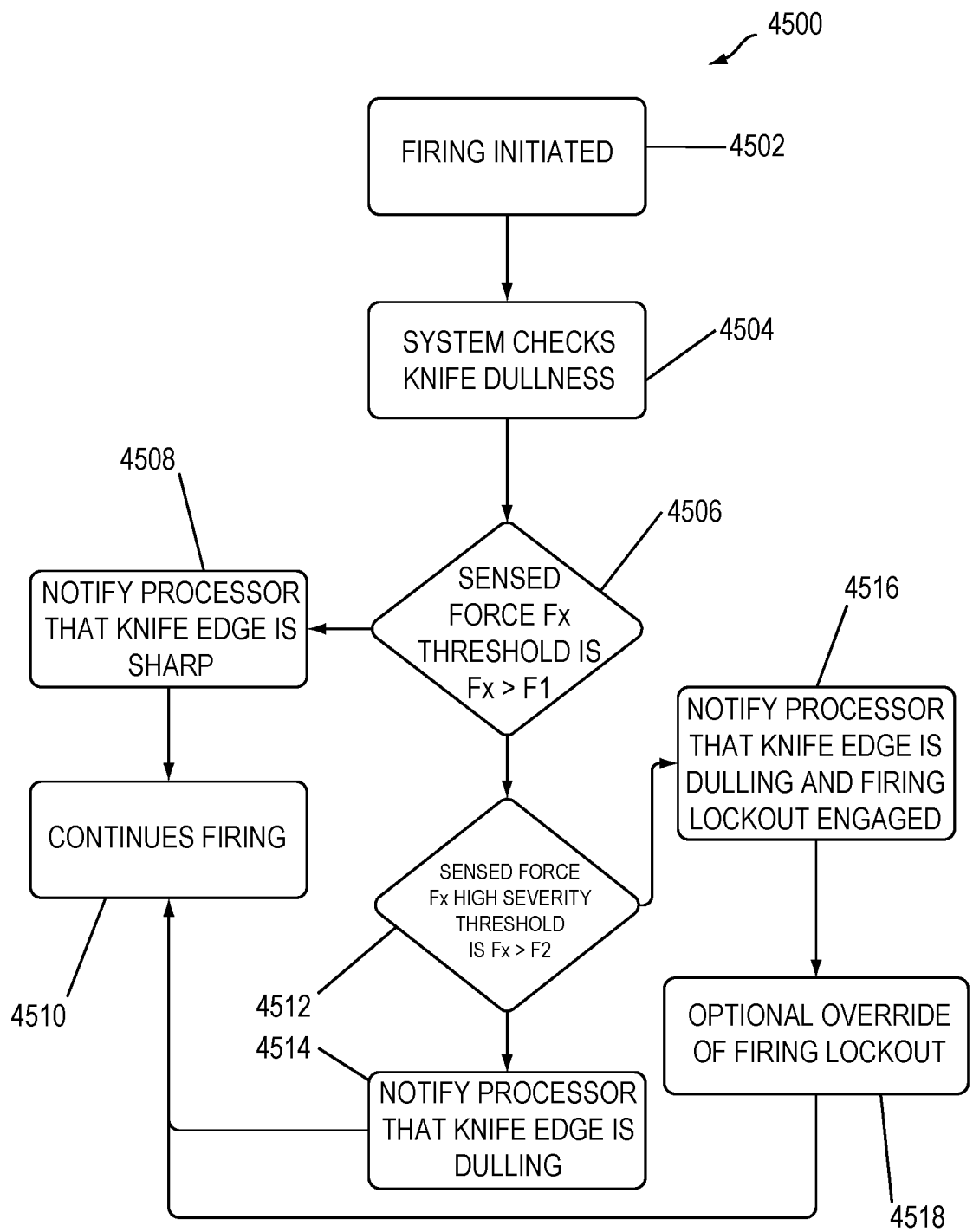
FIG. 87 illustrates a logic diagram outlining a method for evaluating sharpness of a cutting edge of a surgical instrument in accordance with one or more aspects of the present disclosure.

Referring to FIG. 87, a method 4500 is depicted for evaluating the sharpness of the cutting edge 182 of the surgical instrument 10; and various responses are outlined in the event the sharpness of the cutting edge 182 drops to and/or below an alert threshold and/or a high severity threshold, for example. In various instances, a controller such as, for example, the controller 4312 can be configured to implement the method depicted in FIG. 85. In certain instances, the surgical instrument 10 may include a load cell 4334 (FIG. 86); as illustrated in FIG. 84, the controller 4312 may be in communication with the load cell 4334. In certain instances, the load cell 4334 may include a force sensor such as, for example, a strain gauge, which can be operably coupled to the firing bar 172, for example. In certain instances, the controller 4312 may employ the load cell 4334 to monitor the force (Fx) applied to the cutting edge 182 as the cutting edge 182 is advanced during a firing stroke.

Accordingly, when the knife firing is initiated 4502 the system checks 4504 the dullness of the cutting edge 182 of the knife by sensing a force Fx. The sensed force Fx is compared to a threshold force F1 and determines 4506 whether the sensed force Fx is greater than the threshold force F1. When the sensed force Fx is less than or equal to the threshold force F1, the process proceeds along NO branch and displays 4508 nothing and continues 4510 the knife firing process. When the sensed force Fx is greater than the threshold force F1, the process proceeds along YES branch and determines 4512 whether the sensed force Fx exceeds a high severity threshold force F2. When the sensed force Fx is less than or equal to the threshold F2, the process proceeds along NO branch and notifies 4514 the processor that the cutting edge 182 of the knife is dulling and the continues 4510 the knife firing process. When the sensed force Fx is greater than the threshold F2, the process proceeds along YES branch and notifies 4516 the processor that the cutting edge 182 of the knife is dulled and the knife firing lockout is engaged. Subsequently, optionally, the processor may override 4518 the knife firing lockout and continues 4510 the knife firing process if the lockout is overridden.

Figure 88:
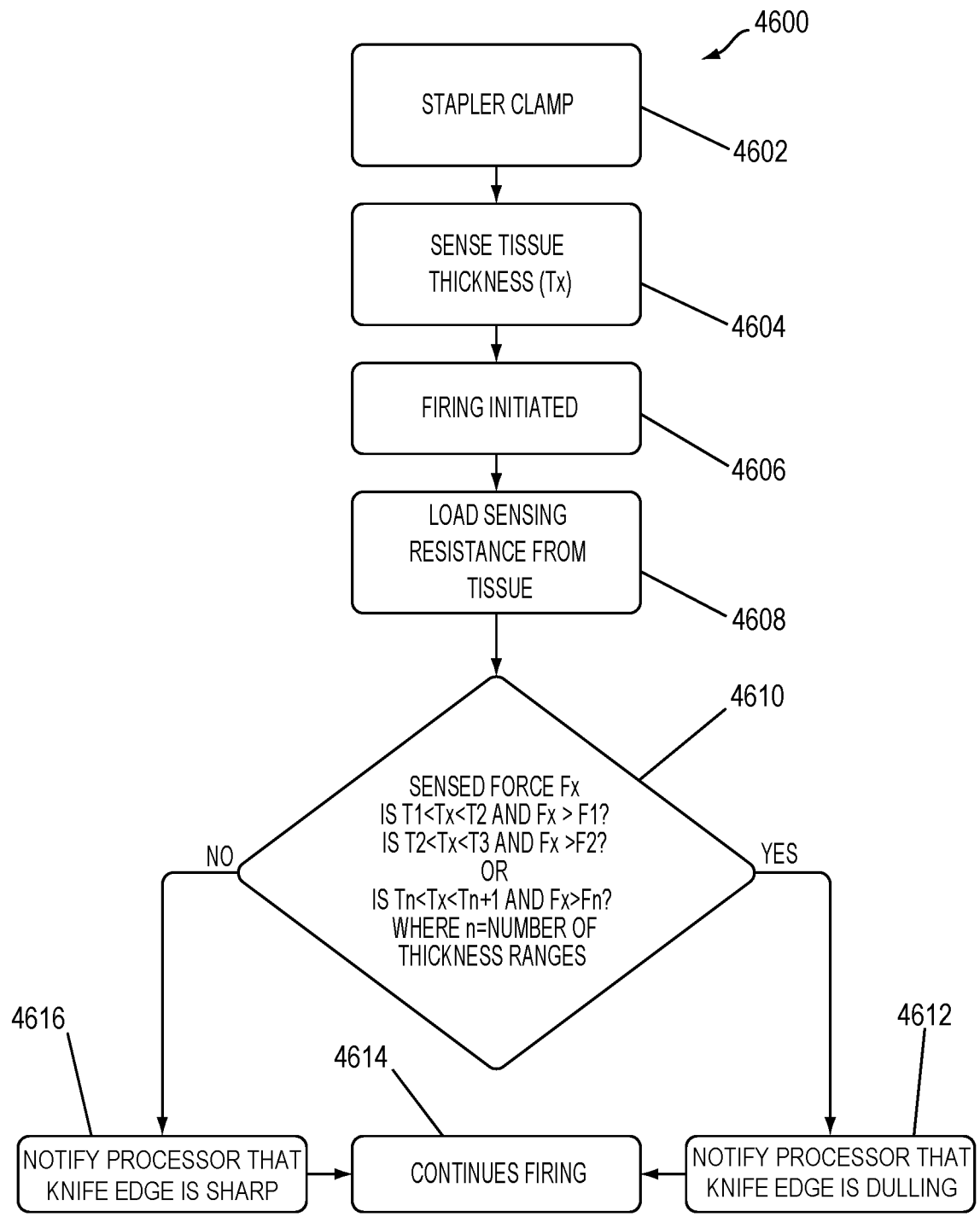
FIG. 88 illustrates a flow chart outlining a method for determining whether a cutting edge of a surgical instrument is sufficiently sharp to transect tissue captured by the surgical instrument in accordance with one or more aspects of the present disclosure.

Referring to FIG. 88, a method 4600 is depicted for determining whether a cutting edge such as, for example, the cutting edge 182 is sufficiently sharp to be employed in transecting a tissue of a particular tissue thickness that is captured by the end effector 300, for example. As described above, repetitive use of the cutting edge 182 may dull or reduce the sharpness of the cutting edge 182 which may increase the force required for the cutting edge 182 to transect the captured tissue. In other words, the sharpness level of the cutting edge 182 can be defined by the force required for the cutting edge 182 to transect the captured tissue, for example. The reader will appreciate that the force required for the cutting edge 182 to transect a captured tissue may also depend on the thickness of the captured tissue. In certain instances, the greater the thickness of the captured tissue, the greater the force required for the cutting edge 182 to transect the captured tissue at the same sharpness level, for example.

Accordingly, initially, the stapler clamps 4602 the tissue between the anvil and the jaw member. The system senses 4604 the tissue thickness Tx and initiates 4606 the knife firing process. Upon initiating the knife firing process, the system senses 4608 the load resistance from the clamped tissue and compares the sensed force Fx and senses thickness Tx against various thresholds and determines 4610 several outcomes based on the evaluation. In one aspect, when the process determines 4610 whether the sensed tissue thickness Tx is within a first tissue thickness range defined between a first tissue thickness threshold T1 and a second tissue thickness threshold T2 AND the sensed force Fx is greater than a first force threshold F1 AND the process determines 4610 whether the sensed tissue thickness Tx is within a second tissue thickness range defined between the second tissue thickness threshold T2 and a third tissue thickness threshold T3 AND the sensed force Fx is greater than a second force threshold F2, the process proceeds along the YES branch and notifies 4612 or alerts the processor that the knife is dulling and then continues 4614 the knife firing process. Otherwise, the process proceeds along the NO branch and the does not notify 4616 the processor and continues the knife firing process. Generally, the process determines whether the sensed tissue thickness Tx is within a tissue thickness range defined between tissue thickness thresholds Tn and Tn+1 AND the sensed force Fx is greater than a force threshold Tn, where n indicates a tissue thickness range. When the process determines 4610 that the sensed tissue thickness Tx is within a first tissue thickness range defined between a first tissue thickness threshold T1 and a second tissue thickness threshold T2 AND the sensed force Fx is greater than a first force threshold F1 AND when the process determines 4610 that the sensed tissue thickness Tx is within a second tissue thickness range defined between the second tissue thickness threshold T2 and a third tissue thickness threshold T3 AND the sensed force Fx is greater than a second force threshold F2, the process continues.

In certain instances, the cutting edge 182 may be sufficiently sharp for transecting a captured tissue comprising a first thickness but may not be sufficiently sharp for transecting a captured tissue comprising a second thickness greater than the first thickness, for example. In certain instances, a sharpness level of the cutting edge 182, as defined by the force required for the cutting edge 182 to transect a captured tissue, may be adequate for transecting the captured tissue if the captured tissue comprises a tissue thickness that is in a particular range of tissue thicknesses, for example.

Figures 89, 90:
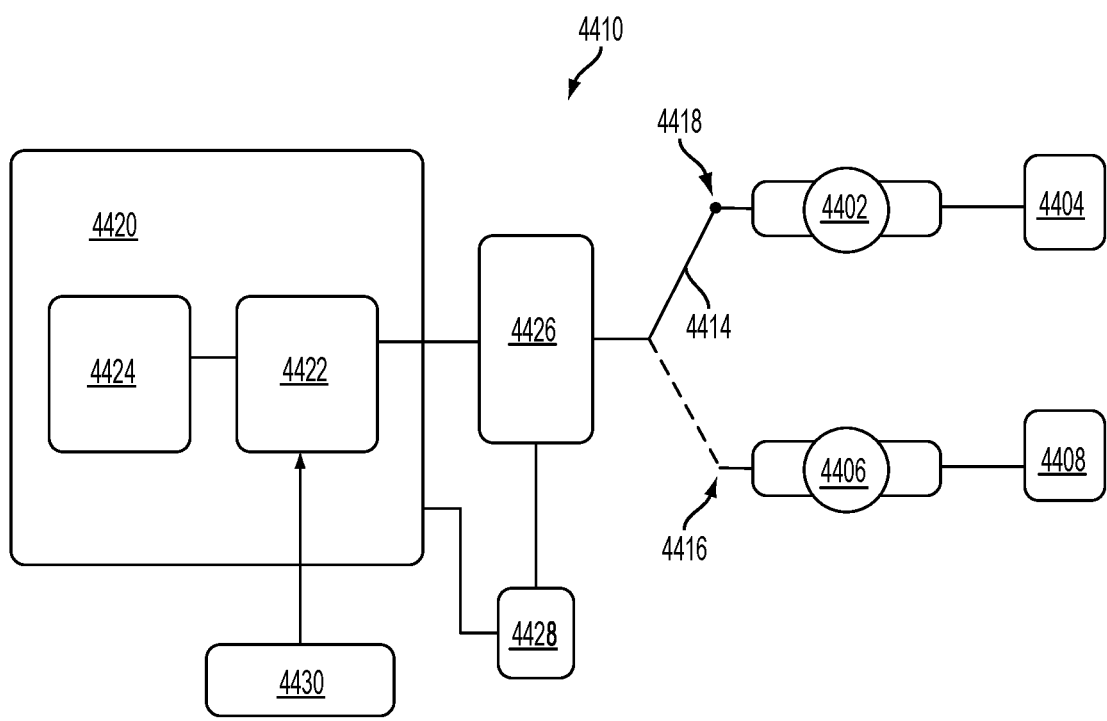
FIG. 89 illustrates a table showing predefined tissue thicknesses and corresponding predefined threshold forces in accordance with one or more aspects of the present disclosure.
FIG. 90 illustrates a logic diagram of a common controller for use with a plurality of motors of a surgical instrument in accordance with one or more aspects of the present disclosure.

In certain instances, as illustrated in FIG. 89, the memory 4316 can store one or more predefined ranges of tissue thicknesses of tissue captured by the end effector 300; and predefined threshold forces associated with the predefined ranges of tissue thicknesses. In certain instances, each predefined threshold force may represent a minimum sharpness level of the cutting edge 182 that is suitable for transecting a captured tissue comprising a tissue thickness (Tx) encompassed by the range of tissue thicknesses that is associated with the predefined threshold force. In certain instances, if the force (Fx) required for the cutting edge 182 to transect the captured tissue, comprising the tissue thickness (Tx), exceeds the predefined threshold force associated with the predefined range of tissue thicknesses that encompasses the tissue thickness (Tx), the cutting edge 182 may not be sufficiently sharp to transect the captured tissue, for example.

In certain instances, the predefined threshold forces and their corresponding predefined ranges of tissue thicknesses can be stored in a database and/or a table on the memory 4316 such as, for example, a table 4342, as illustrated in FIG. 89. In certain instances, the processor 4314 can be configured to receive a measured value of the force (Fx) required for the cutting edge 182 to transect a captured tissue and a measured value of the tissue thickness (Tx) of the captured tissue. The processor 4314 may access the table 4342 to determine the predefined range of tissue thicknesses that encompasses the measured tissue thickness (Tx). In addition, the processor 4314 may compare the measured force (Fx) to the predefined threshold force associated with the predefined range of tissue thicknesses that encompasses the tissue thickness (Tx). In certain instances, if the measured force (Fx) exceeds the predefined threshold force, the processor 4314 may conclude that the cutting edge 182 may not be sufficiently sharp to transect the captured tissue, for example.

Further to the above, the processor 4314 (FIGS. 85, 86) may employ one or more tissue thickness sensing modules such as, for example, a tissue thickness sensing module 4336 to determine the thickness of the captured tissue. Various suitable tissue thickness sensing modules are described in the present disclosure. In addition, various tissue thickness sensing devices and methods, which are suitable for use with the present disclosure, are disclosed in U.S. Patent Application Publication No. 2011/0155781, entitled SURGICAL CUTTING INSTRUMENT THAT ANALYZES TISSUE THICKNESS, now U.S. Pat. No. 8,851,354, which is herein incorporated by reference in its entirety.

In certain instances, the processor 4314 may employ the load cell 4334 to measure the force (Fx) required for the cutting edge 182 to transect a captured tissue comprising a tissue thickness (Tx). The reader will appreciate that that the force applied to the cutting edge 182 by the captured tissue, while the cutting edge 182 is engaged and/or in contact with the captured tissue, may increase as the cutting edge 182 is advanced against the captured tissue up to the force (Fx) at which the cutting edge 182 may transect the captured tissue. In certain instances, the processor 4314 may employ the load cell 4334 to continually monitor the force applied by the captured tissue against the cutting edge 182 as the cutting edge 182 is advanced against the captured tissue. The processor 4314 may continually compare the monitored force to the predefined threshold force associated with the predefined tissue thickness range encompassing the tissue thickness (Tx) of the captured tissue. In certain instances, if the monitored force exceeds the predefined threshold force, the processor 4314 may conclude that the cutting edge is not sufficiently sharp to safely transect the captured tissue, for example.

The method 4600 described in FIG. 88 outline various example actions that can be taken by the controller 4313 in the event it is determined that the cutting edge 182 is not be sufficiently sharp to safely transect the captured tissue, for example. In certain instances, the controller 4312 may warn the user that the cutting edge 182 is too dull for safe use, for example, through the feedback system 1120, for example. In certain instances, the controller 4312 may employ the firing lockout mechanism 1122 to prevent advancement of the cutting edge 182 upon concluding that the cutting edge 182 is not sufficiently sharp to safely transect the captured tissue, for example. In certain instances, the controller 4312 may employ the feedback system 1120 to provide instructions to the user for overriding the firing lockout mechanism 1122, for example.

Figure 91:
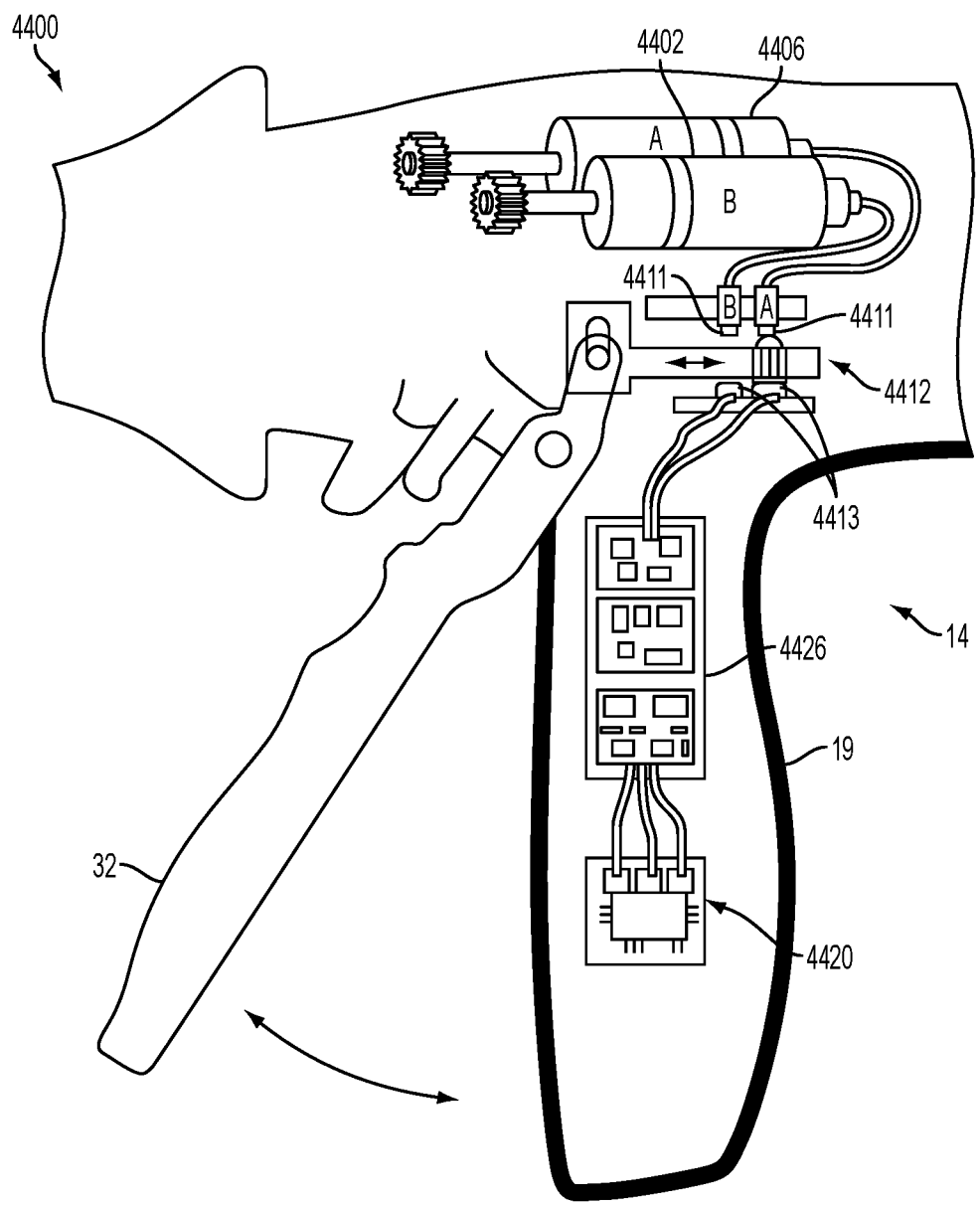
FIG. 91 illustrates a partial elevational view of the handle of the surgical instrument with a removed outer casing in accordance with one or more aspects of the present disclosure.

FIGS. 90, 91 illustrate various aspects of an apparatus, system, and method for employing a common controller with a plurality of motors in connection with a surgical instrument such as, for example, a motor-driven surgical instrument 4400. The surgical instrument 4400 is similar in many respects to other surgical instruments described by the present disclosure such as, for example, the surgical instrument 10 of FIG. 1 which is described in greater detail above. The surgical instrument 4400 includes the housing 12, the handle assembly 14, the closure trigger 32, the interchangeable shaft assembly 200, and the end effector 300. Accordingly, for conciseness and clarity of disclosure, a detailed description of certain features of the surgical instrument 4400, which are common with the surgical instrument 10, will not be repeated here.

Referring still to FIGS. 90, 91, the surgical instrument 4400 may include a plurality of motors which can be activated to perform various functions in connection with the operation of the surgical instrument 4400. In certain instances, a first motor can be activated to perform a first function; a second motor can be activated to perform a second function; and a third motor can be activated to perform a third function. In certain instances, the plurality of motors of the surgical instrument 4400 can be individually activated to cause articulation, closure, and/or firing motions in the end effector 300 (FIGS. 1, 15). The articulation, closure, and/or firing motions can be transmitted to the end effector 300 through the interchangeable shaft assembly 200 (FIG. 1), for example.

In certain instances, as illustrated in FIG. 91, the surgical instrument 4400 may include a firing motor 4402. The firing motor 4402 may be operably coupled to a firing drive assembly 4404 which can be configured to transmit firing motions generated by the firing motor 4402 to the end effector 300 (FIGS. 1, 14). In certain instances, the firing motions generated by the firing motor 4402 may cause the staples 191 to be deployed from the surgical staple cartridge 304 into tissue captured by the end effector 300 and/or the cutting edge 182 to be advanced to cut the captured tissue, for example.

In certain instances, as illustrated in FIG. 91, the surgical instrument 4400 may include an articulation motor 4406, for example. The articulation motor 4406 may be operably coupled to an articulation drive assembly 4408 which can be configured to transmit articulation motions generated by the articulation motor 4406 to the end effector 300 (FIGS. 1, 14). In certain instances, the articulation motions may cause the end effector 300 to articulate relative to the interchangeable shaft assembly 200 (FIG. 1), for example. In certain instances, the surgical instrument 4400 may include a closure motor, for example. The closure motor may be operably coupled to a closure drive assembly which can be configured to transmit closure motions to the end effector 300. In certain instances, the closure motions may cause the end effector 300 to transition from an open configuration to an approximated configuration to capture tissue, for example. The reader will appreciate that the motors described herein and their corresponding drive assemblies are intended as examples of the types of motors and/or driving assemblies that can be employed in connection with the present disclosure. The surgical instrument 4400 may include various other motors which can be utilized to perform various other functions in connection with the operation of the surgical instrument 4400.

As described above, the surgical instrument 4400 may include a plurality of motors which may be configured to perform various independent functions. In certain instances, the plurality of motors of the surgical instrument 4400 can be individually or separately activated to perform one or more functions while the other motors remain inactive. For example, the articulation motor 4406 can be activated to cause the end effector 300 (FIGS. 1, 14) to be articulated while the firing motor 4402 remains inactive. Alternatively, the firing motor 4402 can be activated to fire the plurality of staples 191 (FIG. 14) and/or advance the cutting edge 182 while the articulation motor 4406 remains inactive.

With reference to FIGS. 90, 91, in certain instances, the surgical instrument 4400 may include a common controller 4410 which can be employed with a plurality of motors 4402, 4406 of the surgical instrument 4400. In certain instances, the common controller 4410 may accommodate one of the plurality of motors at a time. For example, the common controller 4410 can be separably couplable to the plurality of motors of the surgical instrument 4400 individually. In certain instances, a plurality of the motors of the surgical instrument 4400 may share one or more common controllers such as the common controller 4410. In certain instances, a plurality of motors of the surgical instrument 4400 can be individually and selectively engaged the common controller 4410. In certain instances, the common controller 4410 can be selectively switched from interfacing with one of a plurality of motors of the surgical instrument 4400 to interfacing with another one of the plurality of motors of the surgical instrument 4400.

In at least one example, the common controller 4410 can be selectively switched between operable engagement with the articulation motor 4406 and operable engagement with the firing motor 4402. In at least one example, as illustrated in FIG. 90, a switch 4414 can be moved or transitioned between a plurality of positions and/or states such as a first position 4416 and a second position 4418, for example. In the first position 4416, the switch 4414 may electrically couple the common controller 4410 to the articulation motor 4406; and in the second position 4418, the switch 4414 may electrically couple the common controller 4410 to the firing motor 4402, for example. In certain instances, the common controller 4410 can be electrically coupled to the articulation motor 4406, while the switch 4414 is in the first position 4416, to control the operation of the articulation motor 4406 to articulate the end effector 300 (FIGS. 1, 15) to a desired position. In certain instances, the common controller 4410 can be electrically coupled to the firing motor 4402, while the switch 4414 is in the second position 4418, to control the operation of the firing motor 4402 to fire the plurality of staples 191 (FIG. 14) and/or advance the cutting edge 182 (FIG. 14), for example. In certain instances, the switch 4414 may be a mechanical switch, an electromechanical switch, a solid state switch, or any suitable switching mechanism.

Referring now to FIG. 91, an outer casing of the handle assembly 14 of the surgical instrument 4400 is removed and several features and elements of the surgical instrument 4400 are also removed for clarity of disclosure. In certain instances, as illustrated in FIG. 91, the surgical instrument 4400 may include an interface 4412 which can be selectively transitioned between a plurality of positions and/or states. In a first position and/or state, the interface 4412 may couple the common controller 4410 (FIG. 90) to a first motor such as, for example, the articulation motor 4406; and in a second position and/or state, the interface 4412 may couple the common controller 4410 to a second motor such as, for example, the firing motor 4402. Additional positions and/or states of the interface 4412 are contemplated by the present disclosure.

In certain instances, the interface 4412 is movable between a first position and a second position, wherein the common controller 4410 (FIG. 90) is coupled to a first motor in the first position and a second motor in the second position. In certain instances, the common controller 4410 is decoupled from first motor as the interface 4412 is moved from the first position; and the common controller 4410 is decoupled from second motor as the interface 4412 is moved from the second position. In certain instances, a switch or a trigger can be configured to transition the interface 4412 between the plurality of positions and/or states. In certain instances, a trigger can be movable to simultaneously effectuate the end effector and transition the common controller 4410 from operable engagement with one of the motors of the surgical instrument 4400 to operable engagement with another one of the motors of the surgical instrument 4400.

In at least one example, as illustrated in FIG. 91, the closure trigger 32 can be operably coupled to the interface 4412 and can be configured to transition the interface 4412 between a plurality of positions and/or states. As illustrated in FIG. 91, the closure trigger 32 can be movable, for example during a closure stroke, to transition the interface 4412 from a first position and/or state to a second position and/or state while transitioning the end effector 300 to an approximated configuration to capture tissue by the end effector, for example.

In certain instances, in the first position and/or state, the common controller 4410 can be electrically coupled to a first motor such as, for example, the articulation motor 4406, and in the second position and/or state, the common controller 4410 can be electrically coupled to a second motor such as, for example, the firing motor 4402. In the first position and/or state, the common controller 4410 may be engaged with the articulation motor 4406 to allow the user to articulate the end effector 300 (FIGS. 1, 15) to a desired position; and the common controller 4410 may remain engaged with the articulation motor 4406 until the closure trigger 32 is actuated. As the user actuates the closure trigger 32 to capture tissue by the end effector 300 at the desired position, the interface 4412 can be transitioned or shifted to transition the common controller 4410 from operable engagement with the articulation motor 4406, for example, to operable engagement with the firing motor 4402, for example. Once operable engagement with the firing motor 4402 is established, the common controller 4410 may take control of the firing motor 4402; and the common controller 4410 may activate the firing motor 4402, in response to user input, to fire the plurality of staples 191 (FIG. 14) and/or advance the cutting edge 182 (FIG. 14), for example.

In certain instances, as illustrated in FIG. 91, the common controller 4410 may include a plurality of electrical and/or mechanical contacts 4411 adapted for coupling engagement with the interface 4412. The plurality of motors of the surgical instrument 4400, which share the common controller 4410, may each comprise one or more corresponding electrical and/or mechanical contacts 4413 adapted for coupling engagement with the interface 4412, for example.

In various instances, the motors of the surgical instrument 4400 can be electrical motors. In certain instances, one or more of the motors of the surgical instrument 4400 can be a DC brushed driving motor having a maximum rotation of, approximately, 25,000 RPM, for example. In other arrangements, the motors of the surgical instrument 4400 may include one or more motors selected from a group of motors comprising a brushless motor, a cordless motor, a synchronous motor, a stepper motor, or any other suitable electric motor.

In various instances, as illustrated in FIG. 90, the common controller 4410 may comprise a motor driver 4426 which may comprise one or more H-Bridge field-effect transistors (FETs). The motor driver 4426 may modulate the power transmitted from a power source 4428 to a motor coupled to the common controller 4410 based on input from a controller 4420 ("microcontroller"), for example. In certain instances, the controller 4420 can be employed to determine the current drawn by the motor, for example, while the motor is coupled to the common controller 4410, as described above.

In certain instances, the controller 4420 may include a processor 4422 ("microprocessor") and one or more computer readable mediums or memory 4424 units ("memory"). In certain instances, the memory 4424 may store various program instructions, which when executed may cause the processor 4422 to perform a plurality of functions and/or calculations described herein. In certain instances, one or more of the memory 4424 may be coupled to the processor 4422, for example.

In certain instances, the power source 4428 can be employed to supply power to the controller 4420, for example. In certain instances, the power source 4428 may comprise a battery (or "battery pack" or "power pack"), such as a Li ion battery, for example. In certain instances, the battery pack may be configured to be releasably mounted to the handle assembly 14 for supplying power to the surgical instrument 4400. A number of battery cells connected in series may be used as the power source 4428. In certain instances, the power source 4428 may be replaceable and/or rechargeable, for example.

In various instances, the processor 4422 may control the motor driver 4426 to control the position, direction of rotation, and/or velocity of a motor that is coupled to the common controller 4410. In certain instances, the processor 4422 can signal the motor driver 4426 to stop and/or disable a motor that is coupled to the common controller 4410. It should be understood that the term processor as used herein includes any suitable processor, controller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system. In one instance, the processor 4422 may be a single core or multicore controller LM4F230H5QR as described in connection with FIGS. 15-17B.

In certain instances, the memory 4424 may include program instructions for controlling each of the motors of the surgical instrument 4400 that are couplable to the common controller 4410. For example, the memory 4424 may include program instructions for controlling the articulation motor 4406. Such program instructions may cause the processor 4422 to control the articulation motor 4406 to articulate the end effector 300 in accordance with user input while the articulation motor 4406 is coupled to the common controller 4410. In another example, the memory 4424 may include program instructions for controlling the firing motor 4402. Such program instructions may cause the processor 4422 to control the firing motor 4402 to fire the plurality of staples 191 and/or advance the cutting edge 182 in accordance with user input while the firing motor 4402 is coupled to the common controller 4410.

In certain instances, one or more mechanisms and/or sensors such as, for example, sensors 4430 can be employed to alert the processor 4422 to the program instructions that should be used in a particular setting. For example, the sensors 4430 may alert the processor 4422 to use the program instructions associated with articulation of the end effector 300 (FIGS. 1, 14) while the common controller 4410 is coupled to the articulation motor 4406; and the sensors 4430 may alert the processor 4422 to use the program instructions associated with firing the surgical instrument 4400 while the common controller 4410 is coupled to the firing motor 4402. In certain instances, the sensors 4430 may comprise position sensors which can be employed to sense the position of the switch 4414, for example. Accordingly, the processor 4422 may use the program instructions associated with articulation of the end effector 300 upon detecting, through the sensors 4430 for example, that the switch 4414 is in the first position 4416; and the processor 4422 may use the program instructions associated with firing the surgical instrument 4400 upon detecting, through the sensors 4430 for example, that the switch 4414 is in the second position 4418.

Figure 92:
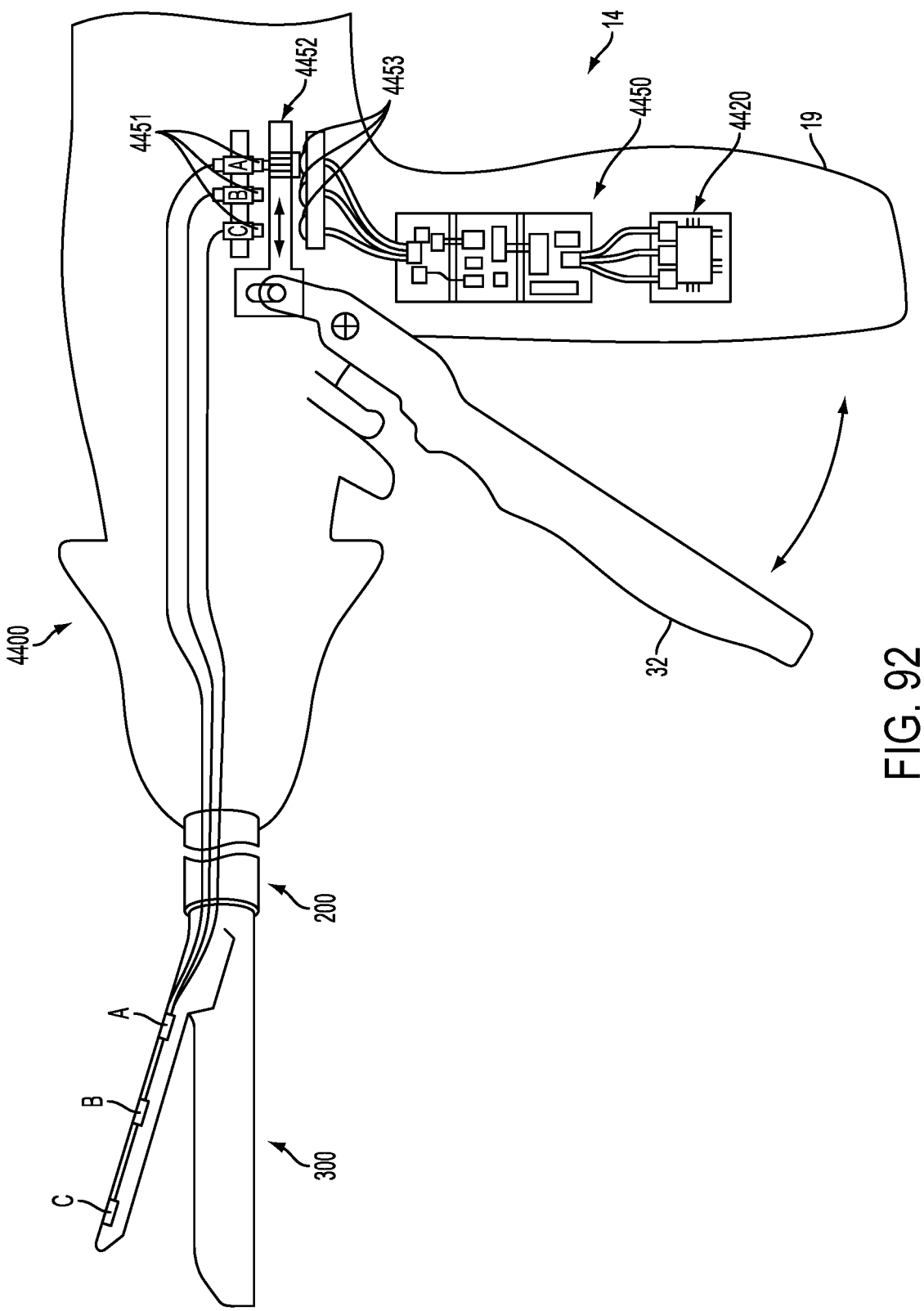
FIG. 92 illustrates a partial elevational view of the surgical instrument with a removed outer casing in accordance with one or more aspects of the present disclosure.

Referring now to FIG. 92, an outer casing of the surgical instrument 4400 is removed and several features and elements of the surgical instrument 4400 are also removed for clarity of disclosure. As illustrated in FIG. 92, the surgical instrument 4400 may include a plurality of sensors which can be employed to perform various functions in connection with the operation of the surgical instrument 4400. For example, as illustrated in FIG. 92, the surgical instrument 4400 may include sensors A, B, and/or C. In certain instances, the sensor A can be employed to perform a first function, for example; the sensor B can be employed to perform a second function, for example; and the sensor C can be employed to perform a third function, for example. In certain instances, the sensor A can be employed to sense a thickness of the tissue captured by the end effector 300 (FIGS. 1, 14) during a first segment of a closure stroke; the sensor B can be employed to sense the tissue thickness during a second segment of the closure stroke following the first segment; and the sensor C can be employed to sense the tissue thickness during a third segment of the closure stroke following the second segment, for example. In certain instances, the sensors A, B, and C can be disposed along the end effector 300, for example.

In certain instances, the sensors A, B, and C can be arranged, as illustrated in FIG. 94, such that the sensor A is disposed proximal to the sensor B, and the sensor C is disposed proximal to the sensor B, for example. In certain instances, as illustrated in FIG. 92, the sensor A can sense the tissue thickness of the tissue captured by the end effector 300 at a first position; the sensor B can sense the tissue thickness of the tissue captured by the end effector 300 at a second position distal to the first position; and the sensor C can sense the tissue thickness of the tissue captured by the end effector 300 at a third position distal to the second position, for example. The reader will appreciate that the sensors described herein are intended as examples of the types of sensors which can be employed in connection with the present disclosure. Other suitable sensors and sensing arrangements can be employed by the present disclosure.

In certain instances, the surgical instrument 4400 may include a controller 4450 which can be similar in many respects to the common controller 4410. For example, the controller 4450, like the common controller 4410, may comprise the controller 4420, the processor 4422, and/or the memory 4424. In certain instances, the power source 4428 can supply power to the controller 4450, for example. In certain instances, the surgical instrument 4400 may include a plurality of sensors such as the sensors A, B, and C, for example, which can activated to perform various functions in connection with the operation of the surgical instrument 4400. In certain instances, one of the sensors A, B, and C, for example, can be individually or separately activated to perform one or more functions while the other sensors remain inactive. In certain instances, a plurality of sensors of the surgical instrument 4400 such as, for example, the sensors A, B, and C may share the controller 4450. In certain instances, only one of the sensors A, B, and C can be coupled to the controller 4450 at a time. In certain instances, the plurality of sensors of the surgical instrument 4400 can be individually and separately couplable to the controller 4450, for example. In at least one example, the controller 4450 can be selectively switched between operable engagement with sensor A, Sensor B, and/or Sensor C.

In certain instances, as illustrated in FIG. 92, the controller 4450 can be disposed in the handle assembly 14, for example, and the sensors that share the controller 4450 can be disposed in the end effector 300 (FIGS. 1, 14), for example. The reader will appreciate that the controller 4450 and/or the sensors that share the controller 4450 are not limited to the above identified positions. In certain instances, the controller 4450 and the sensors that share the controller 4450 can be disposed in the end effector 300, for example. Other arrangements for the positions of the controller 4450 and/or the sensors that share the controller 4450 are contemplated by the present disclosure.

In certain instances, as illustrated in FIG. 92, an interface 4452 can be employed to manage the coupling and/or decoupling of the sensors of the surgical instrument 4400 to the controller 4450. In certain instances, the interface 4452 can be selectively transitioned between a plurality of positions and/or states. In a first position and/or state, the interface 4452 may couple the controller 4450 to the sensor A, for example; in a second position and/or state, the interface 4452 may couple the controller 4450 to the sensor B, for example; and in a third position and/or state, the interface 4452 may couple the controller 4450 to the sensor C, for example. Additional positions and/or states of the interface 4452 are contemplated by the present disclosure.

In certain instances, the interface 4452 is movable between a first position, a second position, and/or a third position, for example, wherein the controller 4450 is coupled to a first sensor in the first position, a second sensor in the second position, and a third sensor in the third position. In certain instances, the controller 4450 is decoupled from first sensor as the interface 4452 is moved from the first position; the controller 4450 is decoupled from second sensor as the interface 4452 is moved from the second position; and the controller 4450 is decoupled from third sensor as the interface 4452 is moved from the third position. In certain instances, a switch or a trigger can be configured to transition the interface 4452 between the plurality of positions and/or states. In certain instances, a trigger can be movable to simultaneously effectuate the end effector and transition the controller 4450 from operable engagement with one of the sensors that share the controller 4450 to operable engagement with another one of the sensors that share the controller 4450, for example.

In at least one example, as illustrated in FIG. 92, the closure trigger 32 can be operably coupled to the interface 4452 and can be configured to transition the interface 4452 between a plurality of positions and/or states. As illustrated in FIG. 92, the closure trigger 32 can be moveable between a plurality of positions, for example during a closure stroke, to transition the interface 4452 between a first position and/or state wherein the controller 4450 is electrically coupled to the sensor A, for example, a second position and/or state wherein the controller 4450 is electrically coupled to the sensor B, for example, and/or a third position and/or state wherein the controller 4450 is electrically coupled to the sensor C, for example.

In certain instances, a user may actuate the closure trigger 32 to capture tissue by the end effector 300. Actuation of the closure trigger may cause the interface 4452 to be transitioned or shifted to transition the controller 4450 from operable engagement with the sensor A, for example, to operable engagement with the sensor B, for example, and/or from operable engagement with sensor B, for example, to operable engagement with sensor C, for example.

In certain instances, the controller 4450 may be coupled to the sensor A while the closure trigger 32 is in a first actuated position. As the closure trigger 32 is actuated past the first actuated position and toward a second actuated position, the controller 4450 may be decoupled from the sensor A. Alternatively, the controller 4450 may be coupled to the sensor A while the closure trigger 32 is in an unactuated position. As the closure trigger 32 is actuated past the unactuated position and toward a second actuated position, the controller 4450 may be decoupled from the sensor A. In certain instances, the controller 4450 may be coupled to the sensor B while the closure trigger 32 is in the second actuated position. As the closure trigger 32 is actuated past the second actuated position and toward a third actuated position, the controller 4450 may be decoupled from the sensor B. In certain instances, the controller 4450 may be coupled to the sensor C while the closure trigger 32 is in the third actuated position.

In certain instances, as illustrated in FIG. 92, the controller 4450 may include a plurality of electrical and/or mechanical contacts 4451 adapted for coupling engagement with the interface 4452. The plurality of sensors of the surgical instrument 4400, which share the controller 4450, may each comprise one or more corresponding electrical and/or mechanical contacts 4453 adapted for coupling engagement with the interface 4452, for example.

In certain instances, the processor 4422 may receive input from the plurality of sensors that share the controller 4450 while the sensors are coupled to the interface 4452. For example, the processor 4422 may receive input from the sensor A while the sensor A is coupled to the controller 4450; the processor 4422 may receive input from the sensor B while the sensor B is coupled to the controller 4450; and the processor 4422 may receive input from the sensor C while the sensor C is coupled to the controller 4450. In certain instances, the input can be a measurement value such as, for example, a measurement value of a tissue thickness of tissue captured by the end effector 300 (FIGS. 1, 15). In certain instances, the processor 4422 may store the input from one or more of the sensors A, B, and C on the memory 4424. In certain instances, the processor 4422 may perform various calculations based on the input provided by the sensors A, B, and C, for example.

Figure 93A:
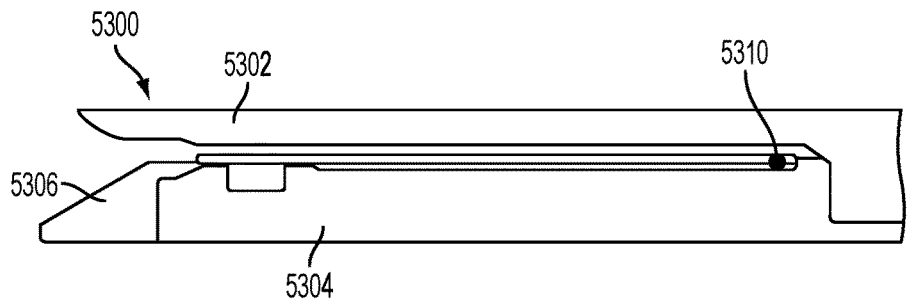
FIG. 93A illustrates a side angle view of an end effector with the anvil in a closed position, illustrating one located on either side of the cartridge deck in accordance with one or more aspects of the present disclosure.
Figure 93B:
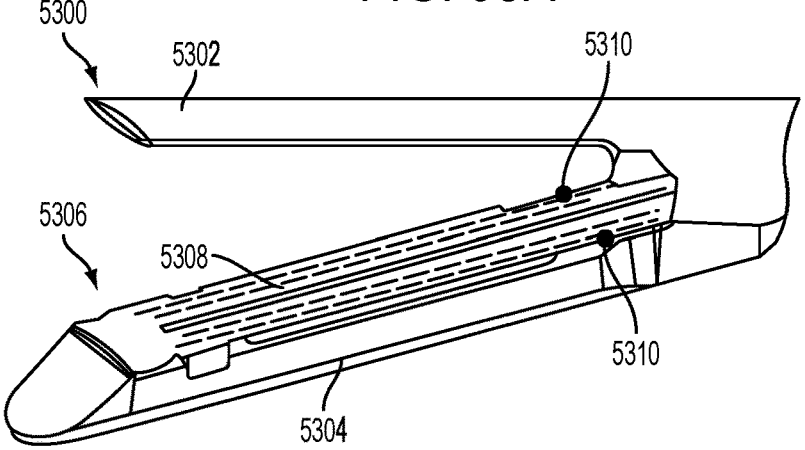
FIG. 93B illustrates a three-quarter angle view of the end effector with the anvil in an open position, and one LED located on either side of the cartridge deck in accordance with one or more aspects of the present disclosure.

FIGS. 93A and 93B illustrate one aspect of an end effector 5300 comprising a staple cartridge 5306 that further comprises two light-emitting diodes 5310 (LEDs). FIG. 93A illustrates an end effector 5300 comprising one LED 5310 located on either side of the cartridge deck 5308. FIG. 91B illustrates a three-quarter angle view of the end effector 5300 with the anvil 5302 in an open position, and one LED 5310 located on either side of the cartridge deck 5308. The end effector 5300 is similar to the end effector 300 (FIGS. 1, 15) described above. The end effector comprises an anvil 5302, pivotally coupled to a jaw member or elongated channel 5304. The elongated channel 5304 is configured to receive the staple cartridge 5306 therein. The staple cartridge 5306 comprises a plurality of staples (not shown). The plurality of staples are deployable from the staple cartridge 5306 during a surgical operation. The staple cartridge 5306 further comprises two LEDs 5310 mounted on the upper surface, or cartridge deck 5308 of the staple cartridge 5306. The LEDs 5310 are mounted such that they will be visible when the anvil 5302 is in a closed position. Furthermore, the LEDs 5310 can be sufficiently bright to be visible through any tissue that may be obscuring a direct view of the LEDs 5310. Additionally, one LED 5310 can be mounted on either side of the staple cartridge 5306 such that at least one LED 5310 is visible from either side of the end effector 5300. The LED 5310 can be mounted near the proximal end of the staple cartridge 530, as illustrated, or may be mounted at the distal end of the staple cartridge 5306.

The LEDs 5310 may be in communication with a processor or controller, such as, for instance, controller 1500 (FIG. 19). The controller 1500 can be configured to detect a property of tissue compressed by the anvil 5302 against the cartridge deck 5308. Tissue that is enclosed by the end effector 5300 may change height as fluid within the tissue is exuded from the tissue's layers. Stapling the tissue before it has sufficiently stabilized may affect the effectiveness of the staples. Tissue stabilization is typically communicates as a rate of change, where the rate of change indicates how rapidly the tissue enclosed by the end effector is changing height.

The LEDs 5310 mounted to the staple cartridge 5306, in the view of the operator of the instrument, can be used to indicate rate at which the enclosed tissue is stabilizing and/or whether the tissue has reached a stable state. The LEDs 5310 can, for example, be configured to flash at a rate that directly correlates to the rate of stabilization of the tissue, that is, can flash quickly initially, flash slower as the tissue stabilizes, and remain steady when the tissue is stable. Alternatively, the LEDs 5310 can flash slowly initially, flash more quickly as the tissue stabilizes, and turn off when the tissue is stable.

The LEDs 5310 mounted on the staple cartridge 5306 can be used additionally or optionally to indicate other information. Examples of other information include, but are not limited to: whether the end effector 5300 is enclosing a sufficient amount of tissue, whether the staple cartridge 5306 is appropriate for the enclosed tissue, whether there is more tissue enclosed than is appropriate for the staple cartridge 5306, whether the staple cartridge 5306 is not compatible with the surgical instrument, or any other indicator that would be useful to the operator of the instrument. The LEDs 5310 can indicate information by either flashing at a particular rate, turning on or off at a particular instance, lighting in different colors for different information. The LEDs 5310 can alternatively or additionally be used to illuminate the area of operation. In some aspects the LEDs 5310 can be selected to emit ultraviolet or infrared light to illuminate information not visible under normal light, where that information is printed on the staple cartridge located in the end effector 5300 or on a tissue compensator (not illustrated). Alternatively or additionally, the staples can be coated with a fluorescing dye and the wavelength of the LEDs 5310 chosen so that the LEDs 5310 cause the fluorescing dye to glow. By illuminating the staples with the LEDs 5310 allows the operator of the instrument to see the staples after they have been driven.

Figure 94A:
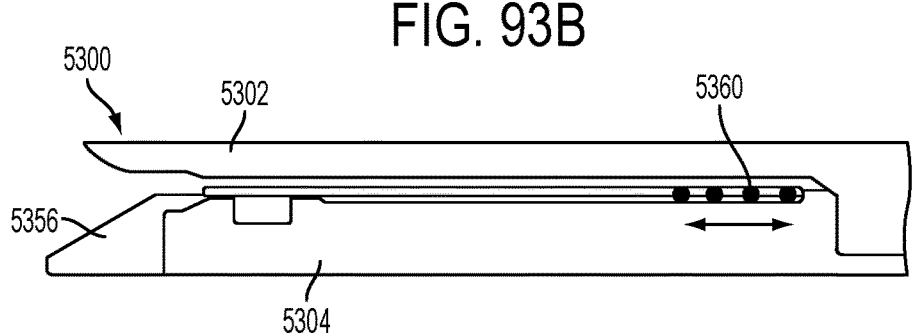
FIG. 94A illustrates a side angle view of an end effector with the anvil in a closed position and a plurality of LEDs located on either side of the cartridge deck in accordance with one or more aspects of the present disclosure.
Figure 94B:
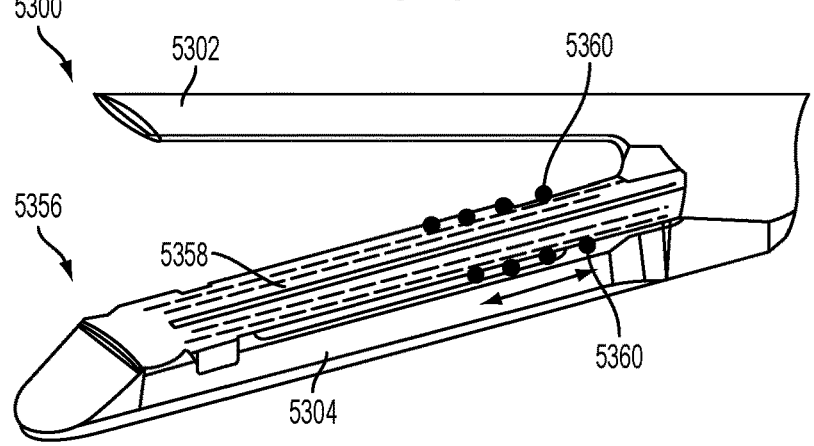
FIG. 94B illustrates a three-quarter angle view of the end effector with the anvil in an open position, and a plurality of LEDs located on either side of the cartridge deck in accordance with one or more aspects of the present disclosure.

FIGS. 94A and 94B illustrate one aspect of the end effector 5300 comprising a staple cartridge 5356 that further comprises a plurality of LEDs 5360. FIG. 92A illustrates a side angle view of the end effector 5300 with the anvil 5302 in a closed position. The illustrated aspect comprises, by way of example, a plurality of LEDs 5360 located on either side of the cartridge deck 5358. FIG. 92B illustrates a three-quarter angle view of the end effector 5300 with the anvil 5302 in an open position, illustrating a plurality of LEDs 5360 located on either side of the cartridge deck 5358. The staple cartridge 5356 comprises a plurality of LEDs 5360 mounted on the cartridge deck 5358 of the staple cartridge 5356. The LEDs 5360 are mounted such that they will be visible when the anvil 5302 is in a closed position. Furthermore, the LEDs6 530 can be sufficiently bright to be visible through any tissue that may be obscuring a direct view of the LEDs 5360. Additionally, the same number of LEDs 5360 can be mounted on either side of the staple cartridge 5356 such that the same number of LEDs 5360 is visible from either side of the end effector 5300. The LEDs 5360 can be mounted near the proximal end of the staple cartridge 5356, as illustrated, or may be mounted at the distal end of the staple cartridge 5356.

The LEDs 5360 may be in communication with a processor or controller, such as, for instance, controller 1500 of FIG. 15. The controller 1500 can be configured to detect a property of tissue compressed by the anvil 5302 against the cartridge deck 5358, such as the rate of stabilization of the tissue, as described above. The LEDs 5360 can be used to indicate the rate at which the enclose tissue is stabilizing and/or whether the tissue has reached a stable state. The LEDs 5360 can be configured, for instance, to light in sequence starting at the proximal end of the staple cartridge 5356 with each subsequent LED 5360 lighting at the rate at which the enclosed tissue is stabilizing; when the tissue is stable, all the LEDs 5360 can be lit. Alternatively, the LEDs 5360 can light in sequence beginning at the distal end of the staple cartridge 5356. Yet another alternative is for the LEDs 5360 to light in a sequential, repeating sequence, with the sequence starting at either the proximal or distal end of the LEDs 5360. The rate at which the LEDs 5360 light and/or the speed of the repeat can indicate the rate at which the enclosed tissue is stabilizing. It is understood that these are only examples of how the LEDs 5360 can indicate information about the tissue, and that other combinations of the sequence in which the LEDs 5360 light, the rate at which they light, and or their on or off state are possible. It is also understood that the LEDs 5360 can be used to communicate some other information to the operator of the surgical instrument, or to light the work area, as described above.

Figure 95A:
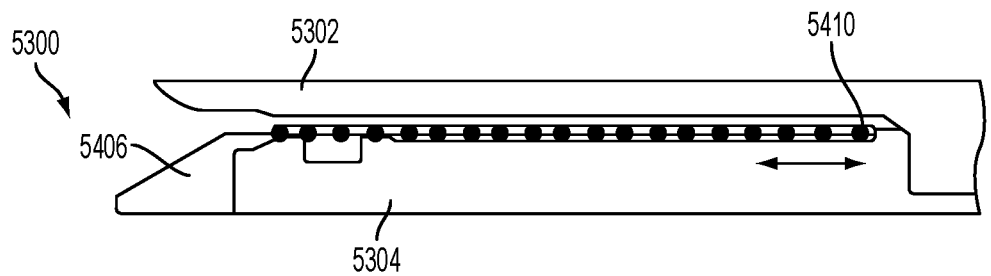
FIG. 95A illustrates a side angle view of an end effector with the anvil in a closed position, and a plurality of LEDs from the proximal to the distal end of the staple cartridge, on either side of the cartridge deck in accordance with one or more aspects of the present disclosure.
Figure 95B:
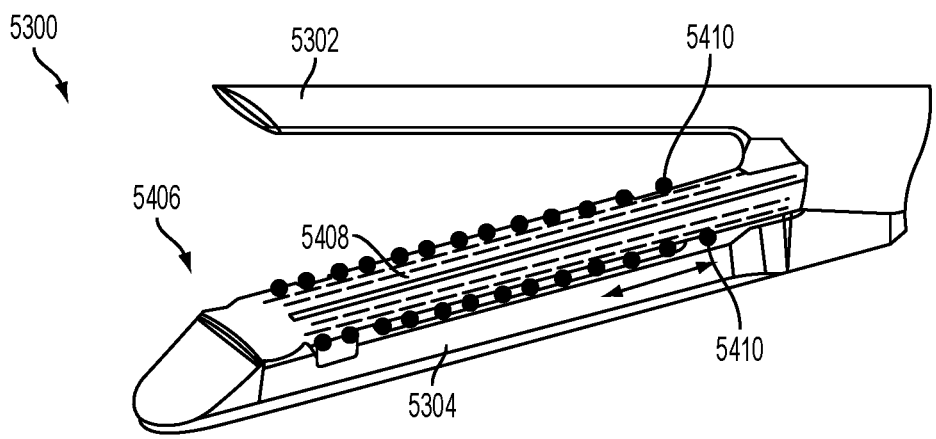
FIG. 95B illustrates a three-quarter angle view of the end effector with the anvil in an open position, illustrating a plurality of LEDs from the proximal to the distal end of the staple cartridge, and on either side of the cartridge deck in accordance with one or more aspects of the present disclosure.

FIGS. 95A and 95B illustrate one aspect of the end effector 5300 comprising a staple cartridge 5406 that further comprises a plurality of LEDs 5410. FIG. 93A illustrates a side angle view of the end effector 5300 with the anvil 5302 in a closed position. The illustrated aspect comprises, by way of example, a plurality of LEDs 5410 from the proximal to the distal end of the staple cartridge 5406, on either side of the cartridge deck 5408. FIG. 93B illustrates a three-quarter angle view of the end effector 5300 with the anvil 5302 in an open position, illustrating a plurality of LEDs 5410 from the proximal to the distal end of the staple cartridge 5406, and on either side of the cartridge deck 5408. The staple cartridge 5406 comprises a plurality of LEDs 5410 mounted on the cartridge deck 5408 of the staple cartridge 5406, with the LEDs 5410 placed continuously from the proximal to the distal end of the staple cartridge 5406. The LEDs 5410 are mounted such that they will be visible when the anvil 5302 is in a closed position. The same number of LEDs 5410 can be mounted on either side of the staple cartridge 5406 such that the same number of LEDs 5410 is visible from either side of the end effector 5300.

The LEDs 5410 can be in communication with a processor or controller, such as, for instance, controller 1500 of FIG. 15. The controller 1500 can be configured to detect a property of tissue compressed by the anvil 5302 against the cartridge deck 5408, such as the rate of stabilization of the tissue, as described above. The LEDs 5410 can be configured to be turned on or off in sequences or groups as desired to indicate the rate of stabilization of the tissue and/or that the tissue is stable. The LEDs 5410 can further be configured communicate some other information to the operator of the surgical instrument, or to light the work area, as described above. Additionally or alternatively, the LEDs 5410 can be configured to indicate which areas of the end effector 5300 contain stable tissue, and or what areas of the end effector 5300 are enclosing tissue, and/or if those areas are enclosing sufficient tissue. The LEDs 5410 can further be configured to indicate if any portion of the enclosed tissue is unsuitable for the staple cartridge 5406.

Figure 96:
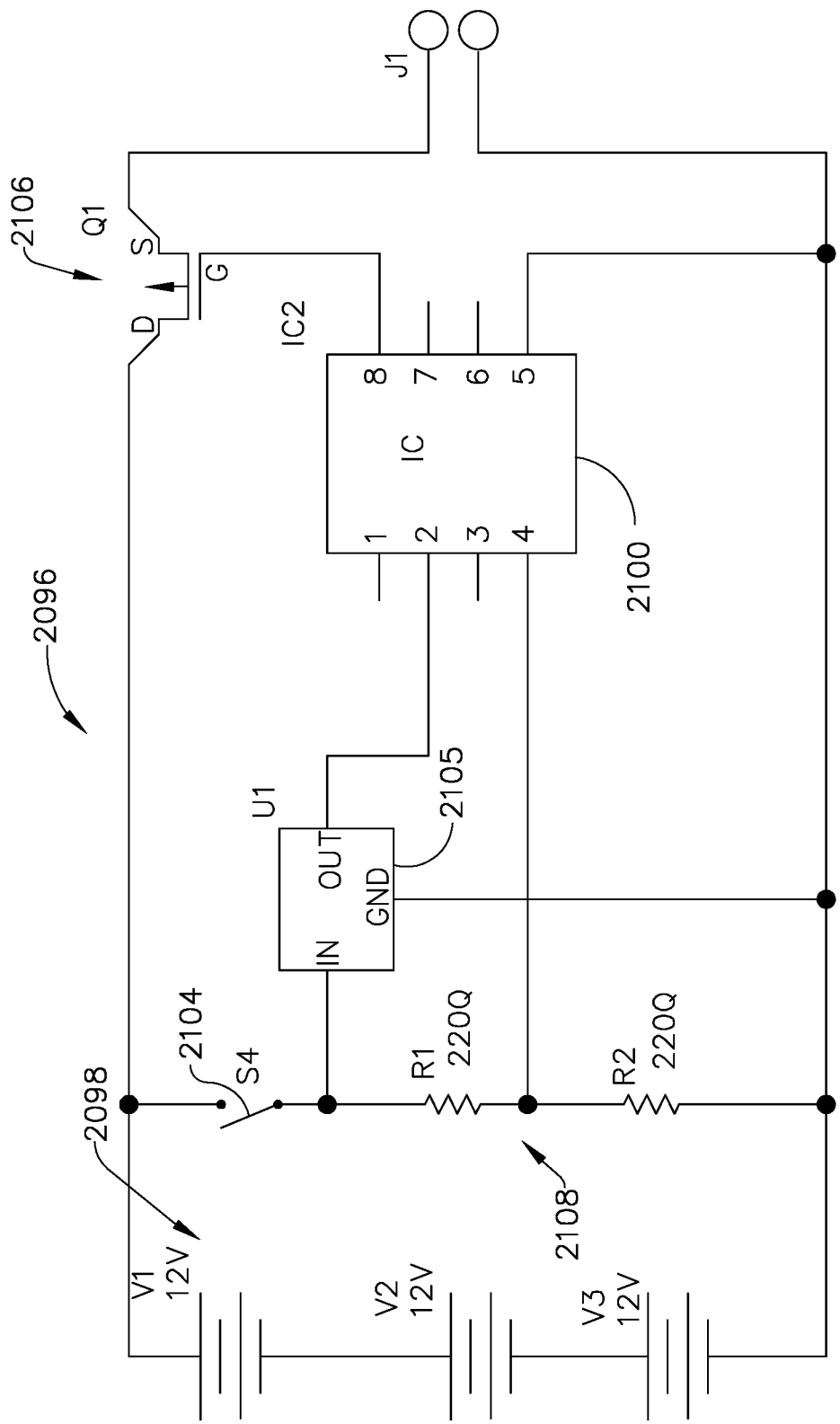
FIG. 96 is a circuit diagram of an example power assembly of a surgical instrument in accordance with one or more aspects of the present disclosure.

Referring now primarily to FIGS. 96 and 97, the power assembly 2096 may include a power modulator control 2106 which may comprise, for example, one or more field-effect transistors (FETs), a Darlington array, an adjustable amplifier, and/or any other power modulator. The power assembly controller 2100 may actuate the power modulator control 2106 to set the power output of the battery 2098 to the power requirement of the interchangeable working assembly 2094 in response to the signal generated by working assembly controller 2102 while the interchangeable working assembly 2094 is coupled to the power assembly 2096.

Still referring primarily to FIGS. 96 and 97, the power assembly controller 2100 can be configured to monitor power transmission from the power assembly 2096 to the interchangeable working assembly 2094 for the one or more signals generated by the working assembly controller 2102 of the interchangeable working assembly 2094 while he interchangeable working assembly 2094 is coupled to the power assembly 2096. As illustrated in FIG. 96, the power assembly controller 2100 may utilize a voltage monitoring mechanism for monitoring the voltage across the battery 2098 to detect the one or more signals generated by the working assembly controller 2102, for example. In certain instances, a voltage conditioner can be utilized to scale the voltage of the battery 2098 to be readable by an Analog to Digital Converter (ADC) of the power assembly controller 2100. As illustrated in FIG. 96, the voltage conditioner may comprise a voltage divider 2108 which can create a reference voltage or a low voltage signal proportional to the voltage of the battery 2098 which can be measured and reported to the power assembly controller 2100 through the ADC, for example.

In other circumstances, as illustrated in FIG. 97, the power assembly 2096 may comprise a current monitoring mechanism for monitoring current transmitted to the interchangeable working assembly 2094 to detect the one or more signals generated by the working assembly controller 2102, for example. In certain instances, the power assembly 2096 may comprise a current sensor 2110 which can be utilized to monitor current transmitted to the interchangeable working assembly 2094. The monitored current can be reported to the power assembly controller 2100 through an ADC, for example. In other circumstances, the power assembly controller 2100 may be configured to simultaneously monitor both of the current transmitted to the interchangeable working assembly 2094 and the corresponding voltage across the battery 2098 to detect the one or more signals generated by the working assembly controller 2102. The reader will appreciate that various other mechanisms for monitoring current and/or voltage can be utilized by the power assembly controller 2100 to detect the one or more signals generated by the working assembly controller 2102; all such mechanisms are contemplated by the present disclosure.

Figure 98:
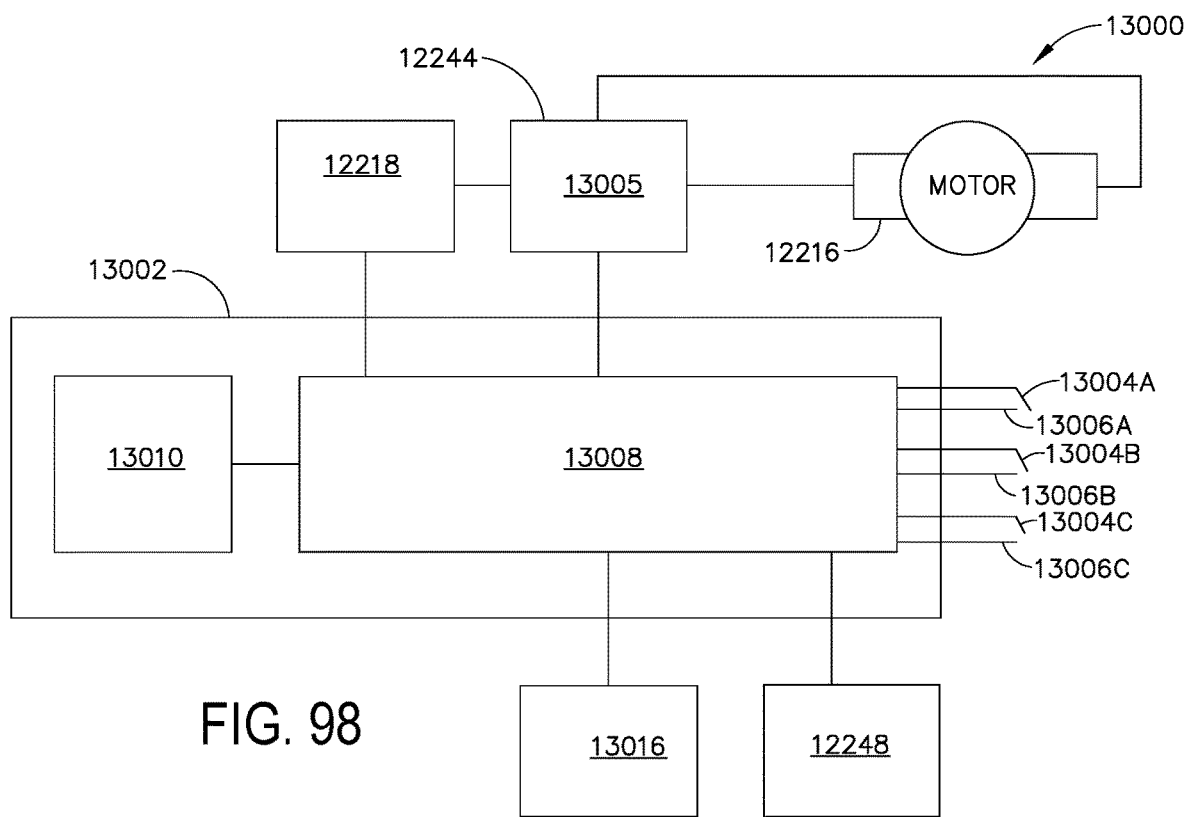
FIG. 98 is a schematic block diagram of a control system of a surgical instrument in accordance with one or more aspects of the present disclosure.

Referring to FIG. 98, the controller 13002 may generally comprise a processor 13008 ("microprocessor") and one or more memory units 13010 operationally coupled to the processor 13008. By executing instruction code stored in the memory 13010, the processor 13008 may control various components of the surgical instrument 12200, such as the motor 12216, various drive systems, and/or a user display, for example. The controller 13002 may be implemented using integrated and/or discrete hardware elements, software elements, and/or a combination of both. Examples of integrated hardware elements may include processors, microprocessors, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controllers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 13002 may include a hybrid circuit comprising discrete and integrated circuit elements or components on one or more substrates, for example. In certain instances, the controller 13002 may be a single core or multicore controller LM4F230H5QR as described in connection with FIGS. 15-17B.

In various forms, the motor 12216 may be a DC brushed driving motor having a maximum rotation of, approximately, 25,000 RPM, for example. In other arrangements, the motor 12216 may include a brushless motor, a cordless motor, a synchronous motor, a stepper motor, or any other suitable electric motor. A battery 12218 (or "power source" or "power pack"), such as a Li ion battery, for example, may be coupled to the housing 12212 to supply power to the motor 12216, for example.

Referring again to FIG. 98, the surgical instrument 12200 may include a motor controller 13005 in operable communication with the controller 13002. The motor controller 13005 can be configured to control a direction of rotation of the motor 12216. In certain instances, the motor controller 13005 may be configured to determine the voltage polarity applied to the motor 12216 by the battery 12218 and, in turn, determine the direction of rotation of the motor 12216 based on input from the controller 13002. For example, the motor 12216 may reverse the direction of its rotation from a clockwise direction to a counterclockwise direction when the voltage polarity applied to the motor 12216 by the battery 12218 is reversed by the motor controller 13005 based on input from the controller 13002. In addition, the motor 12216 can be operably coupled to an articulation drive which can be driven by the motor 12216 distally or proximally depending on the direction in which the motor 12216 rotates, for example. Furthermore, the articulation drive can be operably coupled to the end effector 12208 such that, for example, the axial translation of the articulation drive proximally may cause the end effector 12208 to be articulated in the counterclockwise direction, for example, and/or the axial translation of the articulation drive distally may cause the end effector 12208 to be articulated in the clockwise direction, for example.

Figure 99:
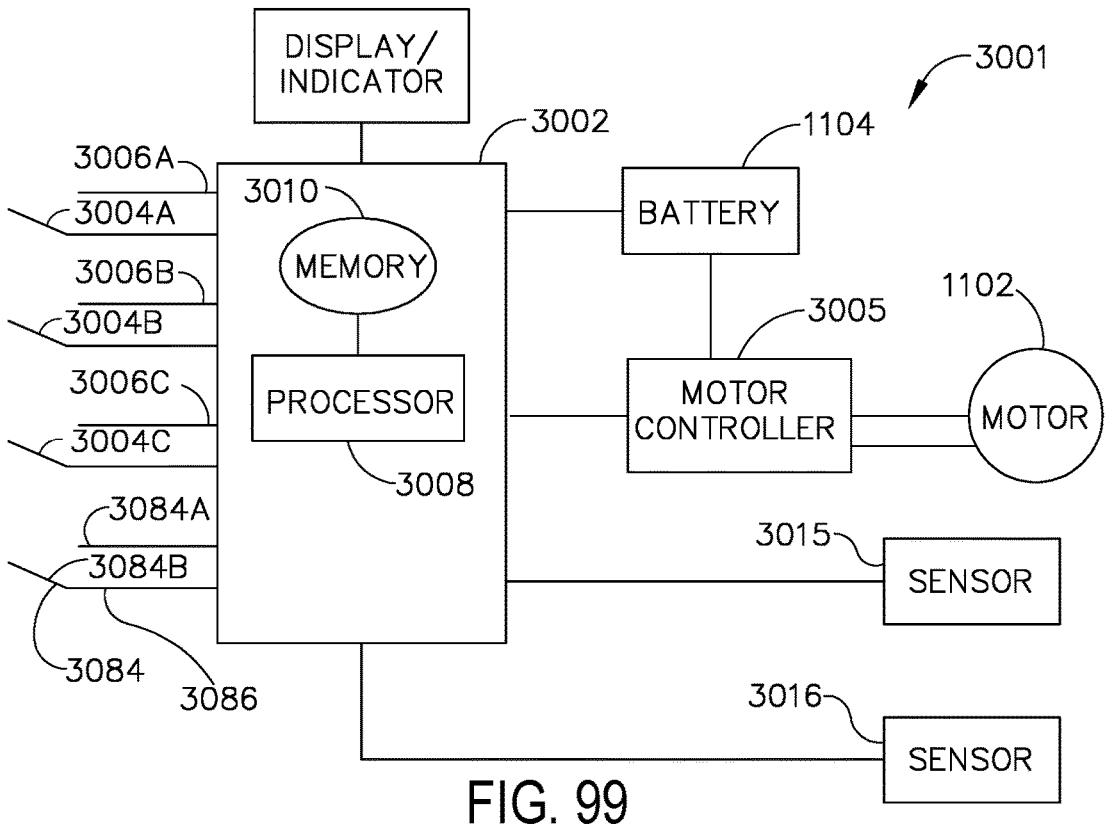
FIG. 99 is a schematic block diagram of a control system of a surgical instrument in accordance with one or more aspects of the present disclosure.

In the aspect illustrated in FIG. 99, an interface 3001 comprises multiple switches 3004A-C, 3084B wherein each of the switches 3004A-C is coupled to the controller 3002 via one of three electrical circuits 3006A-C, respectively, and switch 3084B is coupled to the controller 3002 via circuit 3084A. The reader will appreciate that other combinations of switches and circuits can be utilized with the interface 3001.

Further to the above, the controller 3002 may comprise a processor 3008 and/or one or more memory 3010 units. By executing instruction code stored in the memory 3010, the processor 3008 may control various components of the surgical instrument, such as the electric motor 1102 and/or a user display. The controller 3002 may be implemented using integrated and/or discrete hardware elements, software elements, and/or a combination of both. Examples of integrated hardware elements may include processors, microprocessors, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controller, system-on-chip (SoC), and/or system-in-package (SIP). Examples of discrete hardware elements may include circuits and/or circuit elements (e.g., logic gates, field effect transistors, bipolar transistors, resistors, capacitors, inductors, relay and so forth). In other aspects, the controller 3002 may include a hybrid circuit comprising discrete and integrated circuit elements or components on one or more substrates, for example.

Referring again to FIG. 99, the surgical instrument 1010 may include a motor controller 3005 in operable communication with the controller 3002. The motor controller 3005 can be configured to control a direction of rotation of the electric motor 1102. For example, the electric motor 1102 can be powered by a battery such as, for example, the battery 1104 and the controller 3002 may be configured to determine the voltage polarity applied to the electric motor 1102 by the battery 1104 and, in turn, the direction of rotation of the electric motor 1102 based on input from the controller 3002. For example, the electric motor 1102 may reverse the direction of its rotation from a clockwise direction to a counterclockwise direction when the voltage polarity applied to the electric motor 1102 by the battery 1104 is reversed by the motor controller 3005 based on input from the controller 3002. Examples of suitable motor controllers are described elsewhere in this document and include but are not limited to the driver 7010 (FIG. 100).

In addition, as described elsewhere in this document in greater detail, the electric motor 1102 can be operably coupled to an articulation drive. In use, the electric motor 1102 can drive the proximal articulation drive distally or proximally depending on the direction in which the electric motor 1102 rotates. Furthermore, the proximal articulation drive can be operably coupled to the end effector 1300 such that, for example, the axial translation of the proximal articulation drive 10030 proximally may cause the end effector 1300 to be articulated in the counterclockwise direction, for example, and/or the axial translation of the proximal articulation drive 10030 distally may cause the end effector 1300 to be articulated in the clockwise direction, for example.

Further to the above, referring again to FIG. 99, the interface 3001 can be configured such that the switch 3004A can be dedicated to clockwise articulation of the end effector 1300 and the switch 3004B can be dedicated to counterclockwise articulation of the end effector 1300. For example, the operator may articulate the end effector 1300 in the clockwise direction by closing the switch 3004A which may signal the controller 3002 to cause the electric motor 1102 to rotate in the clockwise direction thereby, as a result, causing the proximal articulation drive 10030 to be advanced distally and causing the end effector 1300 to be articulated in the clockwise direction. In another example, the operator may articulate the end effector 1300 in the counterclockwise direction by closing the switch 3004B which may signal the controller 3002 to cause the electric motor 1102 to rotate in the counterclockwise direction, for example, and retracting the proximal articulation drive 10030 proximally to articulate the end effector 1300 to in the counterclockwise direction.

Figure 100:
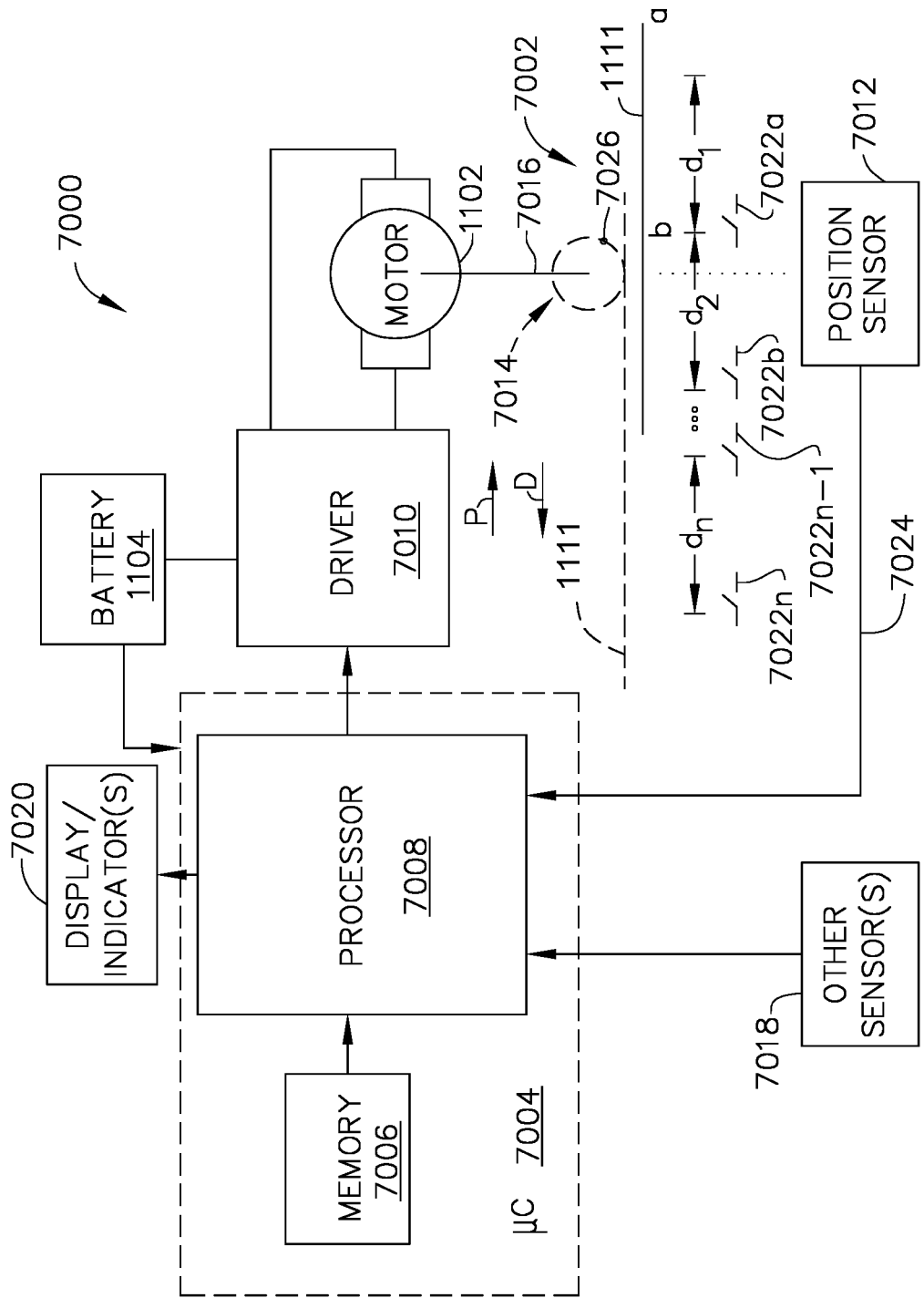
FIG. 100 is a schematic diagram of an absolute positioning system comprising a controlled motor drive circuit arrangement comprising a sensor arrangement in accordance with one or more aspects of the present disclosure.
Figure 101:
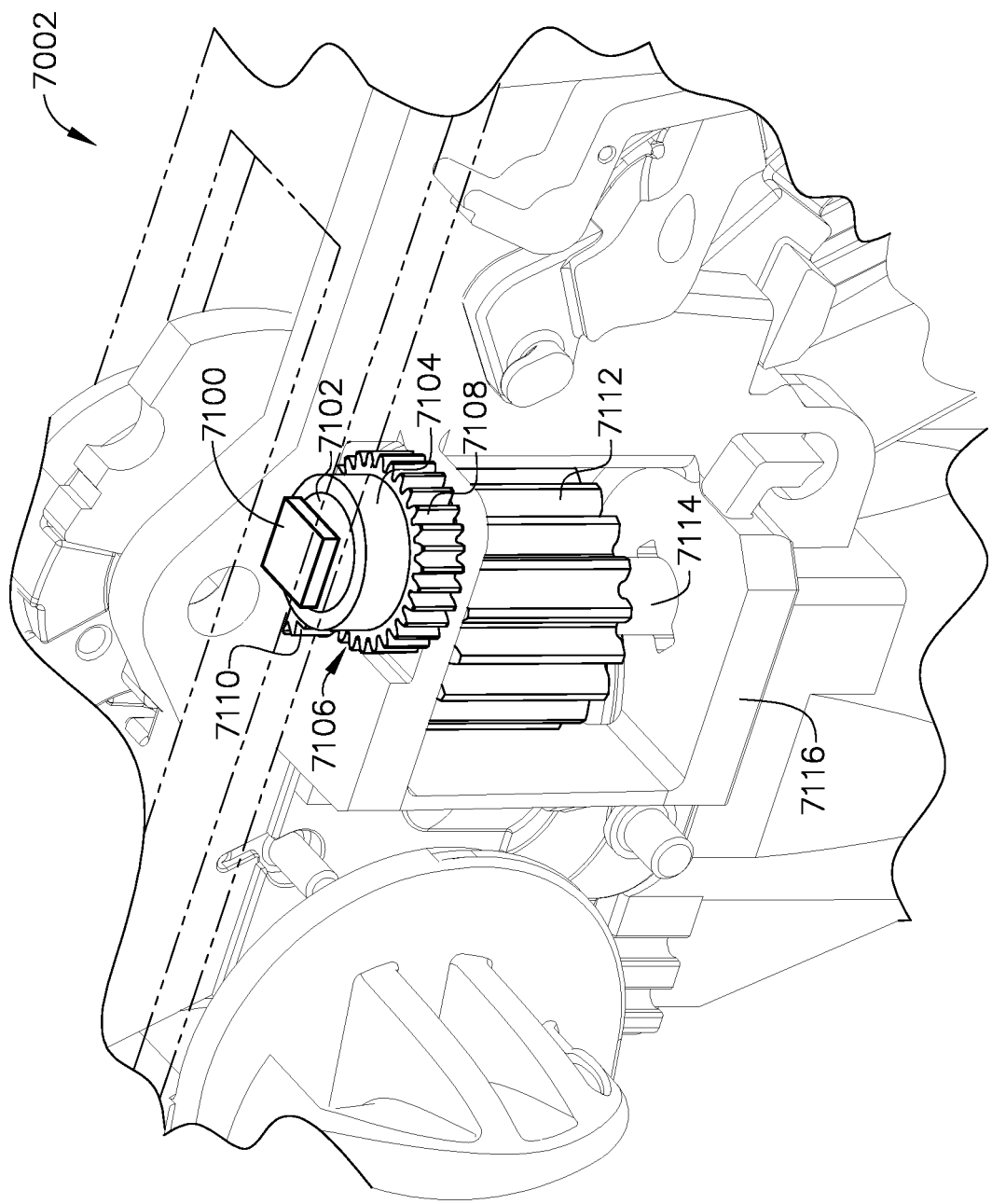
FIG. 101 is a detail perspective view of a sensor arrangement for an absolute positioning system in accordance with one or more aspects of the present disclosure.

As shown in FIG. 100, a sensor arrangement 7002 provides a unique position signal corresponding to the location of the longitudinally-movable drive member 1111. The electric motor 1102 can include a rotatable shaft 7016 that operably interfaces with a gear assembly 7014 that is mounted in meshing engagement with a with a set, or rack, of drive teeth on the longitudinally-movable drive member 1111. With reference also to FIG. 101, the sensor element 7026 may be operably coupled to the gear assembly 7106 such that a single revolution of the sensor element 7026 corresponds to some linear longitudinal translation of the longitudinally-movable drive member 1111, as described in more detail hereinbelow. In one aspect, an arrangement of gearing and sensors can be connected to the linear actuator via a rack and pinion arrangement, or a rotary actuator via a spur gear or other connection. For aspects comprising a rotary screw-drive configuration where a larger number of turns would be required, a high reduction gearing arrangement between the drive member and the sensor, like a worm and wheel, may be employed.

In accordance one aspect of the present disclosure, the sensor arrangement 7002 for the absolute positioning system 7000 provides a position sensor 7012 that is more robust for use with surgical devices. By providing a unique position signal or value for each possible actuator position, such arrangement eliminates the need for a zeroing or calibration step and reduces the possibility of negative design impact in the cases where noise or power brown-out conditions may create position sense errors as in conventional rotary encoder configurations.

In one aspect, the sensor arrangement 7002 for the absolute positioning system 7000 replaces conventional rotary encoders typically attached to the motor rotor and replaces it with a position sensor 7012 which generates a unique position signal for each rotational position in a single revolution of a sensor element associated with the position sensor 7012. Thus, a single revolution of a sensor element associated with the position sensor 7012 is equivalent to a longitudinal linear displacement d1 of the of the longitudinally-movable drive member 1111. In other words, d1 is the longitudinal linear distance that the longitudinally-movable drive member 1111 moves from point "a" to point "b" after a single revolution of a sensor element coupled to the longitudinally-movable drive member 1111. The sensor arrangement 7002 may be connected via a gear reduction that results in the position sensor 7012 completing only a single turn for the full stroke of the longitudinally-movable drive member 1111. With a suitable gear ratio, the full stroke of the longitudinally-movable drive member 1111 can be represented in one revolution of the position sensor 7012.

A series of switches $7022a$ to $7022n$, where n is an integer greater than one, may be employed alone or in combination with gear reduction to provide a unique position signal for more than one revolution of the position sensor 7012. The state of the switches $7022a$-$7022n$ are fed back to a controller 7004 which applies logic to determine a unique position signal corresponding to the longitudinal linear displacement d1+d2+ . . . dn of the longitudinally-movable drive member 1111.

Accordingly, the absolute positioning system 7000 provides an absolute position of the longitudinally-movable drive member 1111 upon power up of the instrument without retracting or advancing the longitudinally-movable drive member 1111 to a reset (zero or home) position as may be required with conventional rotary encoders that merely count the number of steps forwards or backwards that motor has taken to infer the position of a device actuator, drive bar, knife, and the like.

In various aspects, the position sensor 7012 of the sensor arrangement 7002 may comprise one or more magnetic sensor, analog rotary sensor like a potentiometer, array of analog Hall-effect elements, which output a unique combination of position signals or values, among others, for example.

In various aspects, the controller 7004 may be programmed to perform various functions such as precise control over the speed and position of the knife and articulation systems. Using the known physical properties, the controller 7004 can be designed to simulate the response of the actual system in the software of the controller 7004. The simulated response is compared to (noisy and discrete) measured response of the actual system to obtain an "observed" response, which is used for actual feedback decisions. The observed response is a favorable, tuned, value that balances the smooth, continuous nature of the simulated response with the measured response, which can detect outside influences on the system.

In various aspects, the absolute positioning system 7000 may further comprise and/or be programmed to implement the following functionalities. A feedback controller, which can be one of any feedback controllers, including, but not limited to: PID, state feedback and adaptive. A power source converts the signal from the feedback controller into a physical input to the system, in this case voltage. Other examples include, but are not limited to pulse width modulated (PWMed) voltage, current and force. The electric motor 1102 may be a brushed DC motor with a gearbox and mechanical links to an articulation or knife system. Other sensor(s) 7018 may be provided to measure physical parameters of the physical system in addition to position measured by the position sensor 7012. Since it is a digital signal (or connected to a digital data acquisition system) its output will have finite resolution and sampling frequency. A compare and combine circuit may be provided to combine the simulated response with the measured response using algorithms such as, without limitation, weighted average and theoretical control loop that drives the simulated response towards the measured response. Simulation of the physical system takes in account of properties like mass, inertial, viscous friction, inductance resistance, etc. to predict what the states and outputs of the physical system will be by knowing the input. In one aspect, the controller 7004 may be a single core or multicore controller LM4F230H5QR as described in connection with FIGS. 15-17B.

In one aspect, the driver 7010 may be a A3941 available from Allegro Microsystems, Inc. The A3941 driver 7010 is a full-bridge controller for use with external N-channel power metal oxide semiconductor field effect transistors (MOSFETs) specifically designed for inductive loads, such as brush DC motors. The driver 7010 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 7000. Accordingly, the present disclosure should not be limited in this context.

Figure 102:
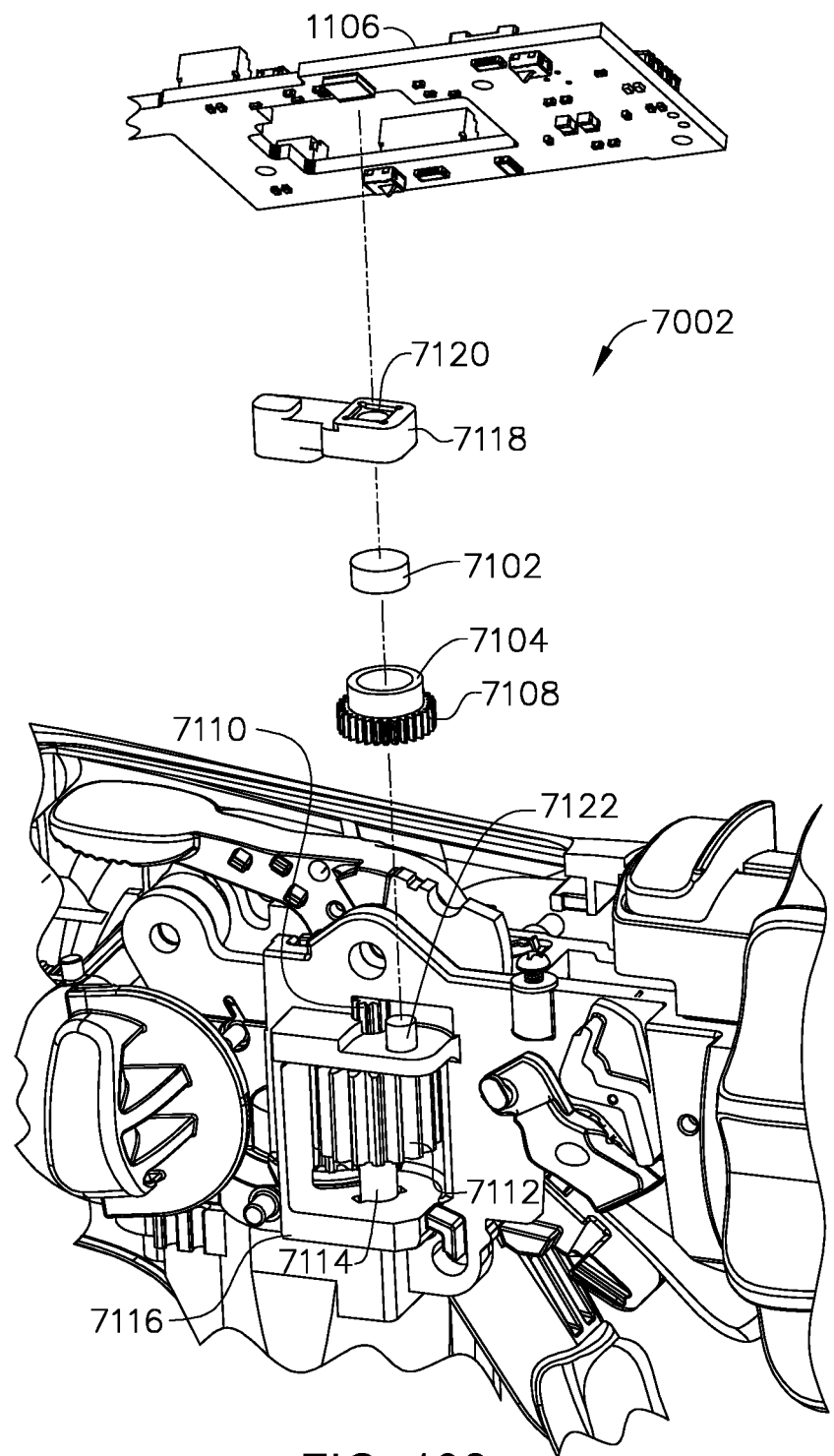
FIG. 102 is an exploded perspective view of the sensor arrangement for an absolute positioning system showing a control circuit board assembly and the relative alignment of the elements of the sensor arrangement in accordance with one or more aspects of the present disclosure.
Figure 103:
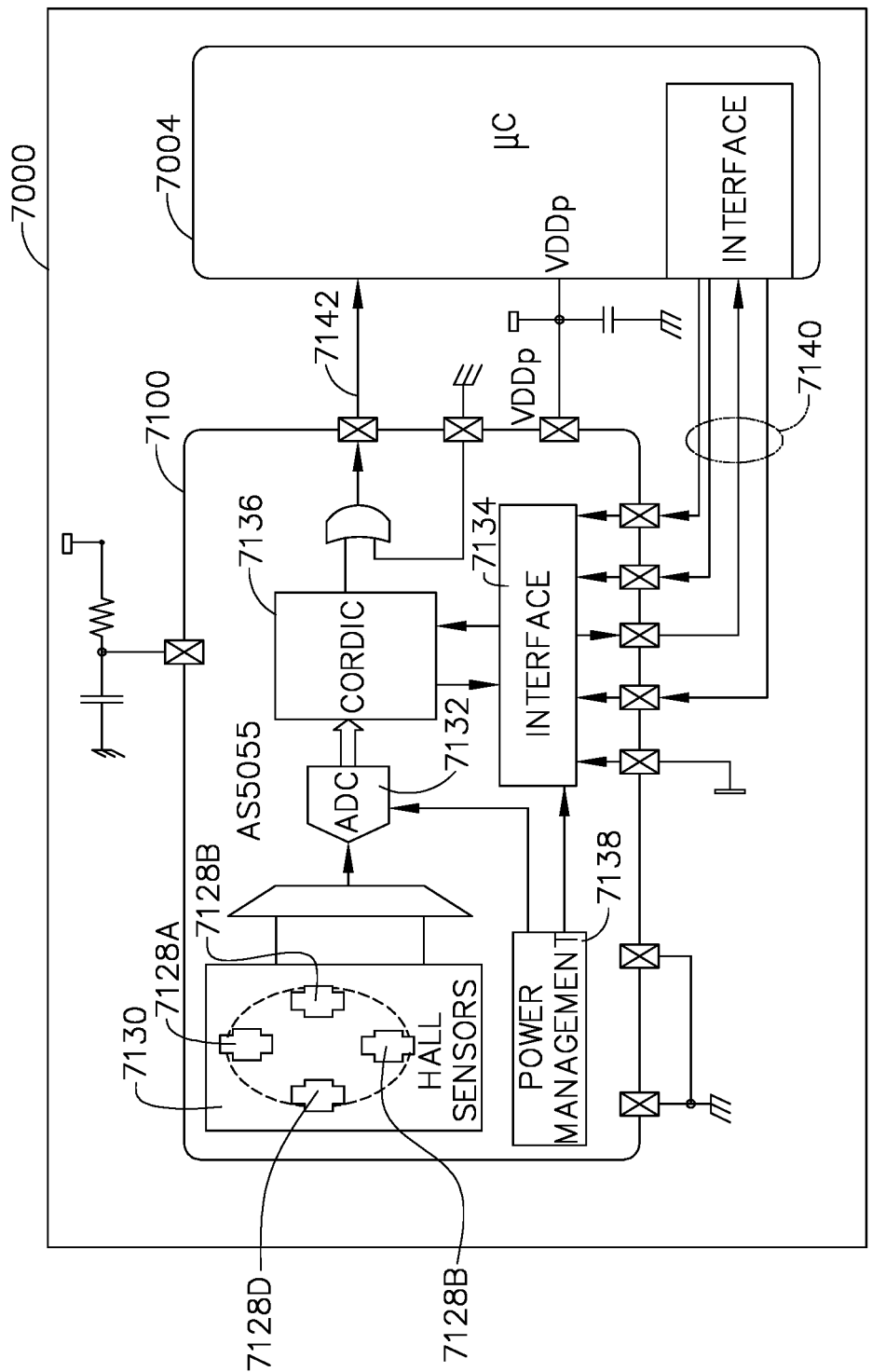
FIG. 103 is a schematic diagram of one aspect of a position sensor for an absolute positioning system comprising a magnetic rotary absolute positioning system in accordance with one or more aspects of the present disclosure.

Having described a general architecture for implementing various aspects of an absolute positioning system 7000 for a sensor arrangement 7002, the disclosure now turns to FIGS. 101-103 for a description of one aspect of a sensor arrangement for the absolute positioning system 7000. In the aspect illustrated in FIG. 101, the sensor arrangement 7002 comprises a position sensor 7100, a magnet 7102 sensor element, a magnet holder 7104 that turns once every full stroke of the longitudinally-movable drive member 1111 (FIG. 100), and a gear assembly 7106 to provide a gear reduction. A structural element such as bracket 7116 is provided to support the gear assembly 7106, the magnet holder 7104, and the magnet 7102. The position sensor 7100 comprises one or more than one magnetic sensing elements such as Hall elements and is placed in proximity to the magnet 7102. Accordingly, as the magnet 7102 rotates, the magnetic sensing elements of the position sensor 7100 determine the absolute angular position of the magnet 7102 over one revolution.

In various aspects, any number of magnetic sensing elements may be employed on the absolute positioning system 7000, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In the illustrated aspect, the gear assembly 7106 comprises a first gear 7108 and a second gear 7110 in meshing engagement to provide a 3:1 gear ratio connection. A third gear 7112 rotates about shaft 7114. The third gear is in meshing engagement with the longitudinally-movable drive member 1111 and rotates in a first direction as the longitudinally-movable drive member 1111 advances in a distal direction D and rotates in a second direction as the longitudinally-movable drive member 1111 retracts in a proximal direction P. The second gear 7110 also rotates about the shaft 7114 and therefore, rotation of the second gear 7110 about the shaft 7114 corresponds to the longitudinal translation of the longitudinally-movable drive member 1111. Thus, one full stroke of the longitudinally-movable drive member 1111 in either the distal or proximal directions D, P corresponds to three rotations of the second gear 7110 and a single rotation of the first gear 7108. Since the magnet holder 7104 is coupled to the first gear 7108, the magnet holder 7104 makes one full rotation with each full stroke of the longitudinally-movable drive member 1111.

FIG. 102 is an exploded perspective view of the sensor arrangement 7002 for the absolute positioning system 7000 showing a circuit 1106 and the relative alignment of the elements of the sensor arrangement 7002, according to one aspect. The position sensor 7100 (not shown in this view) is supported by a position sensor holder 7118 defining an aperture 7120 suitable to contain the position sensor 7100 in precise alignment with a magnet 7102 rotating below. The fixture is coupled to the bracket 7116 and to the circuit 1106 and remains stationary while the magnet 7102 rotates with the magnet holder 7104. A hub 7122 is provided to mate with the first gear 7108 and the magnet holder 7104.

FIG. 103 is a schematic diagram of one aspect of a position sensor 7100 sensor for an absolute positioning system 7000 comprising a magnetic rotary absolute positioning system, according to one aspect. In one aspect, the position sensor 7100 may be implemented as an AS5055EQFT single-chip magnetic rotary position sensor available from Austria Microsystems, AG. The position sensor 7100 is interfaced with the controller 7004 to provide an absolute positioning system 7000. The position sensor 7100 is a low voltage and low power component and includes four Hall-effect elements 7128A, 7128B, 7128C, 7128D in an area 7130 of the position sensor 7100 that is located above the magnet 7102 (FIGS. 99, 100). A high resolution ADC 7132 and a smart power management controller 7138 are also provided on the chip. A CORDIC processor 7136 (for COordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits and magnetic field information are transmitted over a standard serial communication interface such as an SPI interface 7134 to the controller 7004. The position sensor 7100 provides 12 or 14 bits of resolution. The position sensor 7100 may be an AS5055 chip provided in a small QFN 16-pin 4×4×0.85 mm package.

The Hall-effect elements 7128A, 7128B, 7128C, 7128D are located directly above the rotating magnet. The Hall-effect is a well known effect and will not be described in detail herein for the sake of conciseness and clarity of disclosure. Generally, the Hall-effect is the production of a voltage difference (the Hall voltage) across an electrical conductor, transverse to an electric current in the conductor and a magnetic field perpendicular to the current. It was discovered by Edwin Hall in 1879. The Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 7100, the Hall-effect elements 7128A, 7128B, 7128C, 7128D are capable producing a voltage signal that is indicative of the absolute position of the magnet 7102 (FIGS. 186, 187) in terms of the angle over a single revolution of the magnet 7102. This value of the angle, which is unique position signal, is calculated by the CORDIC processor 7136 is stored onboard the AS5055 position sensor 7100 in a register or memory. The value of the angle that is indicative of the position of the magnet 7102 over one revolution is provided to the controller 7004 in a variety of techniques, e.g., upon power up or upon request by the controller 7004.

The AS5055 position sensor 7100 requires only a few external components to operate when connected to the controller 7004. Six wires are needed for a simple application using a single power supply: two wires for power and four wires 7140 for the SPI interface 7134 with the controller 7004. A seventh connection can be added in order to send an interrupt to the controller 7004 to inform that a new valid angle can be read.

Upon power-up, the AS5055 position sensor 7100 performs a full power-up sequence including one angle measurement. The completion of this cycle is indicated as an INT output 7142 and the angle value is stored in an internal register. Once this output is set, the AS5055 position sensor 7100 suspends to sleep mode. The controller 7004 can respond to the INT request at the INT output 7142 by reading the angle value from the AS5055 position sensor 7100 over the SPI interface 7134. Once the angle value is read by the controller 7004, the INT output 7142 is cleared again. Sending a "read angle" command by the SPI interface 7134 by the controller 7004 to the position sensor 7100 also automatically powers up the chip and starts another angle measurement. As soon as the controller 7004 has completed reading of the angle value, the INT output 7142 is cleared and a new result is stored in the angle register. The completion of the angle measurement is again indicated by setting the INT output 7142 and a corresponding flag in the status register.

Due to the measurement principle of the AS5055 position sensor 7100, only a single angle measurement is performed in very short time (~600 μs) after each power-up sequence. As soon as the measurement of one angle is completed, the AS5055 position sensor 7100 suspends to power-down state. An on-chip filtering of the angle value by digital averaging is not implemented, as this would require more than one angle measurement and consequently, a longer power-up time which is not desired in low power applications. The angle jitter can be reduced by averaging of several angle samples in the controller 7004. For example, an averaging of 4 samples reduces the jitter by 6 dB (50%).

As discussed above, the electric motor 1102 positioned within the handle 1042 of surgical instrument system 1000 can be utilized to advance and/or retract the firing system of the shaft assembly 1200, including firing members 1272 and 1280, for example, relative to the end effector 1300 of the shaft assembly 1200 in order to staple and/or incise tissue captured within the end effector 1300. In various circumstances, it may be desirable to advance the firing members 1272 and 1280 at a desired speed, or within a range of desired speeds. Likewise, it may be desirable to retract the firing members 1272 and 1280 at a desired speed, or within a range of desired speeds. In various circumstances, the controller 7004 of the handle 1042, for example, and/or any other suitable controller, can be configured to control the speed of the firing members 1272 and 1280. In some circumstances, the controller can be configured to predict the speed of the firing members 1272 and 1280 based on various parameters of the power supplied to the electric motor 1102, such as voltage and/or current, for example, and/or other operating parameters of the electric motor 1102. The controller can also be configured to predict the current speed of the firing members 1272 and 1280 based on the previous values of the current and/or voltage supplied to the electric motor 1102, and/or previous states of the system like velocity, acceleration, and/or position. Furthermore, the controller can also be configured to sense the speed of the firing members 1272 and 1280 utilizing the absolute positioning sensor system described above, for example. In various circumstances, the controller can be configured to compare the predicted speed of the firing members 1272 and 1280 and the sensed speed of the firing members 1272 and 1280 to determine whether the power to the electric motor 1102 should be increased in order to increase the speed of the firing members 1272 and 1280 and/or decreased in order to decrease the speed of the firing members 1272 and 1280. U.S. Pat. No. 8,210,411, entitled MOTOR-DRIVEN SURGICAL CUTTING INSTRUMENT, which is incorporated herein by reference in its entirety. U.S. Pat. No. 7,845,537, entitled SURGICAL INSTRUMENT HAVING RECORDING CAPABILITIES, which is incorporated herein by reference in its entirety.

Figure 104:
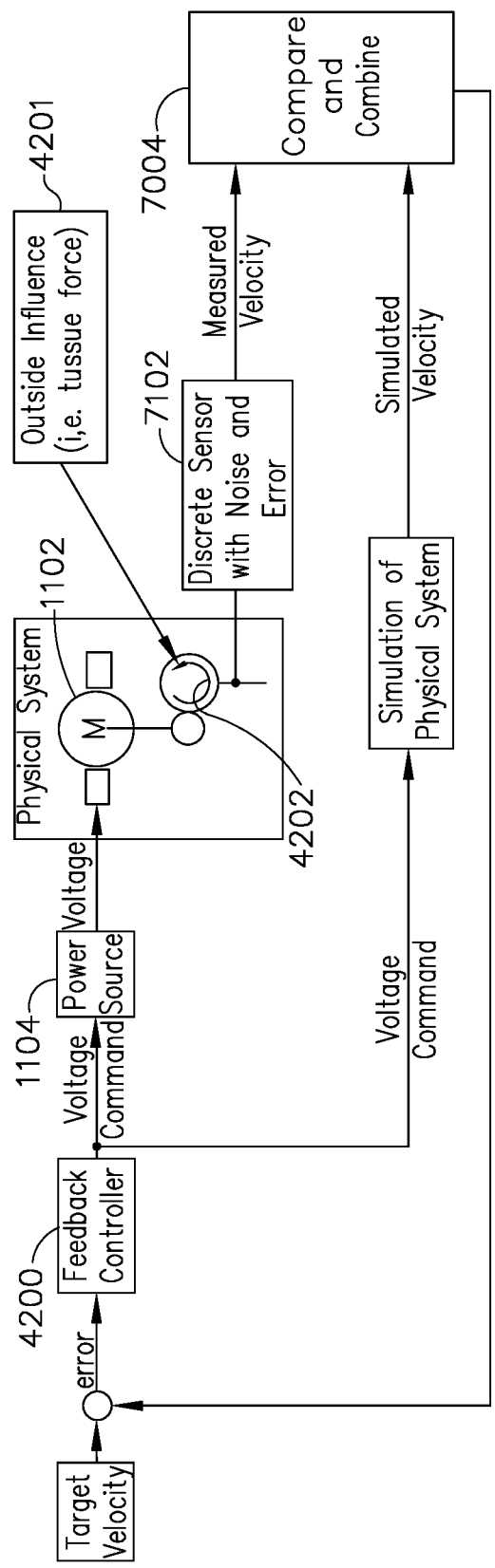
FIG. 104 is a schematic illustrating a system for controlling the speed of a motor and/or the speed of a drivable member of a surgical instrument in accordance with one or more aspects of the present disclosure.
Figure 105:
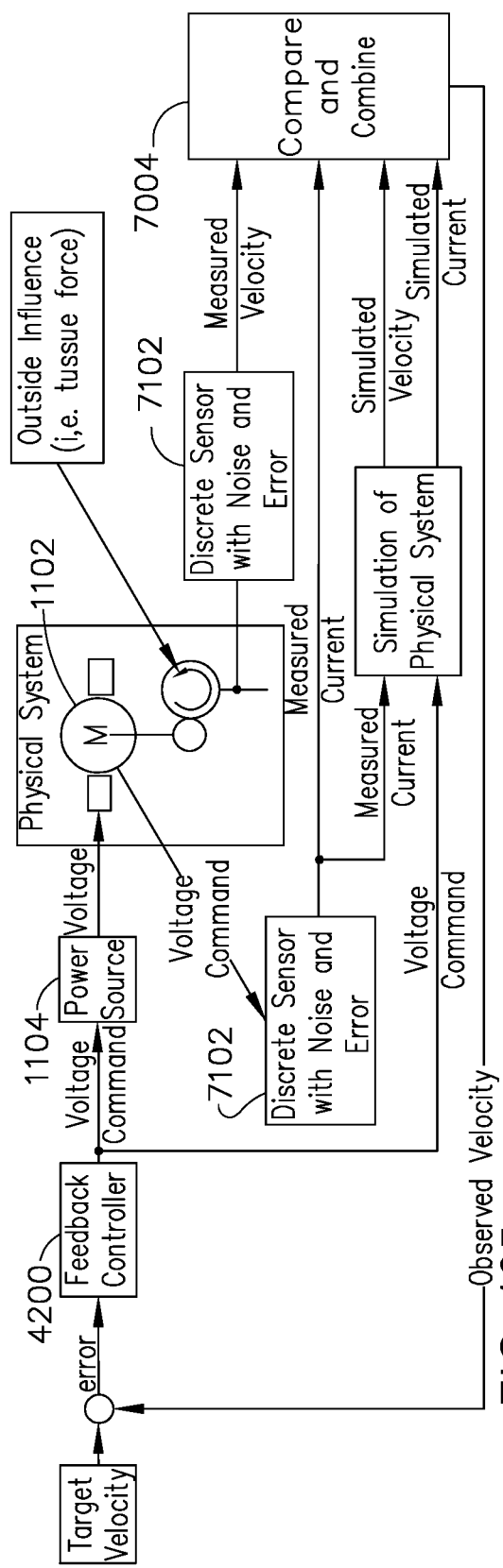
FIG. 105 is a schematic illustrating another system for controlling the speed of a motor and/or the speed of a drivable member of a surgical instrument in accordance with one or more aspects of the present disclosure.

Using the physical properties of the instruments disclosed herein, turning now to FIGS. 104 and 105, a controller, such as controller 7004, for example, can be designed to simulate the response of the actual system of the instrument in the software of the controller. The simulated response is compared to a (noisy and discrete) measured response of the actual system to obtain an "observed" response, which is used for actual feedback decisions. The observed response is a favorable, tuned, value that balances the smooth, continuous nature of the simulated response with the measured response, which can detect outside influences on the system. With regard to FIGS. 104 and 105, a firing element, or cutting element, in the end effector 1300 of the shaft assembly 1200 can be moved at or near a target velocity, or speed. The systems disclosed in FIGS. 102 and 103 can be utilized to move the cutting element at a target velocity. The systems can include a feedback controller 4200, which can be one of any feedback controllers, including, but not limited to a PID, a State Feedback, LQR, and/or an Adaptive controller, for example. The systems can further include a power source. The power source can convert the signal from the feedback controller 4200 into a physical input to the system, in this case voltage, for example. Other examples include, but are not limited to, pulse width modulated (PWM) voltage, frequency modulated voltage, current, torque, and/or force, for example.

With continued reference to FIGS. 104 and 105, the physical system referred to therein is the actual drive system of the instrument configured to drive the firing member, or cutting member. One example is a brushed DC motor with a gearbox and mechanical links to an articulation and/or knife system. Another example is the electric motor 1102 disclosed herein that operates the firing member 10060 and the articulation driver 10030, for example, of an interchangeable shaft assembly. The outside influence 4201 referred to in FIGS. 104 and 105 is the unmeasured, unpredictable influence of things like tissue, surrounding bodies and friction on the physical system, for example. Such outside influence can be referred to as drag and can be represented by a motor 4202 which acts in opposition to the electric motor 1102, for example. In various circumstances, outside influence, such as drag, is the primary cause for deviation of the simulation of the physical system from the actual physical system. The systems depicted in FIGS. 104 and 105 and further discussed below can address the differences between the predicted behavior of the firing member, or cutting member, and the actual behavior of the firing member, or cutting member.

With continued reference to FIGS. 104 and 105, the discrete sensor referred to therein measures physical parameters of the actual physical system. One aspect of such a discrete sensor can include an absolute positioning sensor and system described herein, such as the magnet 7102. As the output of such a discrete sensor can be a digital signal (or connected to a digital data acquisition system) its output may have finite resolution and sampling frequency. The output of the discrete sensor can be supplied to a controller, such as controller 7004, for example. In various circumstances, the controller can combine the simulated, or estimated, response with the measured response. In certain circumstances, it may be useful to use enough measured response to ensure that the outside influence is accounted for without making the observed response unusably noisy. Examples for algorithms that do so include a weighted average and/or a theoretical control loop that drives the simulated response towards the measured response, for example. Ultimately, further to the above, the simulation of the physical system takes in account of properties like mass, inertial, viscous friction, and/or inductance resistance, for example, to predict what the states and outputs of the physical system will be by knowing the input. FIG. 103 shows an addition of evaluating and measuring the current supplied to operate the actual system, which is yet another parameter that can be evaluated for controlling the speed of the cutting member, or firing member, of the shaft assembly 1200, for example. By measuring current in addition to or in lieu of measuring the voltage, in certain circumstances, the physical system can be made more accurate. Nonetheless, the ideas disclosed herein can be extended to the measurement of other state parameters of other physical systems.

Figure 106:
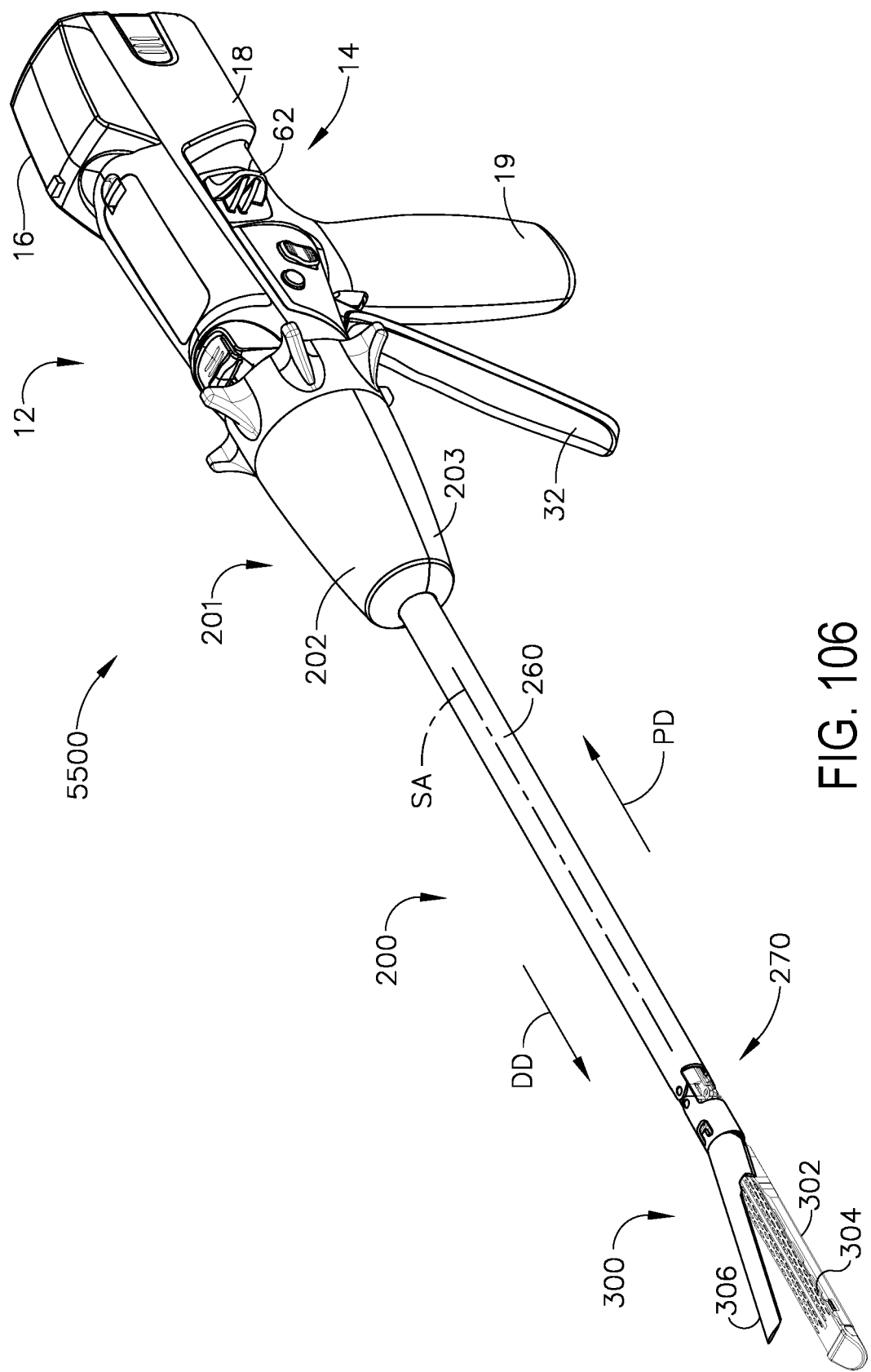
FIG. 106 illustrates a perspective view of a surgical instrument according to various aspects in accordance with one or more aspects of the present disclosure.

FIG. 106 illustrates a perspective view of a surgical instrument 5500 according to various aspects described herein. The surgical instrument 5500 is similar to those described hereinabove in that the surgical instrument 5500 includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5500 is also similar to those described hereinabove in that the surgical instrument 5500 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5500 is also similar to those described hereinabove in that the surgical instrument 5500 also includes algorithms such as closing algorithms, firing algorithms, motor control algorithms, or any combination thereof, which operate to dynamically adjust the operation of the surgical instrument 5500. However, the surgical instrument 5500 is different from those described hereinabove in that the surgical instrument 5500 further includes one or more additional algorithms (in addition to those described hereinabove) which provide additional control functionality for the surgical instrument 5500, as described hereinbelow.

In general, the surgical instrument 5500 may utilize one or more closing algorithms to control a closing motion which clamps the jaws to tissue positioned therebetween and/or one or more firing algorithms to control a firing motion which staples and severs the tissue clamped between the jaws. In operation, a given sensor senses or measures a given parameter (e.g., a closing force, a firing force, and/or any combination thereof) and outputs a signal indicative of the sensed/measured parameter. The output signal can be an analog signal or a digital signal. For instances where the signal output by the sensor is an analog signal, the analog signal is input to an analog-to-digital (A/D) converter which outputs a digital signal indicative of the analog signal. The digital signal is then input to a controller resident in the surgical instrument 5500. For instances where the signal output by the sensor is a digital signal, there is no need for an A/D conversion and the digital signal output by the sensor can be input to the controller. Upon the occurrence of a trigger, a threshold and/or an event, the controller may modify or adjust a closing algorithm, or initiate a different closing algorithm, thereby automatically changing the operation of the surgical instrument 5500 during a closing motion. Similarly, upon the occurrence of a trigger, a threshold and/or an event, the controller may modify or adjust a firing algorithm, or initiate a different firing algorithm, thereby automatically changing the operation of the surgical instrument 5500 during a firing motion.

According to various aspects, the trigger, threshold or event is defined by the sensed/measured closing force. According to other aspects, the trigger, threshold or event is defined by a parameter related to the sensed/measured closing force. Similarly, according to various aspects, the trigger, threshold or event is defined by the sensed/measured firing force. According to other aspects, the trigger, threshold or event is defined by a parameter related to the sensed/measured firing force.

Figure 107:
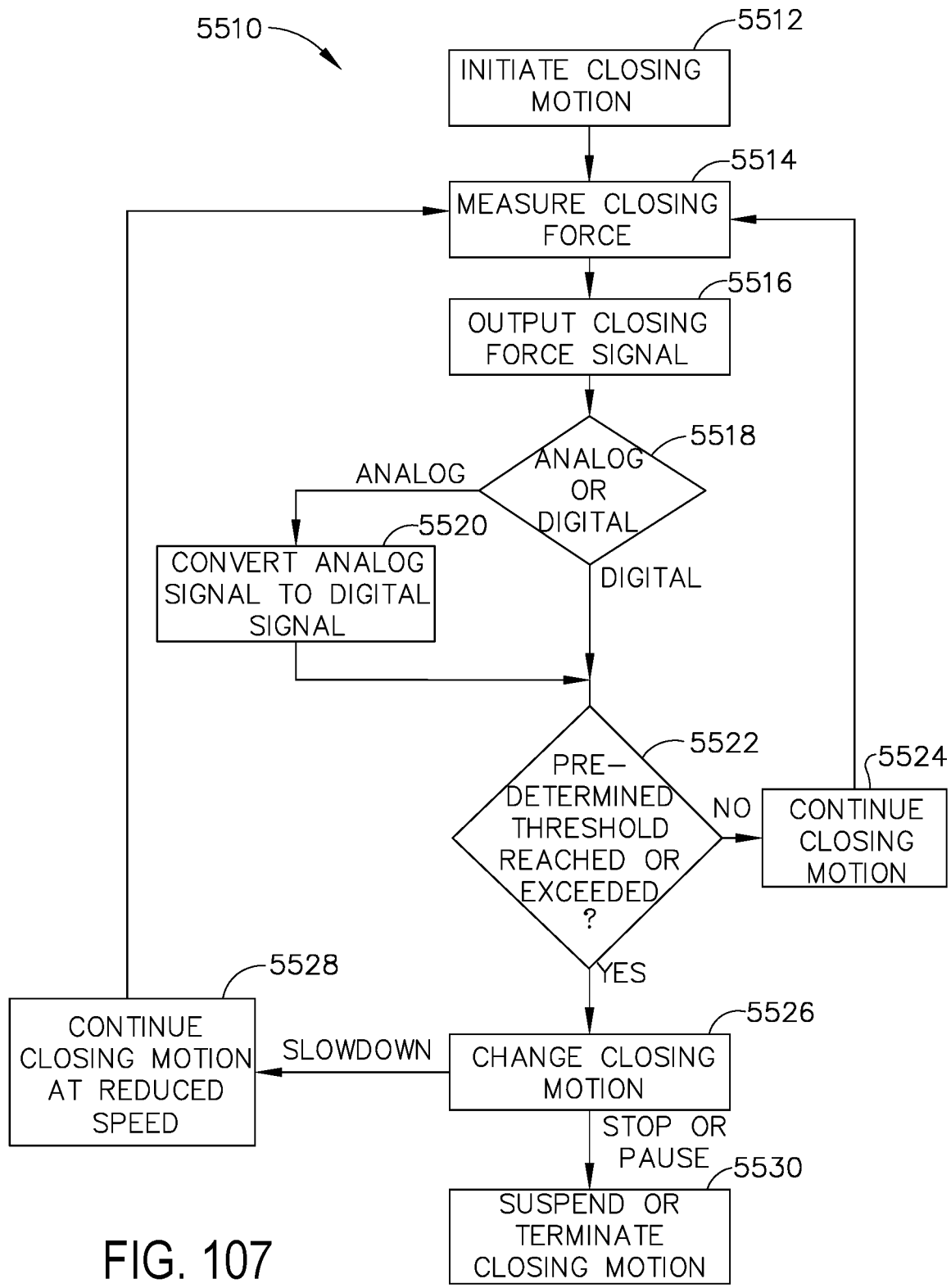
FIG. 107 illustrates a method of controlling a closing motion of the surgical instrument of FIG. 106 according to various aspects in accordance with one or more aspects of the present disclosure.

FIG. 107 illustrates a method 1010 of controlling a closing motion of the surgical instrument 5500 according to various aspects. The process starts when a closing motion is initiated 5512. The closing motion may be initiated, for example, by pulling a closing trigger toward a handle. A sensor resident with the surgical instrument 5500 senses/measures 5514 a closing force. The closing force may be, for example, a force experienced by tissue clamped between the jaws of the surgical instrument 5500, a force experienced by the jaws of the surgical instrument 5500 (e.g., by the anvil and/or the elongated channel), a force experienced by the closure tube of the surgical instrument 5500, and/or any combinations thereof.

In response to the closing force, the sensor outputs 5516 a closing force signal, which is indicative of the closing force sensed/measured 5514 by the sensor. Depending on the configuration of the sensor, the closing force signal can be an analog signal or a digital signal. Upon determining 5518 whether the closing force signal is either an analog signal or a digital signal, the process proceeds along the corresponding branch. When the determination 5518 is that the closing force signal is an analog signal, the process proceeds along the analog branch, where the analog signal is received by an A/D converter, converted 5520 to a digital signal representative of the analog signal by the A/D converter and the digital signal is output by the A/D converter. When the determination 5518 is that the closing force signal is a digital signal, the process proceeds along the digital branch because there is no need for an A/D conversion 5520 when the closing force signal is a digital signal.

The closing force signal which is a digital signal representative of the closing force sensed/measured 5514 by the sensor is received by a controller. The controller utilizes the digital signal and determines 5522 whether the closing force sensed/measured 5514 by the sensor reaches or exceeds a predetermined threshold. The controller may make this determination 5522 based on a comparison of a magnitude of the closing force sensed/measured 5514 by the sensor and the predetermined threshold, based on a comparison of an amplitude of the closing force signal output 5516 by the sensor and a predetermined threshold, or any combination thereof.

When the controller determines 5522 that the closing force sensed/measured 5514 by the sensor has not reached or exceeded the predetermined threshold, the closing motion originally initiated 5512 is continued 5524 along with interim processes 5514-5522. When the controller determines 5522 that the closing force sensed/measured 5514 by the sensor has reached or exceeded the predetermined threshold, the controller changes 5526 the closing motion. According to some aspects, the controller may change the closing motion by modifying or adjusting a closing algorithm being executed by the controller to cause the closing motion to be slowed down, paused or stopped to prevent the surgical instrument 5500 from experiencing excessive forces. According to other aspects, the controller may change the closing motion by executing a different closing algorithm which causes the closing motion to be slowed down, paused or stopped to prevent the surgical instrument 5500 from experiencing excessive forces. In either case, the closing motion may be slowed down, stopped or paused by having the controller communicate a slow down signal, a stop signal or a pause signal to the motor controller to slow down, stop or pause the rotation of the motor(s) which drive the closing of the jaws of the surgical instrument 5500.

Upon changing the closing motion 5526, when the change of the closing motion 5526 is a slowing down of the closing motion (a slowing down of the rotation of the motor(s) which drive the closing of the jaws), the process continues 5528 the closing motion originally initiated 5512 but at a reduced speed and the interim process 5514-5522 is continued but the closing of the jaws occurs at a reduced speed. When the change of the closing motion 5526 is a stopping or pausing of the closing motion (a stopping or pausing of the rotation of the motor(s) which drive the closing of the jaws), the process suspends or terminates 5530 the closing motion.

Figure 108:
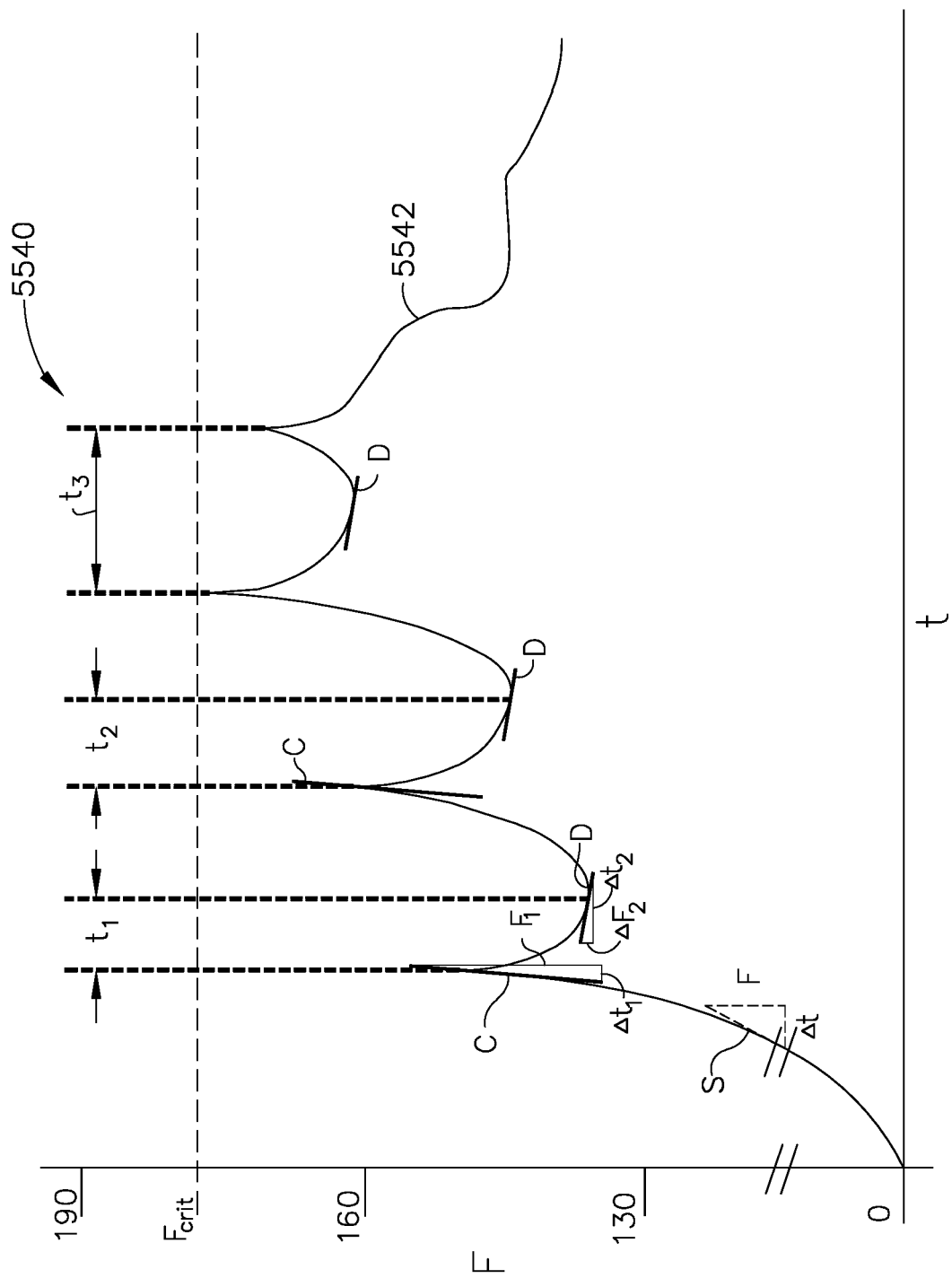
FIG. 108 illustrates an example graph showing a curve representative of a closing force signal over time for various aspects of the surgical instrument of FIG. 106 in accordance with one or more aspects of the present disclosure.

FIG. 108 illustrates an example graph 5540 showing a curve 5542 representative of a closing force F over time t for various aspects of the surgical instrument 5500. The closing force F is shown along the vertical axis and the time t is shown along the horizontal axis. Stated differently, the curve 5542 is a graphical representation of the closing force signal at various times during a closing motion. The curve 5542 may be generated mathematically by the controller based on the closing force signal(s) received by the controller. The closing force F represented on the vertical axis may be a force experienced by tissue clamped between the jaws of the surgical instrument 5500, a force experienced by the jaws of the surgical instrument 5500 (e.g., by the anvil and/or the elongated channel), a force experienced by the closure tube of the surgical instrument 5500, and/or any combinations thereof. The closing force F can be measured in any suitable manner, either directly or indirectly. For example, according to various aspects, the closing force F can be measured directly by a sensor (e.g., a strain gauge) positioned on the anvil, on the elongated channel, on the closure tube, or indirectly by an impedance of the tissue, a current draw of the motor, and/or any combinations thereof.

According to various aspects, the operation of the surgical instrument 5500 may be controlled by monitoring the amplitude of the closing force signal and changing the closing motion when the amplitude of the closing force signal reaches or exceeds a predetermined threshold. With reference to FIG. 107, for example, the closing force amplitude Fcrit may be determined to be an excessive amount of the closing force F experienced by the surgical instrument 5500. Upon the occurrence of the amplitude of the closing force signal reaching or exceeding the closing force amplitude Fcrit, an algorithm, such as the method 1010 of controlling a closing motion of the surgical instrument 5500 according to various aspects illustrated in FIG. 106, may operate to change the closing motion by slowing down, pausing or stopping the motor(s) of the surgical instrument 5500 to prevent the surgical instrument 5500 from experiencing excessive forces.

The curve 5542 provides a useful representation of how the closing force F varies over time t. The change in the closing force F over time t (i.e., the rate of change of the closing force F) may provide useful feedback to the control circuit to control the jaw closing mechanism of the surgical instrument 5500. The change in the closing force F over time t may be represented as a derivative of the curve 5542 and may be approximated over short periods of time by the equation Slope $S = \Delta F / \Delta t$, where $\Delta F$ is the change of the closing force F and $\Delta t$ is the change of the time t. The curve 5542 is representative of an analog signal over time which is sampled and converted to a digital value by an A/D converter as the jaws are closed/opened. Once the analog signal is digitized, the control circuit may thereafter determine the slope of the closing force signal represented by the curve 5542 at any point during the closing motion.

According to various aspects, the operation of the surgical instrument 5500 may be controlled by monitoring the slope of the curve 5542 (the slope of the closing force signal) and changing the closing motion based on the value of the slope. In general, with reference to FIG. 108, the slope of the curve 5542 may be approximated by the equation $S=\Delta F/\Delta t$, where $\Delta F$ is the change of the closing force F and $\Delta t$ is the change of the time t. Those skilled in the art will appreciate that the instantaneous slope may be calculated by taking the derivative of the curve 5542. Over time t, the slope S may be monitored by the control circuit and utilized by the control circuit to control the operation of the surgical instrument 5500. For example, an algorithm of the surgical instrument 5500 may be configured to monitor the change of the closing force F over the time t, stop or pause the closing motion when the slope of the curve 5542 reaches or exceeds a first predetermined threshold, then restart the closing motion when the slope of the curve 5542 reaches or falls below a second predetermined threshold. The value of the slope $C=\Delta F1/\Delta t1$ (a positive value) shown in FIG. 108 may be determined by the controller and may represent the first predetermined threshold. Similarly, the value of the slope $D=\Delta F2/\Delta t2$ (a negative value) shown in FIG. 108 may be determined by the controller and may represent the second predetermined threshold. Thus, according to various aspects, the algorithm can control the operation of the control circuit based on the determined slope, whether instantaneous or approximated.

For the example graph 5540 shown in FIG. 108, at time t=0 the jaws are in the open position and there is no closing force F experienced by the jaws. Once tissue is positioned between the jaws, as the jaws are moved toward a closed position, the jaws come in contact with tissue and begin to compress the tissue. Thus, as the time moves from the time t=0, the closing force F experienced by the jaws begins to increase. An algorithm of the surgical instrument 5500 may automatically stop or pause a further closing of the jaws based on a trigger, a threshold and/or an event. For example, when the change of the closing force F over time t reaches or exceeds a predetermined threshold (e.g., the slope C is greater than the predetermined threshold), the algorithm may automatically stop or pause further closing of the jaws. Alternatively, when the closing force F reaches or exceeds another predetermined threshold (e.g., the closing force F is greater than Fcrit), the algorithm may automatically stop or pause further closing of the jaws.

After the closing of the jaws is stopped or paused, fluid may continue to be displaced from the tissue over time thereby causing the pressure experienced by the jaws to decrease. The control algorithm may automatically re-enable a further closing of the jaws based on a trigger, a threshold or and/or an event. For example, when the change of the closing force F over time t reaches or falls below a predetermined threshold (e.g., the slope D is more negative than the predetermined threshold), the algorithm may automatically restart a further closing of the jaws. A portion of the curve 5542 having the slope D may be indicative of a stabilized tissue condition. Alternatively, when a predetermined period of time has passed since the closing of the jaws was stopped or paused (e.g., the time period t1 in FIG. 108), the algorithm may automatically restart a further closing of the jaws. The predetermined period of time may be considered an adequate amount of time for an adequate amount of tissue creep to occur and/or for the tissue to reach a stabilized condition.

The above-described automatic stopping or pausing and automatic restarting may be repeated any number of times. As more pressure is applied to the tissue (i.e., the jaws experience more force), the amount of time which occurs between an automatic stopping or pausing and an automatic restarting tends to increase (e.g., the time period t3 is greater than the time period t2 which is greater than the time period t1). Once the tissue is deemed to be sufficiently compressed, the jaws of the surgical instrument 5500 can be locked into a closed or clamped position, the closing force F remains essentially constant and the firing motion can be initiated.

Although the example graph 5540 of FIG. 108 was described in the context of various aspects of the surgical instrument 5500, it will be appreciated that the respective illustrations and descriptions of the closing force F can vary for other aspects. For example, in various aspects of the surgical instrument 5500, fewer than or more than three automatic stops or pauses may be required before the tissue is deemed to be sufficiently compressed. Similarly, fewer than or more than three automatic restarts may occur before the tissue is deemed to be sufficiently compressed. Also, although FIG. 108 was described in the context of the closing force F over time t, it will be appreciated that in various aspects, a firing force (not shown) may also be measured/sampled over time. As described in more detail hereinbelow, the firing force measurements and parameters related thereto may be utilized by the control circuit to automatically change a firing motion based on a trigger, a threshold and/or an event.

Figure 109:
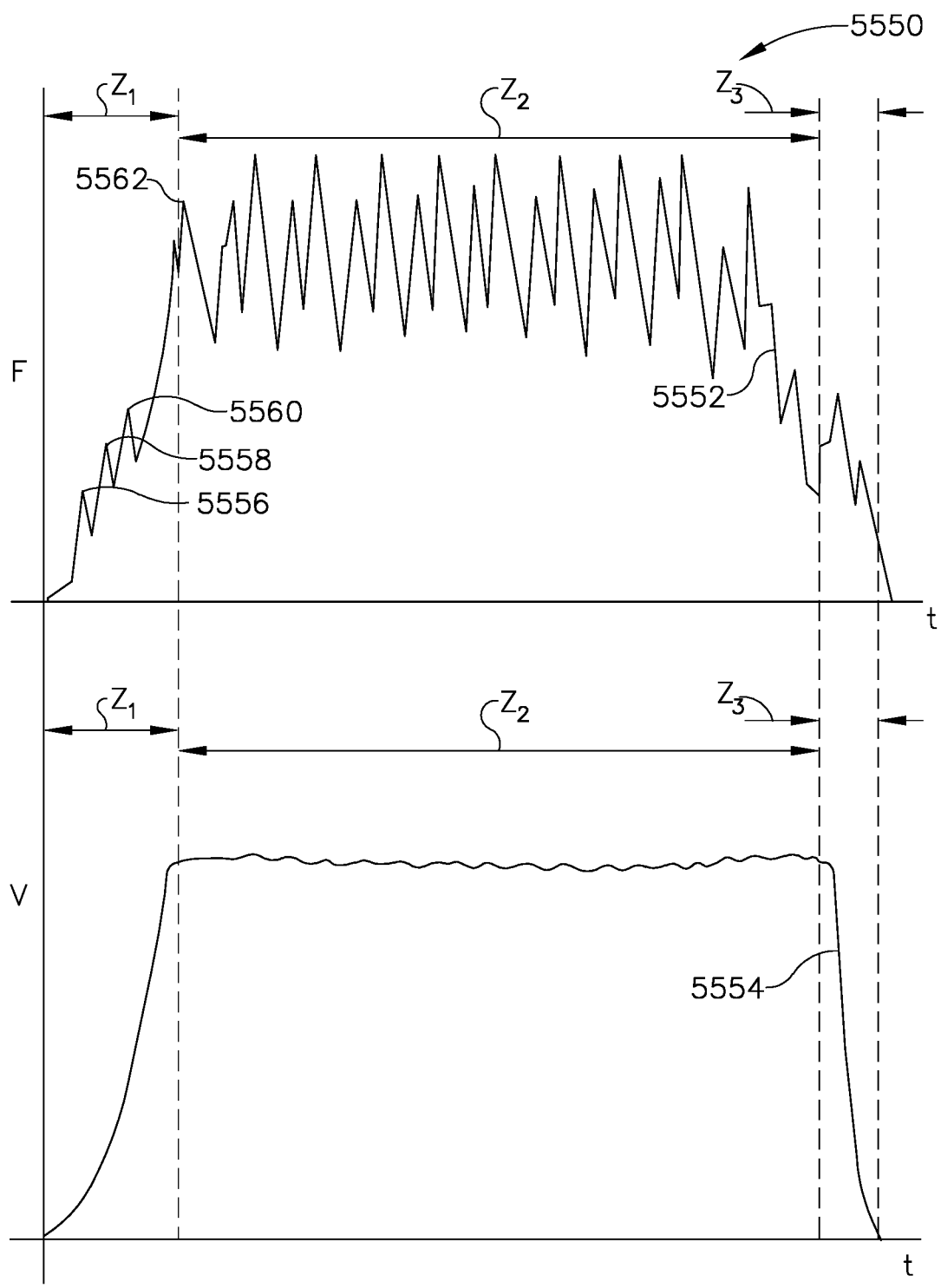
FIG. 109 illustrates an example graph showing a curve representative of a firing force signal over time and a curve representative of a knife velocity over time for various aspects of the surgical instrument of FIG. 106 in accordance with one or more aspects of the present disclosure.

FIG. 109 illustrates an example graph 5550 showing a curve 5552 representative of a firing force F over time t for various aspects of the surgical instrument 5500 and a curve 5554 representative of a knife velocity V over time t for various aspects of the surgical instrument 5500. The firing force F is shown along an upper portion of the vertical axis, the knife velocity V is shown along a lower portion of the vertical axis and the time t is shown along the upper horizontal axis as well as along the lower horizontal axis. Stated differently, the curve 5552 is a representation of the firing force signal at various times during a firing motion and the curve 5554 is a representation of the knife velocity signal at various times during a firing motion. As shown in FIG. 109, the knife transitions over three distinct zones Z1, Z2, Z3. In zone Z1, the knife velocity V and force F are ramping up from a zero initial value. In zone Z2, the knife is traveling at a relatively constant velocity V and spikes in the measured force F are due to the staple driving force. In zone Z3, the knife velocity V and the force F are ramping down to zero.

The curves 5552, 5554 may be generated mathematically by the controller based on the firing force signal(s) and the knife velocity signal(s) received by the controller. The firing force F and the knife velocity V shown in the example graph 5550 of FIG. 109 may be representative of a condition where the thickness and composition of the tissue along the cut line is uniform. The firing force F represented on the upper portion of the vertical axis may be a force experienced by the drive system of the surgical instrument (e.g., by the sled, the knife and/or the firing bar), and/or any combination thereof. The firing force F can be measured in any suitable manner, either directly or indirectly. For example, according to various aspects, the firing force F can be measured directly by a sensor (e.g. a strain gauge) positioned on the sled, on the knife, or indirectly by a current draw of the motor, and/or any combination thereof. The knife velocity V represented on the lower portion of the vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

As explained in more detail hereinbelow (See, e.g., FIG. 110), in various aspects the surgical instrument 5500 can measure and/or determine the following: an instantaneous firing force F, one or more peak values of the firing force F, one or more valley values of the firing force F, an average of the firing force F, a change of the firing force F over time t (i.e., a rate of change of the firing force F), a slope of a line connecting successive peak values of the firing force F, a slope of a line connecting successive valley values of the firing force F, a time between successive peak values of the firing force F, a time between successive valley values of the firing force F, a decrease of the firing force F from a peak value of the firing force F to a following valley value of the firing force F, an increase of the firing force F from a valley value of the firing force F to a following peak value of the firing force F, an instantaneous knife velocity V, one or more peak values of the knife velocity V, one or more valley values of knife velocity V, an average of the knife velocity V, a change of the knife velocity V over time t (i.e., a rate of change of the knife velocity V), and/or any combinations thereof.

For the example graph 5550 shown in FIG. 109, at time t=0 the firing force F is essentially zero, the knife is in the fully retracted position and the knife is stationary (the knife velocity V is zero). Once the firing motion is actuated, the knife begins to advance and initially advances at an increasing velocity. As the knife advances, the sled advances and the staples are driven from the staple cartridge, through the tissue and against the anvil. As the knife and sled advance and the knife velocity V increases, the firing force F increases and reaches a first peak value when a first row of staples is driven from the staple cartridge. At this point in time, the knife is not yet in contact with the tissue. For the example graph 5550 shown in FIG. 109, the first peak 5556 of the firing force F is indicative of the first row of staples being driven from the staple cartridge. According to various aspects, the first row of staples is not driven through the tissue and is thus not driven against the anvil. According to other aspects, the first row of staples is driven through a portion of the tissue which is thinner than the thickest portion of the tissue and against the anvil. According to yet other aspects, the first row of staples is driven through a portion of the tissue which was previously stapled (with staples from another staple cartridge), thereby resulting in that portion of the tissue being double stapled.

After the first row of staples is driven as described hereinabove, the firing force F decreases until a second row of staples is driven, which causes the firing force F to reach a second peak 5558. At this point in time, the knife is not yet in contact with the tissue. For the example graph 5550 shown in FIG. 109, the second peak 5558 is indicative of the second row of staples being driven from the staple cartridge. According to various aspects, the second row of staples is not driven through the tissue and is thus not driven against the anvil. According to other aspects, the second row of staples is driven through a portion of the tissue which is thicker than the portion of tissue through which the first row staples was driven (but thinner than the thickest portion of the tissue) and against the anvil. According to yet other aspects, the second row of staples is driven through a portion of the tissue which was already stapled (with staples from another staple cartridge), thereby resulting in that portion of the tissue being double stapled.

After the second row of staples is driven as described hereinabove, the firing force F decreases until a third row of staples is driven, which causes the firing force F to reach a third peak 5560. At this point in time, the knife is not yet in contact with the tissue. For the example graph 5550 shown in FIG. 109, the third peak 5560 is indicative of the third row of staples being driven from the staple cartridge. According to various aspects, the third row of staples is not driven through the tissue and is thus not driven against the anvil. According to other aspects, the third row of staples is driven through a portion of the tissue which is thicker than the portion of tissue through which the second row staples was driven (but thinner than the thickest portion of the tissue) and against the anvil. According to yet other aspects, the third row of staples is driven through a portion of the tissue which was already stapled (with staples from another staple cartridge), thereby resulting in that portion of the tissue being double stapled.

After the third row of staples is driven as described hereinabove, the firing force F decreases until a fourth row of staples is driven, which causes the firing force F to reach a fourth peak 5562. At some point after the third row of staples is driven, the knife comes into contact with the tissue, begins severing the tissue and advances at a substantially constant velocity. For the example graph 5550 shown in FIG. 109, the fourth peak 5562 is indicative of the knife severing the tissue and the fourth row of staples being driven from the staple cartridge through the tissue and against the anvil.

After the fourth row of staples is driven as described hereinabove, the firing force F continues the cycle of decreasing and increasing as the knife advances through the tissue at a substantially constant velocity and additional rows of staples are driven through the tissue and against the anvil. For the aspects shown in FIG. 109, the knife velocity V is substantially constant from the time the knife comes in contact with the tissue (shortly before the fourth peak value of the firing force is reached) to a time shortly after the knife has severed through the tissue (the last peak value before the last three rows of staples are driven). Shortly after the knife has severed through the tissue, the knife velocity V begins to decrease from the substantially constant velocity to zero. The decrease in the knife velocity V and the lower forces required to drive the last three rows of staples produces lower and lower peak values of the firing force F. There are a number of different reasons why lower forces are required to drive the last three rows of staples. For example, according to various aspects, the last three rows of staples may extend past the tissue (and thus are not driven through the tissue and against the anvil), the last three rows of staples may be driven through a less compressed portion of the tissue (due to the geometry of the anvil and the elongated channel), the last three rows of staples may be driven through a thinner portion of the tissue, and/or any combination thereof. Once all of the staples have been driven and the knife velocity V has reached zero (the knife has stopped advancing), the firing force F is zero.

Although the example graph 5550 of FIG. 109 was described in the context of various aspects of the surgical instrument 5500, it will be appreciated that the respective illustrations and descriptions of the firing force F and the knife velocity V can vary for other aspects. For example, in various aspects of the surgical instrument 5500, the knife may come into contact with the tissue after fewer than or more than three rows of staples have been driven from the staple cartridge. Similarly, fewer than or more than three rows of staples may be driven after the knife has severed through the tissue.

Figure 110:
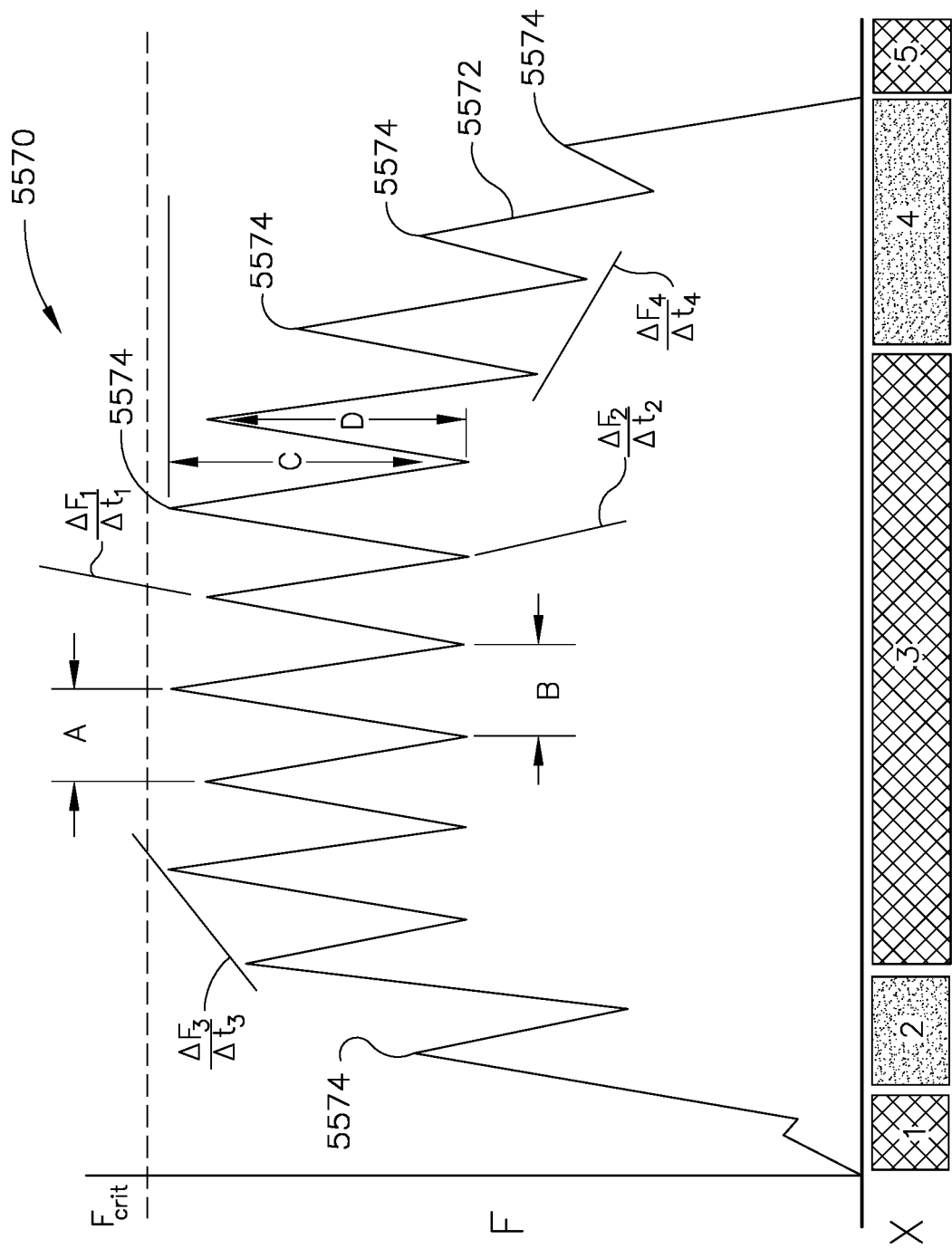
FIG. 110 illustrates an example graph showing a curve representative of a firing force signal and a knife position over time for various aspects of the surgical instrument of FIG. 106 in accordance with one or more aspects of the present disclosure.

FIG. 110 illustrates an example graph 5570 showing a curve 5572 representative of a firing force F and a knife position X over time t for various aspects of the surgical instrument 5500. The firing force F is shown along the vertical axis and the knife position X and the time t are shown along the horizontal axis. As shown along the horizontal axis, the knife position X travels over five Zones 1-5 along the knife channel in the cartridge 304 located in the lower jaw 302 of the end effector 300 of the surgical instrument 5500, as described in more detail hereinbelow. In summary, Zone 1 is a tissue free zone where the knife moves without contacting tissue until it initially contacts tissue in Zone 2. The knife then transects the tissue as it travels along Zone 3. The knife transitions out of the tissue in Zone 4 and in stops in Zone 5, where the knife reaches the end of its travel span in a tissue free region. The spikes 5574 in the various sections 1-5 are due the additional force required to drive staples through the tissue located in the jaws 306, 302 of the end effector 300 portion of the surgical instrument 5500.

Accordingly, the curve 5572 is a representation of the firing force signal at various times during a firing motion in combination with the staple driving force, collectively referred to herein a the driving force F. The curve 5572 may be generated mathematically by the controller based on the firing force signal(s) received by the controller. The firing force F and the knife position X force shown in the example graph 5570 may be representative of a condition where the thickness and composition of the tissue along the cut line is uniform. The firing force F represented on the vertical axis may be a force experienced by the drive system of the surgical instrument 5500 (e.g., by the sled, the knife, and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

According to various aspects, the operation of the surgical instrument 5500 may be controlled by monitoring the amplitude of the firing force signal and the knife position X, and changing the firing motion when the amplitude of the firing force signal reaches or exceeds a predetermined threshold. As previously described, this process may be controlled with an algorithm such as the method 1010 of controlling a closing motion of the surgical instrument 5500 according to various aspects illustrated in FIG. 107. According to some aspects, the changing of the firing motion only proceeds when the knife position is within a predetermined range of positions. With reference to FIG. 110, for example, firing force amplitude Fcrit may be determined to be an excessive amount of the firing force F experienced by the surgical instrument 5500. Upon the occurrence of the amplitude of the firing force signal reaching or exceeding the firing force amplitude Fcrit, an algorithm may operate to change the firing motion by slowing down, pausing or stopping the rotation of the motor(s) which drive the knife of the surgical instrument 5500 to prevent the surgical instrument 5500 from experiencing excessive forces.

The curve 5572 provides a useful representation of how the firing force F and the knife position X vary over time t. The change in the firing force F over time t (i.e., the rate of change of the closing force F) may provide useful feedback to the control circuit to control the firing mechanism of the surgical instrument 5500. The change in the firing force F over time t may be represented as a derivative of the curve 5572 and may be approximated over short periods of time by the equation Slope $S=\Delta F/\Delta t$, where $\Delta F$ is the change of the firing force F and $\Delta t$ is the change of the time t. The slope can have a positive value or a negative value. The slope represented by $\Delta F1/\Delta t1$ of the curve 5572 has a positive value and the slope represented by $\Delta F2/\Delta t2$ of the curve 5572 has a negative value. The curve 5572 is representative of an analog signal over time which is sampled and converted to a digital value by an A/D converter as the firing mechanism is advanced/retracted. Once the analog signal is digitized, the control circuit may thereafter determine the slope of the firing force signal represented by the curve 5542 at any point during the firing motion.

According to various aspects, the operation of the surgical instrument 5500 may be controlled by monitoring the slope of the curve 5572 (the slope of the firing force signal) and the knife position X, and changing the firing motion based on the value of the slope. According to some aspects, the changing of the firing motion only proceeds when the knife position is within a predetermined range of positions. In general, with reference to FIG. 110, the slope of the curve 5572 may be approximated by the equation $S=\Delta F/\Delta t$, where $\Delta F$ is the change of the firing force F and $\Delta t$ is the change of the time t. Those skilled in the art will appreciate that the instantaneous slope may be calculated by taking the derivative of the curve 5572. Over time t, the slope S may be monitored by the control circuit and utilized by the control circuit to control the operation of the surgical instrument 5500. For example, an algorithm of the surgical instrument 5500 may be configured to monitor the change of the firing force F over the time t, stop or pause the firing motion when the slope of the curve 5572 reaches or exceeds a first predetermined threshold, then restart the firing motion when the slope of the curve 5572 reaches or falls below a second predetermined threshold. The value of the slope represented by $\Delta F1/\Delta t1$ (a positive value) shown in FIG. 110 may be determined by the controller and may represent the first predetermined threshold. Similarly, the value of the slope represented by $\Delta F2/\Delta t2$ (a negative value) shown in FIG. 110 may be determined by the controller and may represent the second predetermined threshold. Thus, according to various aspects, the algorithm can control the operation of the control circuit based on the determined slope, whether instantaneous or approximated.

According to various aspects, the operation of the surgical instrument 5500 may be controlled by monitoring a parameter related to the firing force signal and the knife position X, and changing the firing motion based on the value of the parameter. According to some aspects, the changing of the firing motion only proceeds when the knife position is within a predetermined range of positions. With reference to FIG. 110, for example, an algorithm of the surgical instrument 5500 may be configured to monitor first and second parameters (e.g., the slope of a line connecting successive peak values of the firing force signal represented by $\Delta F3/\Delta t3$ and the slope of a line connecting successive valley values of the firing force signal represented by $\Delta F4/\Delta t4$ in FIG. 110), stop or pause the firing motion when the value of the first parameter reaches or exceeds a first predetermined threshold, then restart the firing motion when the value of the second parameter reaches or falls below a second predetermined threshold. The value of the slope represented by $\Delta F3/\Delta t3$ (a positive value) shown in FIG. 110 may be determined by the controller and may represent the first predetermined threshold. Similarly, the value of the slope represented by $\Delta F4/\Delta t4$ (a negative value) shown in FIG. 110 may be determined by the controller and may represent the second predetermined threshold. Thus, according to various aspects, the algorithm, such as the method 1010 of controlling a closing motion of the surgical instrument 5500 according to various aspects shown in FIG. 107, can control the operation of the control circuit based on the determined slopes, whether instantaneous or approximated.

Alternatively, the controller may determine values for other parameters related to the firing force signal and utilize the values of the parameters to change the firing motion. According to some aspects, the changing of the firing motion only proceeds when the knife position is within a predetermined range of positions. With regard to FIG. 110, the other parameters may include, for example, a duration between successive peak values of the firing force signal represented by the time period A shown in FIG. 110, a duration between successive valley values of the firing force signal represented by the time period B shown in FIG. 110, a decrease in the amplitude of the firing force signal from a peak value to a following valley value as represented by the magnitude C shown in FIG. 110 and an increase in the firing force signal from a valley value to a following peak value represented by the magnitude D shown in FIG. 110. The above-described parameters/values determined by the control circuit can be utilized with or without the knife position X to automatically control the firing motion of the surgical instrument 5500. Additionally, the above-described parameters/values determined by the control circuit can be utilized within a limited time/rate window in combination with surgeon variable rate actuation control and feedback.

For the example graph 5570 shown in FIG. 110, at time t=0 the knife is in a fully retracted position near the proximal end of the end effector and over time advances to a fully advanced position near the distal end of the end effector. The overall distance the knife moves from the fully retracted position to the fully advanced position during a firing motion can be divided into predefined zones, with each predefined zone representative of a different operating condition of the surgical instrument 5500. For example, according to various aspects, the overall distance the knife moves from the fully retracted position to the fully advanced position during a firing motion can be divided into five predefined zones and the five zones may be representative of the following: Zone 1 is representative of the knife advancing from a fully retracted position at an increasing velocity but not yet being in contact with tissue positioned between the jaws of the surgical instrument; Zone 2 is representative of the knife advancing at a more rapidly increasing velocity and staples being driven into the tissue (but not into the thickest portion of the tissue); Zone 3 is representative of the knife reaching a maximum or peak velocity, then continuing to advance at a substantially constant velocity and staples being driven into the thickest portion of the tissue; Zone 4 is representative of the knife continuing to advance at a substantial constant velocity, then decreasing in velocity after the tissue has been severed and staples still being driven into the thickest portion of the tissue; and Zone 5 is representative of the knife having reached its fully advanced position (the knife has stopped) and all of the staples have been fired.

Although five zones are shown in FIG. 110, it will be appreciated that the overall distance the knife moves from the fully retracted position to the fully advanced position during a firing motion can be divided into more than or less than five zones, and the respective zones can be representative of operating conditions different from those described hereinabove.

In practice, the thickness and composition of the tissue can vary along the cut line. Thus, it will be appreciated that there are many conditions which can cause the firing force F, the knife velocity V and/or the knife position X to deviate from the firing force F, the knife velocity V and/or the knife position X shown in FIGS. 103 and 104.

Figure 111:
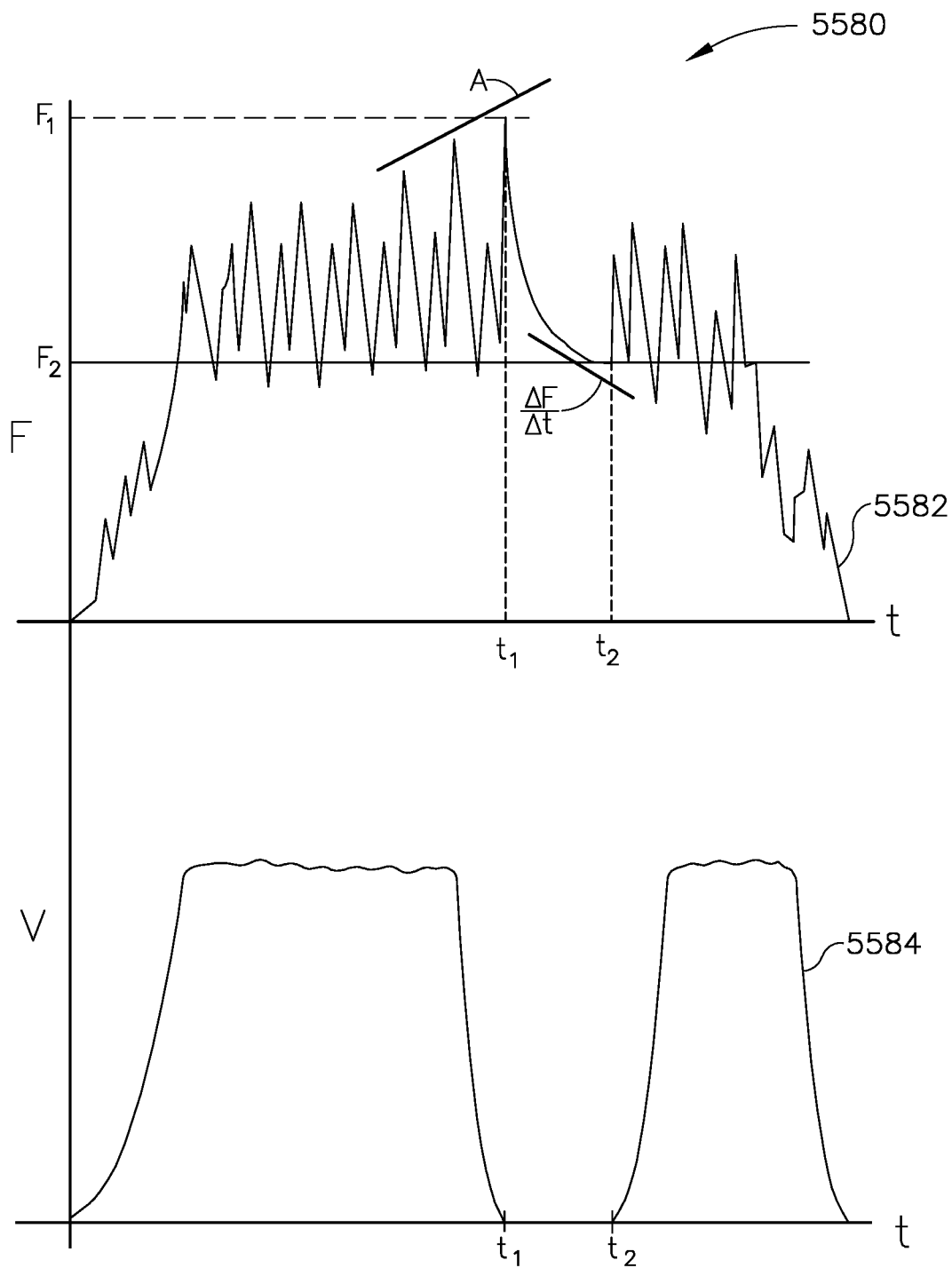
FIG. 111 illustrates an example graph showing a curve representative of a firing force signal and a curve representative of a knife velocity over time for various aspects of the surgical instrument of FIG. 106 in accordance with one or more aspects of the present disclosure.

FIG. 111 illustrates an example graph 5580 showing a curve 5582 representative of a firing force F over time t for various aspects of the surgical instrument 5500 and a curve 5584 representative of a knife velocity V over time t for various aspects of the surgical instrument 5500. Stated differently, the curve 5582 is a representation of the firing force signal at various times during a firing motion and the curve 5584 is a representation of the knife velocity signal at various times during a firing motion. The curves 5582, 5584 may be generated mathematically by the controller based on the firing force signal(s) and the knife velocity signal(s) received by the controller. The firing force F is shown along an upper portion of the vertical axis, the knife velocity V is shown along a lower portion of the vertical axis and the time t is shown along the upper horizontal axis as well as along the lower horizontal axis. The firing force F represented on the upper portion of the vertical axis may be a force experienced by the drive system of the surgical instrument 5500 (e.g., by the sled, the knife and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

The knife velocity V represented on the lower portion of the vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

In addition to the firing force F and the knife velocity V being measured, the firing force measurements (including the parameters/values derived therefrom) and the knife velocity measurements can be stored by a memory of the surgical instrument 5500. An algorithm of the control circuit of the surgical instrument 5500 can utilize the stored measurements to provide automated control of the surgical instrument 5500. For example, according to various aspects, the algorithm can automatically stop or pause a further advancement of the knife based on a trigger, a threshold and/or an event. For example, when a slope of a line connecting successive peak values of the firing force signal (e.g., the slope of the line A shown in FIG. 111) reaches or exceeds a predetermined threshold (e.g., the slope of the line A is greater than the predetermined threshold), the algorithm can automatically stop or pause a further advancement of the knife.

According to other aspects, the algorithm can automatically stop or pause a further advancement of the knife when a slope of a line connecting successive peak values of the firing force signal and the amplitude of the firing force signal reaches or exceeds a second predetermined threshold (e.g., the amplitude is greater than the firing force amplitude F1). According to yet other aspects, the algorithm can automatically stop or pause a further advancement of the knife when the a slope of a line connecting successive peak values of the firing force signal reaches or exceeds a predetermined threshold, the amplitude of the firing force signal reaches or exceeds a second predetermined threshold and the position of the knife is within a predefined zone of operation (e.g., a position where the knife is advancing at a substantially constant velocity). For these aspects, when the combinations are met, the controller signals the motor controller to change the firing motion by slowing down, pausing or stopping the rotation of the motor(s) which drive the knife of the surgical instrument 5500 to prevent the surgical instrument 5500 from experiencing excessive forces. For the example graph 5580 shown in FIG. 111, when the combinations are met, the controller communicates a pause signal or a stop signal to the motor controller to change the firing motion by pausing or stopping the rotation of the motor(s) which drive the knife velocity and the knife velocity is reduced from the substantially constant velocity to zero.

After the advancement of the knife has been stopped or paused, the algorithm may automatically restart the advancement of the knife based on a trigger, a threshold and/or an event. For example, according to various aspects, the algorithm can automatically restart the advancement of the knife when a slope of the curve 5582 (e.g., the slope $\Delta F/\Delta t$ shown in FIG. 111) reaches or falls below a predetermined threshold. The predetermined threshold may be indicative of a stabilized tissue condition. According to other aspects, when a predetermined period of time has passed since the advancement of the knife was stopped or paused (e.g., the period of time between t1 and t2 in FIG. 111), the algorithm may automatically restart a further advancement of the knife. The predetermined period of time may be considered an adequate amount of time for an adequate amount of tissue creep to occur and/or for the tissue to reach a stabilized condition.

According to yet other aspects, when the amplitude of the firing force signal drops a predetermined amount from what the amplitude of the firing force signal was at the time of the initiation of the stop or pause, the algorithm may automatically restart a further advancement of the knife. The predetermined amount of the drop in the amplitude of the firing force signal may be a quantitative amount (e.g., the difference between the firing force amplitude F1 and the firing force amplitude F2 in FIG. 111) or a percentage (e.g., a 10% drop). The predetermined amount of the drop in firing force signal may be considered sufficient enough for an adequate amount of tissue creep to have occurred and/or for the tissue to have reached a stabilized condition.

According to yet other aspects, when the amplitude of the firing force signal drops to a predetermined value (e.g., the firing force amplitude F2 shown in FIG. 111), the algorithm may automatically restart a further advancement of the knife. The predetermined value of the firing force F may be considered low enough for an adequate amount of tissue creep to have occurred and/or for the tissue to have reached a stabilized condition. Regardless of what the restarting of the knife is based on, when the trigger, threshold and/or event occurs, the controller communicates a start signal to the motor controller to restart the firing motion by restarting the rotation of the motor(s) which drive the knife of the surgical instrument 5500, and the restarting of the rotation of the motor(s) causes the knife velocity V to increase from zero to a substantially constant velocity.

After the knife has severed through the tissue, the knife velocity V begins to decrease from the substantially constant velocity to zero. The decrease in the knife velocity V and the lower firing force F required to drive the last few rows of staples produces lower and lower peak values of the firing force signal. Once all of the staples have been driven and the knife velocity V has reached zero (the knife has stopped advancing), the firing force F is zero.

Although the knife position X is not shown in FIG. 111, it will be appreciated that according to some aspects the changing of the firing motion only proceeds when the knife position is within a predetermined range of positions.

FIG. 112 illustrates an example graph 5690 showing a curve 5692 representative of a closing force FC over time t for various aspects of the surgical instrument 5500 and a curve 5694 representative of a firing force FF over time t for various aspects of the surgical instrument 5500. The closing force FC is shown along the "left" vertical axis, the firing force FF is shown along the "right" vertical axis and the time t is shown along the horizontal axis. When viewed together the curves 5692, 5694 reflect the timing of the closing motion and the firing motion relative to one another, where the closing motion is initiated prior to the initiation of the firing motion. Although the example graph 5690 shows a threshold force Fcrit as being the same amplitude for both the closing force FC and the firing force FF, it will be appreciated that the amplitude of the threshold force Fcrit for the closing force FC may be different from the amplitude of the threshold force Fcrit for the firing force FF. Stated differently, the scale of the "left" vertical axis can be different from the scale of the "right" vertical axis.

The curve 5692 is a graphical representation of the closing force signal at various times during a closing motion and may be similar or identical to the curve 5542 of FIG. 108. Thus, as set forth hereinabove, the curve 5692 may be generated mathematically by the controller based on the closing force signal(s) received by the controller. The closing force FC represented on the "left" vertical axis may be a force experienced by tissue clamped between the jaws of the surgical instrument 5500, a force experienced by the jaws of the surgical instrument 5500 (e.g., by the anvil and/or the elongated channel), a force experienced by the closure tube of the surgical instrument 5500, and/or any combinations thereof. The closing force FC can be measured in any suitable manner, either directly or indirectly. For example, according to various aspects, the closing force FC can be measured directly by a sensor (e.g., a strain gauge) positioned on the anvil, on the elongated channel, on the closure tube, or indirectly by an impedance of the tissue, a current draw of the motor, and/or any combinations thereof.

The curve 5694 is a graphical representation of the firing force signal at various times during a firing motion. The curve 5694 may be generated mathematically by the controller based on the firing force signal(s) received by the controller. The firing force FF represented on the "right" vertical axis may be a force experienced by the drive system of the surgical instrument 5500 (e.g., by the sled, the knife, and/or the firing bar), and/or any combination thereof. The firing force FF can be measured in any suitable manner, either directly or indirectly. For example, according to various aspects, the firing force FF can be measured directly by a sensor (e.g., a strain gauge) positioned on the sled, on the knife, or indirectly by a current draw of the motor, and/or any combination thereof. Although not shown for purposes of simplicity, the respective zones of the firing cycle (e.g., zones 1-5 as described hereinabove) could also be shown along the horizontal axis.

For the example graph 5690 in FIG. 112, at some time after the closing motion has commenced, the knife is still in the fully-retracted position and the firing force FF is approximately zero. As the knife and sled advance and the velocity of the knife increases, the firing force FF increases and reaches a first peak value 5696 when a first row of staples is driven from the staple cartridge. After the first row of staples is driven as described hereinabove, the firing force FF decreases until a second row of staples is driven, which causes the firing force FF to reach a second peak value 5698.

At a later point in the firing motion, the slope of the firing force signal reaches or exceeds a predetermined threshold (this condition is shown as the slope A of the firing force signal in FIG. 112) and the amplitude of the firing force FF reaches or exceeds a predetermined amplitude threshold (e.g., the amplitude Fcrit shown in FIG. 112). In response, the control algorithm acts to slow down, stop or pause the further advancement of the knife and the firing force FF begins to decrease.

For the example graph 5690, the slowing down, stopping or pausing of the knife continues until the firing force FF reaches a value which is 10% less than the predetermined amplitude threshold (e.g., Fcrit), at which point the further advancement of the knife is commenced. Of course, according to various aspects, the further advancement of the knife can be commenced when the firing force FF reaches a value which is less than or more than the 10% example shown in FIG. 112. The above-described automatic stopping or pausing and automatic restarting may be repeated any number of times. For the example graph 5690, once the further advancement of the knife is commenced, the knife advances towards its fully advanced position and the firing force FF eventually decreases to zero as indicated at the far right side.

Figure 113:
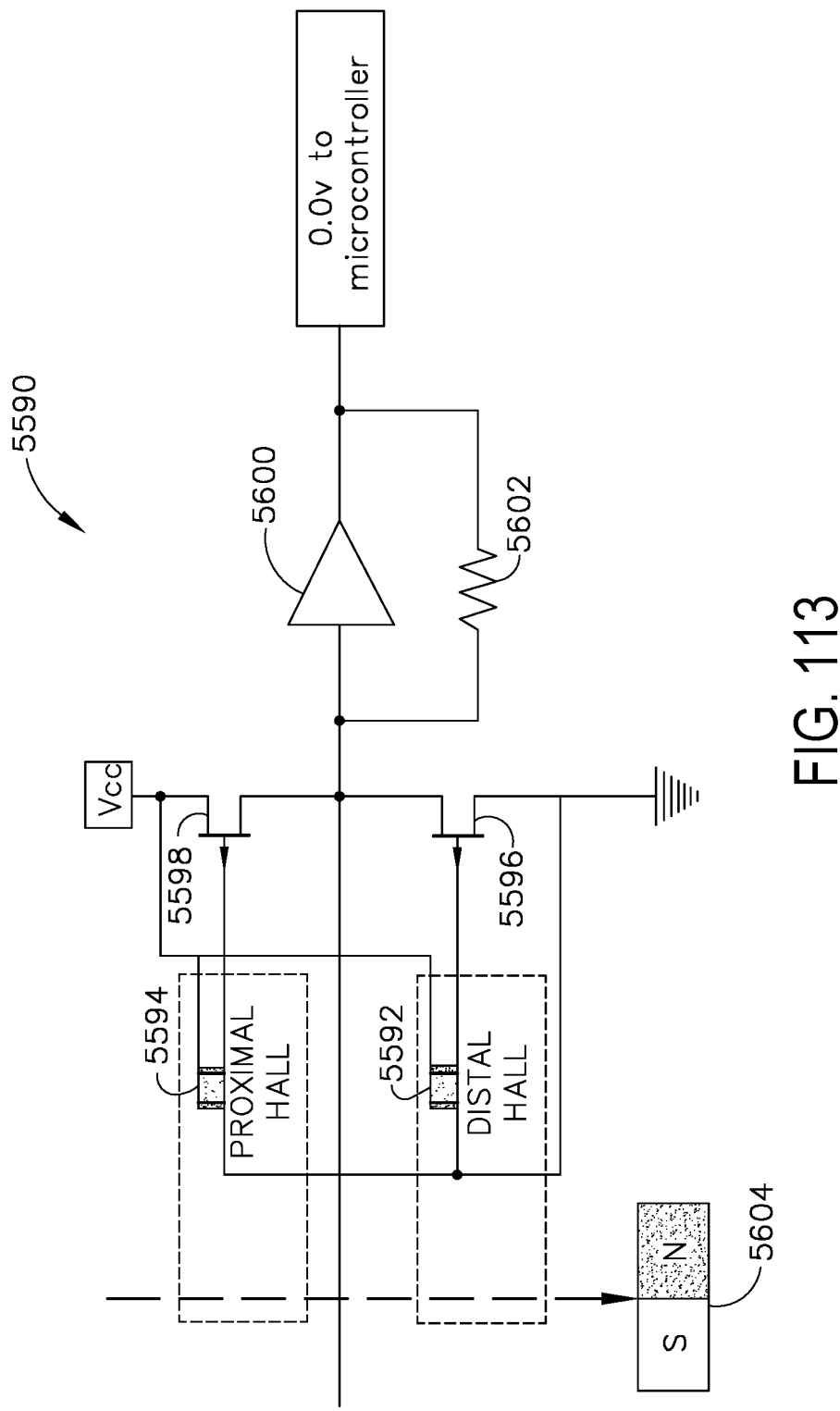
FIG. 113 illustrates various aspects of a direction sensor of the surgical instrument of FIG. 106 in accordance with one or more aspects of the present disclosure.
Figure 114:
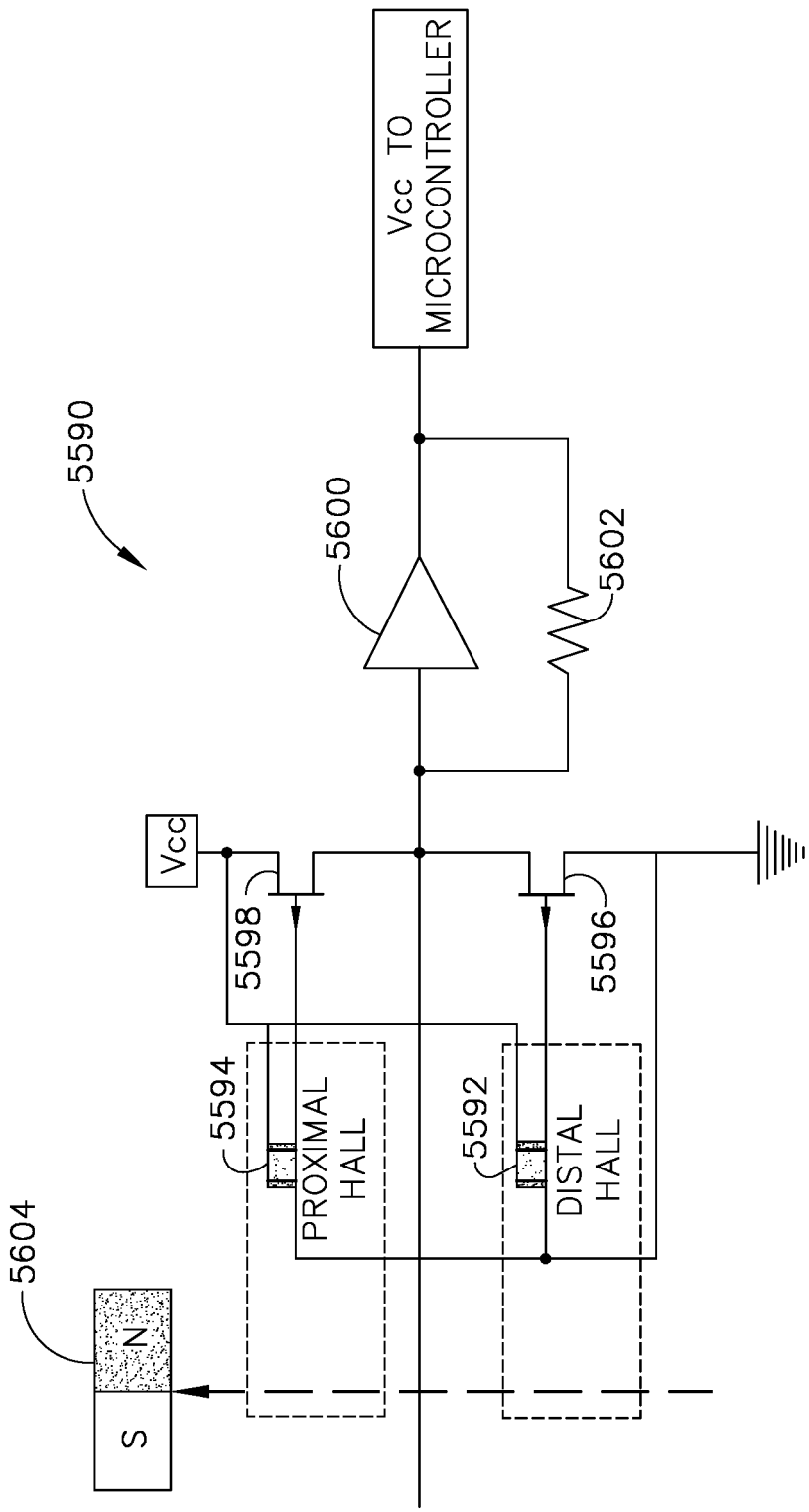
FIG. 114 illustrates various aspects of a direction sensor of the surgical instrument of FIG. 106 in accordance with one or more aspects of the present disclosure.

FIGS. 113, 114 illustrate various aspects of a direction sensor 5590 of the surgical instrument 5500. According to various aspects, the control circuit of the surgical instrument 5500 may be configured to stop an advancement of the knife when a staple cartridge is not positioned or properly positioned in the elongated channel. For such aspects, the control circuit may include the direction sensor 5590, a main processor and a safety processor, each positioned in the shaft assembly, as described above in connection with FIGS. 16A-17B. The direction sensor 5590 is electrically connected to the main processor and/or the safety processor of the shaft assembly. The main processor and/or the safety processor of the shaft assembly may be electrically connected to the main processor and/or the safety processor of the handle assembly. The direction sensor 5590 is positioned at a location relative to a starting point of the tissue transection, and is configured to sense movement of the firing bar and output a signal (e.g., a voltage) related to the sensed position of the firing bar to the main processor and/or safety processor of the shaft assembly. Based on the sensed movement of the firing bar, the main processor and/or the safety processor of the shaft assembly can determine and track a status of the movement and the direction of the movement of the firing bar as the firing bar moves distally and proximally of the starting point of the tissue transection. The main processor and/or the safety processor of the shaft assembly can signal the motor controller to power, cycle and/or reboot the electric motor to control the movement and the direction of the movement of the firing bar, and thus the movement and the direction of the movement of the knife, all while continuing to determine the relevant position of the firing bar based on the output signal of the direction sensor 5590.

As shown in FIGS. 113, 114, the direction sensor 5590 includes first and second sensors 5592, 5594, first and second transistors 5596, 5598, an operational amplifier 5600 and a resistive element 5602. The first and second sensors 5592, 5594 may be Hall-effect sensors, with each of the first and second Hall-effect sensors being positioned a set distance from the tissue transection or cut line. Collectively, the first and second transistors 5596, 5598, the operational amplifier 5600 and the resistive element 5602 comprise a latching circuit, where the latching circuit outputs only the voltage related to the last Hall-effect sensor that was activated.

FIG. 113 indicates a firing stroke in which the magnet 5604 moves from an initial proximal position to a distal position. In FIG. 113, the magnet 5604 is shown in the final distal position and the output of the operational amplifier 5600 indicates the distal position of the magnet 5604. In operation, as the firing bar moves distally from a proximal starting point of the tissue transection as shown in FIG. 113, a magnet 5604 positioned on the firing bar moves past the first Hall-effect sensor 5594 then past the second Hall-effect sensor 5592. As the magnet 5604 moves past the first Hall-effect sensor 5594, the first Hall-effect sensor 5594 outputs a signal which is indicative of the movement of the firing bar to a gate of the first transistor 5598 to drive the latching circuit to a first stable state Vcc. As the magnet 5604 moves past the second Hall-effect sensor 5592, the second Hall-effect sensor 5592 outputs a signal which is indicative of the movement of the firing bar to a gate of the second transistor 5596 to drive the latching circuit to a second stable state 0.0 V. The latching circuit outputs a signal (e.g., a voltage 0.0 V) indicative of the second stable state to the main processor and/or the safety processor of the shaft assembly indicating that the firing bar is in the distal fired position.

FIG. 114 indicates a retracting stroke in which the magnet 5604 moves from an initial distal position to a final proximal position. In FIG. 114, the magnet 5604 is shown in the final proximal position and the output of the operational amplifier 5600 indicates the proximal position of the magnet 5604. In operation, as the firing bar moves proximally toward the starting point of the tissue transection as shown in FIG. 114, the magnet 5604 positioned on the firing bar moves past the second Hall-effect sensor 5592 then past the first Hall-effect sensor 5594. As the magnet 5604 moves past the second Hall-effect sensor 5592, the second Hall-effect sensor 5592 outputs a signal which is indicative of the movement of the firing bar to the gate of the second transistor 5596 to drive the latching circuit to the second stable state of 0.0 V. As the magnet 5604 moves past the first Hall-effect sensor 5594, the first Hall-effect sensor 5594 outputs a signal which is indicative of the movement of the firing bar to the gate of the first transistor 5598 to drive the latching circuit to the first stable state Vcc. The latching circuit outputs a signal (e.g., a voltage of Vcc) indicative of the first stable state to the main processor and/or the safety processor of the shaft assembly indicating that the firing bar is in the proximal retracted position.

Figure 115:
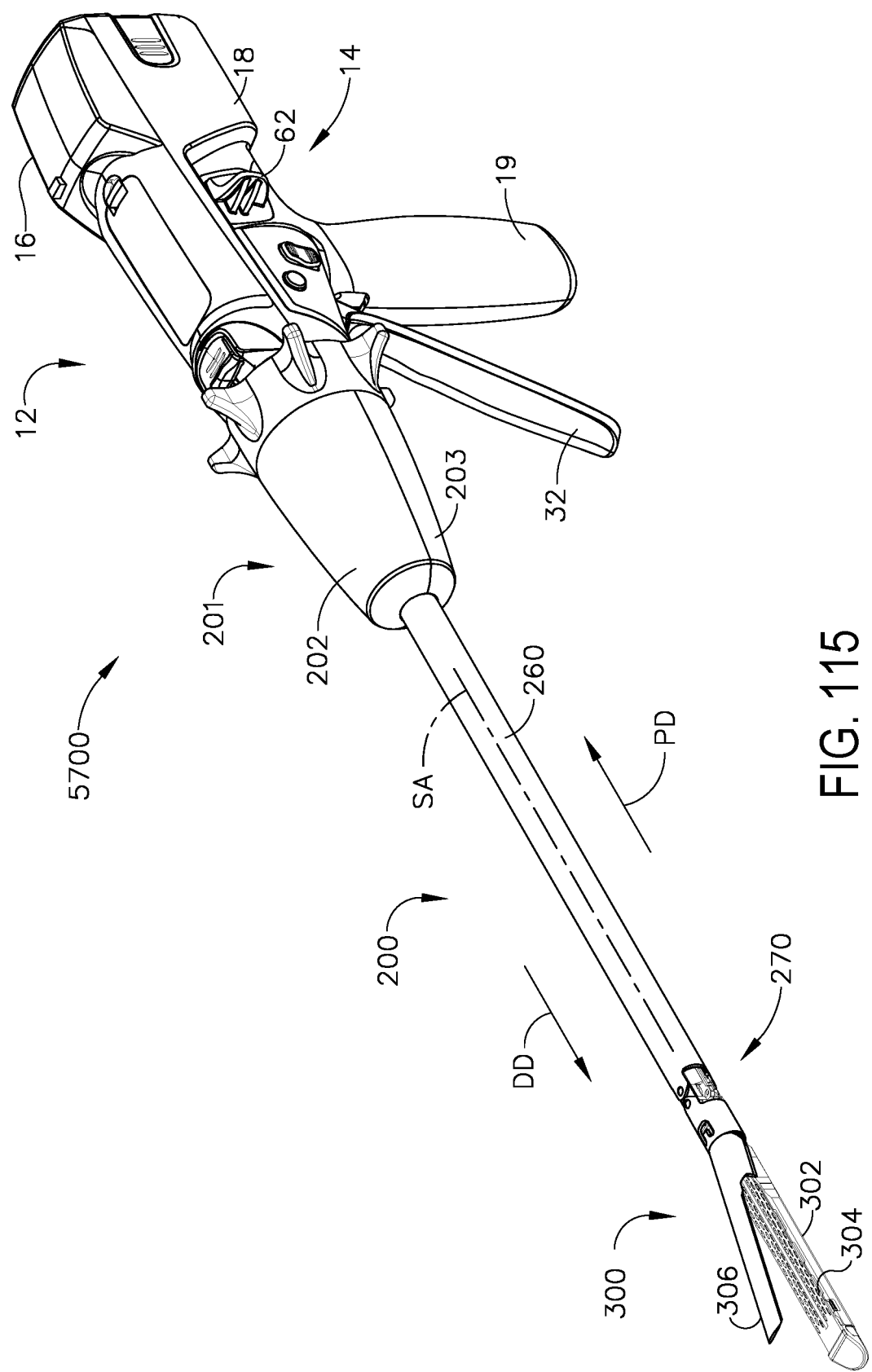
FIG. 115 illustrates a perspective view of another surgical instrument in accordance with one or more aspects of the present disclosure.

FIG. 115 illustrates a perspective view of a surgical instrument 5700 in accordance with one or more aspects described herein. The surgical instrument 5700 is similar to the surgical instrument 5500 and includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5700 is also similar to the surgical instrument 5500 in that the surgical instrument 5700 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5700 is also similar to the surgical instrument 5500 in that the surgical instrument 5700 also includes algorithms such as closing algorithms, firing algorithms, motor control algorithms, or any combination thereof, which operate to dynamically adjust the operation of the surgical instrument 5700. However, the surgical instrument 5700 is different from the surgical instrument 5500 in that the surgical instrument 5700 further includes one or more additional algorithms (in addition to those described hereinabove) which provide additional control functionality for the surgical instrument 5700, as described hereinbelow.

In certain situations, it may be desirable for the surgical instrument 5700 to ignore the occurrence of one or more of the above-described triggers, thresholds and/or events associated with the firing force. In accordance with one or more aspects, the surgical instrument 5700 includes one or more control algorithms which are configured to ignore certain triggers, thresholds and/or events if the triggers, thresholds and/or events occur before an amplitude of the firing force has reached or exceeded a predetermined threshold, if the triggers, thresholds and/or events occur within certain zones of the firing motion, and combinations thereof. As described hereinabove, the zones of the firing motion are related to the position of the knife. In other words, the control algorithms can vary the firing force triggers, thresholds and/or events (e.g., values of the thresholds) based on the position of the knife within the firing motion.

Figure 116:
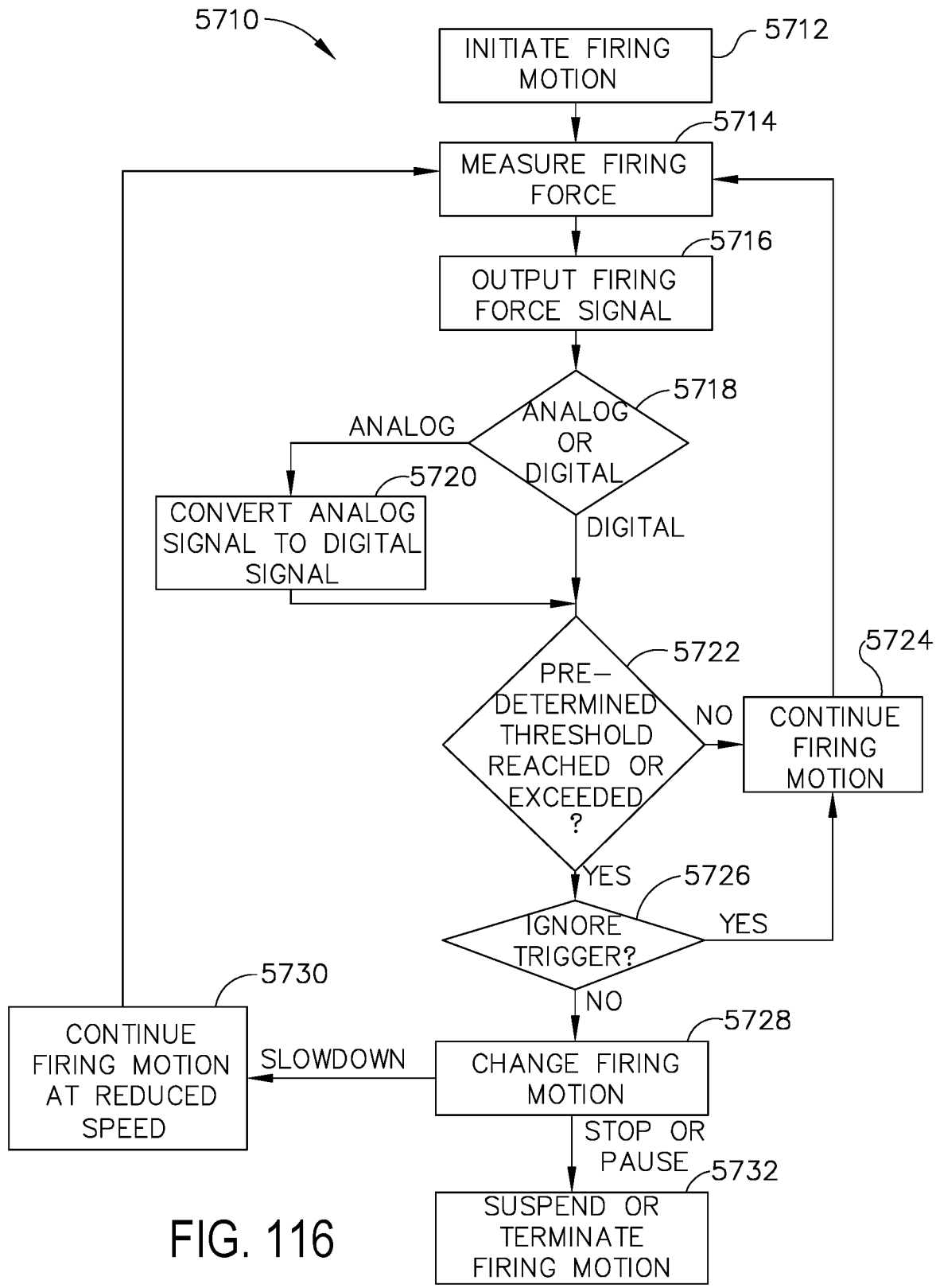
FIG. 116 illustrates a method of controlling a firing motion of the surgical instrument of FIG. 115 in accordance with one or more aspects of the present disclosure.

FIG. 116 illustrates a method 5710 of controlling a firing motion of the surgical instrument 5700 in accordance with one or more aspects. The process starts when a firing motion is initiated 5712. The closing motion may be initiated, for example, by pulling a firing trigger toward a handle. A sensor resident with the surgical instrument 5700 senses/measures 5714 a firing force. The firing force may be, for example, a force experienced by the drive system of the surgical instrument (e.g., by the sled, the knife and/or the firing bar), and/or any combination thereof. The firing force F can be measured in any suitable manner, either directly or indirectly. For example, in accordance with one or more aspects, the firing force F can be measured directly by a sensor (e.g. a strain gauge) positioned on the sled, on the knife, or indirectly by a current draw of the motor.

In response to the firing force, the sensor outputs 5716 a firing force signal, which is indicative of the firing force sensed/measured 5714 by the sensor. Depending on the configuration of the sensor, the firing force signal can be an analog signal or a digital signal. Upon determining 5718 whether the firing force signal is either an analog signal or a digital signal, the process proceeds along the corresponding branch. When the determination 5718 is that the firing force signal is an analog signal, the process proceeds along the analog branch, where the analog signal is received by an A/D converter, converted 5720 to a digital signal representative of the analog signal by the A/D converter and the digital signal is output by the A/D converter. When the determination 5718 is that the firing force signal is a digital signal, the process proceeds along the digital branch because there is no need for an A/D conversion 5720 when the firing force signal is a digital signal.

The firing force signal which is a digital signal representative of the firing force sensed/measured 5714 by the sensor is received by a controller. The controller utilizes the digital signal and determines 5722 whether the firing force sensed/measured 5714 by the sensor reaches or exceeds a predetermined threshold. The controller may make this determination 5722 based on a comparison of a magnitude of the firing force sensed/measured 5714 by the sensor and the predetermined threshold, based on a comparison of an amplitude of the firing force signal output 5716 by the sensor and a predetermined threshold, or any combination thereof.

When the controller determines 5722 that the firing force sensed/measured 5714 by the sensor has not reached or exceeded the predetermined threshold, the firing motion originally initiated 5712 is continued 5724 along with interim processes 5714-5722. When the controller determines 5722 that the firing force sensed/measured 5714 by the sensor has reached or exceeded the predetermined threshold, the controller then determines 5726 whether or not to ignore the fact that the firing force has reached or exceeded the predetermined threshold. This determination 5726 can be based, for example, on whether or not the amplitude of the firing force signal has reached or exceeded a predetermined threshold, based on the position of the sled, the knife and/or the firing bar, or any combinations thereof. For example, as described in more detail hereinbelow, in certain aspects the controller may determine 5726 to ignore the fact that the slope of the firing force signal has reached or exceeded a predetermined slope threshold if the amplitude of the firing force signal has not yet reached or exceeded a predetermined amplitude threshold. In other aspects, the controller may determine 5726 to ignore the fact that the slope of the firing force signal has reached or exceeded a predetermined slope threshold based on the position of the sled, the knife, the firing bar, or any combination thereof when the knife is in a certain zone (e.g., Zone 1 or Zone 5) of the firing motion. For instances when the controller determines 5726 to ignore the fact that a parameter of the firing force signal has reached or exceeded a predetermined threshold, the firing motion originally initiated 5712 is continued 5724 along with interim processes 5714-5722.

In other aspects, the controller may determine 5726 not to ignore the fact that a parameter of the firing force signal has reached or exceeded a predetermined threshold. The determination 5726 not to ignore the fact that a parameter of the firing force signal has reached or exceeded the predetermined threshold can be based, for example, on whether or not the amplitude of the firing force signal has reached or exceeded a predetermined threshold, based on the position of the sled, the knife and/or the firing bar, or any combinations thereof. For instances when the controller determines 5726 not to ignore the fact that a parameter of the firing force signal has reached or exceeded the predetermined threshold the controller changes 5730 the firing motion. According to some aspects, the controller may change the firing motion by modifying or adjusting a firing algorithm being executed by the controller to cause the firing motion to be slowed down, paused or stopped to prevent the surgical instrument 5700 from experiencing excessive forces. According to other aspects, the controller may change the firing motion by executing a different firing algorithm which causes the firing motion to be slowed down, paused or stopped to prevent the surgical instrument 5700 from experiencing excessive forces. In either case, the firing motion may be slowed down, stopped or paused by having the controller communicate a slow down signal, a stop signal or a pause signal to the motor controller to slow down, stop or pause the rotation of the motor(s) which drive the sled, knife, firing bar or any combination thereof of the surgical instrument 5700.

Upon changing the firing motion 5728, when the change of the firing motion 5728 is a slowing down of the firing motion (a slowing down of the rotation of the motor(s) which drive the sled, knife and/or firing bar), the process continues 5730 the closing motion originally initiated 5712 but at a reduced speed and the interim process 5714-5726 is continued but the firing of the sled, knife and/or firing bar occurs at a reduced speed. When the change of the firing motion 5728 is a stopping or pausing of the firing motion (a stopping or pausing of the rotation of the motor(s) which drive the sled, knife and/or firing bar), the process suspends or terminates 5732 the firing motion.

In accordance with one or more aspects, the operation of the surgical instrument 5700 may be controlled by monitoring parameters of the firing force signal (e.g., the amplitude, the slope, etc.) and in cases where a predetermined threshold is reached or exceeded, deciding whether change the firing motion based on the monitored parameters or to ignore the reaching or exceeding of the predetermined threshold. For example, in accordance with one or more aspects, if the change of the firing force F over time t (e.g., the slope of the firing force signal) reaches or exceeds a predetermined threshold before the firing force F reaches or exceeds a first firing force threshold, the control algorithm may ignore the fact that the slope of the firing force signal reached or exceeded the predetermined threshold and allow the operation of the surgical instrument 5700 to proceed as if the slope of the firing force signal had never reached or exceed the predetermined threshold.

Figure 117:
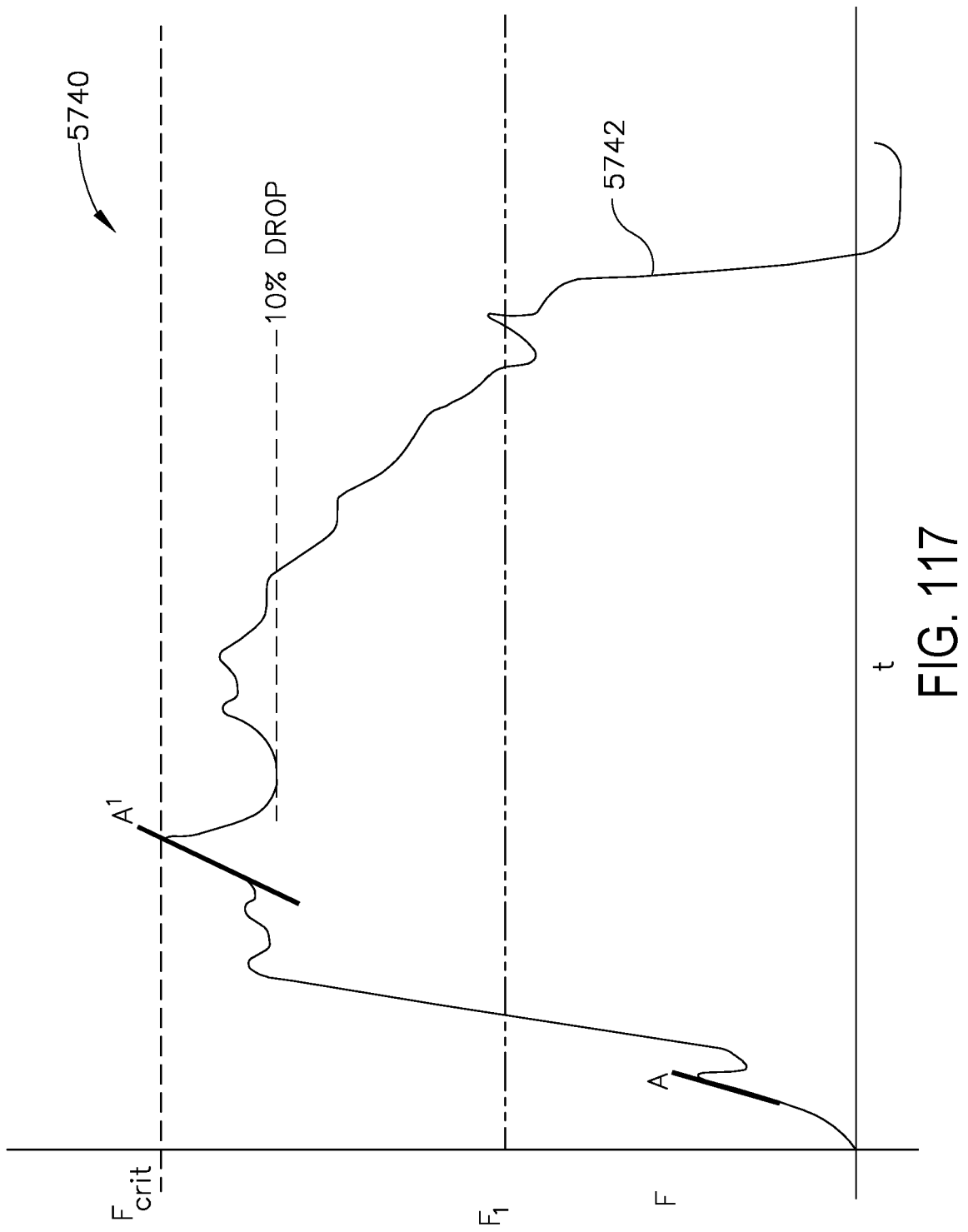

FIG. 117 illustrates an example graph 5740 showing a curve 5742 representative of a firing force F over time t for various aspects of the surgical instrument 5700. The firing force F is shown along the vertical axis and the time t is shown along the horizontal axis. Stated differently, the curve 5742 is a graphical representation of the firing force signal at various times during a firing motion. The curve 5742 may be generated mathematically by the controller based on the firing force signal(s) received by the controller. The firing force F shown in the example graph 5740 may be representative of a condition where the thickness and composition of the tissue along the cut line is uniform. The firing force F represented on the vertical axis may be a force experienced by the drive system of the surgical instrument 1000 (e.g., by the sled, the knife, and/or the firing bar), and/or any combination thereof. The firing force F can be measured in any suitable manner, either directly or indirectly. For example, in accordance with one or more aspects, the firing force F can be measured directly by a sensor (e.g., a strain gauge) positioned on the sled, on the knife, or indirectly by a current draw of the motor, and/or any combination thereof.

For the example graph 5740 shown in FIG. 117, at time t=0, the knife is in a fully retracted position near the proximal end of the end effector and over time advances to a fully advanced position near the distal end of the end effector. As described hereinabove, the overall distance the knife moves from the fully retracted position to the fully advanced position during a firing motion can be divided into predefined zones, with each zone being representative of a different operating condition of the surgical instrument 5700. Although not shown in FIG. 117 for purposes of simplicity, the respective zones of the firing motion (e.g., zones 1-5 as described hereinabove) could also be shown along the horizontal axis of FIG. 117.

Shortly after the knife moves from its fully retracted position towards its fully advanced position, the change of the firing force F over time t reaches or exceeds a predetermined slope threshold (this condition is shown as the slope A of the firing force signal in FIG. 117). As the slope A occurs in this example prior to the firing force F reaching or exceeding a first firing force threshold (shown as F1 in FIG. 117), the control algorithm may ignore the fact that the slope A reached or exceeded the predetermined threshold and allow the operation of the surgical instrument 5700 to proceed as if the slope A had never reached or exceed the predetermined threshold. Similarly, the control algorithm could also ignore the Slope A trigger, threshold or event based on the position of the knife (e.g., if the knife was in zone 2 of the firing motion when the predetermined slope threshold was reached or exceeded).

Due to the slope A trigger, threshold and/or event effectively being ignored, the knife continues to advance toward the fully advanced position and the firing force F continues to rise over time t. As shown in FIG. 117, the slope of the firing force signal again reaches or exceeds the predetermined slope threshold (this instance is shown as the slope A1 of the firing force signal in FIG. 117). In accordance with one or more aspects, the reaching or exceeding of the predetermined slope threshold alone is sufficient for the control algorithm to change the firing motion to slow down, stop or pause the further advancement of the knife. According to other aspects, the reaching or exceeding of the predetermined amplitude threshold (e.g., the amplitude Fcrit shown in FIG. 117) alone is sufficient for the control algorithm to change the firing motion to slow down, stop or pause the further advancement of the knife. According to yet other aspects, the combination of the reaching or exceeding of the predetermined slope threshold and the reaching or exceeding of the predetermined amplitude threshold causes the control algorithm to change the firing motion to slow down, stop or pause the further advancement of the knife. As shown in FIG. 117, when the slope A1 of the firing force signal reaches or exceeds the predetermined slope threshold and the amplitude of the firing force signal reaches or exceeds the predetermined amplitude threshold (e.g., Fcrit), the control algorithm changes the firing motion to slow down, stop or pause the further advancement of the knife and the firing force F begins to decrease.

The slowing down, stopping or pausing of the knife continues until the firing force F reaches a value which is 10% less than the predetermined amplitude threshold (e.g., Fcrit), at which point the further advancement of the knife is commenced. Of course, in accordance with one or more aspects, the further advancement of the knife can be commenced when the firing force reaches a value which is less than or more than the 10% example shown in FIG. 117. For the example graph 5742, once the further advancement of the knife is commenced, the knife advances to its fully advanced position and the firing force decreases to zero as indicated at the far right side of FIG. 117.

According to other aspects, the decision to change the firing motion or to ignore the reaching or exceeding of the predetermined threshold may be further based on the position of the sled, knife, firing bar or combinations thereof. For example, in accordance with one or more aspects, if the change of the firing force over time t reaches or exceeds a predetermined threshold while the knife is within a certain zone of the firing motion (e.g., zone 2 or zone 4), the control algorithm may ignore the fact that the slope of the firing force signal reached or exceeded the predetermined threshold and allow the operation of the surgical instrument 5700 to proceed as if the slope of the firing force signal had never reached or exceed the predetermined threshold.

Figure 118:
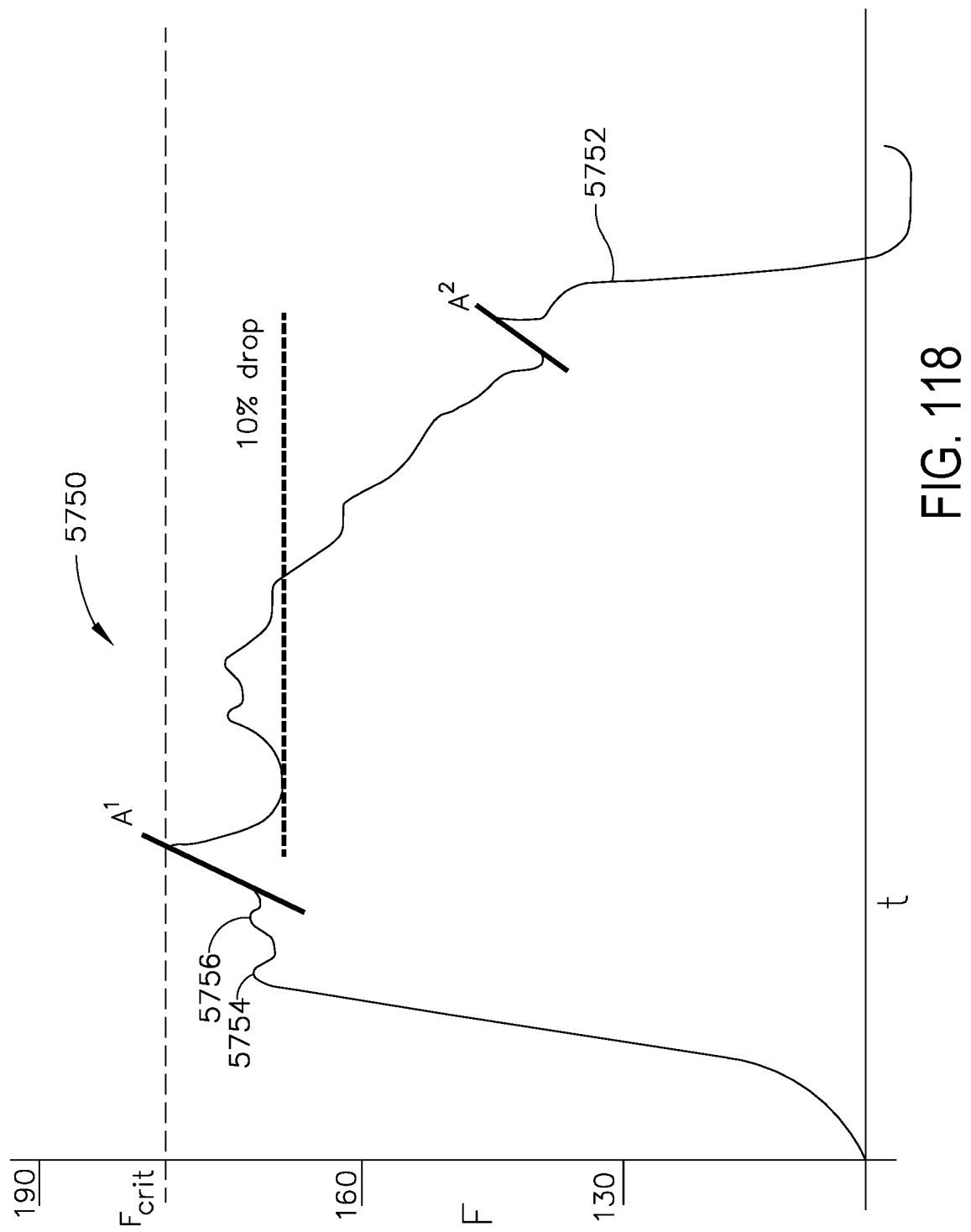

FIG. 118 illustrates an example graph 5750 showing a curve 5752 representative of a firing force F over time t for various aspects of the surgical instrument 5700. The curve 5752 may be generated mathematically by the controller based on the firing force signal(s) received by the controller. The firing force F shown in the example graph 5750 may be representative of a condition where the thickness and composition of the tissue along the cut line is uniform. The firing force F represented on the vertical axis may be a force experienced by the drive system of the surgical instrument 5700 (e.g., by the sled, the knife, and/or the firing bar), and/or any combination thereof. Although not shown for purposes of simplicity, the respective zones of the firing cycle (e.g., zones 1-5 as described hereinabove) could also be shown along the horizontal axis.

The firing force F can be measured in any suitable manner, either directly or indirectly. For example, in accordance with one or more aspects, the firing force F can be measured directly by a sensor (e.g., a strain gauge) positioned on the sled, on the knife, or indirectly by a current draw of the motor, and/or any combination thereof.

For the example graph 5750 in FIG. 118, at time t=0 the knife is in the fully-retracted position and the firing force F is zero. As the knife and sled advance and the velocity of the knife increases, the firing force F increases and reaches a first peak value 5754 when a first row of staples is driven from the staple cartridge. After the first row of staples is driven as described hereinabove, the firing force F decreases until a second row of staples is driven, which causes the firing force F to reach a second peak value 5756.

At a later point in the firing motion, the slope of the firing force signal reaches or exceeds a predetermined threshold (this condition is shown as the slope A1 of the firing force signal in FIG. 118) and the amplitude of the firing force F reaches or exceeds a predetermined amplitude threshold (e.g., the amplitude Fcrit shown in FIG. 118). In response, the control algorithm acts to slow down, stop or pause the further advancement of the knife and the firing force F begins to decrease.

For the example graph 5752, the slowing down, stopping or pausing of the knife continues until the firing force F reaches a value which is 10% less than the predetermined amplitude threshold (e.g., Fcrit), at which point the further advancement of the knife is commenced. Of course, in accordance with one or more aspects, the further advancement of the knife can be commenced when the firing force reaches a value which is less than or more than the 10% example shown in FIG. 118. The above-described automatic stopping or pausing and automatic restarting may be repeated any number of times.

For the example graph 5752, once the further advancement of the knife is commenced, as the knife advances towards its fully advanced position the slope of the firing force signal once again reaches or exceeds the predetermined slope threshold (this condition is shown as the slope A2 of the firing force signal in FIG. 118). However, because the predetermined slope threshold was reached or exceeded while the knife was in zone 4 of the firing motion, the control algorithm ignores this "slope" trigger and continues advancing the knife to its fully advanced position, resulting in the firing force decreasing to zero as indicated at the far right side of FIG. 118.

In addition to ignoring triggers, thresholds and/or events based on where the triggers, thresholds and/or events occur within the firing motion, the control algorithms may also vary or modify the triggers, thresholds and/or events based on where the triggers, thresholds and/or events occur within the firing motion. For example, in accordance with one or more aspects, the control algorithms may set the value for a predetermined slope threshold at a first value for zone 1 of the firing motion, at a second value for zone 2 of the firing motion, at a third value for zone 3 of the firing motion, etc.

Figure 119:
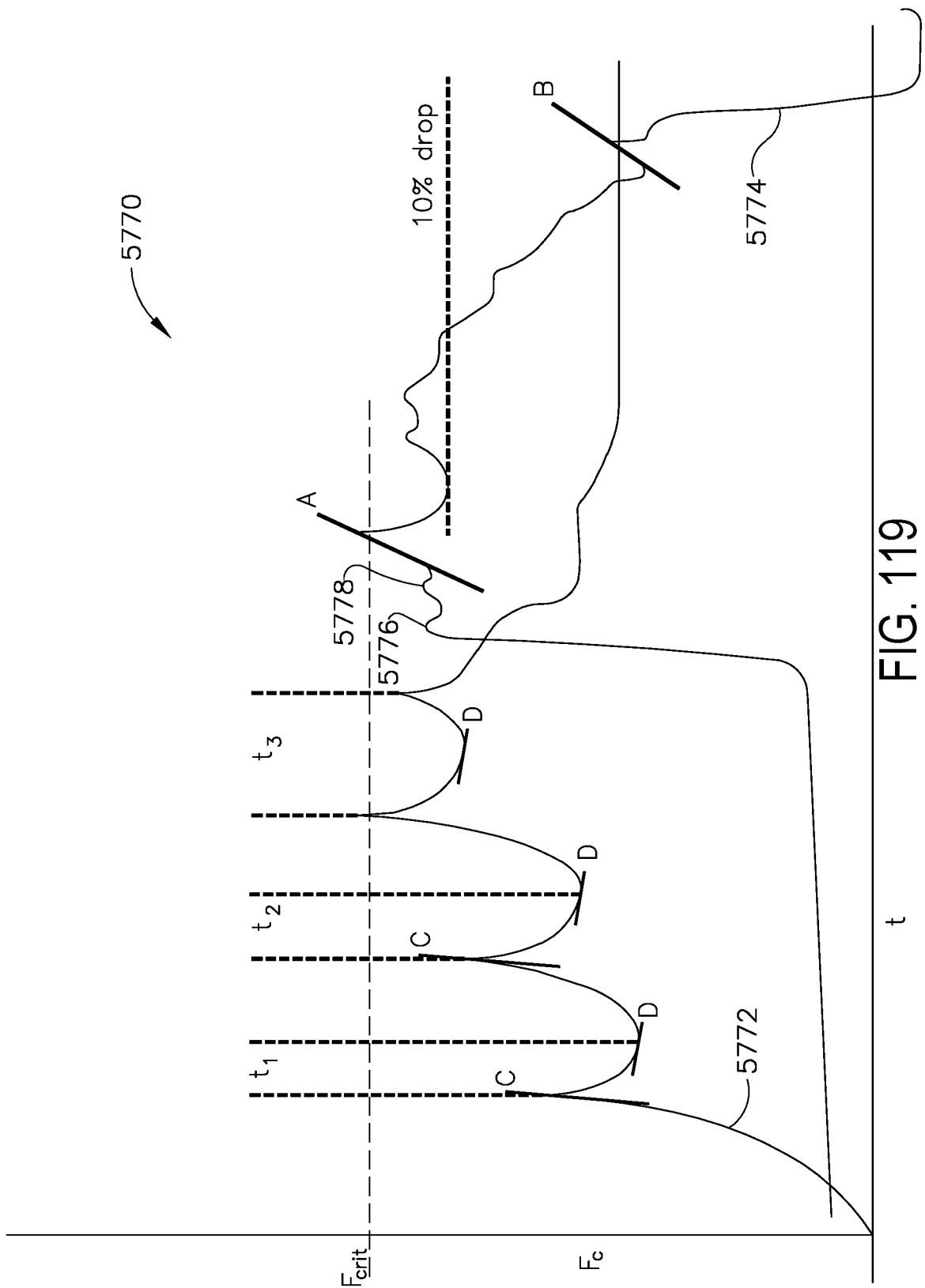

FIG. 119 illustrates an example graph 5770 showing a curve representative of a closing force FC over time t for various aspects of the surgical instrument and a curve representative of a firing force FF over time t for the surgical instrument 5700 of FIG. 115. FIG. 119 illustrates an example graph 5770 showing a curve 5772 representative of a closing force FC over time t for various aspects of the surgical instrument 5700 and a curve 5774 representative of a firing force FF over time t for various aspects of the surgical instrument 5700. The closing force FC is shown along the "left" vertical axis, the firing force FF is shown along the "right" vertical axis and the time t is shown along the horizontal axis. When viewed together the curves 5772, 5774 reflect the timing of the closing motion and the firing motion relative to one another, where the closing motion is initiated prior to the initiation of the firing motion. Although the example graph 5770 shows a threshold force Fcrit as being the same amplitude for both the closing force FC and the firing force FF, it will be appreciated that the amplitude of the threshold force Fcrit for the closing force FC may be different from the amplitude of the threshold force Fcrit for the firing force FF. Stated differently, the scale of the "left" vertical axis can be different from the scale of the "right" vertical axis.

The curve 5772 is a graphical representation of the closing force signal at various times during a closing motion. Thus, as set forth hereinabove, the curve 5772 may be generated mathematically by the controller based on the closing force signal(s) received by the controller. The closing force FC represented on the "left" vertical axis may be a force experienced by tissue clamped between the jaws of the surgical instrument 5700, a force experienced by the jaws of the surgical instrument 5700 (e.g., by the anvil and/or the elongated channel), a force experienced by the closure tube of the surgical instrument 5700, and/or any combinations thereof. The closing force FC can be measured in any suitable manner, either directly or indirectly. For example, according to various aspects, the closing force FC can be measured directly by a sensor (e.g., a strain gauge) positioned on the anvil, on the elongated channel, on the closure tube, or indirectly by an impedance of the tissue, a current draw of the motor, and/or any combinations thereof.

The curve 5774 is a graphical representation of the firing force signal at various times during a firing motion and may be similar or identical to the curve 5752 of FIG. 109. Thus, as set forth hereinabove, the curve 5774 may be generated mathematically by the controller based on the firing force signal(s) received by the controller. The firing force FF represented on the "right" vertical axis may be a force experienced by the drive system of the surgical instrument 5700 (e.g., by the sled, the knife, and/or the firing bar), and/or any combination thereof. The firing force FF can be measured in any suitable manner, either directly or indirectly. For example, according to various aspects, the firing force FF can be measured directly by a sensor (e.g., a strain gauge) positioned on the sled, on the knife, or indirectly by a current draw of the motor, and/or any combination thereof.

Although not shown for purposes of simplicity, the respective zones of the firing cycle (e.g., zones 1-5 as described hereinabove) could also be shown along the horizontal axis.

For the example graph 5770 in FIG. 110, at some time after the closing motion has commenced, the knife is still in the fully-retracted position and the firing force FF is approximately zero. As the knife and sled advance and the velocity of the knife increases, the firing force FF increases and reaches a first peak value 5776 when a first row of staples is driven from the staple cartridge. After the first row of staples is driven as described hereinabove, the firing force FF decreases until a second row of staples is driven, which causes the firing force FF to reach a second peak value 5778.

At a later point in the firing motion, the slope of the firing force signal reaches or exceeds a predetermined threshold (this condition is shown as the slope A of the firing force signal in FIG. 117) and the amplitude of the firing force FF reaches or exceeds a predetermined amplitude threshold (e.g., the amplitude Fcrit shown in FIG. 117). In response, the control algorithm acts to slow down, stop or pause the further advancement of the knife and the firing force FF begins to decrease.

For the example graph 5770, the slowing down, stopping or pausing of the knife continues until the firing force FF reaches a value which is 10% less than the predetermined amplitude threshold (e.g., Fcrit), at which point the further advancement of the knife is commenced. Of course, according to various aspects, the further advancement of the knife can be commenced when the firing force FF reaches a value which is less than or more than the 10% example shown in FIG. 117. The above-described automatic stopping or pausing and automatic restarting may be repeated any number of times.

For the example graph 5770, once the further advancement of the knife is commenced, as the knife advances towards its fully advanced position the slope of the firing force signal once again reaches or exceeds the predetermined slope threshold (this condition is shown as the slope B of the firing force signal in FIG. 117). However, because the predetermined slope threshold was reached or exceeded while the knife was in zone 4 (not shown) of the firing motion, the control algorithm ignores this "slope" trigger and continues advancing the knife to its fully advanced position, resulting in the firing force decreasing to zero as indicated at the far right side of FIG. 117.

Figure 120:
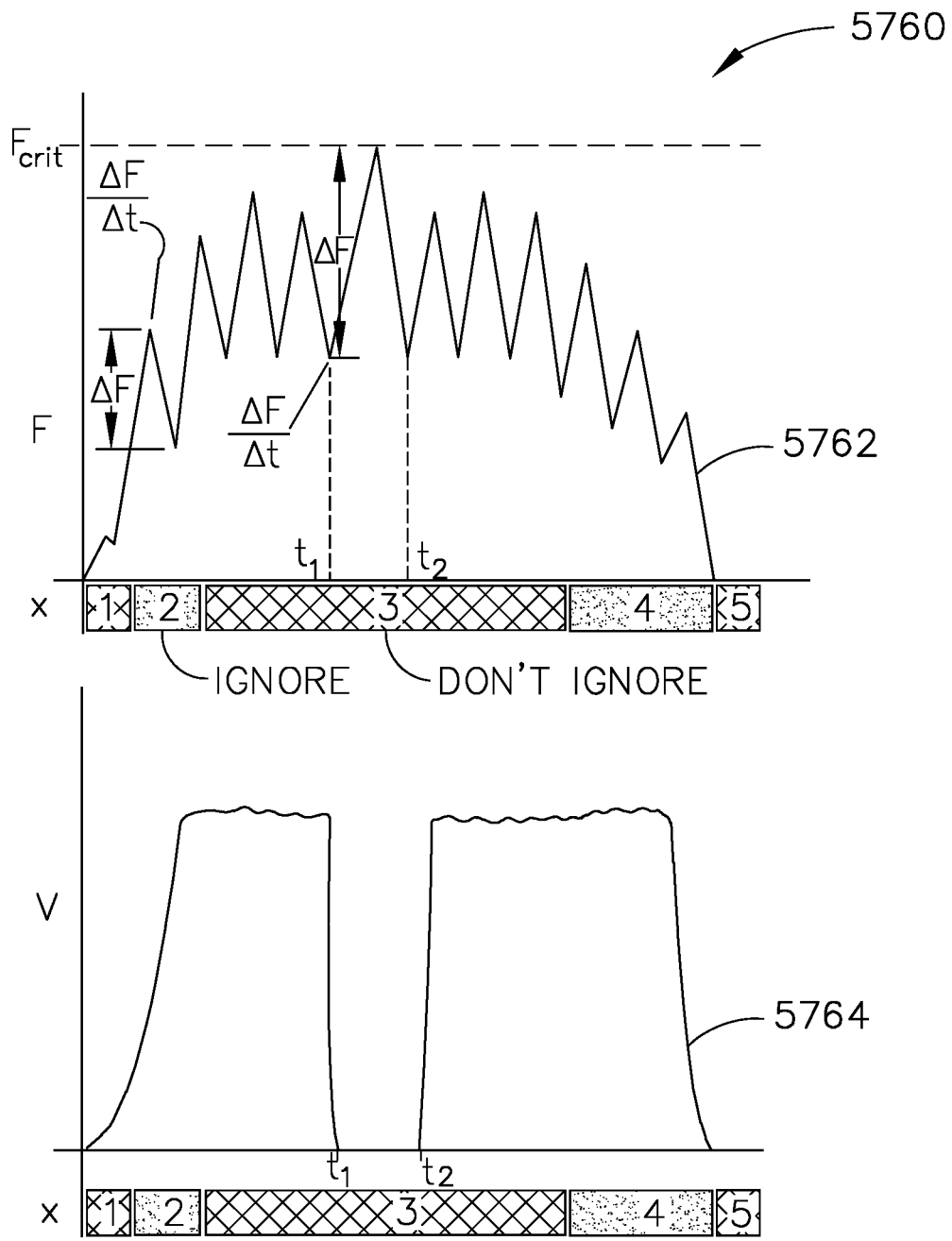

FIG. 120 illustrates an example graph 5760 showing a first curve 5762 representative of a firing force F over time t for various aspects of the surgical instrument 5700, a knife position X over time t for various aspects of the surgical instrument 5700 and a second curve 5764 representative of knife velocity V over time t for various aspects of the surgical instrument 5700. The firing force F is shown along the top vertical axis, the knife velocity V is shown along the bottom vertical axis, the knife position X is shown along the top horizontal axis and the time t are shown along both the top and bottom the horizontal axes. As shown along the top horizontal axis, the knife position X travels over five Zones 1-5 along the knife channel in the cartridge 304 located in the lower jaw 302 of the end effector 300 of the surgical instrument 5700. The knife velocity V and the firing force F shown in FIG. 120 may be based on the assumption that the thickness and composition of the tissue along the cut line is uniform.

Accordingly, the curve 5762 is a representation of the firing force signal at various times during a firing motion and the curve 5764 is a representation of the knife velocity signal at various times during a firing motion. The curves 5762, 5764 may be generated mathematically by the controller based on the firing force signal(s) and the knife velocity signal(s) received by the controller. The firing force F represented on the top vertical axis may be a force experienced by the drive system of the surgical instrument 5500 (e.g., by the sled, the knife and/or the firing bar), and/or any combination thereof. The firing force F can be measured in any suitable manner, either directly or indirectly. For example, in accordance with one or more aspects, the firing force F can be measured directly by a sensor (e.g., a strain gauge) positioned on the sled, on the knife, or indirectly by a current draw of the motor, and/or any combination thereof.

The knife velocity V represented on the bottom vertical axis may be a velocity of the knife, a velocity of the sled, a velocity of another component of the drive system (e.g., the firing bar), and/or any combination thereof. The knife velocity V can be measured in any suitable manner, either directly or indirectly. For example, in accordance with one or more aspects, the knife velocity V can be measured directly by a combination of a magnet positioned on the firing bar and a Hall-effect sensor or indirectly by a current draw of the motor, an encoder coupled to the shaft of the motor, and/or any combination thereof.

For the example graph 5764, the knife velocity V is shown as increasing from zero to a substantially maximum velocity while the knife advances from its fully retracted position through zone 1 and into zone 2 of the firing motion. Even if the change of the firing force F over time (e.g., the slope ΔF/Δt shown occurring in zone 1 and/or zone 2) reaches or exceeds a predetermined threshold, the control algorithm may ignore this trigger, threshold and/or event and allow the knife to continue advancing as shown by the knife velocity V in FIG. 120. Once the substantially maximum velocity is reached in zone 2, the knife continues to advance in zone 2 and zone 3 until another trigger, threshold and/or event prompts the control algorithm to automatically stop the advancement of the knife. For the example graph 5762, this occurs in zone 3 when the firing force F exceeds the predetermined threshold Fcrit. According to other aspects, the trigger, threshold and/or event could be a change of firing force F over time t reaching or exceeding a certain value, a combination of the change of firing force F over time t reaching or exceeding a certain value and the firing force F reaching or exceeding a certain value, a change of a peak-to-peak firing force over time t reaching or exceeding a certain value, a combination of a change of a peak-to-peak firing force over time t reaching or exceeding a certain value and the firing force F reaching or exceeding a certain value, etc.

Once the firing force F reaches or exceeds the predetermined threshold Fcrit and the knife is in a position associated with zone 3 of the firing motion, the control algorithm automatically stops or pauses the further advancement of the knife and the knife velocity V falls from a substantially constant velocity to zero at time t1. In other words, instead of ignoring the trigger, the control algorithm acts on the trigger and changes the firing motion. After a predefined period of time (e.g., the time period t2−t1) as shown in FIG. 120 or a predefined drop in the amplitude of the firing force F, the control algorithm automatically restarts the advancement of the knife and the knife velocity V increases from zero at time t2 to a substantially maximum velocity, then continues in zone 3 and zone 4 at a substantially constant velocity. At some point in zone 4, the knife velocity drops from a substantially constant velocity to zero and the firing force also drops to zero.

Although FIG. 120 depicts the control algorithm as not acting on a firing force trigger, threshold and/or event which occurs in zone 2 of the firing motion and acting on a firing force trigger, threshold and/or event which occurs in zone 3 of the firing motion, it will be appreciated that the control algorithm can be configured to act or not act on firing force triggers, thresholds and/or events which occur in other zones of the firing motion. For example, as described hereinabove with respect to FIG. 118, the control algorithm can be configured to not act (ignore) a firing force trigger, threshold and/or event which occurs in zone 4 of the firing motion.

Furthermore, although the functionality of the control algorithms described in connection with FIGS. 115-120 were described in the context of ignoring or varying triggers, thresholds and/or events during the firing motion, it will be appreciated that the control algorithms of the surgical instrument 5700 may also be configured to ignore or vary triggers, thresholds and/or events during the closing cycle (i.e., the closing of the jaws).

Figure 121:
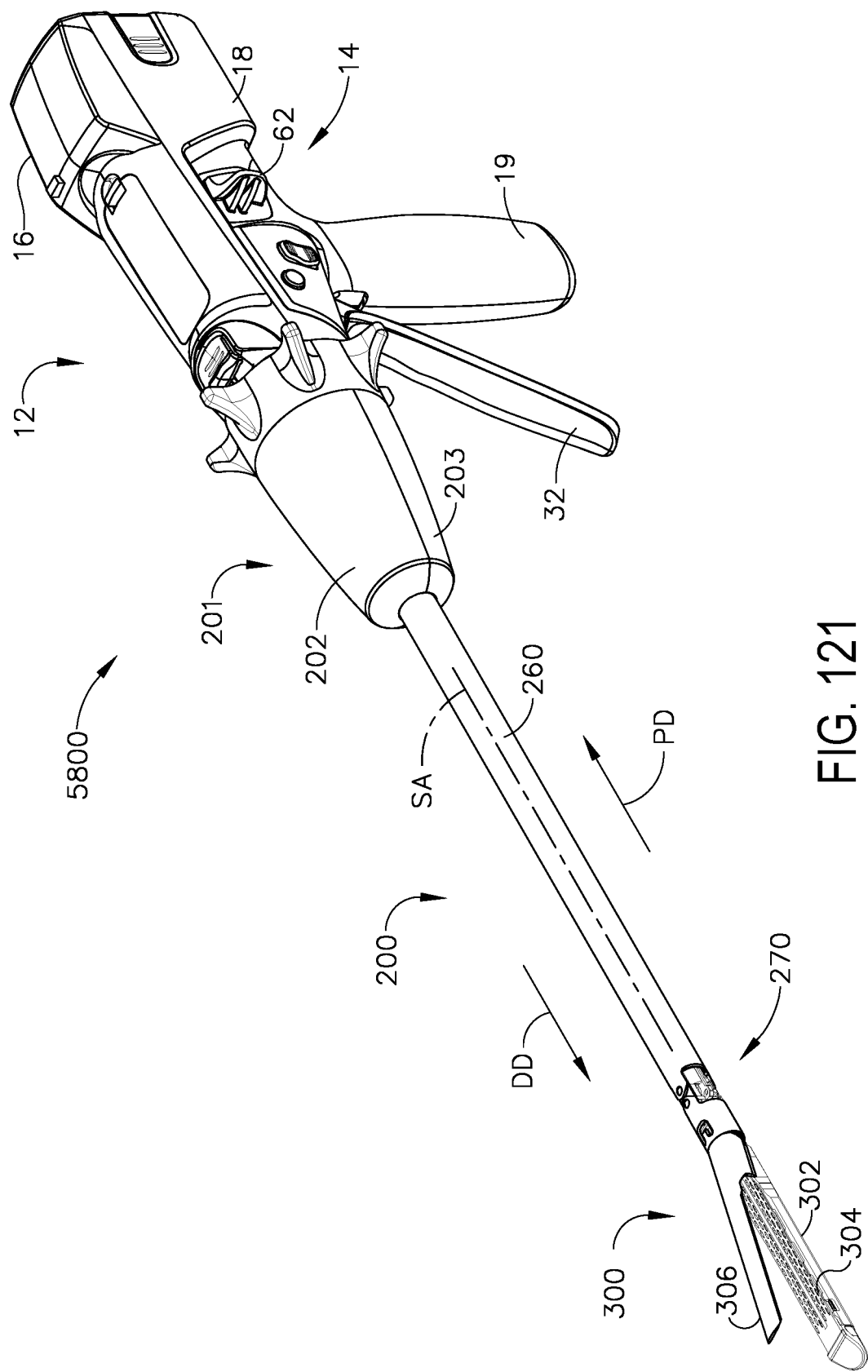

FIG. 121 illustrates a perspective view of a surgical instrument 5800 according to various aspects described herein. The surgical instrument 5800 is similar to the surgical instrument 5500 and includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5800 is also similar to the surgical instrument 5500 in that the surgical instrument 5800 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5500 is also similar to the surgical instrument 5800 in that the surgical instrument 5800 also includes algorithms such as closing algorithms, firing algorithms, motor control algorithms, or any combination thereof, which operate to dynamically adjust the operation of the surgical instrument 5800. However, the surgical instrument 5800 is different from the surgical instrument 5500 in that the surgical instrument 5800 further includes one or more additional algorithms (in addition to those described hereinabove) which provide additional control functionality for the surgical instrument 5800, as described herein below.

In certain aspects, for different circumstances, the control algorithms are configured to automatically invoke different adjustments to the closing motion and/or the firing motion. For example, in certain aspects, a control algorithm is configured to adjust the firing motion based on how fast the load is increasing or decreasing as it approaches a predefined staged threshold. For such aspects, a first adjustment to the firing motion may be invoked when the load is increasing at a first rate as it approaches a predefined threshold, and a second adjustment to the firing motion may be invoked when the load is increasing at a second rate as it approaches a predefined threshold. In other aspects, the control algorithms are configured to adjust the closure algorithm and/or the firing algorithm based on how fast aspects of the closing force, the closure tube velocity, the firing force, the knife velocity, the motor current and combinations thereof are increasing or decreasing as they approaches respective predefined staged thresholds.

Figure 122:
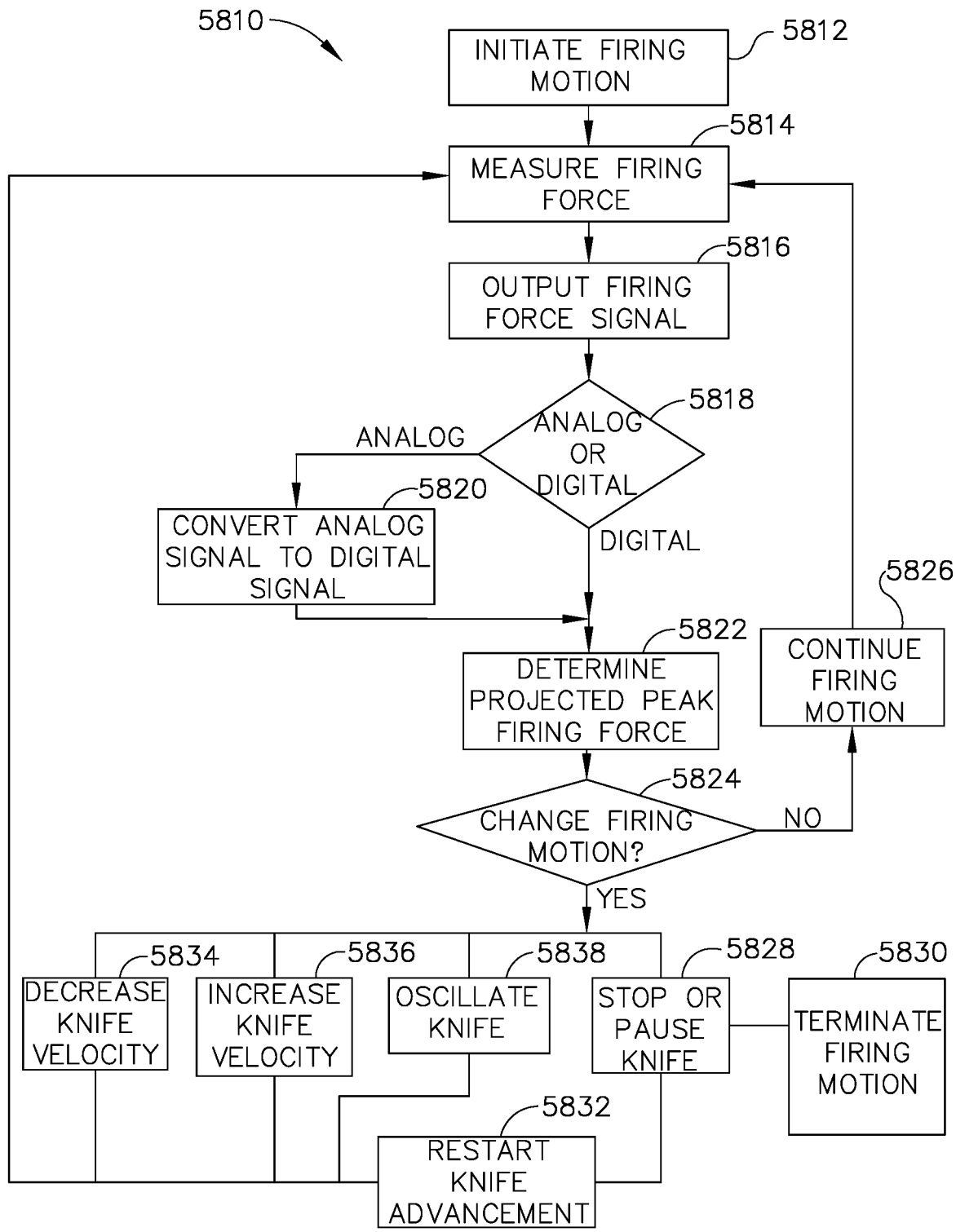

FIG. 122 illustrates a method 5810 of controlling a firing motion of the surgical instrument 5800 according to various aspects. The process starts when a firing motion is initiated 5812. The firing motion may be initiated, for example, by pulling a firing trigger toward a handle. A sensor resident with the surgical instrument 5800 senses/measures 5814 a firing force. The firing force may be, for example, a force experienced by the drive system of the surgical instrument (e.g., by the sled, the knife and/or the firing bar), and/or any combination thereof. The firing force F can be measured in any suitable manner, either directly or indirectly. For example, according to various aspects, the firing force F can be measured directly by a sensor (e.g. a strain gauge) positioned on the sled, on the knife, or indirectly by a current draw of the motor.

In response to the firing force, the sensor outputs 5816 a firing force signal, which is indicative of the firing force sensed/measured 5814 by the sensor. Depending on the configuration of the sensor, the firing force signal can be an analog signal or a digital signal. Upon determining 5818 whether the firing force signal is either an analog signal or a digital signal, the process proceeds along the corresponding branch. When the determination 5818 is that the firing force signal is an analog signal, the process proceeds along the analog branch, where the analog signal is received by an A/D converter, converted 5820 to a digital signal representative of the analog signal by the A/D converter and the digital signal is output by the A/D converter. When the determination 5818 is that the firing force signal is a digital signal, the process proceeds along the digital branch because there is no need for an A/D conversion 5820 when the firing force signal is a digital signal.

The firing force signal which is a digital signal representative of the firing force sensed/measured 5814 by the sensor is received by a controller. The controller utilizes the digital signal and determines 5822 a projected peak firing force. According to various aspects, the projected peak firing force is determined by constructing a straight line which passes through the two most recent peak values of the firing force signal, projecting when the next peak firing force will occur and determining the value of the firing force on the straight line at that time. The straight line is representative of a change of peak firing force values over time and may thus be considered a slope of the peak firing force values. The controller may project when the next peak firing force will occur in any suitable manner. For example, according to various aspects, the controller may utilize the time lapse between the last two peak firing forces, the average of the time lapses between each of the peak firing forces which have occurred in a given firing motion, the pattern or trend of the time lapses between each of the peak firing forces which have occurred in a given firing motion and combinations thereof.

After the controller determines 5822 that the projected peak firing force, the controller then determines 5824 whether or not the firing motion should be changed. The determination 5824 may be based, for example, on how fast or slow the projected peak firing force is approaching a predetermined threshold, on the amplitude of the firing force and how fast or slow the projected peak firing force is approaching a predetermined threshold, and combinations thereof. In other words, the determination 5824 may be based on the amplitude of the firing force and the value of the slope of the peak firing force values as the slope is approaching a predetermined threshold. The predetermined threshold may be any suitable threshold such as, for example, a predetermined firing force threshold. When the controller determines 5824 that the firing motion should not be changed, the firing motion originally initiated 5812 is continued 5826 along with interim processes 5814-5824. When the controller determines 5824 that the motion should be changed, the firing motion may be changed in a multitude of different ways, with the particular way determined based on how fast or slow the projected peak firing force is approaching a predetermined threshold.

According to various aspects, when the projected peak firing force is approaching a predetermined threshold at a first rate, the controller may stop or pause 5828 the firing motion by communicating a stop signal or a pause signal to the motor controller to stop or pause the rotation of the motor(s) which drive the sled, knife, firing bar or any combination thereof of the surgical instrument 5800. After the firing motion is stopped or paused, the firing motion may be subsequently terminated 5830 or the controller may restart 5832 the firing motion by communicating a restart signal to the motor controller to restart the rotation of the motor(s) which drive the sled, knife, firing bar or any combination thereof of the surgical instrument 5800. The firing motion may be restarted 5832 based on, for example, a period of time, a predetermined drop in the firing force and combinations thereof. After the firing motion is restarted 5832, interim processes 5814-5824 of the firing motion originally initiated 5812 are continued.

According to various aspects, when the projected peak firing force is approaching a predetermined threshold at a second rate, the controller may change the firing motion to decrease the knife velocity 5834 by communicating a slow down signal to the motor controller to slow down the rotation of the motor(s) which drive the sled, knife, firing bar or any combination thereof of the surgical instrument 5800. Similarly, according to various aspects, when the projected peak firing force is approaching a predetermined threshold at a third rate, the controller may change the firing motion to increase the knife velocity 5836 by communicating a speed up signal to the motor controller to speed up the rotation of the motor(s) which drive the sled, knife, firing bar or any combination thereof of the surgical instrument 5800.

According to various aspects, when the projected peak firing force is approaching a predetermined threshold at a fourth rate, the controller may change the firing motion to oscillate the knife 5838 by communicating an oscillation signal to the motor controller to alternate the rotation of the motor(s) which drive the sled, knife, firing bar or any combination thereof of the surgical instrument 5800 in a clockwise direction and a counterclockwise direction, thereby producing a back and forth motion of the sled, knife, firing bar or any combination thereof.

Figure 123:
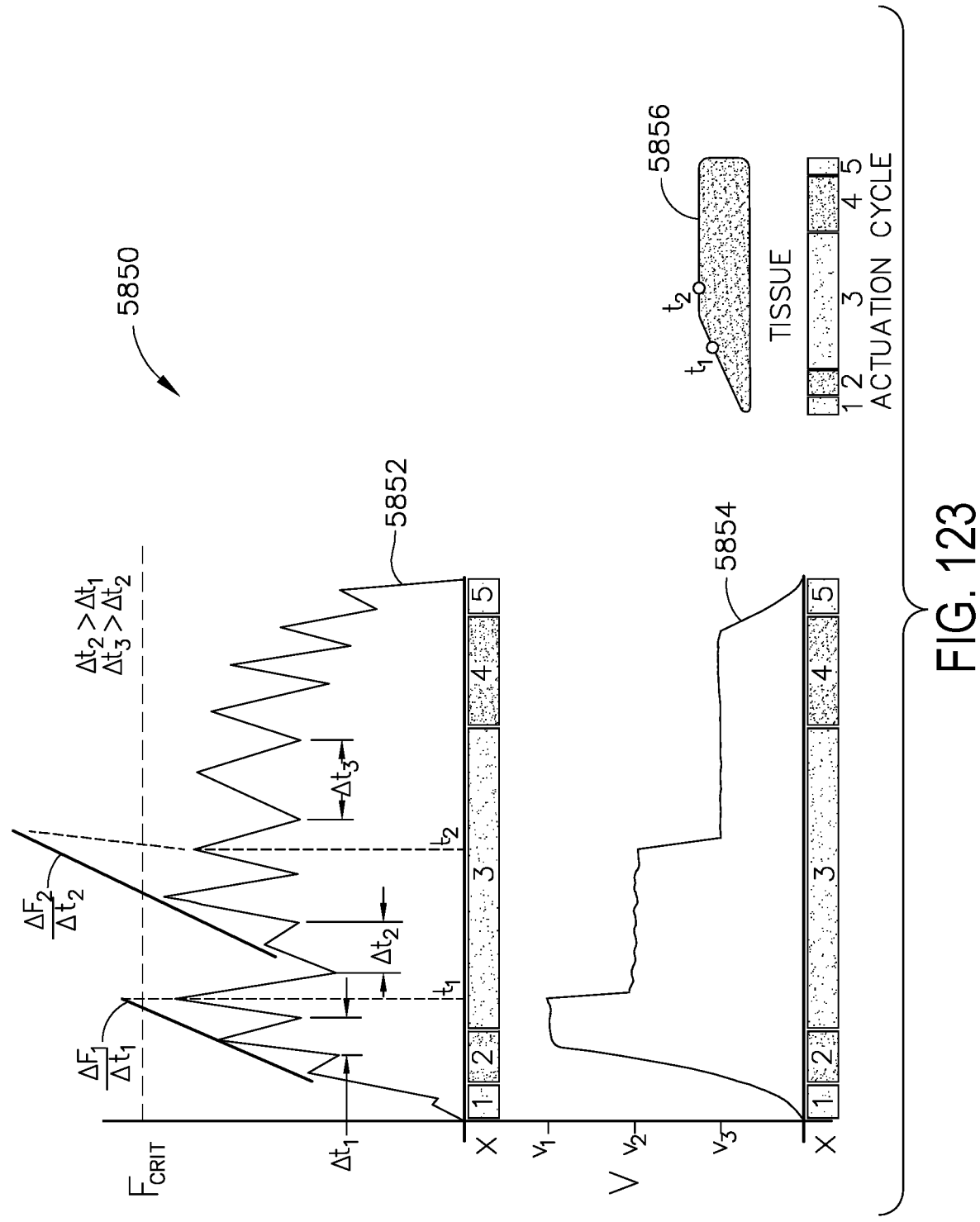

FIG. 123 illustrates an example graph 5850 showing a first curve 5852 representative of a firing force F over time t for various aspects of the surgical instrument 5800, a knife position X over time t for various aspects of the surgical instrument 5800 and a second curve 5854 representative of knife velocity V over time t for various aspects of the surgical instrument 5800. The firing force F is shown along the top vertical axis, the knife velocity V is shown along the bottom vertical axis, the knife position X is shown along both the top and bottom horizontal axes and the time t is shown along both the top and bottom the horizontal axes. As shown along the top an bottom horizontal axes, the knife position X travels over five zones (zones 1-5) along the knife channel in the cartridge 304 located in the lower jaw 302 of the end effector 300 of the surgical instrument 5800. The knife velocity V and the firing force F shown in FIG. 123 may be based on the assumption that the thickness and composition of the tissue 5856 along the cut line is non-uniform as shown on the far right side of FIG. 123.

Accordingly, the curve 5852 is a representation of the firing force signal at various times during a firing motion and the curve 5854 is a representation of the knife velocity signal at various times during a firing motion. The curves 5852, 5854 may be generated mathematically by the controller based on the firing force signal(s) and the knife velocity signal(s) received by the controller. The firing force F represented on the top vertical axis may be a force experienced by the drive system of the surgical instrument 5800 (e.g., by the sled, the knife and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

The knife velocity V represented on the bottom vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

For the example graph 5840, the curve 5854 shows the knife velocity V increasing from zero at time t=0 to a substantially maximum velocity V1 while the knife advances from its fully retracted position through zone 1 and into zone 2 of the firing motion. Once the substantially maximum velocity V1 is reached in zone 2, the knife continues to advance in zone 2 and zone 3 until a trigger, threshold and/or event prompts the control algorithm to automatically change the firing motion, in this case decreasing the knife velocity V. Such a trigger, threshold or event is shown in the curve 5852, where the projected peak firing force on the slope ($\Delta F1/\Delta t1$) reaches or exceeds a predetermined threshold (e.g., the firing force value Fcrit) at the time t1. As shown in FIG. 123, the time t1 may correspond to the knife cutting through a portion of tissue 5856 which is less than a full thickness of the tissue 5856.

Once the projected peak firing force on the slope ($\Delta F1/\Delta t1$) reaches or exceeds the predetermined threshold Fcrit and the knife is in a position associated with zone 3 of the firing motion at time t1, the control algorithm changes the firing motion to decrease the knife velocity from the substantially maximum velocity V1 to the reduced velocity V2. Although the velocity V2 is shown as being approximately ⅔ of the velocity V1, it will be appreciated that the decrease in the knife velocity V can be more or less than ⅓ of the maximum velocity V1. According to various aspects, the amount of the decrease is based on the value of the slope ($\Delta F1/\Delta t1$), essentially how quickly the peak firing forces are approaching the predetermined threshold. The knife then advances at the reduced velocity V2 in zone 3 until another trigger, threshold and/or event prompts the control algorithm to automatically change the firing motion, in this case further decreasing the knife velocity V. Such a trigger, threshold or event is shown in the curve 5852, where the projected peak firing force on the slope ($\Delta F2/\Delta t2$) reaches or exceeds a predetermined threshold (e.g., the firing force value Fcrit) at the time t2. As shown in FIG. 123, the time t2 may correspond to the knife cutting through a portion of tissue 5856 which is the full thickness of the tissue 5856.

Once the projected peak firing force on the slope ($\Delta F2/\Delta t2$) reaches or exceeds the predetermined threshold Fcrit and the knife is in a position associated with zone 3 of the firing motion at time t2, the control algorithm again changes the firing motion to further decrease the knife velocity from the reduced V2 to the further reduced velocity V3. Although the velocity V3 is shown as being approximately ⅓ of the velocity V1 and ½ of the velocity V2, it will be appreciated that the further decrease in the knife velocity V can be more or less than ⅓ of the maximum velocity V1 or more or less than ½ of the previous velocity V2. According to various aspects, the amount of the decrease is based on the value of the slope ($\Delta F2/\Delta t2$), essentially how quickly the peak firing forces are approaching the predetermined threshold.

After the time t2, the knife continues advancing through zones 3 and 4 of the firing motion at the velocity V2, then begins dropping in zone 4 and reaches zero in zone 5 of the firing motion. As shown in the curve 5852, the firing force F also drops to zero in zone 5. Due to the differences in the knife velocity V brought about by the controller, it will be appreciated that the time period $\Delta t1$, the time between successive valley firing force values when the knife is in zone 2 of the firing motion and advancing at the velocity V1, is less than the time period $\Delta t2$, the time between successive valley firing force values when the knife is in zone 3 of the firing motion and advancing at the velocity V2, which is less than the time period $\Delta t3$, the time between successive valley firing force values when the knife is in zone 3 of the firing motion and advancing at the velocity V3.

Although FIG. 123 depicts the control algorithm as acting to reduce the knife velocity V based on triggers, thresholds and/or events which occur in zones 2 and/or 3 of the firing motion, it will be appreciated that the control algorithm can be configured to act to increase the knife velocity, oscillate the knife and combinations thereof in zones 2 and 3 of the firing motion and/or in other zones of the firing motion. For example, when the peak firing forces are rapidly approaching a predetermined threshold (i.e., the slope is steep), the firing algorithm may interpret this as an obstruction to the knife and change the firing motion to stop the advancement of the knife then create an oscillating motion. The stop, backup, re-advance, stop, backup, re-advance pattern assists the knife in moving through the obstruction.

Furthermore, although the functionality of the control algorithms described in connection with FIG. 123 were described in the context of adjusting the knife velocity V, it will be appreciated that the control algorithms of the surgical instrument 5800 may also be configured to adjust the closure tube velocity during the closing motion (i.e., the closing of the jaws). Similarly, the control algorithms may operate to change the closing motion such that the anvil vibrates/oscillates toward a fully closed position to improve compression of the tissue 5856.

Figure 124:
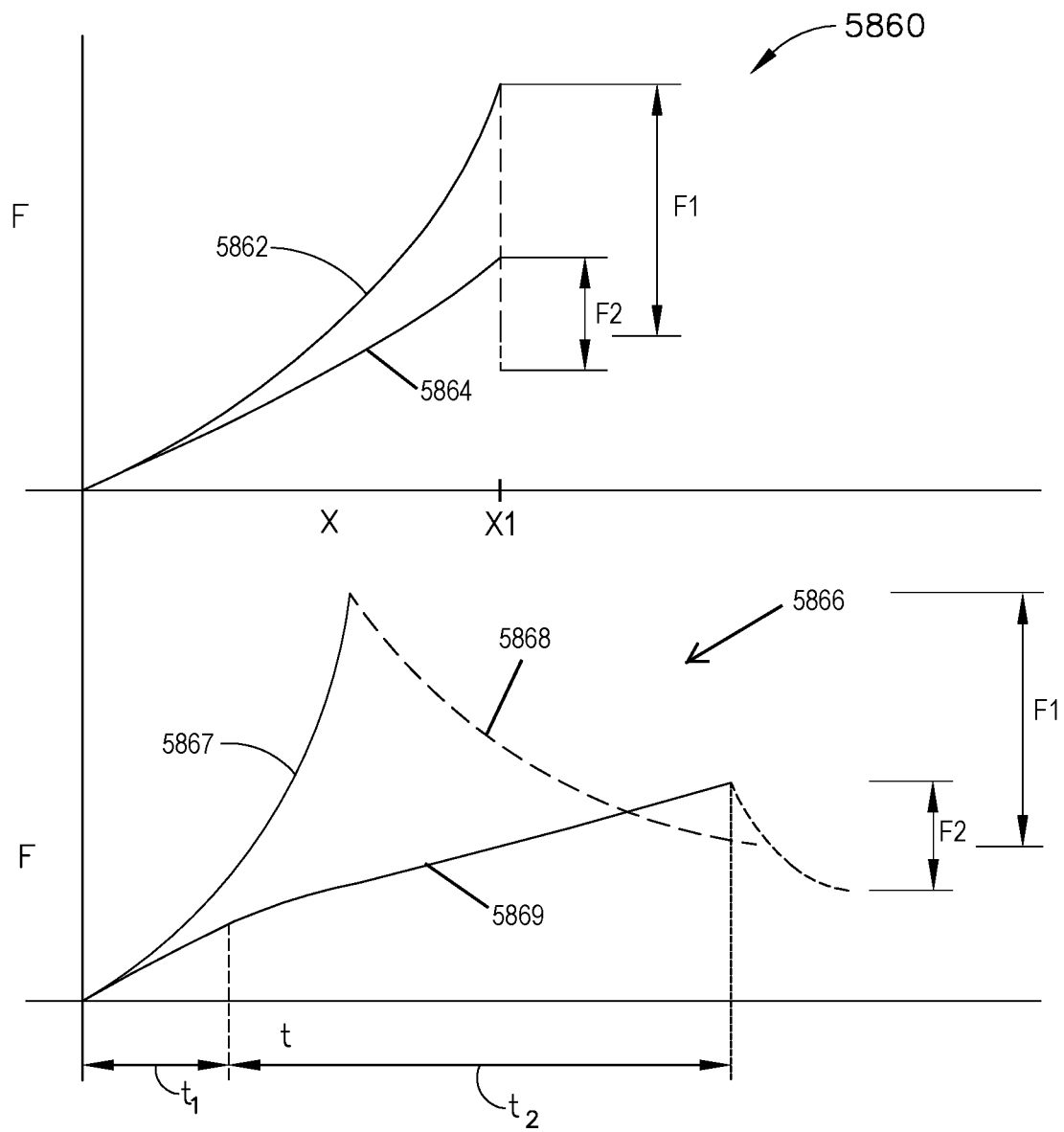

FIG. 124 illustrates the rate of closure of the jaws (jaws closure speed) for the surgical instrument of FIG. 121 in accordance with one or more aspects of the present disclosure. In other words, the rate of closure of the anvil 306 closing onto the staple cartridge 304 with tissue located therebetween. The top graph 5860 represents the jaws closing at a constant speed where the jaw closing force (F) is represented along the vertical axis as the knife advances over a longitudinal distance (X) in the cartridge 304, as represented along the horizontal axis, until the stop trigger is actuated by the control program at X1. The stop trigger stops the jaws from closing for a period of time prior to initiating the firing stroke. As previously described herein, this enables the jaws to squeeze excess moisture from the tissue prior to initiating the firing stroke after a brief delay period of 5 to 20 seconds and preferably about 15 seconds. At X1, the jaws closing force reaches a peak amplitude and the gap between the jaws is set to a predetermined distance. Still with reference to the top graph 5860, the first curve 5862 represents the force over distance as the jaws close at a first constant speed until the stop trigger stops the jaws from closing at X1. At this point, the force F reaches a peak force of F1 and the gap between the jaws is set to a first distance. The second curve 5864 represents the force over distance as the jaws close at a second speed, which is less than the first speed, until the stop trigger stops the jaws from closing at X1. The first jaw closing speed is adjusted to the second closing speed by the control circuit when the control circuit predicts that the closing force will be too high. At X1, the force F reaches a peak force of F2, which is less than F1, and the gap between the jaws is set to a second distance which is less than the first distance.

With reference still to FIG. 124, the bottom graph 5866 represents the jaws closing force (F) along the vertical axis and time (t) along the horizontal axis. The first curve 5867 represents the jaws closing force over time as the jaws close at a constant speed. As shown by the first curve 5867, when the jaws closing speed is constant, the jaws can experience a force that reaches a maximum F1 that is too high and reaches this peak force F1 before the stop trigger is activated. Accordingly, when the control circuit predicts that the jaws closing force will be high, the control circuit slows down the jaws closure speed after a period of t1. At the lower jaw closing speed the second curve 5869 can lead to a lower force (and a lower gap) and ultimately a lower peak force F2 (and gap) after a period t2 prior to initiating a firing stroke. As shown, the stop trigger actually changes speed the keep the jaws closing force F below the slope threshold 5868.

In various aspects, the control algorithms operate to effectively take control of the surgical instrument during the closing and/or firing motions. In certain aspects, a control algorithm automatically operates the surgical instrument in a cutting mode which optimizes staple form. For example, an exemplary control algorithm advances the knife in three incremental stages to optimize staple form. In the first stage, the knife is advanced distally a small increment (e.g., 3 mm) and is then stopped. Pressure applied to the tissue near the knife operates to force fluid out of the tissue. The knife remains stopped until a predetermined time passes, a sensor (pressure, distance, etc.) in the distal shaft indicates an asymptote, and combinations thereof. In the second stage, the knife is retracted proximally a smaller distance (e.g., 1 mm) from the first stage stopping point and is then stopped. The distance between the first stage stopping point and the second stage stopping point allows for the knife acceleration which occurs in the third stage. In the third stage, the knife is driven distally at a rapid speed until sufficient knife advancement is made to drive/form one staple (or one row of staples). The high speed move forms the staple quickly, reducing the chances of staple buckling and improving form quality. High speed forming is a technique used in nail guns, particularly in finishing nails that are extremely prone to buckling. The three stages are repeated for each row of staples for the length of the cut, effectively ratcheting through the tissue.

According to certain aspects, the surgical instrument includes a button which can be utilized by an operator to selectively enable or disable the above-described cutting mode. The button may be positioned on the shaft. Although the cutting mode was described as a cutting mode which optimizes staple form, it will be appreciated that according to other aspects the control algorithm may operate the surgical instrument in a cutting mode which is different than that described hereinabove.

In certain instances, in lieu of the closing motion or the firing motion being changed or modified based on upon the occurrence of a single trigger, threshold and/or event, the closing motion or the firing motion may be changed or modified based on a combination of triggers, thresholds, events and/or combinations thereof.

Figure 125:
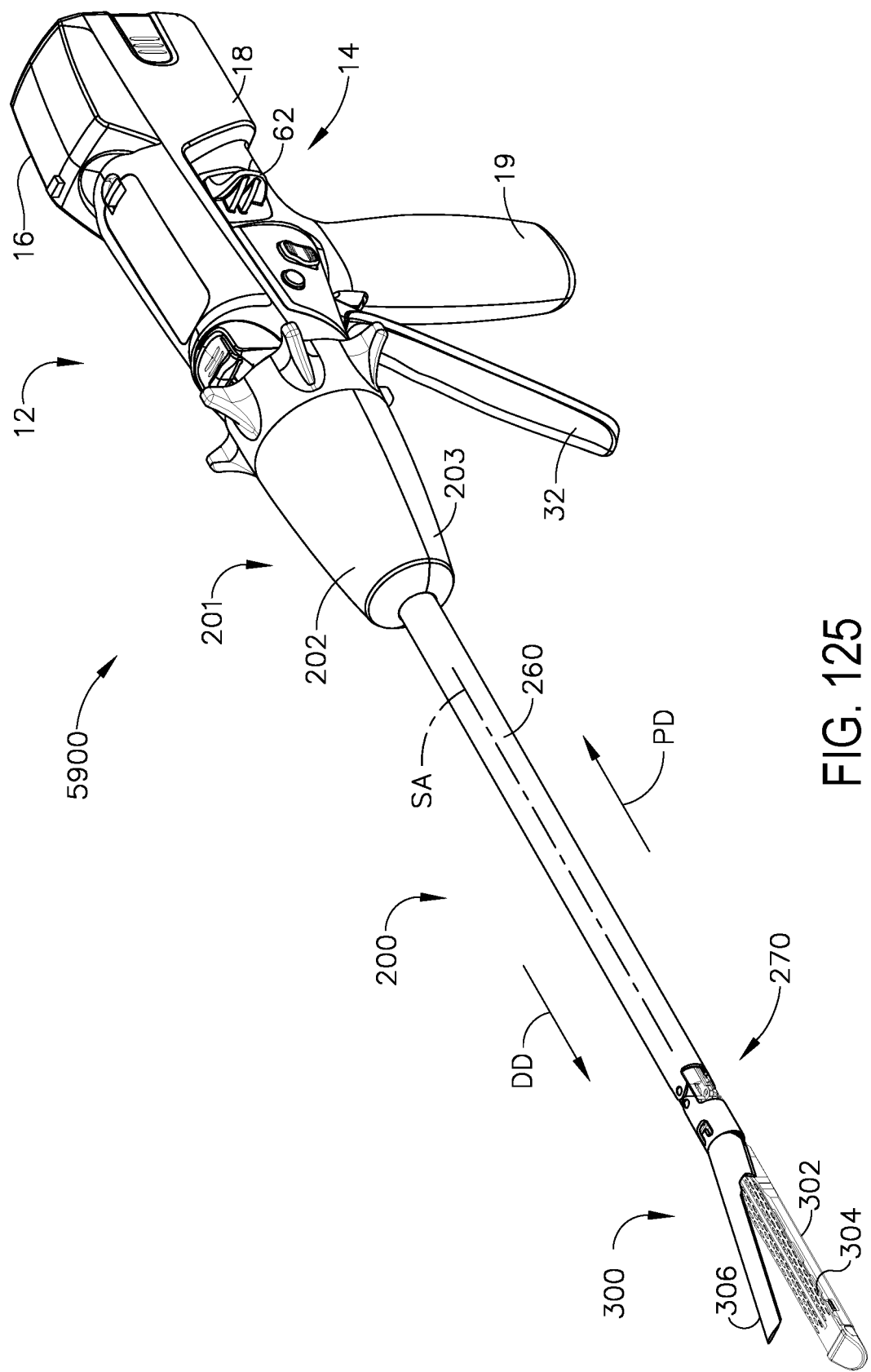

FIG. 125 illustrates a perspective view of a surgical instrument 5900 according to various aspects described herein. The surgical instrument 5900 is similar to the surgical instrument 5500 and includes an elongated channel configured to support a staple cartridge, an anvil pivotably connected to the elongated channel, a closure member mechanically coupled to the anvil, a knife mechanically coupled to the staple cartridge, an electric motor mechanically coupled to the closure member and/or the knife, a motor controller electrically coupled to the motor, and a control circuit electrically coupled to the motor controller. The surgical instrument 5900 is also similar to the surgical instrument 5500 in that the surgical instrument 5900 also includes sensors which are collectively configured to sense or measure a closing force, a firing force, a current drawn by the electric motor, an impedance of tissue positioned between the elongated channel and the anvil, a position of the anvil relative to the elongated channel, a position of the knife, or any combination thereof. The surgical instrument 5900 is also similar to the surgical instrument 5500 in that the surgical instrument 5900 also includes algorithms such as closing algorithms, firing algorithms, motor control algorithms, or any combination thereof, which operate to dynamically adjust the operation of the surgical instrument 5900. However, the surgical instrument 5900 is different from the surgical instrument 5500 in that the surgical instrument 5900 further includes one or more additional algorithms (in addition to those described hereinabove) which provide additional control functionality for the surgical instrument 5900, as described hereinbelow.

In certain aspects, the control algorithms are configured to automatically invoke different adjustments to the closing motion and/or the firing motion based on a combination of different triggers. For example, in certain aspects, a control algorithm is configured to adjust the firing motion to limit the maximum velocity of the knife, reduce the knife velocity by 50%, apply a pre-programmed knife velocity profile, only halt the firing motion and retract the knife, only complete the current firing motion, etc. based on a combination of different triggers. Such triggers may include, for example, a slope value of the firing force signal at the time a threshold is reached or exceeded, a slope value of the peak firing force values, a number of thresholds reached or exceeded within a given time interval, and thresholds reached or exceeded for multiple parameters (e.g., current, force, velocity, acceleration).

Figure 126A:
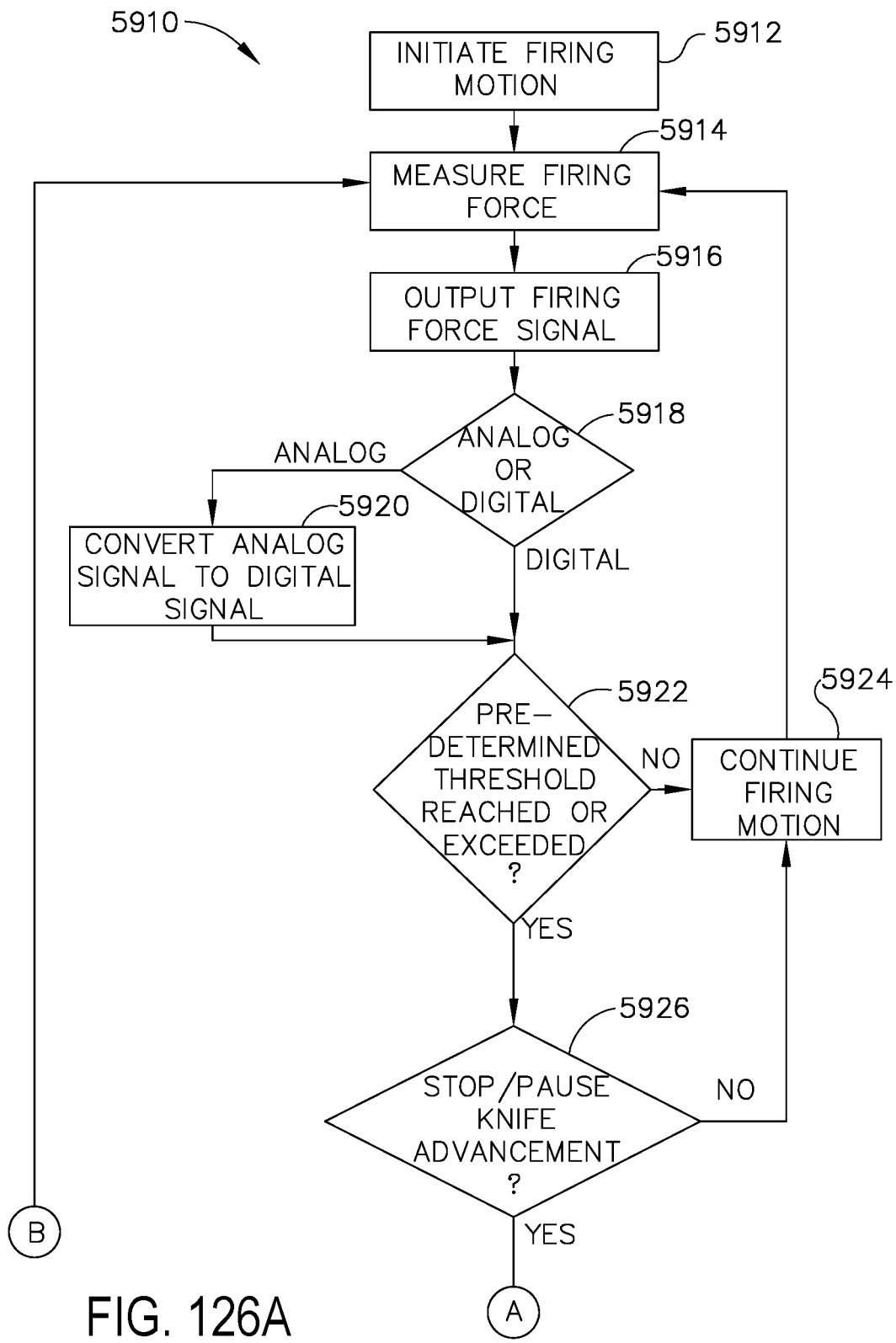
Figure 126B:
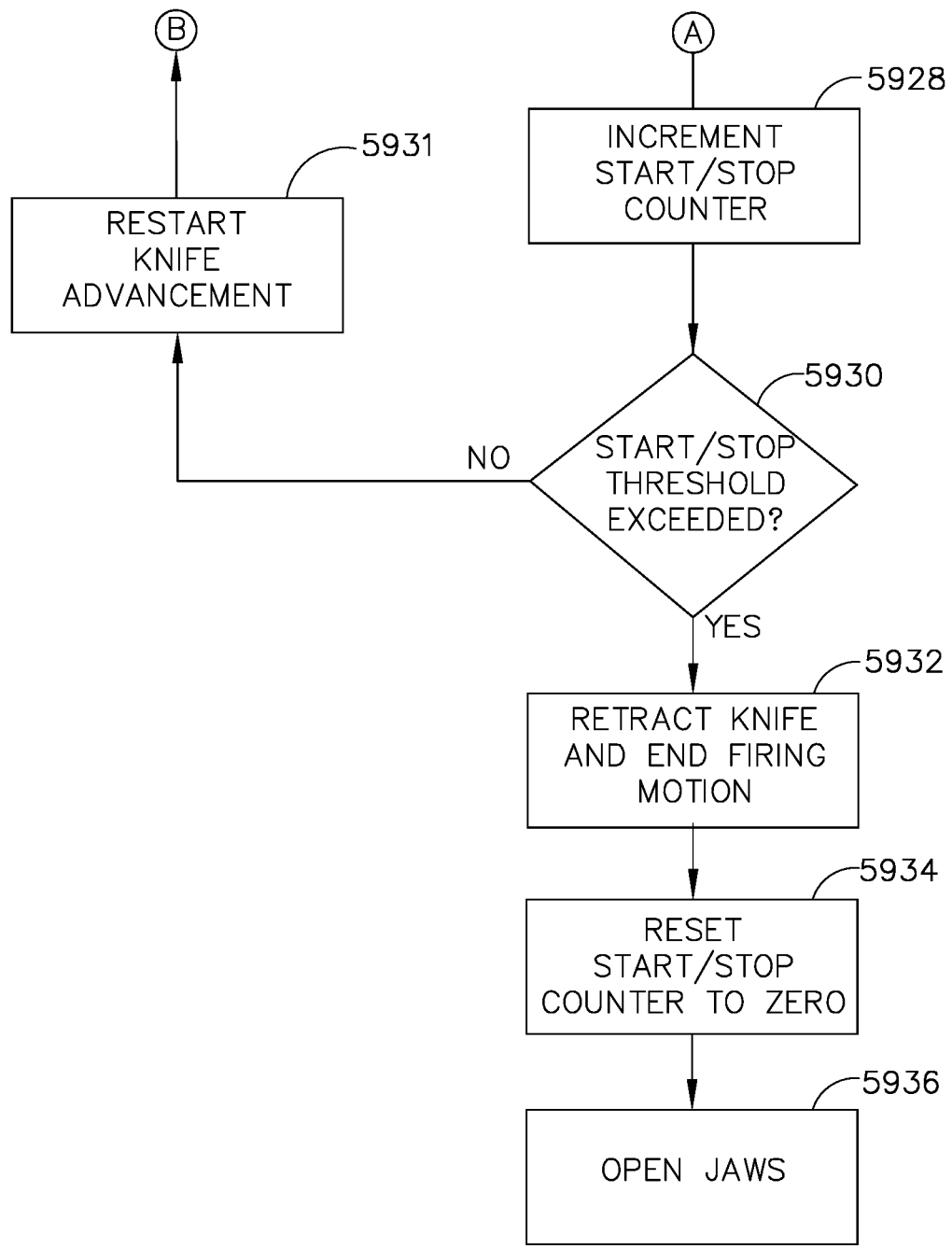

FIGS. 126A and 126B illustrate a method 5910 of controlling a firing motion of the surgical instrument 5900 according to various aspects. The process starts when a firing motion is initiated 5912. The firing motion may be initiated, for example, by pulling a firing trigger toward a handle. A start/stop counter of the surgical instrument 5900 is initially set to zero prior to or at the time the firing motion is originally initiated 5912. A sensor resident with the surgical instrument 5900 senses/measures 5914 a firing force. The firing force may be, for example, a force experienced by the drive system of the surgical instrument (e.g., by the sled, the knife and/or the firing bar), and/or any combination thereof. The firing force can be measured in any suitable manner, either directly or indirectly. For example, according to various aspects, the firing force can be measured directly by a sensor (e.g. a strain gauge) positioned on the sled, on the knife, or indirectly by a current draw of the motor.

In response to the firing force, the sensor outputs 5916 a firing force signal, which is indicative of the firing force sensed/measured 5914 by the sensor. Depending on the configuration of the sensor, the firing force signal can be an analog signal or a digital signal. Upon determining 5918 whether the firing force signal is either an analog signal or a digital signal, the process proceeds along the corresponding branch. When the determination 5918 is that the firing force signal is an analog signal, the process proceeds along the analog branch, where the analog signal is received by an A/D converter, converted 5920 to a digital signal representative of the analog signal by the A/D converter and the digital signal is output by the A/D converter. When the determination 5918 is that the firing force signal is a digital signal, the process proceeds along the digital branch because there is no need for an A/D conversion 5920 when the firing force signal is a digital signal.

The firing force signal which is a digital signal representative of the firing force sensed/measured 5914 by the sensor is received by a controller. The controller utilizes the digital signal and determines 5922 whether the firing force sensed/measured 5914 by the sensor reaches or exceeds a predetermined threshold. Of course according to various aspects, the predetermined threshold can be other than a firing force threshold. For example, according to various aspects, the predetermined threshold can be a given amplitude of the firing force signal, a slope value of the peak firing force values, how fast or slow a slope of the peak firing forces is approaching a predetermined threshold, a current drawn by the motor, and combinations thereof.

When the controller determines 5922 that a predetermined threshold has not been reached or exceeded, the firing motion originally initiated 5912 is continued 5924 along with interim processes 5914-5922. When the controller determines 5922 that a predetermined threshold has been reached or exceeded, the controller then determines 5926 if the knife advancement should be stopped/paused. In certain instances, depending on the position of the knife (which zone of the firing motion the knife is in), the advancement of the knife may be continued even if a predetermined threshold has been reached or exceeded. When the controller determines 5926 the advancement of the knife should not be paused/stopped, the firing motion originally initiated 5912 is continued 5924 along with interim processes 5914-5922.

When the controller determines 5926 the advancement of the knife should be paused/stopped (i.e., the trigger is not ignored), the controller communicates a stop signal or a pause signal to the motor controller to stop or pause the rotation of the motor(s) which drive the knife of the surgical instrument 5900 and the controller increments 5928 the start/stop counter from zero to one. The controller reads the start/stop counter and determines 5930 whether the count of the start/stop counter has reached or exceed a predetermined threshold. The predetermined threshold may be any suitable whole number. For example, according to various aspects, the predetermined threshold for the value of the start/stop counter is three.

When the controller determines 5930 the count of the start/stop counter has not reached or exceed the predetermined threshold, the advancement of the knife may be restarted after a predetermined period of time, once the firing force has dropped a predetermined amount, and combinations thereof, and the interim processes 5914-5930 are continued. When the controller determines 5930 the count of the start/stop counter has reached or exceed the predetermined threshold, the controller ends 5932 the firing motion by communicating signals to the motor controller to reverse the rotation of the motor(s) which drive the knife of the surgical instrument 5900, thereby retracting the knife to its fully proximal position then (2) stop the "reversing" rotation of the motor(s), thereby ending 5932 the firing motion originally initiated 5912. When the firing motion is ended 5932, the controller may reset 5934 the start/stop counter to zero and the jaws of the surgical instrument 5900 may then be opened and removed from the tissue site.

FIG. 127 illustrates an example graph 5950 showing a first curve 5952 representative of a firing force F over time t for various aspects of the surgical instrument 5900, a knife position X over time t for various aspects of the surgical instrument 5900 and a second curve 5954 representative of knife velocity V over time t for various aspects of the surgical instrument 5900. The firing force F is shown along the top vertical axis, the knife velocity V is shown along the bottom vertical axis, the knife position X is shown along both the top and bottom horizontal axes and the time t is shown along both the top and bottom horizontal axes. As shown along the top and bottom horizontal axes, the knife position X travels over five zones (zones 1-5) along the knife channel in the cartridge 304 located in the lower jaw 302 of the end effector 300 of the surgical instrument 5900. The knife velocity V and the firing force F shown in FIG. 127 may be based on the assumption that the thickness and composition of the tissue along the cut line is non-uniform.

Accordingly, the curve 5952 is a representation of the firing force signal at various times during a firing motion and the curve 5954 is a representation of the knife velocity signal at various times during a firing motion. The curves 5952, 5954 may be generated mathematically by the controller based on the firing force signal(s) and the knife velocity signal(s) received by the controller. The firing force F represented on the top vertical axis may be a force experienced by the drive system of the surgical instrument 5900 (e.g., by the sled, the knife and/or the firing bar), and/or any combination thereof. The firing force F can be measured in any suitable manner, either directly or indirectly. For example, according to various aspects, the firing force F can be measured directly by a sensor (e.g., a strain gauge) positioned on the sled, on the knife, or indirectly by a current draw of the motor, and/or any combination thereof.

The knife velocity V represented on the bottom vertical axis may be a velocity of the knife, a velocity of the sled, a velocity of another component of the drive system (e.g., the firing bar), and/or any combination thereof. The knife velocity V can be measured in any suitable manner, either directly or indirectly. For example, according to various aspects, the knife velocity V can be measured directly by a combination of a magnet positioned on the firing bar and a Hall-effect sensor or indirectly by a current draw of the motor, an encoder coupled to the shaft of the motor, and/or any combination thereof.

For the example graph 5950, the curve 5954 shows the knife velocity V increasing from zero at time t=0 to a substantially maximum velocity V1 while the knife advances from its fully retracted position through zone 1 and into zone 2 of the firing motion. Once the substantially maximum velocity V1 is reached in zone 2, the knife continues to advance in zone 2 and zone 3 until a trigger, threshold and/or event prompts the control algorithm to automatically change the firing motion. In this case, as shown in the curve 5952, the firing force F reaches or exceeds a predetermined threshold (the firing force value Fcrit) at the time t1, thereby causing the controller to signal the motor controller to stop the rotation of the motor(s) which drive the knife of the surgical instrument 5900, thereby causing the knife velocity to go from the knife velocity V1 to zero as shown in the curve 5954. When the controller signals for the advancement of the knife to stop, the controller may increment a start/stop counter which was initially set to zero. In other words, the start/stop counter is incremented to one to reflect that one start/stop cycle has occurred in this particular firing motion.

After the advancement of the knife is stopped at the time t1 or shortly thereafter, upon the occurrence of another trigger such as, for example, a predetermined period of time (t2-t1), a drop of the firing force F a predetermined amount, a slope of the firing force signal reaching or exceeding a predetermined threshold, and combinations thereof, the controller may signal the motor controller to restart rotation of the motor(s) which drive the knife of the surgical instrument 5900. As shown in the curve 5954, advancement of the knife may be started again at the time t2 or shortly thereafter.

As shown in the curve 5954, at the time t2 or shortly thereafter, the knife velocity begins at zero and increases as the knife continues advancing in zone 3 of the firing motion until another trigger, threshold and/or event prompts the control algorithm to automatically change the firing motion. In this case, as shown in the curve 5952, the firing force F reaches or exceeds a predetermined threshold (the firing force value Fcrit) at the time t3, thereby causing the controller to signal the motor controller to stop the rotation of the motor(s) which drive the knife of the surgical instrument 5900, thereby causing the knife velocity to go from the knife velocity V2, which is less than the knife velocity V1, to zero. When the controller signals for the advancement of the knife to stop, the controller may increment the start/stop counter from 1 to 2 to reflect that two start/stop cycles have occurred in this particular firing motion.

After the advancement of the knife is stopped at the time t3 or shortly thereafter, upon the occurrence of another trigger such as, for example, a predetermined period of time (t4-t3), a drop of the firing force F a predetermined amount, a slope of the firing force signal reaching or exceeding a predetermined threshold, and combinations thereof, the controller may signal the motor controller to restart rotation of the motor(s) which drive the knife of the surgical instrument 5900. As shown in the curve 5954, advancement of the knife may be started again at the time t4 or shortly thereafter.

As shown in the curve 5954, at the time t4 or shortly thereafter, the knife velocity begins at zero and increases as the knife continues advancing in zone 3 of the firing motion until another trigger, threshold and/or event prompts the control algorithm to automatically change the firing motion. In this case, as shown in the curve 5952, the firing force F reaches or exceeds a predetermined threshold (the firing force value Fcrit) at the time t5, thereby causing the controller to signal the motor controller to stop the rotation of the motor(s) which drive the knife of the surgical instrument 5900, thereby causing the knife velocity to go from the knife velocity V2 to zero. When the controller signals for the advancement of the knife to stop, the controller may increment the start/stop counter from 2 to 3 to reflect that three start/stop cycles have occurred in this particular firing motion.

According to various aspects, after the third start/stop cycle has occurred, the controller signals the motor controller to reverse the rotation of the motor(s) which drive the knife of the surgical instrument 5900, effectively ceasing further advancement of the knife and returning the knife to its fully retracted position. This is shown conceptually in the curve 5954 as the knife velocity V stopping at zero at time t5 while the knife is in zone 3 of the firing motion and in the curve 5952 as the firing force F stopping at zero shortly after time t5 while the knife is in zone 3 of the firing motion. In the example graph 5950, the three start/stop cycles is deemed to be indicative of a situation where the surgical instrument 5900 has determined there is an insufficient possibility of completing the firing motion (e.g., due to an obstruction) so the knife is returned to the fully retracted state, thereby allowing the jaws of the surgical instrument 5900 to be opened and removed from the tissue site. According to other aspects, the number of start/stop cycles deemed to be indicative of a situation where the surgical instrument 5900 has determined there is an insufficient possibility of completing the firing motion can be more than three or less than three.

Although the example graph 5950 reflects the control algorithm deeming there to be an insufficient possibility of a successful firing motion after the firing force threshold Fcrit was reached or exceeded three consecutive times while the knife is in zone 3 of the firing motion, it will be appreciated that any number of different criteria may be utilized to deem that there is an insufficient possibility of a successful firing motion. For example, according to some aspects, the breaches may be based on a rate of change of a velocity of the knife, on a rate of change of the load, on a rate of change of the firing force, etc., and the deeming may be based on more than three or less than three consecutive breaches, on the knife being in zone 3 or another zone when the breaches occur, etc.

Furthermore, although the functionality of the control algorithms described in connection with FIGS. 117, 118A and 118B were described in the context of the firing motion, it will be appreciated that the control algorithms of the surgical instrument 5900 may also be configured to change, adjust or modify the closing motion in a similar manner. For example, if the closure force reaches or exceeds a predetermined threshold three consecutive times while tissue is being compressed between the jaws of the surgical instrument 5900, the control algorithms may deem that there is an insufficient possibility of a successful closing motion and automatically adjust the closing motion to stop the closing motion and open the jaws of the surgical instrument 5900.

In certain aspects, based on the real-time or continuous determination of the defect density of the staple form, the control algorithms can automatically make changes to various closing and/or firing parameters (e.g., clamp pressure, speed of firing, timing of a pause in firing, duration of a firing pause, etc.) to affect staple form.

The information obtained from the sensor array can be analyzed by determining the defect density at any location along the staple line. The defect density can be analyzed as a running number along the entirety of the staple line. Alternatively, staple line integrity could be determined at each opportunity along the length of the staple line.

The defect density can be used to inform the surgeon of possible issues prior to unclamping the surgical instrument 5900. If certain thresholds of defect density are encountered, the surgical instrument 5900 can respond in different ways.

For example, if the detected defect density or rate is above a first decision point, the surgical instrument 5900 may slow down the velocity of the closure tube to allow more time for tissue flow and presumably better staple form. The detection of malforms (lack of detection of good form) can also be used to change the closing and/or firing parameters in real time to result in better staple formation with the remainder of the staple line. If the detected defect density or defect rate is above a second decision point, the surgical instrument 5900 may display a warning to the surgeon prior to the unclamping of the jaws of the surgical instrument 5900, so that the surgeon can be prepared with additional therapies to treat potential bleeding or stabilize the tissue as appropriate.

While various details have been set forth in the foregoing description, it will be appreciated that the various aspects of the motorized surgical instruments may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a processor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects of the aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, those skilled in the art will appreciate that the mechanisms of the subject matter described herein are capable of being distributed as a program product in a variety of forms, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

In summary, numerous benefits have been described which result from employing the concepts described herein. The foregoing description of the one or more aspects has been presented for purposes of illustration and description. It is not intended to be exhaustive or limiting to the precise form disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

What is claimed is:

1. A surgical system, comprising:
   an end effector, comprising:
      a first jaw; and
      a second jaw rotatable relative to said first jaw between an open position and a closed position;
   a firing driver driveable through the end effector from a first position toward a second position during a firing stroke;
   a force sensor to measure a force to drive the firing driver;
   a position sensor to detect a position of the firing driver; and
   a control circuit to communicate with the force sensor and the position sensor, wherein the control circuit is to:
      advance the firing driver toward the second position; and
      select between maintaining advancement of the firing driver toward the second position and pausing advancement of the firing driver based on:
         the measured force exceeding a force threshold; and
         the detected position of the firing driver.

2. The surgical system of claim 1, wherein the end effector defines a proximal zone, a medial zone distal to the proximal zone, and a distal zone distal to the medial zone, and wherein the control circuit is to maintain advancement of the firing driver based on:
   the measured force exceeding the force threshold; and
   a detection of the firing driver being positioned in the proximal zone or the distal zone.

3. The surgical system of claim 2, wherein the control circuit is to pause advancement of the firing driver based on:
   the measured force exceeding the force threshold; and
   a detection of the firing driver being positioned in the medial zone.

4. The surgical system of claim 1, wherein the firing driver comprises a sled.

5. The surgical system of claim 1, wherein the firing driver comprises a knife.

6. The surgical system of claim 1, wherein the force sensor comprises a strain gauge.

7. The surgical system of claim 1, further comprising a motor to driver the firing driver through the firing stroke, and wherein the force sensor comprises a current sensor to measure a current draw of the motor.

8. A surgical system, comprising:
   an end effector;
   a firing driver driveable through the end effector from a first position toward a second position during a firing stroke;
   a force sensor to measure a force to drive the firing driver;
   a position sensor to detect a position of the firing driver; and
   a control circuit to communicate with the force sensor and the position sensor, wherein the control circuit is to:
      advance the firing driver toward the second position; and
      maintain advancement of the firing driver toward the second position based on:
         the measured force exceeding a force threshold; and
         the detected position of the firing driver.

9. The surgical system of claim 8, wherein the end effector defines a proximal zone, a medial zone distal to the proximal zone, and a distal zone distal to the medial zone, and wherein the control circuit is to maintain advancement of the firing driver toward the second position based on:
   the measured force exceeding the force threshold; and
   a detection of the firing driver being positioned in the proximal zone or the distal zone.

10. The surgical system of claim 9, wherein the control circuit is to pause advancement of the firing driver based on:
   the measured force exceeding the force threshold; and
   a detection of the firing driver being positioned in the medial zone.

11. The surgical system of claim 8, wherein the firing driver comprises a sled.

12. The surgical system of claim 8, wherein the firing driver comprises a knife.

13. The surgical system of claim 8, wherein the force sensor comprises a strain gauge.

14. The surgical system of claim 8, further comprising a motor to driver the firing driver through the firing stroke, and wherein the force sensor comprises a current sensor to measure a current draw of the motor.

15. A surgical system, comprising:
an end effector;
a firing driver driveable through the end effector from a first position toward a second position during a firing stroke;
a force sensor to measure a force to drive the firing driver;
a position sensor to detect a position of the firing driver; and
a control circuit to communicate with the force sensor and the position sensor, wherein the control circuit is to:
advance the firing driver toward the second position;
determine a rate of change of the measured force; and
select between maintaining advancement of the firing driver and pausing advancement of the firing driver based on:
the determined rate of change exceeding a rate of change threshold; and
the detected position of the firing driver.

16. The surgical system of claim 15, wherein the control circuit is to select between maintaining advancement of the firing driver and pausing advancement of the firing driver further based on a comparison of the determined rate of change to a firing force threshold.

17. The surgical system of claim 15, wherein the end effector defines a proximal zone, a medial zone distal to the proximal zone, and a distal zone distal to the medial zone, and wherein the control circuit is to maintain advancement of the firing driver based on:
the determined rate of change exceeding the rate of change threshold; and
a detection of the firing driver being positioned in the proximal zone or the distal zone.

18. The surgical system of claim 17, wherein the control circuit is to pause advancement of the firing driver based on:
the determined rate of change exceeding the rate of change threshold; and
a detection of the firing driver being positioned in the medial zone.

19. The surgical system of claim 15, wherein the force sensor comprises a strain gauge.

20. The surgical system of claim 15, further comprising a motor to driver the firing driver through the firing stroke, and wherein the force sensor comprises a current sensor to measure a current draw of the motor.

\* \* \* \* \*